US011129615B2

(12) United States Patent
Scheib et al.

(10) Patent No.: US 11,129,615 B2
(45) Date of Patent: Sep. 28, 2021

(54) SURGICAL STAPLING SYSTEM

(71) Applicant: Cilag GmbH International, Zug (CH)

(72) Inventors: Charles J. Scheib, Loveland, OH (US); Gary S. Jaworek, Cincinnati, OH (US); Steven G. Hall, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 468 days.

(21) Appl. No.: 14/551,390

(22) Filed: Nov. 24, 2014

(65) Prior Publication Data

US 2015/0083782 A1 Mar. 26, 2015

Related U.S. Application Data

(63) Continuation of application No. 13/835,592, filed on Mar. 15, 2013, now abandoned, which is a (Continued)

(51) Int. Cl.
*A61B 17/10* (2006.01)
*A61B 17/068* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC ................ A61B 17/068; A61B 17/072; A61B 17/07207; A61B 17/105;
(Continued)

(56) References Cited

U.S. PATENT DOCUMENTS

| | | | |
|---|---|---|---|
| 66,052 | A | 6/1867 | Smith |
| 662,587 | A | 11/1900 | Blake |

(Continued)

FOREIGN PATENT DOCUMENTS

| | | | |
|---|---|---|---|
| AU | 2008207624 | A1 | 3/2009 |
| AU | 2010214687 | A1 | 9/2010 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Robert F Long
*Assistant Examiner* — Eduardo R Ferrero

(57) ABSTRACT

A surgical stapling system comprising a stapling assembly, a firing member, a shaft, an articulation joint, and a handle is disclosed. The stapling assembly comprises a distal end, a staple cartridge, and an anvil. The stapling assembly is configurable in an open configuration and a closed configuration by a closure member. The shaft is rotatable in first and second rotation directions. The stapling assembly is articulatable about the articulation joint in first and second articulation directions. The handle comprises a firing actuator configured to move the firing member toward the distal end, and a rotation actuator comprising a first initial position. The handle further comprises an articulation actuator comprising a second initial position. The handle further comprises means for preventing the articulation of the stapling assembly and the rotation of the shaft when the firing actuator is being actuated. The means is independent from the closure member.

1 Claim, 50 Drawing Sheets

906 CCW CW 920 922 994 992 PWM 993 OUTPUT DSP INPUT 123 990 121 991 949 941b 931 990 949 925 949 940b 947b 930 932 941b 940a 947a 941a

Related U.S. Application Data continuation of application No. 12/366,538, filed on Feb. 5, 2009, now Pat. No. 8,517,239.

(51) Int. Cl.
*A61B 17/072* (2006.01)
*A61B 17/29* (2006.01)
*A61B 17/00* (2006.01)

(52) U.S. Cl.
CPC ............... *A61B 2017/00398* (2013.01); *A61B 2017/2927* (2013.01); *A61B 2017/2929* (2013.01)

(58) Field of Classification Search
CPC .. A61B 2017/00398; A61B 2017/2929; A61B 2017/2927
See application file for complete search history.

(56) References Cited

U.S. PATENT DOCUMENTS 670,748 A 3/1901 Weddeler
719,487 A 2/1903 Minor
804,229 A 11/1905 Hutchinson
951,393 A 3/1910 Hahn
1,075,556 A 10/1913 Fenoughty
1,188,721 A 6/1916 Bittner
1,306,107 A 6/1919 Elliott
1,314,601 A 9/1919 McCaskey
1,677,337 A 7/1928 Grove
1,794,907 A 3/1931 Kelly
1,849,427 A 3/1932 Hook
1,944,116 A 1/1934 Stratman
1,954,048 A 4/1934 Jeffrey et al.
2,028,635 A 1/1936 Wappler
2,037,727 A 4/1936 La Chapelle
2,132,295 A 10/1938 Hawkins
2,161,632 A 6/1939 Nattenheimer
D120,434 S 5/1940 Gold
2,211,117 A 8/1940 Hess
2,214,870 A 9/1940 West
2,224,882 A 12/1940 Peck
2,318,379 A 5/1943 Davis et al.
2,329,440 A 9/1943 La Place
2,377,581 A 6/1945 Shaffrey
2,406,389 A 8/1946 Lee
2,441,096 A 5/1948 Happe
2,448,741 A 9/1948 Scott et al.
2,450,527 A 10/1948 Smith et al.
2,491,872 A 12/1949 Neuman
2,507,872 A 5/1950 Unsinger
2,526,902 A 10/1950 Rublee
2,527,256 A 10/1950 Jackson
2,578,686 A 12/1951 Fish
2,638,901 A 5/1953 Sugarbaker
2,674,149 A 4/1954 Benson
2,701,489 A 2/1955 Osborn
2,711,461 A 6/1955 Happe
2,724,289 A 11/1955 Wight
2,742,955 A 4/1956 Dominguez
2,804,848 A 9/1957 O'Farrell et al.
2,808,482 A 10/1957 Zanichkowsky et al.
2,853,074 A 9/1958 Olson
2,856,192 A 10/1958 Schuster
2,887,004 A 5/1959 Stewart
2,957,353 A 10/1960 Lewis
2,959,974 A 11/1960 Emrick
3,026,744 A 3/1962 Rouse
3,032,769 A 5/1962 Palmer
3,060,972 A 10/1962 Sheldon
3,075,062 A 1/1963 Iaccarino
3,078,465 A 2/1963 Bobrov
3,079,606 A 3/1963 Bobrov et al.
3,080,564 A 3/1963 Strekopitov et al.
3,166,072 A 1/1965 Sullivan, Jr.
3,180,236 A 4/1965 Beckett
3,196,869 A 7/1965 Scholl
3,204,731 A 9/1965 Bent et al.
3,266,494 A 8/1966 Brownrigg et al.
3,269,630 A 8/1966 Fleischer
3,269,631 A 8/1966 Takaro
3,275,211 A 9/1966 Hirsch et al.
3,317,103 A 5/1967 Cullen et al.
3,317,105 A 5/1967 Astafjev et al.
3,357,296 A 12/1967 Lefever
3,359,978 A 12/1967 Smith, Jr.
3,377,893 A 4/1968 Shorb
3,480,193 A 11/1969 Ralston
3,490,675 A 1/1970 Green et al.
3,494,533 A 2/1970 Green et al.
3,499,591 A 3/1970 Green
3,503,396 A 3/1970 Pierie et al.
3,509,629 A 5/1970 Kidokoro
3,551,987 A 1/1971 Wilkinson
3,568,675 A 3/1971 Harvey
3,572,159 A 3/1971 Tschanz
3,583,393 A 6/1971 Takahashi
3,589,589 A 6/1971 Akopov
3,598,943 A 8/1971 Barrett
3,608,549 A 9/1971 Merrill
3,618,842 A 11/1971 Bryan
3,638,652 A 2/1972 Kelley
3,640,317 A 2/1972 Panfili
3,643,851 A 2/1972 Green et al.
3,650,453 A 3/1972 Smith, Jr.
3,661,339 A 5/1972 Shimizu
3,661,666 A 5/1972 Foster et al.
3,662,939 A 5/1972 Bryan
3,688,966 A 9/1972 Perkins et al.
3,695,646 A 10/1972 Mommsen
3,709,221 A 1/1973 Riely
3,717,294 A 2/1973 Green
3,724,237 A 4/1973 Wood
3,726,755 A 4/1973 Shannon
3,727,904 A 4/1973 Gabbey
3,734,207 A 5/1973 Fishbein
3,740,994 A 6/1973 DeCarlo, Jr.
3,744,495 A 7/1973 Johnson
3,746,002 A 7/1973 Haller
3,747,603 A 7/1973 Adler
3,747,692 A 7/1973 Davidson
3,751,902 A 8/1973 Kingsbury et al.
3,752,161 A 8/1973 Bent
3,799,151 A 3/1974 Fukaumi et al.
3,808,452 A 4/1974 Hutchinson
3,815,476 A 6/1974 Green et al.
3,819,100 A 6/1974 Noiles et al.
3,821,919 A 7/1974 Knohl
3,826,978 A 7/1974 Kelly
3,836,171 A * 9/1974 Hayashi ................ B60R 22/343 242/384
3,837,555 A 9/1974 Green
3,841,474 A 10/1974 Maier
3,851,196 A 11/1974 Hinds
3,863,639 A 2/1975 Kleaveland
3,863,940 A 2/1975 Cummings
3,883,624 A 5/1975 McKenzie et al.
3,885,491 A 5/1975 Curtis
3,887,393 A 6/1975 La Rue, Jr.
3,892,228 A 7/1975 Mitsui
3,894,174 A 7/1975 Cartun
3,902,247 A 9/1975 Fleer et al.
3,940,844 A 3/1976 Colby et al.
3,944,163 A * 3/1976 Hayashi ................ B60R 22/353 242/382.1
3,950,686 A 4/1976 Randall
3,952,747 A 4/1976 Kimmell, Jr.
3,955,581 A 5/1976 Spasiano et al.
3,959,879 A 6/1976 Sellers
RE28,932 E 8/1976 Noiles et al.
3,972,734 A 8/1976 King
3,973,179 A 8/1976 Weber et al.
3,981,051 A 9/1976 Brumlik
3,999,110 A 12/1976 Ramstrom et al.

(56) References Cited

U.S. PATENT DOCUMENTS 4,025,216 A 5/1977 Hives
4,027,746 A 6/1977 Kine
4,034,143 A 7/1977 Sweet
4,038,987 A 8/1977 Komiya
4,054,108 A 10/1977 Gill
4,060,089 A 11/1977 Noiles
4,066,133 A 1/1978 Voss
4,085,337 A 4/1978 Moeller
4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale
4,154,122 A 5/1979 Severin
4,160,857 A 7/1979 Nardella et al.
4,169,990 A 10/1979 Lerdman
4,180,285 A 12/1979 Reneau
4,185,701 A 1/1980 Boys
4,190,042 A 2/1980 Sinnreich
4,198,734 A 4/1980 Brumlik
4,198,982 A 4/1980 Fortner et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A * 11/1982 Kochera ................ B62K 21/16 403/93
4,366,544 A 12/1982 Shima et al.
4,369,013 A 1/1983 Abildgaard et al.
4,373,147 A 2/1983 Carlson, Jr.
4,376,380 A * 3/1983 Burgess .................. E05B 37/08 70/303 A
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Siegel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,520,817 A 6/1985 Green
4,522,327 A 6/1985 Korthoff et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles et al.
4,580,712 A 4/1986 Green

(56) References Cited

U.S. PATENT DOCUMENTS 4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang

(56) References Cited

U.S. PATENT DOCUMENTS 4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A * 5/1992 Hufnagle ................ F16D 11/12 74/366
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman et al.
5,173,053 A 12/1992 Swanson et al.
5,173,133 A 12/1992 Morin et al.
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D338,729 S 8/1993 Sprecklemeier et al.
5,234,447 A 8/1993 Kaster et al.
5,236,269 A 8/1993 Handy

(56) References Cited

U.S. PATENT DOCUMENTS 5,236,424 A 8/1993 Imran
5,236,440 A 8/1993 Hlavacek
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,714 A 3/1994 Kramer
5,303,606 A 4/1994 Kokinda
5,304,204 A 4/1994 Bregen
D347,474 S 5/1994 Olson
5,307,976 A 5/1994 Olson et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller née Degwitz et al.
5,314,466 A 5/1994 Stern et al.
5,318,221 A 6/1994 Green et al.
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A * 7/1994 Hassler .................. A61B 17/29 600/564
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Iacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,250 A 10/1994 Christensen
5,354,303 A 10/1994 Spaeth et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.

(56) References Cited

U.S. PATENT DOCUMENTS 5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson, IV et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,654 A 7/1995 Nic
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Schichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,509,596 A 4/1996 Green et al.
5,509,916 A 4/1996 Taylor
5,509,918 A 4/1996 Romano
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.

(56) References Cited

U.S. PATENT DOCUMENTS 5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,945 A 8/1996 Fritzsch
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A * 3/1997 Kolesa .................. A61B 17/29 606/170
5,611,709 A 3/1997 McAnulty
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A * 5/1997 Sklar ............. A61B 17/320016 606/170
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida

(56) References Cited

U.S. PATENT DOCUMENTS 5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Costellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
5,758,814 A 6/1998 Gallagher et al.
5,762,255 A 6/1998 Chrisman et al.
5,762,256 A 6/1998 Mastri et al.
5,765,565 A 6/1998 Adair
5,766,188 A 6/1998 Igaki
5,766,205 A 6/1998 Zvenyatsky et al.
5,769,303 A 6/1998 Knodel et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A * 7/1998 Koukline ........... A61B 17/0686 227/119
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.

(56) References Cited

U.S. PATENT DOCUMENTS 5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A * 11/1998 Kolesa .................. A61B 17/29 600/564
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,760 A 2/1999 McGuckin, Jr.
5,868,790 A 2/1999 Vincent et al.
5,871,135 A 2/1999 Williamson, IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,878 A 4/1999 Pierce
5,894,979 A 4/1999 Powell
5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,984,949 A 11/1999 Levin
5,988,479 A 11/1999 Palmer
5,990,379 A 11/1999 Gregory
5,993,466 A 11/1999 Yoon
5,997,528 A 12/1999 Bisch et al.

(56) References Cited

U.S. PATENT DOCUMENTS 5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Törmälä et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
H1904 H 10/2000 Yates et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,149,660 A 11/2000 Laufer et al.
6,151,323 A 11/2000 O'Connell et al.
6,152,935 A 11/2000 Kammerer et al.
6,155,473 A 12/2000 Tompkins et al.
6,156,056 A 12/2000 Kearns et al.
6,157,169 A 12/2000 Lee
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.

(56) References Cited

U.S. PATENT DOCUMENTS 6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balázs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.

(56) References Cited

U.S. PATENT DOCUMENTS 6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,625,517 B1 9/2003 Bogdanov et al.
6,626,834 B2 9/2003 Dunne et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Toni
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.

(56) References Cited

U.S. PATENT DOCUMENTS 6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Würsch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush

(56) References Cited

U.S. PATENT DOCUMENTS 6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 * 10/2005 Milliman ......... A61B 17/07207 227/175.1
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 * 4/2006 Ohta ................... A01B 33/082 74/340
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.

(56) References Cited

U.S. PATENT DOCUMENTS 7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.

(56) References Cited

U.S. PATENT DOCUMENTS

D541,418 S 4/2007 Schechter et al.
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 * 4/2007 Frecker ................. A61B 17/29 606/167
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapius
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,313,430 B2 12/2007 Urquhart et al.
7,314,473 B2 1/2008 Jinno et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu

(56) References Cited

U.S. PATENT DOCUMENTS 7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 * 7/2008 Smith .............. A61B 17/07207 227/175.1
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 * 10/2008 Boudreaux ...... A61B 17/07207 227/176.1
7,442,201 B2 10/2008 Pugsley et al.
7,443,547 B2 10/2008 Moreno et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.

(56) References Cited

U.S. PATENT DOCUMENTS 7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,783 B2 1/2010 Roberts et al.
7,644,848 B2 * 1/2010 Swayze ............ A61B 17/07207 227/2
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh, II et al.
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shelton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.

(56) References Cited

U.S. PATENT DOCUMENTS 7,731,724 B2 6/2010 Huitema et al.
7,735,703 B2 6/2010 Morgan et al.
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,879,063 B2 2/2011 Khosravi
7,879,070 B2 2/2011 Ortiz et al.
7,883,461 B2 2/2011 Albrecht et al.
7,883,465 B2 2/2011 Donofrio et al.
7,883,540 B2 2/2011 Niwa et al.

(56) References Cited

U.S. PATENT DOCUMENTS 7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,102 B2 7/2011 Patel et al.
7,981,132 B2 7/2011 Dubrul et al.
7,987,405 B2 7/2011 Turner et al.
7,988,015 B2 8/2011 Mason, II et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.
8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.

(56) References Cited

U.S. PATENT DOCUMENTS 8,016,858 B2 9/2011 Whitman
8,016,881 B2 9/2011 Furst
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,882 B2 10/2011 Viola
8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 * 10/2011 Smith .............. A61B 17/07207
227/176.1
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,636 B2 11/2011 Moll et al.
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.
8,074,858 B2 12/2011 Marczyk
8,074,859 B2 12/2011 Kostrzewski
8,074,861 B2 12/2011 Ehrenfels et al.
8,075,476 B2 12/2011 Vargas
8,075,571 B2 12/2011 Vitali et al.
8,079,950 B2 12/2011 Stern et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,102,138 B2 1/2012 Sekine et al.
8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.

(56) References Cited

U.S. PATENT DOCUMENTS 8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,041 B2 7/2012 Marczyk et al.
8,231,042 B2 7/2012 Hessler et al.
8,231,043 B2 7/2012 Tarinelli et al.
8,235,272 B2 8/2012 Nicholas et al.
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai

(56) References Cited

U.S. PATENT DOCUMENTS 8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,381,828 B2 2/2013 Whitman et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel

(56) References Cited

U.S. PATENT DOCUMENTS 8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 * 11/2013 Smith .............. A61B 17/07207
227/175.1
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.

(56) References Cited

U.S. PATENT DOCUMENTS 8,608,745 B2 12/2013 Guzman et al.
8,613,383 B2 12/2013 Beckman et al.
8,616,427 B2 12/2013 Viola
8,616,431 B2 12/2013 Timm et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.

(56) References Cited

U.S. PATENT DOCUMENTS 8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roβkamp et al.
8,869,913 B2 10/2014 Matthias et al.
8,870,050 B2 10/2014 Hodgkinson
8,870,867 B2 10/2014 Walberg et al.
8,870,912 B2 10/2014 Brisson et al.
8,875,971 B2 11/2014 Hall et al.
8,875,972 B2 11/2014 Weisenburgh, II et al.
8,876,857 B2 11/2014 Burbank
8,876,858 B2 11/2014 Braun
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,936,614 B2 1/2015 Allen, IV
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.
8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.

(56) References Cited

U.S. PATENT DOCUMENTS 8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.
8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux
8,982,195 B2 3/2015 Claus et al.
8,984,711 B2 3/2015 Ota et al.
8,985,240 B2 3/2015 Winnard
8,985,429 B2 3/2015 Balek et al.
8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,005,230 B2 4/2015 Yates et al.
9,005,238 B2 4/2015 DeSantis et al.
9,005,243 B2 4/2015 Stopek et al.
9,010,606 B2 4/2015 Aranyi et al.
9,010,608 B2 4/2015 Casasanta, Jr. et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.

(56) References Cited

U.S. PATENT DOCUMENTS 9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni

(56) References Cited

U.S. PATENT DOCUMENTS 9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,226 B2 6/2016 Zemlok et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,669 B2 7/2016 Karkanias et al.
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.

(56) References Cited

U.S. PATENT DOCUMENTS 9,451,958 B2 9/2016 Shelton, IV et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,523 B2 10/2016 Meade et al.
9,474,540 B2 10/2016 Stokes et al.
9,475,180 B2 10/2016 Eshleman et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,566,061 B2 2/2017 Aronhalt et al.
9,566,062 B2 2/2017 Boudreaux
9,566,065 B2 2/2017 Knodel
9,566,067 B2 2/2017 Milliman et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.
9,610,412 B2 4/2017 Zemlok et al.
9,614,258 B2 4/2017 Takahashi et al.
9,615,826 B2 4/2017 Shelton, IV et al.
9,622,745 B2 4/2017 Ingmanson et al.
9,622,746 B2 4/2017 Simms et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell

(56) References Cited

U.S. PATENT DOCUMENTS 9,636,850 B2 5/2017 Stopek et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,116 B2 5/2017 Smith et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,731,410 B2 8/2017 Hirabayashi et al.
9,733,663 B2 8/2017 Leimbach et al.
9,737,297 B2 8/2017 Racenet et al.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.

(56) References Cited

U.S. PATENT DOCUMENTS 9,801,627 B2 10/2017 Harris et al.
9,801,628 B2 10/2017 Harris et al.
9,801,634 B2 10/2017 Shelton, IV et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter et al.
9,833,239 B2 12/2017 Yates et al.
9,833,241 B2 12/2017 Huitema et al.
9,833,242 B2 12/2017 Baxter et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach
9,883,861 B2 2/2018 Shelton, IV et al.
9,884,456 B2 2/2018 Schellin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.

(56) References Cited

U.S. PATENT DOCUMENTS 9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,003 B2 6/2018 Timm et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,284 B2 6/2018 Boudreaux
9,999,423 B2 6/2018 Schuckmann et al.
9,999,472 B2 6/2018 Weir et al.
10,004,500 B2 6/2018 Shelton, IV et al.
10,004,506 B2 6/2018 Shelton, IV et al.
D822,206 S 7/2018 Shelton, IV et al.
10,010,395 B2 7/2018 Puckett et al.
10,016,656 B2 7/2018 Devor et al.
10,022,123 B2 7/2018 Williams et al.
10,022,125 B2 7/2018 (Prommersberger) Stopek et al.
10,024,407 B2 7/2018 Aranyi et al.
10,028,744 B2 7/2018 Shelton, IV et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,532 B2 8/2018 Srinivas et al.
10,039,545 B2 8/2018 Sadowski et al.
10,041,822 B2 8/2018 Zemlok
10,045,778 B2 8/2018 Yates et al.
10,045,782 B2 8/2018 Murthy Aravalli
10,045,869 B2 8/2018 Forsell
10,052,102 B2 8/2018 Baxter, III et al.
10,052,164 B2 8/2018 Overmyer
10,058,317 B2 8/2018 Fan et al.
10,058,373 B2 8/2018 Takashino et al.
10,058,395 B2 8/2018 Devengenzo et al.
10,064,620 B2 9/2018 Gettinger et al.
10,064,639 B2 9/2018 Ishida et al.
10,064,649 B2 9/2018 Golebieski et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,128 B2 10/2018 Cooper et al.
10,105,136 B2 10/2018 Yates et al.
10,105,139 B2 10/2018 Yates et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,698 B2 10/2018 Scheib et al.
10,111,702 B2 10/2018 Kostrzewski
D833,608 S 11/2018 Miller et al.
10,117,650 B2 11/2018 Nicholas et al.
10,117,653 B2 11/2018 Leimbach et al.
10,117,654 B2 11/2018 Ingmanson et al.
10,124,493 B2 11/2018 Rothfuss et al.
10,130,361 B2 11/2018 Yates et al.
10,130,367 B2 11/2018 Cappola et al.
10,130,738 B2 11/2018 Shelton, IV et al.
10,130,830 B2 11/2018 Miret Carceller et al.
10,133,248 B2 11/2018 Fitzsimmons et al.
10,136,879 B2 11/2018 Ross et al.
10,136,889 B2 11/2018 Shelton, IV et al.
10,136,891 B2 11/2018 Shelton, IV et al.
D835,659 S 12/2018 Anzures et al.
D836,124 S 12/2018 Fan
10,143,474 B2 12/2018 Bucciaglia et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,506 B2 12/2018 Boudreaux et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,026 B2 1/2019 Shelton, IV et al.
10,172,611 B2 1/2019 Shelton, IV et al.
10,172,615 B2 1/2019 Marczyk et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,182,813 B2 1/2019 Leimbach et al.
10,182,815 B2 1/2019 Williams et al.
10,182,818 B2 1/2019 Hensel et al.
10,182,868 B2 1/2019 Meier et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,381 B2 2/2019 Zergiebel et al.
10,206,676 B2 2/2019 Shelton, IV
10,206,748 B2 2/2019 Burbank
10,210,244 B1 2/2019 Branavan et al.
10,211,586 B2 2/2019 Adams et al.
10,213,202 B2 2/2019 Flanagan et al.
10,213,203 B2 2/2019 Swayze et al.
10,213,204 B2 2/2019 Aranyi et al.

(56) References Cited

U.S. PATENT DOCUMENTS

D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,251 B2 3/2019 Scheib et al.
10,226,274 B2 3/2019 Worrell et al.
10,231,634 B2 3/2019 Zand et al.
10,231,734 B2 3/2019 Thompson et al.
10,231,794 B2 3/2019 Shelton, IV et al.
10,238,386 B2 3/2019 Overmyer et al.
10,238,389 B2 3/2019 Yates et al.
10,238,390 B2 3/2019 Harris et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,029 B2 4/2019 Hunter et al.
10,245,030 B2 4/2019 Hunter et al.
10,245,034 B2 4/2019 Shelton, IV et al.
10,245,038 B2 4/2019 Hopkins et al.
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,331 B2 4/2019 Shelton, IV et al.
10,258,332 B2 4/2019 Schmid et al.
10,258,418 B2 4/2019 Shelton, IV et al.
10,264,797 B2 4/2019 Zhang et al.
10,265,068 B2 4/2019 Harris et al.
10,265,073 B2 4/2019 Scheib et al.
10,265,090 B2 4/2019 Ingmanson et al.
10,271,840 B2 4/2019 Sapre
10,271,844 B2 4/2019 Valentine et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,702 B2 5/2019 Shelton, IV et al.
10,278,703 B2 5/2019 Nativ et al.
10,278,707 B2 5/2019 Thompson et al.
10,278,780 B2 5/2019 Shelton, IV
10,285,695 B2 5/2019 Jaworek et al.
10,285,699 B2 5/2019 Vendely et al.
10,285,705 B2 5/2019 Shelton, IV et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,878 B2 5/2019 Shelton, IV et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,590 B2 6/2019 Shelton, IV et al.
10,315,566 B2 6/2019 Choi et al.
10,321,927 B2 6/2019 Hinman
10,327,743 B2 6/2019 St. Goar et al.
10,327,767 B2 6/2019 Shelton, IV et al.
10,327,769 B2 6/2019 Overmyer et al.
10,327,777 B2 6/2019 Harris et al.
D854,032 S 7/2019 Jones et al.
D854,151 S 7/2019 Shelton, IV et al.
10,335,145 B2 7/2019 Harris et al.
10,335,147 B2 7/2019 Rector et al.
10,335,149 B2 7/2019 Baxter, III et al.
10,337,148 B2 7/2019 Rouse et al.
10,342,535 B2 7/2019 Scheib et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 7/2019 Shelton, IV et al.
10,357,247 B2 7/2019 Shelton, IV et al.
10,357,248 B2 7/2019 Dalessandro et al.
10,357,252 B2 7/2019 Harris et al.
10,363,033 B2 7/2019 Timm et al.
10,363,036 B2 7/2019 Yates et al.
10,363,037 B2 7/2019 Aronhalt et al.
D855,634 S 8/2019 Kim
D856,359 S 8/2019 Huang et al.
10,368,838 B2 8/2019 Williams et al.
10,368,861 B2 8/2019 Baxter, III et al.
10,368,863 B2 8/2019 Timm et al.
10,368,864 B2 8/2019 Harris et al.
10,368,865 B2 8/2019 Harris et al.
10,368,867 B2 8/2019 Harris et al.
10,368,892 B2 8/2019 Stulen et al.
10,376,263 B2 8/2019 Morgan et al.
10,383,626 B2 8/2019 Soltz
10,383,628 B2 8/2019 Kang et al.
10,383,634 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D860,219 S 9/2019 Rasmussen et al.
D861,035 S 9/2019 Park et al.
10,398,434 B2 9/2019 Shelton, IV et al.
10,398,460 B2 9/2019 Overmyer
10,404,136 B2 9/2019 Oktavec et al.
10,405,859 B2 9/2019 Harris et al.
10,405,863 B2 9/2019 Wise et al.
10,405,914 B2 9/2019 Manwaring et al.
10,405,932 B2 9/2019 Overmyer
10,405,937 B2 9/2019 Black et al.
10,413,291 B2 9/2019 Worthington et al.
10,413,293 B2 9/2019 Shelton, IV et al.
10,413,294 B2 9/2019 Shelton, IV et al.
10,413,297 B2 9/2019 Harris et al.
10,413,370 B2 9/2019 Yates et al.
10,413,373 B2 9/2019 Yates et al.
10,420,548 B2 9/2019 Whitman et al.
10,420,549 B2 9/2019 Yates et al.
10,420,550 B2 9/2019 Shelton, IV
10,420,552 B2 9/2019 Shelton, IV et al.
10,420,554 B2 9/2019 Collings et al.
10,420,555 B2 9/2019 Shelton, IV et al.
10,420,558 B2 9/2019 Nalagatla et al.
10,420,559 B2 9/2019 Marczyk et al.
10,420,577 B2 9/2019 Chowaniec et al.
D861,707 S 10/2019 Yang
D862,518 S 10/2019 Niven et al.
D863,343 S 10/2019 Mazlish et al.
D864,388 S 10/2019 Barber
10,426,466 B2 10/2019 Contini et al.
10,426,467 B2 10/2019 Miller et al.
10,426,468 B2 10/2019 Contini et al.

(56) References Cited

U.S. PATENT DOCUMENTS 10,426,469 B2 10/2019 Shelton, IV et al.
10,426,471 B2 10/2019 Shelton, IV et al.
10,426,481 B2 10/2019 Aronhalt et al.
10,426,555 B2 10/2019 Crowley et al.
10,433,837 B2 10/2019 Worthington et al.
10,433,839 B2 10/2019 Scheib et al.
10,433,840 B2 10/2019 Shelton, IV et al.
10,433,845 B2 10/2019 Baxter, III et al.
10,433,846 B2 10/2019 Vendely et al.
10,433,849 B2 10/2019 Shelton, IV et al.
10,441,281 B2 10/2019 Shelton, IV et al.
10,441,286 B2 10/2019 Shelton, IV et al.
10,441,345 B2 10/2019 Aldridge et al.
10,448,948 B2 10/2019 Shelton, IV et al.
10,448,950 B2 10/2019 Shelton, IV et al.
10,448,952 B2 10/2019 Shelton, IV et al.
10,456,122 B2 10/2019 Koltz et al.
10,456,132 B2 10/2019 Gettinger et al.
10,456,137 B2 10/2019 Vendely et al.
10,456,140 B2 10/2019 Shelton, IV et al.
D865,796 S 11/2019 Xu et al.
10,463,367 B2 11/2019 Kostrzewski et al.
10,463,370 B2 11/2019 Yates et al.
10,463,371 B2 11/2019 Kostrzewski
10,463,372 B2 11/2019 Shelton, IV et al.
10,463,373 B2 11/2019 Mozdzierz et al.
10,463,382 B2 11/2019 Ingmanson et al.
10,463,384 B2 11/2019 Shelton, IV et al.
10,470,764 B2 11/2019 Baxter, III et al.
10,470,767 B2 11/2019 Gleiman et al.
10,470,769 B2 11/2019 Shelton, IV et al.
10,471,282 B2 11/2019 Kirk et al.
10,471,576 B2 11/2019 Totsu
10,478,181 B2 11/2019 Shelton, IV et al.
10,478,182 B2 11/2019 Taylor
10,478,185 B2 11/2019 Nicholas
10,478,187 B2 11/2019 Shelton, IV et al.
10,478,188 B2 11/2019 Harris et al.
10,478,189 B2 11/2019 Bear et al.
10,478,190 B2 11/2019 Miller et al.
10,478,207 B2 11/2019 Lathrop
10,485,537 B2 11/2019 Yates et al.
10,485,539 B2 11/2019 Shelton, IV et al.
10,485,542 B2 11/2019 Shelton, IV et al.
10,485,543 B2 11/2019 Shelton, IV et al.
10,485,547 B2 11/2019 Shelton, IV et al.
D869,655 S 12/2019 Shelton, IV et al.
D870,742 S 12/2019 Cornell
10,492,783 B2 12/2019 Shelton, IV et al.
10,492,785 B2 12/2019 Overmyer et al.
10,492,847 B2 12/2019 Godara et al.
10,492,851 B2 12/2019 Hughett, Sr. et al.
10,498,269 B2 12/2019 Zemlok et al.
10,499,914 B2 12/2019 Huang et al.
10,499,917 B2 12/2019 Scheib et al.
10,499,918 B2 12/2019 Schellin et al.
10,508,720 B2 12/2019 Nicholas
10,512,461 B2 12/2019 Gupta et al.
10,517,590 B2 12/2019 Giordano et al.
10,517,592 B2 12/2019 Shelton, IV et al.
10,517,595 B2 12/2019 Hunter et al.
10,517,596 B2 12/2019 Hunter et al.
10,517,599 B2 12/2019 Baxter, III et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.
10,531,874 B2 1/2020 Morgan et al.
10,531,887 B2 1/2020 Shelton, IV et al.
10,537,324 B2 1/2020 Shelton, IV et al.
10,537,325 B2 1/2020 Bakos et al.
10,537,351 B2 1/2020 Shelton, IV et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,991 B2 1/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,418 B2 2/2020 Richard et al.
10,561,419 B2 2/2020 Beardsley
10,561,420 B2 2/2020 Harris et al.
10,561,432 B2 2/2020 Estrella et al.
10,561,474 B2 2/2020 Adams et al.
10,562,160 B2 2/2020 Iwata et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,569,071 B2 2/2020 Harris et al.
D879,808 S 3/2020 Harris et al.
D879,809 S 3/2020 Harris et al.
10,580,320 B2 3/2020 Kamiguchi et al.
10,582,928 B2 3/2020 Hunter et al.
10,588,625 B2 3/2020 Weaner et al.
10,588,626 B2 3/2020 Overmyer et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
10,610,224 B2 4/2020 Shelton, IV et al.
10,610,236 B2 4/2020 Baril
10,610,313 B2 4/2020 Bailey et al.
10,617,411 B2 4/2020 Williams
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,624,616 B2 4/2020 Mukherjee et al.
10,624,630 B2 4/2020 Deville et al.
10,624,633 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,089 B2 5/2020 Manwaring et al.
10,639,115 B2 5/2020 Shelton, IV et al.
10,646,220 B2 5/2020 Shelton, IV et al.
10,653,413 B2 5/2020 Worthington et al.
10,653,435 B2 5/2020 Shelton, IV et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,675,021 B2 6/2020 Harris et al.

(56) References Cited

U.S. PATENT DOCUMENTS 10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,677,035 B2 6/2020 Balan et al.
10,682,134 B2 6/2020 Shelton, IV et al.
10,682,136 B2 6/2020 Harris et al.
10,682,138 B2 6/2020 Shelton, IV et al.
10,682,141 B2 6/2020 Moore et al.
10,682,142 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,904 B2 6/2020 Harris et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,123 B2 6/2020 Allen, IV
10,695,187 B2 6/2020 Moskowitz et al.
D890,784 S 7/2020 Shelton, IV et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
10,729,432 B2 8/2020 Shelton, IV et al.
10,729,436 B2 8/2020 Shelton, IV et al.
10,729,443 B2 8/2020 Cabrera et al.
10,729,458 B2 8/2020 Stoddard et al.
10,729,501 B2 8/2020 Leimbach et al.
10,729,509 B2 8/2020 Shelton, IV et al.
10,736,616 B2 8/2020 Scheib et al.
10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,644 B2 8/2020 Windolf et al.
10,743,851 B2 8/2020 Swayze et al.
10,743,868 B2 8/2020 Shelton, IV et al.
10,743,870 B2 8/2020 Hall et al.
10,743,872 B2 8/2020 Leimbach et al.
10,743,873 B2 8/2020 Overmyer et al.
10,743,874 B2 8/2020 Shelton, IV et al.
10,743,875 B2 8/2020 Shelton, IV et al.
10,743,877 B2 8/2020 Shelton, IV et al.
10,743,930 B2 8/2020 Nagtegaal
10,751,048 B2 8/2020 Whitman et al.
10,751,053 B2 8/2020 Harris et al.
10,751,076 B2 8/2020 Laurent et al.
10,751,138 B2 8/2020 Giordano et al.
10,758,229 B2 9/2020 Shelton, IV et al.
10,758,230 B2 9/2020 Shelton, IV et al.
10,758,232 B2 9/2020 Shelton, IV et al.
10,758,259 B2 9/2020 Demmy et al.
10,765,425 B2 9/2020 Yates et al.
10,765,427 B2 9/2020 Shelton, IV et al.
10,765,429 B2 9/2020 Leimbach et al.
10,765,430 B2 9/2020 Wixey
10,765,432 B2 9/2020 Moore et al.
10,765,442 B2 9/2020 Strobl
10,772,625 B2 9/2020 Shelton, IV et al.
10,772,628 B2 9/2020 Chen et al.
10,772,629 B2 9/2020 Shelton, IV et al.
10,772,630 B2 9/2020 Wixey
10,772,631 B2 9/2020 Zergiebel et al.
10,772,632 B2 9/2020 Kostrzewski
10,772,651 B2 9/2020 Shelton, IV et al.
10,779,818 B2 9/2020 Zemlok et al.
10,779,820 B2 9/2020 Harris et al.
10,779,821 B2 9/2020 Harris et al.
10,779,823 B2 9/2020 Shelton, IV et al.
10,779,824 B2 9/2020 Shelton, IV et al.
10,779,825 B2 9/2020 Shelton, IV et al.
10,779,826 B2 9/2020 Shelton, IV et al.
10,779,903 B2 9/2020 Wise et al.
10,780,539 B2 9/2020 Shelton, IV et al.
10,786,248 B2 9/2020 Rousseau et al.
10,786,253 B2 9/2020 Shelton, IV et al.
10,792,038 B2 10/2020 Becerra et al.
10,796,471 B2 10/2020 Leimbach et al.
10,799,240 B2 10/2020 Shelton, IV et al.
10,799,306 B2 10/2020 Robinson et al.
10,806,451 B2 10/2020 Harris et al.
10,813,683 B2 10/2020 Baxter, III et al.
10,842,473 B2 11/2020 Scheib et al.
D906,355 S 12/2020 Messerly et al.
10,849,621 B2 12/2020 Whitfield et al.
10,849,623 B2 12/2020 Dunki-Jacobs et al.
10,849,697 B2 12/2020 Yates et al.
10,874,392 B2 12/2020 Scirica et al.
10,874,393 B2 12/2020 Satti, III et al.
D907,647 S 1/2021 Siebel et al.
D907,648 S 1/2021 Siebel et al.
10,892,899 B2 1/2021 Shelton, IV et al.
D910,847 S 2/2021 Shelton, IV et al.
10,905,415 B2 2/2021 DiNardo et al.
10,912,562 B2 2/2021 Dunki-Jacobs et al.
D914,878 S 3/2021 Shelton, IV et al.
10,932,804 B2 3/2021 Scheib et al.
10,932,872 B2 3/2021 Shelton, IV et al.
10,944,728 B2 3/2021 Wiener et al.
10,952,708 B2 3/2021 Scheib et al.
10,952,728 B2 3/2021 Shelton, IV et al.
10,966,791 B2 4/2021 Harris et al.
10,973,520 B2 4/2021 Shelton, IV et al.
10,980,535 B2 4/2021 Yates et al.
2001/0000531 A1 4/2001 Casscells et al.
2001/0005786 A1* 6/2001 Michelson ......... A61B 10/0096
606/83
2001/0025183 A1 9/2001 Shahidi
2001/0025184 A1 9/2001 Messerly
2001/0034530 A1 10/2001 Malackowski et al.
2001/0044637 A1 11/2001 Jacobs et al.
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0026126 A1 2/2002 Burdorff et al.
2002/0029032 A1 3/2002 Arkin
2002/0029036 A1 3/2002 Goble et al.
2002/0042620 A1 4/2002 Julian et al.
2002/0049472 A1 4/2002 Coleman et al.
2002/0087048 A1 7/2002 Brock et al.
2002/0091374 A1 7/2002 Cooper
2002/0095175 A1 7/2002 Brock et al.
2002/0103494 A1 8/2002 Pacey
2002/0111624 A1 8/2002 Witt et al.
2002/0116063 A1 8/2002 Giannetti et al.
2002/0117534 A1 8/2002 Green et al.
2002/0127265 A1 9/2002 Bowman et al.
2002/0128552 A1 9/2002 Nowlin et al.
2002/0128633 A1 9/2002 Brock et al.
2002/0134811 A1 9/2002 Napier et al.
2002/0135474 A1 9/2002 Sylliassen

(56) References Cited

U.S. PATENT DOCUMENTS

2002/0143340 A1 10/2002 Kaneko
2002/0151770 A1 10/2002 Noll et al.
2002/0157481 A1 10/2002 Kogiso et al.
2002/0158593 A1 10/2002 Henderson et al.
2002/0165541 A1 11/2002 Whitman
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2002/0193808 A1 12/2002 Belef et al.
2003/0009193 A1 1/2003 Corsaro
2003/0011245 A1 1/2003 Fiebig
2003/0012805 A1 1/2003 Chen et al.
2003/0023316 A1 1/2003 Brown et al.
2003/0040670 A1 2/2003 Govari
2003/0045835 A1 3/2003 Anderson et al.
2003/0066858 A1 4/2003 Holgersson
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0094356 A1 5/2003 Waldron
2003/0096158 A1 5/2003 Takano et al.
2003/0105478 A1 6/2003 Whitman et al.
2003/0114851 A1 6/2003 Truckai et al.
2003/0121586 A1 7/2003 Mitra et al.
2003/0130677 A1 7/2003 Whitman et al.
2003/0139741 A1 7/2003 Goble et al.
2003/0149406 A1 8/2003 Martineau et al.
2003/0153908 A1 8/2003 Goble et al.
2003/0153968 A1 8/2003 Geis et al.
2003/0163085 A1 8/2003 Tanner et al.
2003/0164172 A1 9/2003 Chumas et al.
2003/0181900 A1 9/2003 Long
2003/0190584 A1 10/2003 Heasley
2003/0195387 A1 10/2003 Kortenbach et al.
2003/0202901 A1 10/2003 Stetzel
2003/0205029 A1 11/2003 Chapolini et al.
2003/0212005 A1 11/2003 Petito et al.
2003/0216732 A1 11/2003 Truckai et al.
2003/0220660 A1 11/2003 Kortenbach et al.
2003/0236505 A1 12/2003 Bonadio et al.
2004/0002726 A1 1/2004 Nunez et al.
2004/0006335 A1 1/2004 Garrison
2004/0006340 A1 1/2004 Latterell et al.
2004/0006372 A1 1/2004 Racenet et al.
2004/0006861 A1 1/2004 Haytayan
2004/0007608 A1 1/2004 Ehrenfels et al.
2004/0024457 A1 2/2004 Boyce et al.
2004/0028502 A1 2/2004 Cummins
2004/0030333 A1 2/2004 Goble
2004/0032345 A1 2/2004 Kazuya et al.
2004/0034357 A1 2/2004 Beane et al.
2004/0034369 A1 2/2004 Sauer et al.
2004/0044295 A1 3/2004 Reinert et al.
2004/0044364 A1 3/2004 DeVries et al.
2004/0049121 A1 3/2004 Yaron
2004/0049172 A1 3/2004 Root et al.
2004/0059362 A1 3/2004 Knodel et al.
2004/0068161 A1 4/2004 Couvillon, Jr.
2004/0068224 A1 4/2004 Couvillon, Jr. et al.
2004/0068307 A1 4/2004 Goble
2004/0070369 A1 4/2004 Sakahibara
2004/0073222 A1 4/2004 Koseki
2004/0078037 A1 4/2004 Batchelor et al.
2004/0082952 A1 4/2004 Dycus et al.
2004/0085180 A1 5/2004 Juang
2004/0092992 A1 5/2004 Adams et al.
2004/0093024 A1 5/2004 Lousararian et al.
2004/0094597 A1 5/2004 Whitman et al.
2004/0097987 A1 5/2004 Pugsley et al.
2004/0098040 A1 5/2004 Taniguchi et al.
2004/0101822 A1 5/2004 Weisner et al.
2004/0102783 A1 5/2004 Sutterlin, III et al.
2004/0108357 A1 6/2004 Milliman et al.
2004/0110439 A1 6/2004 Chaikof et al.
2004/0111081 A1 6/2004 Whitman et al.
2004/0115022 A1 6/2004 Albertson et al.
2004/0116952 A1 6/2004 Sakurai et al.
2004/0119185 A1 6/2004 Chen
2004/0122419 A1 6/2004 Neuberger
2004/0122423 A1 6/2004 Dycus et al.
2004/0133095 A1 7/2004 Dunki-Jacobs et al.
2004/0133189 A1 7/2004 Sakurai
2004/0143297 A1 7/2004 Ramsey
2004/0147909 A1 7/2004 Johnston et al.
2004/0153100 A1 8/2004 Ahlberg et al.
2004/0158261 A1 8/2004 Vu
2004/0164123 A1 8/2004 Racenet et al.
2004/0166169 A1 8/2004 Malaviya et al.
2004/0167572 A1 8/2004 Roth et al.
2004/0173659 A1 9/2004 Green et al.
2004/0181219 A1 9/2004 Goble et al.
2004/0186470 A1 9/2004 Goble et al.
2004/0193189 A1 9/2004 Kortenbach et al.
2004/0197367 A1 10/2004 Rezania et al.
2004/0199181 A1 10/2004 Knodel et al.
2004/0204735 A1 10/2004 Shiroff et al.
2004/0218451 A1 11/2004 Said et al.
2004/0222268 A1 11/2004 Bilotti et al.
2004/0225186 A1 11/2004 Horne, Jr. et al.
2004/0230214 A1 11/2004 Donofrio et al.
2004/0232201 A1 11/2004 Wenchell et al.
2004/0236352 A1 11/2004 Wang et al.
2004/0243147 A1 12/2004 Lipow
2004/0243151 A1 12/2004 Demmy et al.
2004/0243163 A1 12/2004 Casiano et al.
2004/0243176 A1 12/2004 Hahnen et al.
2004/0247415 A1 12/2004 Mangone, Jr.
2004/0249366 A1 12/2004 Kunz
2004/0254455 A1 12/2004 Iddan
2004/0254566 A1 12/2004 Plicchi et al.
2004/0254590 A1 12/2004 Hoffman et al.
2004/0254608 A1 12/2004 Huitema et al.
2004/0260315 A1 12/2004 Dell et al.
2004/0267297 A1 12/2004 Malackowski
2004/0267310 A1 12/2004 Racenet et al.
2005/0010158 A1 1/2005 Brugger et al.
2005/0010213 A1 1/2005 Stad et al.
2005/0021078 A1 1/2005 Vleugels et al.
2005/0032511 A1 2/2005 Malone et al.
2005/0033352 A1 2/2005 Zeph et al.
2005/0033357 A1 2/2005 Braun
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0070929 A1 3/2005 Dalessandro et al.
2005/0075561 A1 4/2005 Golden
2005/0080342 A1 4/2005 Gilreath et al.
2005/0080454 A1 4/2005 Drews et al.
2005/0085693 A1 4/2005 Belson et al.
2005/0090817 A1 4/2005 Phan
2005/0096683 A1 5/2005 Ellins et al.
2005/0103819 A1 5/2005 Racenet et al.
2005/0107814 A1 5/2005 Johnston et al.
2005/0107824 A1 5/2005 Hillstead et al.
2005/0113820 A1 5/2005 Goble et al.
2005/0116673 A1 6/2005 Carl et al.
2005/0119525 A1 6/2005 Takemoto
2005/0119669 A1 6/2005 Demmy
2005/0124855 A1 6/2005 Jaffe et al.
2005/0125009 A1 6/2005 Perry et al.
2005/0125897 A1 6/2005 Wyslucha et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131437 A1 6/2005 Johnston et al.
2005/0131457 A1 6/2005 Douglas et al.
2005/0137454 A1 6/2005 Saadat et al.

(56) References Cited

U.S. PATENT DOCUMENTS

2005/0137455 A1 6/2005 Ewers et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145675 A1 7/2005 Hartwick et al.
2005/0150928 A1 7/2005 Kameyama et al.
2005/0154258 A1 7/2005 Tartaglia et al.
2005/0154406 A1 7/2005 Bombard et al.
2005/0159184 A1 7/2005 Kerner et al.
2005/0159778 A1 7/2005 Heinrich et al.
2005/0165419 A1 7/2005 Sauer et al.
2005/0165435 A1 7/2005 Johnston et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177249 A1 8/2005 Kladakis et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0187572 A1 8/2005 Johnston et al.
2005/0187576 A1 8/2005 Whitman et al.
2005/0189397 A1 9/2005 Jankowski
2005/0192609 A1 9/2005 Whitman et al.
2005/0192628 A1 9/2005 Viola
2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0240222 A1 10/2005 Shipp
2005/0245965 A1 11/2005 Orban, III et al.
2005/0246881 A1 11/2005 Kelly et al.
2005/0251063 A1 11/2005 Basude
2005/0251128 A1 11/2005 Amoah
2005/0256452 A1 11/2005 DeMarchi et al.
2005/0256522 A1 11/2005 Francischelli et al.
2005/0261676 A1 11/2005 Hall et al.
2005/0261677 A1 11/2005 Hall et al.
2005/0263563 A1 12/2005 Racenet et al.
2005/0267455 A1 12/2005 Eggers et al.
2005/0267530 A1 12/2005 Cummins
2005/0272973 A1 12/2005 Kawano et al.
2005/0274034 A1 12/2005 Hayashida et al.
2005/0274768 A1 12/2005 Cummins et al.
2005/0283188 A1 12/2005 Loshakove et al.
2005/0283226 A1 12/2005 Haverkost
2006/0004407 A1 1/2006 Hiles et al.
2006/0008787 A1 1/2006 Hayman et al.
2006/0011699 A1 1/2006 Olson et al.
2006/0015009 A1 1/2006 Jaffe et al.
2006/0020247 A1 1/2006 Kagan et al.
2006/0020258 A1 1/2006 Strauss et al.
2006/0020336 A1 1/2006 Liddicoat
2006/0025811 A1 2/2006 Shelton, IV
2006/0025812 A1 2/2006 Shelton, IV
2006/0041188 A1 2/2006 Dirusso et al.
2006/0047275 A1 3/2006 Goble
2006/0047303 A1 3/2006 Ortiz et al.
2006/0047307 A1 3/2006 Ortiz et al.
2006/0047308 A1* 3/2006 Ortiz ................ A61B 17/07207
606/219
2006/0049229 A1 3/2006 Milliman et al.
2006/0052824 A1 3/2006 Ransick et al.
2006/0052825 A1 3/2006 Ransick et al.
2006/0060630 A1 3/2006 Shelton, IV et al.
2006/0064086 A1 3/2006 Odom
2006/0079115 A1 4/2006 Aranyi et al.
2006/0079735 A1 4/2006 Martone et al.
2006/0079874 A1 4/2006 Faller et al.
2006/0079879 A1 4/2006 Faller et al.
2006/0085031 A1 4/2006 Bettuchi
2006/0085033 A1 4/2006 Criscuolo et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0108393 A1 5/2006 Heinrich et al.
2006/0111711 A1 5/2006 Goble
2006/0111723 A1 5/2006 Chapolini et al.
2006/0116634 A1 6/2006 Shachar
2006/0122636 A1 6/2006 Bailly et al.
2006/0142772 A1 6/2006 Ralph et al.
2006/0144898 A1 7/2006 Bilotti et al.
2006/0149163 A1 7/2006 Hibner et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton, IV et al.
2006/0185682 A1 8/2006 Marczyk
2006/0199999 A1 9/2006 Ikeda et al.
2006/0200123 A1 9/2006 Ryan
2006/0201989 A1 9/2006 Ojeda
2006/0206100 A1 9/2006 Eskridge et al.
2006/0212069 A1 9/2006 Shelton, IV
2006/0217729 A1 9/2006 Eskridge et al.
2006/0226196 A1 10/2006 Hueil et al.
2006/0235368 A1 10/2006 Oz
2006/0235469 A1 10/2006 Viola
2006/0241655 A1 10/2006 Viola
2006/0241666 A1 10/2006 Briggs et al.
2006/0241692 A1 10/2006 McGuckin, Jr. et al.
2006/0244460 A1 11/2006 Weaver
2006/0252981 A1 11/2006 Matsuda et al.
2006/0252990 A1 11/2006 Kubach
2006/0252993 A1 11/2006 Freed et al.
2006/0253069 A1 11/2006 Li et al.
2006/0258904 A1 11/2006 Stefanchik et al.
2006/0258910 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264927 A1 11/2006 Ryan
2006/0264929 A1 11/2006 Goble et al.
2006/0271042 A1 11/2006 Latterell et al.
2006/0271102 A1 11/2006 Bosshard et al.
2006/0278680 A1 12/2006 Viola et al.
2006/0278681 A1 12/2006 Viola et al.
2006/0282064 A1 12/2006 Shimizu et al.
2006/0284730 A1 12/2006 Schmid et al.
2006/0287576 A1 12/2006 Tsuji et al.
2006/0289602 A1 12/2006 Wales et al.
2006/0291981 A1 12/2006 Viola et al.
2007/0009570 A1 1/2007 Kim et al.
2007/0010702 A1 1/2007 Wang et al.
2007/0010838 A1 1/2007 Shelton, IV et al.
2007/0016235 A1 1/2007 Tanaka et al.
2007/0018958 A1 1/2007 Tavakoli et al.
2007/0023476 A1 2/2007 Whitman et al.
2007/0023477 A1 2/2007 Whitman et al.
2007/0026039 A1 2/2007 Drumheller et al.
2007/0026040 A1 2/2007 Crawley et al.
2007/0027468 A1 2/2007 Wales et al.
2007/0027472 A1 2/2007 Hiles et al.

(56) References Cited

U.S. PATENT DOCUMENTS

2007/0027551 A1 2/2007 Farnsworth et al.
2007/0027553 A1 2/2007 Biran et al.
2007/0034668 A1 2/2007 Holsten et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055219 A1 3/2007 Whitman et al.
2007/0055228 A1 3/2007 Berg et al.
2007/0066981 A1 3/2007 Meagher
2007/0070574 A1 3/2007 Nerheim et al.
2007/0073341 A1 3/2007 Smith
2007/0073389 A1 3/2007 Bolduc et al.
2007/0078328 A1 4/2007 Ozaki et al.
2007/0078484 A1 4/2007 Talarico et al.
2007/0083193 A1 4/2007 Werneth et al.
2007/0084897 A1 4/2007 Shelton, IV et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton, IV
2007/0103437 A1 5/2007 Rosenberg
2007/0106113 A1 5/2007 Ravo
2007/0106317 A1 5/2007 Shelton, IV et al.
2007/0118115 A1 5/2007 Artale et al.
2007/0118175 A1 5/2007 Butler et al.
2007/0129605 A1 6/2007 Schaaf
2007/0134251 A1 6/2007 Ashkenazi et al.
2007/0135686 A1 6/2007 Pruitt, Jr. et al.
2007/0135803 A1 6/2007 Belson
2007/0152612 A1 7/2007 Chen et al.
2007/0155010 A1 7/2007 Farnsworth et al.
2007/0158358 A1 7/2007 Mason, II et al.
2007/0170225 A1 7/2007 Shelton, IV et al.
2007/0173687 A1 7/2007 Shima et al.
2007/0173806 A1 7/2007 Orszulak et al.
2007/0173813 A1 7/2007 Odom
2007/0173872 A1 7/2007 Neuenfeldt
2007/0175950 A1 8/2007 Shelton, IV et al.
2007/0175951 A1 8/2007 Shelton, IV et al.
2007/0175955 A1 8/2007 Shelton, IV et al.
2007/0179477 A1 8/2007 Danger
2007/0179528 A1 8/2007 Soltz et al.
2007/0181632 A1 8/2007 Milliman
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0194079 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0219571 A1 9/2007 Balbierz et al.
2007/0225562 A1 9/2007 Spivey et al.
2007/0233163 A1 10/2007 Bombard et al.
2007/0239028 A1 10/2007 Houser et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0249999 A1 10/2007 Sklar et al.
2007/0250113 A1 10/2007 Hegeman et al.
2007/0260132 A1 11/2007 Sterling
2007/0260278 A1 11/2007 Wheeler et al.
2007/0262592 A1 11/2007 Hwang et al.
2007/0270660 A1 11/2007 Caylor et al.
2007/0270784 A1 11/2007 Smith et al.
2007/0270884 A1 11/2007 Smith et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0287993 A1* 12/2007 Hinman ............... A61B 17/062 606/1
2007/0288044 A1 12/2007 Jinno et al.
2007/0290027 A1 12/2007 Maatta et al.
2007/0296286 A1 12/2007 Avenell
2007/0299427 A1 12/2007 Yeung et al.
2008/0003196 A1 1/2008 Jonn et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0035701 A1 2/2008 Racenet et al.
2008/0039746 A1 2/2008 Hissong et al.
2008/0041916 A1 2/2008 Milliman et al.
2008/0041917 A1 2/2008 Racenet et al.
2008/0042861 A1 2/2008 Dacquay et al.
2008/0048002 A1* 2/2008 Smith .............. A61B 17/07207 227/175.1
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0071328 A1 3/2008 Haubrich et al.
2008/0077158 A1 3/2008 Haider et al.
2008/0078802 A1 4/2008 Hess et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083808 A1 4/2008 Scirica
2008/0083813 A1 4/2008 Zemlok et al.
2008/0085296 A1 4/2008 Powell et al.
2008/0086078 A1 4/2008 Powell et al.
2008/0091072 A1 4/2008 Omori et al.
2008/0097563 A1 4/2008 Petrie et al.
2008/0108443 A1 5/2008 Jinno et al.
2008/0114250 A1 5/2008 Urbano et al.
2008/0114315 A1 5/2008 Voegele et al.
2008/0114385 A1 5/2008 Byrum et al.
2008/0125634 A1 5/2008 Ryan et al.
2008/0125749 A1 5/2008 Olson
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Linvneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0172088 A1 7/2008 Smith et al.
2008/0177392 A1 7/2008 Williams et al.
2008/0183193 A1 7/2008 Omori et al.
2008/0185419 A1 8/2008 Smith et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0200949 A1 8/2008 Hiles et al.
2008/0206186 A1 8/2008 Butler et al.
2008/0208058 A1 8/2008 Sabata et al.
2008/0223903 A1* 9/2008 Marczyk ............. A61B 17/072 227/175.1
2008/0228029 A1 9/2008 Mikkaichi et al.
2008/0234709 A1 9/2008 Houser

(56) References Cited

U.S. PATENT DOCUMENTS

2008/0241667 A1 10/2008 Kohn et al.
2008/0242939 A1 10/2008 Johnston
2008/0245841 A1 10/2008 Smith et al.
2008/0249536 A1 10/2008 Stahler et al.
2008/0249608 A1 10/2008 Dave
2008/0251568 A1 10/2008 Zemlok et al.
2008/0251569 A1 10/2008 Smith et al.
2008/0255413 A1 10/2008 Zemlok et al.
2008/0255607 A1* 10/2008 Zemlok ............ A61B 17/07207
600/127
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281254 A1 11/2008 Humayun et al.
2008/0281332 A1 11/2008 Taylor
2008/0283570 A1 11/2008 Boyden et al.
2008/0287944 A1 11/2008 Pearson et al.
2008/0287988 A1 11/2008 Smith et al.
2008/0290134 A1 11/2008 Bettuchi et al.
2008/0293910 A1 11/2008 Kapiamba et al.
2008/0294179 A1 11/2008 Balbierz et al.
2008/0296346 A1 12/2008 Shelton, IV et al.
2008/0297287 A1 12/2008 Shachar et al.
2008/0298784 A1 12/2008 Kastner
2008/0308602 A1 12/2008 Timm et al.
2008/0308603 A1 12/2008 Shelton, IV et al.
2008/0308608 A1 12/2008 Prommersberger
2008/0312686 A1 12/2008 Ellingwood
2008/0312687 A1 12/2008 Blier
2008/0314955 A1* 12/2008 Boudreaux ...... A61B 17/07207
227/175.2
2008/0314957 A1* 12/2008 Boudreaux ...... A61B 17/07207
227/175.2
2008/0314960 A1 12/2008 Marczyk et al.
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0012534 A1 1/2009 Madhani et al.
2009/0015195 A1 1/2009 Loth-Krausser
2009/0018553 A1 1/2009 McLean et al.
2009/0020958 A1 1/2009 Soul
2009/0047329 A1 2/2009 Stucky et al.
2009/0048583 A1 2/2009 Williams et al.
2009/0048589 A1 2/2009 Takashino et al.
2009/0048612 A1 2/2009 Farritor et al.
2009/0054908 A1 2/2009 Zand et al.
2009/0069842 A1 3/2009 Lee et al.
2009/0076506 A1 3/2009 Baker
2009/0078736 A1 3/2009 Van Lue
2009/0081313 A1 3/2009 Aghion et al.
2009/0082789 A1 3/2009 Milliman et al.
2009/0088659 A1 4/2009 Graham et al.
2009/0088774 A1 4/2009 Swarup et al.
2009/0090763 A1 4/2009 Zemlok et al.
2009/0092651 A1 4/2009 Shah et al.
2009/0093728 A1 4/2009 Hyde et al.
2009/0099579 A1 4/2009 Nentwick et al.
2009/0099876 A1 4/2009 Whitman
2009/0108048 A1 4/2009 Zemlok et al.
2009/0110533 A1 4/2009 Jinno
2009/0112229 A1 4/2009 Omori et al.
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0131819 A1 5/2009 Ritchie et al.
2009/0132400 A1 5/2009 Conway
2009/0137952 A1 5/2009 Ramamurthy et al.
2009/0143805 A1 6/2009 Palmer et al.
2009/0143855 A1 6/2009 Weber et al.
2009/0149871 A9 6/2009 Kagan et al.
2009/0157067 A1 6/2009 Kane et al.
2009/0157087 A1 6/2009 Wei et al.
2009/0171147 A1 7/2009 Lee et al.
2009/0177218 A1 7/2009 Young et al.
2009/0177226 A1 7/2009 Reinprecht et al.
2009/0179757 A1 7/2009 Cohn et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0213685 A1 8/2009 Mak et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248007 A1 10/2009 Falkenstein et al.
2009/0248038 A1 10/2009 Blumenkranz et al.
2009/0248100 A1 10/2009 Vaisnys et al.
2009/0253959 A1 10/2009 Yoshie et al.
2009/0255974 A1 10/2009 Viola
2009/0255975 A1 10/2009 Zemlok et al.
2009/0255976 A1 10/2009 Marczyk et al.
2009/0255977 A1 10/2009 Zemlok
2009/0255978 A1 10/2009 Viola et al.
2009/0261141 A1 10/2009 Stratton et al.
2009/0262078 A1 10/2009 Pizzi
2009/0270895 A1 10/2009 Churchill et al.
2009/0277949 A1 11/2009 Viola et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0005035 A1 1/2010 Carpenter et al.
2010/0010511 A1 1/2010 Harris et al.
2010/0012703 A1 1/2010 Calabrese et al.
2010/0012704 A1 1/2010 Tarinelli Racenet et al.
2010/0015104 A1 1/2010 Fraser et al.
2010/0016852 A1 1/2010 Manzo et al.
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0032179 A1 2/2010 Hanspers et al.
2010/0036370 A1 2/2010 Mirel et al.
2010/0041945 A1 2/2010 Isbell, Jr.
2010/0049084 A1 2/2010 Nock et al.
2010/0051668 A1 3/2010 Milliman et al.
2010/0057087 A1 3/2010 Cha
2010/0057107 A1 3/2010 Sorrentino et al.
2010/0057118 A1 3/2010 Dietz et al.
2010/0065604 A1 3/2010 Weng
2010/0069942 A1 3/2010 Shelton, IV
2010/0072254 A1 3/2010 Aranyi et al.
2010/0076483 A1 3/2010 Imuta
2010/0076489 A1 3/2010 Stopek et al.
2010/0081883 A1 4/2010 Murray et al.
2010/0087840 A1 4/2010 Ebersole et al.
2010/0094289 A1 4/2010 Taylor et al.
2010/0094340 A1 4/2010 Stopek et al.
2010/0096431 A1 4/2010 Smith et al.
2010/0100123 A1 4/2010 Bennett
2010/0100124 A1 4/2010 Calabrese et al.
2010/0108740 A1 5/2010 Pastorelli et al.
2010/0108741 A1 5/2010 Hessler et al.

(56) References Cited

U.S. PATENT DOCUMENTS

2010/0116519 A1 5/2010 Gareis
2010/0122339 A1 5/2010 Boccacci
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0147923 A1 6/2010 D'Agostino et al.
2010/0159435 A1 6/2010 Mueller et al.
2010/0163598 A1 7/2010 Belzer
2010/0179022 A1 7/2010 Shirokoshi
2010/0179540 A1 7/2010 Marczyk et al.
2010/0180711 A1 7/2010 Kilibarda et al.
2010/0186219 A1 7/2010 Smith
2010/0191262 A1 7/2010 Harris et al.
2010/0191292 A1 7/2010 DeMeo et al.
2010/0193566 A1 8/2010 Schieb et al.
2010/0200637 A1 8/2010 Beetel
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0228250 A1 9/2010 Brogna
2010/0230465 A1 9/2010 Smith et al.
2010/0234687 A1 9/2010 Azarbarzin et al.
2010/0241137 A1 9/2010 Doyle et al.
2010/0243707 A1 9/2010 Olson et al.
2010/0243708 A1 9/2010 Aranyi et al.
2010/0245102 A1 9/2010 Yokoi
2010/0249497 A1 9/2010 Peine et al.
2010/0249519 A1 9/2010 Park et al.
2010/0249759 A1 9/2010 Hinman et al.
2010/0249947 A1 9/2010 Lesh et al.
2010/0256675 A1 10/2010 Romans
2010/0258327 A1 10/2010 Esenwein et al.
2010/0258611 A1 10/2010 Smith et al.
2010/0267662 A1 10/2010 Fielder et al.
2010/0268030 A1 10/2010 Viola et al.
2010/0274160 A1 10/2010 Yachi et al.
2010/0276471 A1 11/2010 Whitman
2010/0292540 A1 11/2010 Hess et al.
2010/0294827 A1 11/2010 Boyden et al.
2010/0298636 A1 11/2010 Casto et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0320252 A1 12/2010 Viola et al.
2010/0331856 A1 12/2010 Carlson et al.
2010/0331880 A1 12/2010 Stopek
2011/0003528 A1 1/2011 Lam
2011/0006101 A1 1/2011 Hall et al.
2011/0009694 A1 1/2011 Schultz et al.
2011/0009890 A1 1/2011 Palmer et al.
2011/0011916 A1 1/2011 Levine
2011/0016960 A1 1/2011 Debrailly
2011/0017799 A1 1/2011 Whitman et al.
2011/0021871 A1 1/2011 Berkelaar
2011/0022032 A1 1/2011 Zemlok et al.
2011/0024477 A1 2/2011 Hall et al.
2011/0024478 A1 2/2011 Shelton, IV
2011/0025311 A1 2/2011 Chauvin et al.
2011/0029270 A1 2/2011 Mueglitz
2011/0034910 A1 2/2011 Ross et al.
2011/0034918 A1 2/2011 Reschke
2011/0036887 A1 2/2011 Zemlok et al.
2011/0036890 A1 2/2011 Ma
2011/0036891 A1 2/2011 Zemlok et al.
2011/0045047 A1 2/2011 Bennett et al.
2011/0046666 A1 2/2011 Sorrentino et al.
2011/0046667 A1 2/2011 Culligan et al.
2011/0052660 A1 3/2011 Yang et al.
2011/0056717 A1 3/2011 Herisse
2011/0060356 A1 3/2011 Reschke et al.
2011/0060363 A1 3/2011 Hess et al.
2011/0066156 A1 3/2011 McGahan et al.
2011/0082538 A1 4/2011 Dahlgren et al.
2011/0084112 A1 4/2011 Kostrzewski
2011/0087276 A1 4/2011 Bedi et al.
2011/0087279 A1 4/2011 Shah et al.
2011/0088921 A1 4/2011 Forgues et al.
2011/0091515 A1 4/2011 Zilberman et al.
2011/0095064 A1 4/2011 Taylor et al.
2011/0095068 A1 4/2011 Patel
2011/0101065 A1 5/2011 Milliman
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0118778 A1 5/2011 Burbank
2011/0121049 A1 5/2011 Malinouskas et al.
2011/0125138 A1 5/2011 Malinouskas et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144640 A1 6/2011 Heinrich et al.
2011/0144764 A1 6/2011 Bagga et al.
2011/0147433 A1 6/2011 Shelton, IV et al.
2011/0155786 A1 6/2011 Shelton, IV
2011/0160725 A1 6/2011 Kabaya et al.
2011/0163146 A1 7/2011 Ortiz et al.
2011/0167619 A1 7/2011 Smith et al.
2011/0172495 A1 7/2011 Armstrong
2011/0174099 A1 7/2011 Ross et al.
2011/0174861 A1 7/2011 Shelton, IV et al.
2011/0178536 A1 7/2011 Kostrzewski
2011/0184459 A1 7/2011 Malkowski et al.
2011/0192882 A1 8/2011 Hess et al.
2011/0199225 A1 8/2011 Touchberry et al.
2011/0208093 A1 8/2011 Gross et al.
2011/0210156 A1 9/2011 Smith et al.
2011/0218400 A1 9/2011 Ma et al.
2011/0218550 A1 9/2011 Ma
2011/0220381 A1 9/2011 Friese et al.
2011/0225105 A1 9/2011 Scholer et al.
2011/0230713 A1 9/2011 Kleemann et al.
2011/0238044 A1 9/2011 Main et al.
2011/0241597 A1 10/2011 Zhu et al.
2011/0253765 A1 10/2011 Nicholas et al.
2011/0256266 A1 10/2011 Orme et al.
2011/0257650 A1 10/2011 Deville et al.
2011/0264119 A1 10/2011 Bayon et al.
2011/0271186 A1 11/2011 Owens
2011/0275901 A1 11/2011 Shelton, IV
2011/0276083 A1 11/2011 Shelton, IV et al.
2011/0278343 A1 11/2011 Knodel et al.
2011/0279268 A1 11/2011 Konishi et al.
2011/0282446 A1 11/2011 Schulte et al.
2011/0290856 A1 12/2011 Shelton, IV et al.
2011/0290858 A1 12/2011 Whitman et al.
2011/0293690 A1 12/2011 Griffin et al.
2011/0295295 A1 12/2011 Shelton, IV et al.
2011/0307023 A1 12/2011 Tweden et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0007550 A1 1/2012 Juergens
2012/0016239 A1 1/2012 Barthe et al.
2012/0016413 A1 1/2012 Timm et al.
2012/0016467 A1 1/2012 Chen et al.
2012/0018326 A1 1/2012 Racenet et al.
2012/0022523 A1 1/2012 Smith et al.
2012/0022630 A1 1/2012 Wübbeling
2012/0029272 A1 2/2012 Shelton, IV et al.
2012/0033360 A1 2/2012 Hsu
2012/0045303 A1 2/2012 Macdonald
2012/0046692 A1 2/2012 Smith et al.
2012/0059286 A1 3/2012 Hastings et al.
2012/0062171 A1 3/2012 Smith et al.
2012/0064483 A1 3/2012 Lint et al.

(56) References Cited

U.S. PATENT DOCUMENTS

2012/0074200 A1 3/2012 Schmid et al.
2012/0078071 A1 3/2012 Bohm et al.
2012/0078244 A1 3/2012 Worrell et al.
2012/0078278 A1 3/2012 Bales, Jr. et al.
2012/0080336 A1 4/2012 Shelton, IV et al.
2012/0080340 A1 4/2012 Shelton, IV et al.
2012/0080344 A1 4/2012 Shelton, IV
2012/0080475 A1 4/2012 Smith et al.
2012/0080478 A1 4/2012 Morgan et al.
2012/0080498 A1 4/2012 Shelton, IV et al.
2012/0086276 A1 4/2012 Sawyers
2012/0089131 A1 4/2012 Zemlok et al.
2012/0095458 A1 4/2012 Cybulski et al.
2012/0109186 A1 5/2012 Parrott et al.
2012/0110810 A1 5/2012 Houser et al.
2012/0116261 A1 5/2012 Mumaw et al.
2012/0116262 A1 5/2012 Houser et al.
2012/0116265 A1 5/2012 Houser et al.
2012/0116266 A1 5/2012 Houser et al.
2012/0116367 A1 5/2012 Houser et al.
2012/0116381 A1 5/2012 Houser et al.
2012/0116388 A1 5/2012 Houser et al.
2012/0116391 A1 5/2012 Houser et al.
2012/0116395 A1 5/2012 Madan et al.
2012/0118595 A1 5/2012 Pellenc
2012/0123203 A1 5/2012 Riva
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0138658 A1 6/2012 Ullrich et al.
2012/0171539 A1 7/2012 Rejman et al.
2012/0175398 A1 7/2012 Sandborn et al.
2012/0187179 A1 7/2012 Gleiman
2012/0197272 A1 8/2012 Oray et al.
2012/0209289 A1 8/2012 Duque et al.
2012/0211542 A1 8/2012 Racenet
2012/0220990 A1 8/2012 Mckenzie et al.
2012/0223121 A1 9/2012 Viola et al.
2012/0228355 A1 9/2012 Combrowski et al.
2012/0234895 A1 9/2012 O'Connor et al.
2012/0234897 A1 9/2012 Shelton, IV et al.
2012/0234899 A1 9/2012 Scheib et al.
2012/0239068 A1 9/2012 Morris et al.
2012/0241492 A1 9/2012 Shelton, IV et al.
2012/0241493 A1 9/2012 Baxter, III et al.
2012/0248167 A1 10/2012 Flanagan et al.
2012/0248169 A1 10/2012 Widenhouse et al.
2012/0251861 A1 10/2012 Liang et al.
2012/0253328 A1 10/2012 Cunningham et al.
2012/0253329 A1 10/2012 Zemlok et al.
2012/0265176 A1 10/2012 Braun
2012/0271285 A1 10/2012 Sholev et al.
2012/0271327 A1 10/2012 West et al.
2012/0273550 A1 11/2012 Scirica
2012/0277780 A1 11/2012 Smith et al.
2012/0283707 A1 11/2012 Giordano et al.
2012/0286021 A1 11/2012 Kostrzewski et al.
2012/0289811 A1 11/2012 Viola et al.
2012/0289979 A1 11/2012 Eskaros et al.
2012/0292367 A1 11/2012 Morgan et al.
2012/0296333 A1 11/2012 Twomey
2012/0296342 A1 11/2012 Haglund Wendelschafer
2012/0298722 A1 11/2012 Hess et al.
2012/0301498 A1 11/2012 Altreuter et al.
2012/0310255 A1 12/2012 Brisson et al.
2012/0310256 A1 12/2012 Brisson
2012/0325892 A1 12/2012 Kostrzewski
2012/0330329 A1 12/2012 Harris et al.
2013/0006227 A1 1/2013 Takashino
2013/0008937 A1 1/2013 Viola
2013/0012983 A1 1/2013 Kleyman
2013/0018361 A1 1/2013 Bryant
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0026973 A1 1/2013 Luke et al.
2013/0030462 A1 1/2013 Keating et al.
2013/0030608 A1 1/2013 Taylor et al.
2013/0032626 A1 2/2013 Smith et al.
2013/0037596 A1 2/2013 Bear et al.
2013/0041292 A1 2/2013 Cunningham
2013/0046290 A1 2/2013 Palmer et al.
2013/0057162 A1 3/2013 Pollischansky
2013/0060278 A1 3/2013 Bozung et al.
2013/0062391 A1 3/2013 Boudreaux et al.
2013/0068816 A1 3/2013 Mandakolathur Vasudevan et al.
2013/0075446 A1 3/2013 Wang et al.
2013/0079814 A1 3/2013 Hess et al.
2013/0087597 A1 4/2013 Shelton, IV et al.
2013/0087599 A1 4/2013 Krumanaker et al.
2013/0087602 A1 4/2013 Olson et al.
2013/0090534 A1 4/2013 Burns et al.
2013/0096568 A1 4/2013 Justis
2013/0098970 A1 4/2013 Racenet et al.
2013/0103023 A1 4/2013 Monson et al.
2013/0103024 A1 4/2013 Monson et al.
2013/0105548 A1 5/2013 Hodgkinson et al.
2013/0105552 A1 5/2013 Weir et al.
2013/0106352 A1 5/2013 Nagamine
2013/0116668 A1 5/2013 Shelton, IV et al.
2013/0116669 A1 5/2013 Shelton, IV et al.
2013/0119108 A1 5/2013 Altman et al.
2013/0123816 A1 5/2013 Hodgkinson et al.
2013/0123822 A1 5/2013 Wellman et al.
2013/0126202 A1 5/2013 Oomori et al.
2013/0126379 A1 5/2013 Medhal et al.
2013/0131476 A1 5/2013 Siu et al.
2013/0131651 A1 5/2013 Strobl et al.
2013/0136969 A1 5/2013 Yasui et al.
2013/0146641 A1 6/2013 Shelton, IV et al.
2013/0146642 A1 6/2013 Shelton, IV et al.
2013/0150832 A1 6/2013 Belson et al.
2013/0153633 A1 6/2013 Casasanta, Jr. et al.
2013/0153634 A1 6/2013 Carter et al.
2013/0153635 A1 6/2013 Hodgkinson
2013/0153636 A1 6/2013 Shelton, IV et al.
2013/0153638 A1 6/2013 Carter et al.
2013/0153641 A1 6/2013 Shelton, IV et al.
2013/0158390 A1 6/2013 Tan et al.
2013/0162198 A1 6/2013 Yokota et al.
2013/0168431 A1 7/2013 Zemlok et al.
2013/0169217 A1 7/2013 Watanabe et al.
2013/0172878 A1 7/2013 Smith
2013/0172929 A1 7/2013 Hess et al.
2013/0175317 A1 7/2013 Yates et al.
2013/0175322 A1 7/2013 Yates et al.
2013/0181033 A1 7/2013 Shelton, IV et al.
2013/0181034 A1 7/2013 Shelton, IV et al.
2013/0186933 A1 7/2013 Shelton, IV et al.
2013/0186934 A1 7/2013 Shelton, IV et al.
2013/0190733 A1 7/2013 Giordano et al.
2013/0190757 A1 7/2013 Yates et al.
2013/0193188 A1 8/2013 Shelton, IV et al.
2013/0193189 A1 8/2013 Swensgard et al.
2013/0197556 A1 8/2013 Shelton, IV et al.
2013/0211244 A1 8/2013 Nathaniel
2013/0214025 A1 8/2013 Zemlok et al.
2013/0214030 A1 8/2013 Aronhalt et al.
2013/0215449 A1 8/2013 Yamasaki
2013/0221059 A1 8/2013 Racenet et al.
2013/0221063 A1 8/2013 Aronhalt et al.
2013/0221064 A1 8/2013 Aronhalt et al.
2013/0221065 A1 8/2013 Aronhalt et al.
2013/0233905 A1 9/2013 Sorrentino et al.
2013/0233906 A1 9/2013 Hess et al.
2013/0233908 A1 9/2013 Knodel et al.
2013/0238021 A1 9/2013 Gross et al.
2013/0248578 A1 9/2013 Arteaga Gonzalez
2013/0253480 A1 9/2013 Kimball et al.

(56) References Cited

U.S. PATENT DOCUMENTS

2013/0256371 A1 10/2013 Shelton, IV et al.
2013/0256373 A1 10/2013 Schmid et al.
2013/0256374 A1 10/2013 Shelton, IV et al.
2013/0256375 A1 10/2013 Shelton, IV et al.
2013/0256377 A1 10/2013 Schmid et al.
2013/0256378 A1 10/2013 Schmid et al.
2013/0256379 A1 10/2013 Schmid et al.
2013/0256380 A1 10/2013 Schmid et al.
2013/0256382 A1 10/2013 Swayze et al.
2013/0256383 A1 10/2013 Aronhalt et al.
2013/0261648 A1 10/2013 Laurent et al.
2013/0267945 A1 10/2013 Behnke et al.
2013/0267978 A1 10/2013 Trissel
2013/0270322 A1 10/2013 Scheib et al.
2013/0277410 A1 10/2013 Fernandez et al.
2013/0277412 A1 10/2013 Gresham et al.
2013/0282052 A1 10/2013 Aranyi et al.
2013/0306704 A1 11/2013 Balbierz et al.
2013/0310873 A1 11/2013 Stopek et al.
2013/0313304 A1 11/2013 Shelton, IV et al.
2013/0313306 A1 11/2013 Shelton, IV et al.
2013/0317753 A1 11/2013 Kamen et al.
2013/0319706 A1 12/2013 Nicholas et al.
2013/0324981 A1 12/2013 Smith et al.
2013/0324982 A1 12/2013 Smith et al.
2013/0327552 A1 12/2013 Lovelass et al.
2013/0327809 A1 12/2013 Shelton, IV et al.
2013/0327810 A1 12/2013 Swayze et al.
2013/0333910 A1 12/2013 Tanimoto et al.
2013/0334280 A1 12/2013 Krehel et al.
2013/0334283 A1 12/2013 Swayze et al.
2013/0334284 A1 12/2013 Swayze et al.
2013/0334285 A1 12/2013 Swayze et al.
2013/0334286 A1 12/2013 Swayze et al.
2013/0334287 A1 12/2013 Shelton, IV
2013/0334288 A1 12/2013 Shelton, IV
2013/0341374 A1 12/2013 Shelton, IV et al.
2014/0001231 A1 1/2014 Shelton, IV et al.
2014/0001234 A1 1/2014 Shelton, IV et al.
2014/0001237 A1 1/2014 Shelton, IV et al.
2014/0001238 A1 1/2014 Shelton, IV et al.
2014/0001239 A1 1/2014 Shelton, IV et al.
2014/0001240 A1 1/2014 Shelton, IV et al.
2014/0005640 A1 1/2014 Shelton, IV et al.
2014/0005678 A1 1/2014 Shelton, IV et al.
2014/0005681 A1 1/2014 Gee et al.
2014/0005693 A1 1/2014 Shelton, IV et al.
2014/0005694 A1 1/2014 Shelton, IV et al.
2014/0005702 A1 1/2014 Timm et al.
2014/0005703 A1 1/2014 Stulen et al.
2014/0005718 A1 1/2014 Shelton, IV et al.
2014/0008414 A1 1/2014 Shelton, IV et al.
2014/0012237 A1 1/2014 Pribanic et al.
2014/0012238 A1 1/2014 Chen et al.
2014/0012289 A1 1/2014 Snow et al.
2014/0014704 A1 1/2014 Onukuri et al.
2014/0014705 A1 1/2014 Baxter, III
2014/0014707 A1 1/2014 Onukuri et al.
2014/0015782 A1 1/2014 Kim et al.
2014/0018832 A1 1/2014 Shelton, IV
2014/0022283 A1 1/2014 Chan et al.
2014/0025046 A1 1/2014 Williams et al.
2014/0039549 A1 2/2014 Belsky et al.
2014/0042205 A1 2/2014 Baxter, III et al.
2014/0048580 A1 2/2014 Merchant et al.
2014/0061279 A1 3/2014 Laurent et al.
2014/0061280 A1 3/2014 Ingmanson et al.
2014/0081176 A1 3/2014 Hassan
2014/0094681 A1 4/2014 Valentine et al.
2014/0100558 A1 4/2014 Schmitz et al.
2014/0103093 A1 4/2014 Koch, Jr. et al.
2014/0107640 A1 4/2014 Yates et al.
2014/0110455 A1 4/2014 Ingmanson et al.
2014/0114327 A1 4/2014 Boudreaux et al.
2014/0115229 A1 4/2014 Kothamasu et al.
2014/0128850 A1 5/2014 Kerr et al.
2014/0131418 A1 5/2014 Kostrzewski
2014/0135832 A1 5/2014 Park et al.
2014/0138423 A1 5/2014 Whitfield et al.
2014/0151431 A1 6/2014 Hodgkinson et al.
2014/0151433 A1 6/2014 Shelton, IV et al.
2014/0158747 A1 6/2014 Measamer et al.
2014/0166722 A1 6/2014 Hess et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0171966 A1 6/2014 Giordano et al.
2014/0175147 A1 6/2014 Manoux et al.
2014/0175150 A1 6/2014 Shelton et al.
2014/0175152 A1 6/2014 Hess et al.
2014/0175154 A1 6/2014 Shelton, IV et al.
2014/0181710 A1 6/2014 Baalu et al.
2014/0188091 A1 7/2014 Vidal et al.
2014/0188159 A1 7/2014 Steege
2014/0191014 A1 7/2014 Shelton, IV
2014/0191015 A1 7/2014 Shelton, IV
2014/0203061 A1 7/2014 Hodgkinson
2014/0205637 A1 7/2014 Widenhouse et al.
2014/0207124 A1 7/2014 Aldridge et al.
2014/0207125 A1 7/2014 Applegate et al.
2014/0207166 A1 7/2014 Shelton, IV et al.
2014/0209658 A1 7/2014 Skalla et al.
2014/0213848 A1 7/2014 Moskowitz et al.
2014/0224857 A1 8/2014 Schmid
2014/0228632 A1 8/2014 Sholev et al.
2014/0228867 A1 8/2014 Thomas et al.
2014/0230595 A1 8/2014 Butt et al.
2014/0232316 A1 8/2014 Philipp
2014/0236184 A1 8/2014 Leimbach et al.
2014/0239036 A1 8/2014 Zerkle et al.
2014/0239038 A1 8/2014 Leimbach et al.
2014/0239047 A1 8/2014 Hodgkinson et al.
2014/0243865 A1 8/2014 Swayze et al.
2014/0246472 A1 9/2014 Kimsey et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0252066 A1 9/2014 Shelton, IV et al.
2014/0252068 A1 9/2014 Shelton, IV et al.
2014/0259591 A1 9/2014 Shelton, IV et al.
2014/0263541 A1 9/2014 Leimbach et al.
2014/0263552 A1 9/2014 Hall et al.
2014/0263554 A1 9/2014 Leimbach et al.
2014/0263558 A1 9/2014 Hausen et al.
2014/0263562 A1 9/2014 Patel et al.
2014/0263564 A1 9/2014 Leimbach et al.
2014/0263572 A1 9/2014 Shelton, IV et al.
2014/0276730 A1 9/2014 Boudreaux et al.
2014/0277017 A1 9/2014 Leimbach et al.
2014/0284371 A1 9/2014 Morgan et al.
2014/0284373 A1 9/2014 Shelton, IV et al.
2014/0288460 A1 9/2014 Ouyang et al.
2014/0291378 A1 10/2014 Shelton, IV et al.
2014/0291379 A1 10/2014 Schellin et al.
2014/0291380 A1 10/2014 Weaner et al.
2014/0291382 A1 10/2014 Lloyd et al.
2014/0291383 A1 10/2014 Spivey et al.
2014/0296873 A1 10/2014 Morgan et al.
2014/0296874 A1 10/2014 Morgan et al.
2014/0299648 A1 10/2014 Shelton, IV et al.
2014/0303645 A1 10/2014 Morgan et al.
2014/0303646 A1 10/2014 Morgan et al.
2014/0303660 A1 10/2014 Boyden et al.
2014/0305987 A1 10/2014 Parihar et al.
2014/0305988 A1 10/2014 Boudreaux et al.
2014/0305989 A1 10/2014 Parihar et al.
2014/0305990 A1 10/2014 Shelton, IV et al.
2014/0305991 A1 10/2014 Parihar et al.
2014/0305992 A1 10/2014 Kimsey et al.
2014/0305994 A1 10/2014 Parihar et al.
2014/0309665 A1 10/2014 Parihar et al.
2014/0309666 A1 10/2014 Shelton, IV et al.

(56) References Cited

U.S. PATENT DOCUMENTS

2014/0330161 A1 11/2014 Swayze et al.
2014/0330298 A1 11/2014 Arshonsky et al.
2014/0330579 A1 11/2014 Cashman et al.
2014/0339286 A1 11/2014 Motooka et al.
2014/0352463 A1 12/2014 Parihar
2014/0353358 A1 12/2014 Shelton, IV et al.
2014/0367445 A1 12/2014 Ingmanson et al.
2014/0367447 A1 12/2014 Woodard, Jr. et al.
2014/0374130 A1 12/2014 Nakamura et al.
2014/0378950 A1 12/2014 Chiu
2015/0002089 A1 1/2015 Rejman et al.
2015/0008248 A1 1/2015 Giordano et al.
2015/0025549 A1 1/2015 Kilroy et al.
2015/0034696 A1 2/2015 Shelton, IV et al.
2015/0038961 A1 2/2015 Clark et al.
2015/0038986 A1 2/2015 Swensgard et al.
2015/0041518 A1 2/2015 Shelton, IV et al.
2015/0053737 A1 2/2015 Leimbach et al.
2015/0053738 A1 2/2015 Morgan et al.
2015/0053739 A1 2/2015 Morgan et al.
2015/0053740 A1 2/2015 Shelton, IV
2015/0053741 A1 2/2015 Shelton, IV et al.
2015/0053742 A1 2/2015 Shelton, IV et al.
2015/0053743 A1 2/2015 Yates et al.
2015/0053744 A1 2/2015 Swayze et al.
2015/0053745 A1 2/2015 Yates et al.
2015/0053746 A1 2/2015 Shelton, IV et al.
2015/0053748 A1 2/2015 Yates et al.
2015/0060518 A1 3/2015 Shelton, IV et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0076207 A1 3/2015 Boudreaux et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0076212 A1 3/2015 Shelton, IV
2015/0080868 A1 3/2015 Kerr
2015/0082624 A1 3/2015 Craig et al.
2015/0083780 A1 3/2015 Shelton, IV et al.
2015/0083781 A1 3/2015 Giordano et al.
2015/0083783 A1 3/2015 Shelton, IV et al.
2015/0087952 A1 3/2015 Albert et al.
2015/0088127 A1 3/2015 Craig et al.
2015/0088547 A1 3/2015 Balram et al.
2015/0090759 A1 4/2015 Spivey et al.
2015/0090760 A1 4/2015 Giordano et al.
2015/0090761 A1 4/2015 Giordano et al.
2015/0090762 A1 4/2015 Giordano et al.
2015/0090763 A1 4/2015 Murray et al.
2015/0108199 A1 4/2015 Shelton, IV et al.
2015/0122869 A1 5/2015 Aronhalt et al.
2015/0127021 A1 5/2015 Harris et al.
2015/0134077 A1 5/2015 Shelton, IV et al.
2015/0136830 A1 5/2015 Baxter, III et al.
2015/0136831 A1 5/2015 Baxter, III et al.
2015/0136832 A1 5/2015 Baxter, III et al.
2015/0136833 A1 5/2015 Shelton, IV et al.
2015/0136835 A1 5/2015 Shelton, IV et al.
2015/0150620 A1 6/2015 Miyamoto et al.
2015/0157354 A1 6/2015 Bales, Jr. et al.
2015/0173744 A1 6/2015 Shelton, IV et al.
2015/0173745 A1 6/2015 Baxter, III et al.
2015/0173746 A1 6/2015 Baxter, III et al.
2015/0173747 A1 6/2015 Baxter, III et al.
2015/0173749 A1 6/2015 Shelton, IV et al.
2015/0173750 A1 6/2015 Shelton, IV et al.
2015/0173751 A1 6/2015 Shelton, IV et al.
2015/0173755 A1 6/2015 Baxter, III et al.
2015/0173756 A1 6/2015 Baxter, III et al.
2015/0173760 A1 6/2015 Shelton, IV et al.
2015/0173761 A1 6/2015 Shelton, IV et al.
2015/0173762 A1 6/2015 Shelton, IV et al.
2015/0173789 A1 6/2015 Baxter, III et al.
2015/0182220 A1 7/2015 Yates et al.
2015/0182222 A1 7/2015 Swayze et al.
2015/0196295 A1 7/2015 Shelton, IV et al.
2015/0196296 A1 7/2015 Swayze et al.
2015/0196299 A1 7/2015 Swayze et al.
2015/0196347 A1 7/2015 Yates et al.
2015/0196348 A1 7/2015 Yates et al.
2015/0201918 A1 7/2015 Kumar et al.
2015/0201932 A1 7/2015 Swayze et al.
2015/0201935 A1 7/2015 Weisenburgh, II et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209031 A1 7/2015 Shelton, IV et al.
2015/0209038 A1 7/2015 Shelton, IV et al.
2015/0209039 A1 7/2015 Shelton, IV et al.
2015/0209041 A1 7/2015 Milliman et al.
2015/0209045 A1 7/2015 Hodgkinson et al.
2015/0222212 A1 8/2015 Iwata
2015/0223809 A1 8/2015 Scheib et al.
2015/0223816 A1 8/2015 Morgan et al.
2015/0223868 A1 8/2015 Brandt et al.
2015/0230697 A1 8/2015 Phee et al.
2015/0230783 A1 8/2015 Shelton, IV et al.
2015/0230784 A1 8/2015 Shelton, IV et al.
2015/0231409 A1 8/2015 Racenet et al.
2015/0238118 A1 8/2015 Legassey et al.
2015/0239180 A1 8/2015 Schellin et al.
2015/0265276 A1 9/2015 Huitema et al.
2015/0265357 A1 9/2015 Shelton, IV et al.
2015/0272557 A1 10/2015 Overmyer et al.
2015/0272569 A1 10/2015 Leimbach et al.
2015/0272570 A1 10/2015 Lytle, IV et al.
2015/0272571 A1 10/2015 Leimbach et al.
2015/0272572 A1 10/2015 Overmyer et al.
2015/0272574 A1 10/2015 Leimbach et al.
2015/0272575 A1 10/2015 Leimbach et al.
2015/0272578 A1 10/2015 Leimbach et al.
2015/0272579 A1 10/2015 Leimbach et al.
2015/0272580 A1 10/2015 Leimbach et al.
2015/0272581 A1 10/2015 Leimbach et al.
2015/0272582 A1 10/2015 Leimbach et al.
2015/0272583 A1 10/2015 Leimbach et al.
2015/0277471 A1 10/2015 Leimbach et al.
2015/0280384 A1 10/2015 Leimbach et al.
2015/0280424 A1 10/2015 Leimbach et al.
2015/0282809 A1 10/2015 Shelton, IV et al.
2015/0282810 A1 10/2015 Shelton, IV et al.
2015/0289873 A1 10/2015 Shelton, IV et al.
2015/0289874 A1 10/2015 Leimbach et al.
2015/0297200 A1 10/2015 Fitzsimmons et al.
2015/0297210 A1 10/2015 Widenhouse et al.
2015/0297217 A1 10/2015 Huitema et al.
2015/0297218 A1 10/2015 Shelton, IV et al.
2015/0297219 A1 10/2015 Shelton, IV et al.
2015/0297221 A1 10/2015 Kerr et al.
2015/0297222 A1 10/2015 Huitema et al.
2015/0297223 A1 10/2015 Huitema et al.
2015/0297224 A1 10/2015 Hall et al.
2015/0297225 A1 10/2015 Huitema et al.
2015/0297226 A1 10/2015 Hall et al.
2015/0297227 A1 10/2015 Huitema et al.
2015/0297228 A1 10/2015 Huitema et al.
2015/0297229 A1 10/2015 Schellin et al.
2015/0297230 A1 10/2015 Schellin et al.
2015/0297231 A1 10/2015 Huitema et al.
2015/0297232 A1 10/2015 Huitema et al.
2015/0297233 A1 10/2015 Huitema et al.
2015/0297234 A1 10/2015 Schellin et al.
2015/0297235 A1 10/2015 Harris et al.
2015/0297236 A1 10/2015 Harris et al.
2015/0303417 A1 10/2015 Koeder et al.
2015/0305744 A1 10/2015 Moore et al.
2015/0305745 A1 10/2015 Baxter, III et al.
2015/0313591 A1 11/2015 Baxter, III et al.

(56) References Cited

U.S. PATENT DOCUMENTS

2015/0313594 A1 11/2015 Shelton, IV et al.
2015/0324317 A1 11/2015 Collins et al.
2015/0327853 A1 11/2015 Aronhalt et al.
2015/0327864 A1 11/2015 Hodgkinson et al.
2015/0335328 A1 11/2015 Shelton, IV et al.
2015/0335329 A1 11/2015 Shelton, IV et al.
2015/0342606 A1 12/2015 Schmid et al.
2015/0342607 A1 12/2015 Shelton, IV et al.
2015/0352699 A1 12/2015 Sakai et al.
2015/0359536 A1 12/2015 Cropper et al.
2015/0366585 A1 12/2015 Lemay et al.
2015/0367497 A1 12/2015 Ito et al.
2015/0372265 A1 12/2015 Morisaku et al.
2015/0374367 A1 12/2015 Hall et al.
2015/0374368 A1 12/2015 Swayze et al.
2015/0374369 A1 12/2015 Yates et al.
2015/0374372 A1 12/2015 Zergiebel et al.
2015/0374374 A1 12/2015 Shelton, IV et al.
2015/0374375 A1 12/2015 Shelton, IV et al.
2015/0374376 A1 12/2015 Shelton, IV
2015/0374377 A1 12/2015 Shelton, IV
2015/0374378 A1 12/2015 Giordano et al.
2015/0374379 A1 12/2015 Shelton, IV
2016/0000430 A1 1/2016 Ming et al.
2016/0000431 A1 1/2016 Giordano et al.
2016/0000432 A1 1/2016 Huang et al.
2016/0000437 A1 1/2016 Giordano et al.
2016/0000438 A1 1/2016 Swayze et al.
2016/0000439 A1 1/2016 Weisenburgh, II et al.
2016/0000440 A1 1/2016 Weisenburgh, II et al.
2016/0000441 A1 1/2016 Shelton, IV et al.
2016/0000442 A1 1/2016 Shelton, IV
2016/0000452 A1 1/2016 Yates et al.
2016/0000453 A1 1/2016 Yates et al.
2016/0000513 A1 1/2016 Shelton, IV et al.
2016/0007992 A1 1/2016 Yates et al.
2016/0008023 A1 1/2016 Yates et al.
2016/0015390 A1 1/2016 Timm et al.
2016/0015391 A1 1/2016 Shelton, IV et al.
2016/0030042 A1 2/2016 Heinrich et al.
2016/0051257 A1 2/2016 Shelton, IV et al.
2016/0051316 A1 2/2016 Boudreaux
2016/0058443 A1 3/2016 Yates et al.
2016/0066911 A1 3/2016 Baber et al.
2016/0066912 A1 3/2016 Baber et al.
2016/0066913 A1 3/2016 Swayze et al.
2016/0066915 A1 3/2016 Baber et al.
2016/0069449 A1 3/2016 Kanai et al.
2016/0074038 A1 3/2016 Leimbach et al.
2016/0074040 A1 3/2016 Widenhouse et al.
2016/0074103 A1 3/2016 Sartor
2016/0082161 A1 3/2016 Zilberman et al.
2016/0089137 A1 3/2016 Hess et al.
2016/0089141 A1 3/2016 Harris et al.
2016/0089142 A1 3/2016 Harris et al.
2016/0089143 A1 3/2016 Harris et al.
2016/0089146 A1 3/2016 Harris et al.
2016/0089147 A1 3/2016 Harris et al.
2016/0089148 A1 3/2016 Harris et al.
2016/0089149 A1 3/2016 Harris et al.
2016/0100837 A1 4/2016 Huang et al.
2016/0106426 A1 4/2016 Shelton, IV et al.
2016/0106427 A1 4/2016 Shelton, IV et al.
2016/0106431 A1 4/2016 Shelton, IV et al.
2016/0113653 A1 4/2016 Zingman
2016/0120544 A1 5/2016 Shelton, IV et al.
2016/0120545 A1 5/2016 Shelton, IV et al.
2016/0120547 A1 5/2016 Schmid et al.
2016/0128694 A1 5/2016 Baxter, III et al.
2016/0135812 A1 5/2016 Shelton, IV et al.
2016/0135835 A1 5/2016 Onuma
2016/0135895 A1 5/2016 Faasse et al.
2016/0166256 A1 6/2016 Baxter, III et al.
2016/0174969 A1 6/2016 Kerr et al.
2016/0174970 A1 6/2016 Shelton, IV et al.
2016/0174971 A1 6/2016 Baxter, III et al.
2016/0174972 A1 6/2016 Shelton, IV et al.
2016/0174973 A1 6/2016 Shelton, IV et al.
2016/0174974 A1 6/2016 Schmid et al.
2016/0174975 A1 6/2016 Shelton, IV et al.
2016/0174976 A1 6/2016 Morgan et al.
2016/0174983 A1 6/2016 Shelton, IV et al.
2016/0174984 A1 6/2016 Smith et al.
2016/0174985 A1 6/2016 Baxter, III et al.
2016/0183939 A1 6/2016 Shelton, IV et al.
2016/0183943 A1 6/2016 Shelton, IV
2016/0183944 A1 6/2016 Swensgard et al.
2016/0183945 A1 6/2016 Shelton, IV et al.
2016/0183947 A1 6/2016 Shelton, IV et al.
2016/0183948 A1 6/2016 Shelton, IV et al.
2016/0183950 A1 6/2016 Shelton, IV et al.
2016/0184039 A1 6/2016 Shelton, IV et al.
2016/0192916 A1 7/2016 Shelton, IV et al.
2016/0192917 A1 7/2016 Shelton, IV et al.
2016/0192918 A1 7/2016 Shelton, IV et al.
2016/0192929 A1 7/2016 Schmid et al.
2016/0192933 A1 7/2016 Shelton, IV
2016/0192936 A1 7/2016 Leimbach et al.
2016/0192960 A1 7/2016 Bueno et al.
2016/0192996 A1 7/2016 Spivey et al.
2016/0192997 A1 7/2016 Spivey et al.
2016/0199059 A1 7/2016 Shelton, IV et al.
2016/0199061 A1 7/2016 Shelton, IV et al.
2016/0199063 A1 7/2016 Mandakolathur Vasudevan et al.
2016/0199064 A1 7/2016 Shelton, IV et al.
2016/0199088 A1 7/2016 Shelton, IV et al.
2016/0199089 A1 7/2016 Hess et al.
2016/0199956 A1 7/2016 Shelton, IV et al.
2016/0206309 A1 7/2016 Hess et al.
2016/0206310 A1 7/2016 Shelton, IV
2016/0206314 A1 7/2016 Scheib et al.
2016/0220246 A1 8/2016 Timm et al.
2016/0220247 A1 8/2016 Timm et al.
2016/0220248 A1 8/2016 Timm et al.
2016/0220249 A1 8/2016 Shelton, IV et al.
2016/0220254 A1 8/2016 Baxter, III et al.
2016/0220266 A1 8/2016 Shelton, IV et al.
2016/0220268 A1 8/2016 Shelton, IV et al.
2016/0235403 A1 8/2016 Shelton, IV et al.
2016/0235404 A1 8/2016 Shelton, IV
2016/0235405 A1 8/2016 Shelton, IV et al.
2016/0235406 A1 8/2016 Shelton, IV et al.
2016/0235408 A1 8/2016 Shelton, IV et al.
2016/0235409 A1 8/2016 Shelton, IV et al.
2016/0235494 A1 8/2016 Shelton, IV et al.
2016/0238108 A1 8/2016 Kanai et al.
2016/0242768 A1 8/2016 Moore et al.
2016/0242769 A1 8/2016 Moore et al.
2016/0242770 A1 8/2016 Moore et al.
2016/0242775 A1 8/2016 Shelton, IV et al.
2016/0242776 A1 8/2016 Shelton, IV et al.
2016/0242777 A1 8/2016 Shelton, IV et al.
2016/0242780 A1 8/2016 Shelton, IV et al.
2016/0242781 A1 8/2016 Shelton, IV et al.
2016/0242782 A1 8/2016 Shelton, IV et al.
2016/0242783 A1 8/2016 Shelton, IV et al.
2016/0249908 A1 9/2016 Shelton, IV et al.
2016/0249909 A1 9/2016 Shelton, IV et al.
2016/0249910 A1 9/2016 Shelton, IV et al.
2016/0249911 A1 9/2016 Timm et al.
2016/0249915 A1 9/2016 Beckman et al.
2016/0249916 A1 9/2016 Shelton, IV et al.
2016/0249917 A1 9/2016 Beckman et al.
2016/0249918 A1 9/2016 Shelton, IV et al.
2016/0249919 A1 9/2016 Savage et al.
2016/0249922 A1 9/2016 Morgan et al.
2016/0249927 A1 9/2016 Beckman et al.
2016/0249930 A1 9/2016 Hall et al.
2016/0249945 A1 9/2016 Shelton, IV et al.
2016/0256071 A1 9/2016 Shelton, IV et al.
2016/0256153 A1 9/2016 Shelton, IV et al.
2016/0256154 A1 9/2016 Shelton, IV et al.
2016/0256155 A1 9/2016 Shelton, IV et al.
2016/0256156 A1 9/2016 Shelton, IV et al.

(56) References Cited

U.S. PATENT DOCUMENTS

2016/0256159 A1 9/2016 Pinjala et al.
2016/0256160 A1 9/2016 Shelton, IV et al.
2016/0256161 A1 9/2016 Overmyer et al.
2016/0256162 A1 9/2016 Shelton, IV et al.
2016/0256163 A1 9/2016 Shelton, IV et al.
2016/0256184 A1 9/2016 Shelton, IV et al.
2016/0256185 A1 9/2016 Shelton, IV et al.
2016/0256186 A1 9/2016 Shelton, IV et al.
2016/0256187 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262746 A1 9/2016 Shelton, IV et al.
2016/0262760 A1 9/2016 Shelton, IV et al.
2016/0262921 A1 9/2016 Balbierz et al.
2016/0270780 A1 9/2016 Hall et al.
2016/0278771 A1 9/2016 Shelton, IV et al.
2016/0287249 A1 10/2016 Alexander, III et al.
2016/0287250 A1 10/2016 Shelton, IV et al.
2016/0287251 A1 10/2016 Shelton, IV et al.
2016/0287253 A1 10/2016 Shelton, IV et al.
2016/0287254 A1 10/2016 Baxter, III et al.
2016/0287265 A1 10/2016 Macdonald et al.
2016/0287279 A1 10/2016 Bovay et al.
2016/0310143 A1 10/2016 Bettuchi
2016/0314716 A1 10/2016 Grubbs
2016/0331375 A1 11/2016 Shelton, IV et al.
2016/0345976 A1 12/2016 Gonzalez et al.
2016/0367122 A1 12/2016 Ichimura et al.
2017/0000553 A1 1/2017 Wiener et al.
2017/0007244 A1 1/2017 Shelton, IV et al.
2017/0007245 A1 1/2017 Shelton, IV et al.
2017/0007250 A1 1/2017 Shelton, IV et al.
2017/0007347 A1 1/2017 Jaworek et al.
2017/0014125 A1 1/2017 Shelton, IV et al.
2017/0014129 A1 1/2017 Shelton, IV et al.
2017/0027572 A1 2/2017 Nalagatla et al.
2017/0049444 A1 2/2017 Schellin et al.
2017/0049448 A1 2/2017 Widenhouse et al.
2017/0055819 A1 3/2017 Hansen et al.
2017/0056000 A1 3/2017 Nalagatla et al.
2017/0056002 A1 3/2017 Nalagatla et al.
2017/0056005 A1 3/2017 Shelton, IV et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086831 A1 3/2017 Shelton, IV et al.
2017/0086838 A1 3/2017 Harris et al.
2017/0086842 A1 3/2017 Shelton, IV et al.
2017/0086930 A1 3/2017 Thompson et al.
2017/0105733 A1 4/2017 Scheib et al.
2017/0172382 A1 6/2017 Nir et al.
2017/0172662 A1 6/2017 Panescu et al.
2017/0182195 A1 6/2017 Wagner
2017/0182211 A1 6/2017 Raxworthy et al.
2017/0196556 A1 7/2017 Shah et al.
2017/0196558 A1 7/2017 Morgan et al.
2017/0196637 A1 7/2017 Shelton, IV et al.
2017/0196649 A1 7/2017 Yates et al.
2017/0202571 A1 7/2017 Shelton, IV et al.
2017/0202770 A1 7/2017 Friedrich et al.
2017/0209145 A1 7/2017 Swayze et al.
2017/0215881 A1 8/2017 Shelton, IV et al.
2017/0224332 A1 8/2017 Hunter et al.
2017/0224334 A1 8/2017 Worthington et al.
2017/0224339 A1 8/2017 Huang et al.
2017/0231627 A1 8/2017 Shelton, IV et al.
2017/0231628 A1 8/2017 Shelton, IV et al.
2017/0238928 A1 8/2017 Morgan et al.
2017/0238962 A1 8/2017 Hansen et al.
2017/0249431 A1 8/2017 Shelton, IV et al.
2017/0262110 A1 9/2017 Polishchuk et al.
2017/0265774 A1 9/2017 Johnson et al.
2017/0265856 A1 9/2017 Shelton, IV et al.
2017/0281171 A1 10/2017 Shelton, IV et al.
2017/0281173 A1 10/2017 Shelton, IV et al.
2017/0281186 A1 10/2017 Shelton, IV et al.
2017/0281187 A1 10/2017 Shelton, IV et al.
2017/0281189 A1 10/2017 Nalagatla et al.
2017/0290584 A1 10/2017 Jasemian et al.
2017/0290585 A1 10/2017 Shelton, IV et al.
2017/0296169 A1 10/2017 Yates et al.
2017/0296173 A1 10/2017 Shelton, IV et al.
2017/0296177 A1 10/2017 Harris et al.
2017/0296185 A1 10/2017 Swensgard et al.
2017/0296213 A1 10/2017 Swensgard et al.
2017/0311944 A1 11/2017 Morgan et al.
2017/0312041 A1 11/2017 Giordano et al.
2017/0312042 A1 11/2017 Giordano et al.
2017/0319201 A1 11/2017 Morgan et al.
2017/0333034 A1 11/2017 Morgan et al.
2017/0333035 A1 11/2017 Morgan et al.
2017/0348010 A1 12/2017 Chiang
2017/0348043 A1 12/2017 Wang et al.
2017/0354413 A1 12/2017 Chen et al.
2017/0354415 A1 12/2017 Casasanta, Jr. et al.
2017/0358052 A1 12/2017 Yuan
2017/0360439 A1 12/2017 Chen et al.
2017/0360441 A1 12/2017 Sgroi
2017/0367695 A1 12/2017 Shelton, IV et al.
2017/0367697 A1 12/2017 Shelton, IV et al.
2018/0000545 A1 1/2018 Giordano et al.
2018/0008356 A1 1/2018 Giordano et al.
2018/0008357 A1 1/2018 Giordano et al.
2018/0028185 A1 2/2018 Shelton, IV et al.
2018/0042611 A1 2/2018 Swayze et al.
2018/0055513 A1 3/2018 Shelton, IV et al.
2018/0055526 A1 3/2018 Shelton, IV et al.
2018/0064440 A1 3/2018 Shelton, IV et al.
2018/0064441 A1 3/2018 Shelton, IV et al.
2018/0064442 A1 3/2018 Shelton, IV et al.
2018/0064443 A1 3/2018 Shelton, IV et al.
2018/0070942 A1 3/2018 Shelton, IV et al.
2018/0078268 A1 3/2018 Messerly et al.
2018/0085116 A1 3/2018 Yates et al.
2018/0085117 A1 3/2018 Shelton, IV et al.
2018/0092710 A1 4/2018 Bosisio et al.
2018/0103955 A1 4/2018 Shelton, IV et al.
2018/0110520 A1 4/2018 Shelton, IV et al.
2018/0110521 A1 4/2018 Shelton, IV et al.
2018/0110522 A1 4/2018 Shelton, IV et al.
2018/0110523 A1 4/2018 Shelton, IV
2018/0110574 A1 4/2018 Shelton, IV et al.
2018/0110575 A1 4/2018 Shelton, IV et al.
2018/0114591 A1 4/2018 Pribanic et al.
2018/0116658 A1 5/2018 Aronhalt, IV et al.
2018/0116662 A1 5/2018 Shelton, IV et al.
2018/0125481 A1 5/2018 Yates et al.
2018/0125487 A1 5/2018 Beardsley
2018/0125488 A1 5/2018 Morgan et al.
2018/0125489 A1 5/2018 Leimbach et al.
2018/0125590 A1 5/2018 Giordano et al.
2018/0125594 A1 5/2018 Beardsley
2018/0126504 A1 5/2018 Shelton, IV et al.
2018/0132845 A1 5/2018 Schmid et al.
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0140299 A1 5/2018 Weaner et al.
2018/0146960 A1 5/2018 Shelton, IV et al.
2018/0150153 A1 5/2018 Yoon et al.
2018/0153542 A1 6/2018 Shelton, IV et al.
2018/0161034 A1 6/2018 Scheib et al.
2018/0168575 A1 6/2018 Simms et al.
2018/0168577 A1 6/2018 Aronhalt et al.
2018/0168578 A1 6/2018 Aronhalt et al.
2018/0168579 A1 6/2018 Aronhalt et al.
2018/0168584 A1 6/2018 Harris et al.
2018/0168586 A1 6/2018 Shelton, IV et al.
2018/0168589 A1 6/2018 Swayze et al.
2018/0168590 A1 6/2018 Overmyer et al.
2018/0168592 A1 6/2018 Overmyer et al.

(56) References Cited

U.S. PATENT DOCUMENTS

2018/0168593 A1 6/2018 Overmyer et al.
2018/0168597 A1 6/2018 Fanelli et al.
2018/0168598 A1 6/2018 Shelton, IV et al.
2018/0168601 A1 6/2018 Bakos et al.
2018/0168603 A1 6/2018 Morgan et al.
2018/0168605 A1 6/2018 Baber et al.
2018/0168607 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168614 A1 6/2018 Shelton, IV et al.
2018/0168615 A1 6/2018 Shelton, IV et al.
2018/0168617 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168627 A1 6/2018 Weaner et al.
2018/0168628 A1 6/2018 Hunter et al.
2018/0168629 A1 6/2018 Shelton, IV et al.
2018/0168632 A1 6/2018 Harris et al.
2018/0168633 A1 6/2018 Shelton, IV et al.
2018/0168639 A1 6/2018 Shelton, IV et al.
2018/0168646 A1 6/2018 Shelton, IV et al.
2018/0168647 A1 6/2018 Shelton, IV et al.
2018/0168648 A1 6/2018 Shelton, IV et al.
2018/0168649 A1 6/2018 Shelton, IV et al.
2018/0168650 A1 6/2018 Shelton, IV et al.
2018/0168651 A1 6/2018 Shelton, IV et al.
2018/0168715 A1 6/2018 Strobl
2018/0206843 A1 7/2018 Yates et al.
2018/0214147 A1 8/2018 Merchant et al.
2018/0221050 A1 8/2018 Kostrzewski et al.
2018/0228490 A1 8/2018 Richard et al.
2018/0242962 A1 8/2018 Walen et al.
2018/0250001 A1 9/2018 Aronhalt et al.
2018/0250086 A1 9/2018 Grubbs
2018/0271520 A1 9/2018 Shelton, IV et al.
2018/0271604 A1 9/2018 Grout et al.
2018/0273597 A1 9/2018 Stimson
2018/0289369 A1 10/2018 Shelton, IV et al.
2018/0289371 A1 10/2018 Wang et al.
2018/0296211 A1 10/2018 Timm et al.
2018/0296216 A1 10/2018 Shelton, IV et al.
2018/0296217 A1 10/2018 Moore et al.
2018/0303482 A1 10/2018 Shelton, IV et al.
2018/0310935 A1 11/2018 Wixey
2018/0317919 A1 11/2018 Shelton, IV et al.
2018/0333155 A1 11/2018 Hall et al.
2018/0333169 A1 11/2018 Leimbach et al.
2018/0344319 A1 12/2018 Shelton, IV et al.
2018/0353170 A1 12/2018 Overmyer et al.
2018/0353176 A1 12/2018 Shelton, IV et al.
2018/0353177 A1 12/2018 Shelton, IV et al.
2018/0353178 A1 12/2018 Shelton, IV et al.
2018/0353179 A1 12/2018 Shelton, IV et al.
2018/0360443 A1 12/2018 Shelton, IV et al.
2018/0360445 A1 12/2018 Shelton, IV et al.
2018/0360446 A1 12/2018 Shelton, IV et al.
2018/0360449 A1 12/2018 Shelton, IV et al.
2018/0360452 A1 12/2018 Shelton, IV et al.
2018/0360454 A1 12/2018 Shelton, IV et al.
2018/0360455 A1 12/2018 Shelton, IV et al.
2018/0360456 A1 12/2018 Shelton, IV et al.
2018/0360471 A1 12/2018 Parfett et al.
2018/0360472 A1 12/2018 Harris et al.
2018/0360473 A1 12/2018 Shelton, IV et al.
2018/0360549 A1 12/2018 Hares et al.
2018/0368833 A1 12/2018 Shelton, IV et al.
2018/0368837 A1 12/2018 Morgan et al.
2018/0368838 A1 12/2018 Shelton, IV et al.
2018/0368839 A1 12/2018 Shelton, IV et al.
2018/0368841 A1 12/2018 Shelton, IV et al.
2018/0368842 A1 12/2018 Shelton, IV et al.
2018/0368843 A1 12/2018 Shelton, IV et al.
2018/0368844 A1 12/2018 Bakos et al.
2018/0368845 A1 12/2018 Bakos et al.
2018/0368846 A1 12/2018 Shelton, IV et al.
2019/0000446 A1 1/2019 Shelton, IV et al.
2019/0000448 A1 1/2019 Shelton, IV et al.
2019/0000450 A1 1/2019 Shelton, IV et al.
2019/0000454 A1 1/2019 Swayze et al.
2019/0000457 A1 1/2019 Shelton, IV et al.
2019/0000459 A1 1/2019 Shelton, IV et al.
2019/0000461 A1 1/2019 Shelton, IV et al.
2019/0000462 A1 1/2019 Shelton, IV et al.
2019/0000466 A1 1/2019 Shelton, IV et al.
2019/0000467 A1 1/2019 Shelton, IV et al.
2019/0000468 A1 1/2019 Adams et al.
2019/0000469 A1 1/2019 Shelton, IV et al.
2019/0000470 A1 1/2019 Yates et al.
2019/0000471 A1 1/2019 Shelton, IV et al.
2019/0000472 A1 1/2019 Shelton, IV et al.
2019/0000474 A1 1/2019 Shelton, IV et al.
2019/0000475 A1 1/2019 Shelton, IV et al.
2019/0000476 A1 1/2019 Shelton, IV et al.
2019/0000477 A1 1/2019 Shelton, IV et al.
2019/0000478 A1 1/2019 Messerly et al.
2019/0000479 A1 1/2019 Harris et al.
2019/0000481 A1 1/2019 Harris et al.
2019/0000525 A1 1/2019 Messerly et al.
2019/0000530 A1 1/2019 Yates et al.
2019/0000531 A1 1/2019 Messerly et al.
2019/0000534 A1 1/2019 Messerly et al.
2019/0000538 A1 1/2019 Widenhouse et al.
2019/0000565 A1 1/2019 Shelton, IV et al.
2019/0008511 A1 1/2019 Kerr et al.
2019/0015096 A1 1/2019 Shelton, IV et al.
2019/0015102 A1 1/2019 Baber et al.
2019/0015165 A1 1/2019 Giordano et al.
2019/0029675 A1 1/2019 Yates et al.
2019/0029676 A1 1/2019 Yates et al.
2019/0029681 A1 1/2019 Swayze et al.
2019/0029682 A1 1/2019 Huitema et al.
2019/0029701 A1 1/2019 Shelton, IV et al.
2019/0033955 A1 1/2019 Leimbach et al.
2019/0038279 A1 2/2019 Shelton, IV et al.
2019/0038281 A1 2/2019 Shelton, IV et al.
2019/0038282 A1 2/2019 Shelton, IV et al.
2019/0038283 A1 2/2019 Shelton, IV et al.
2019/0038292 A1 2/2019 Zhang
2019/0038371 A1 2/2019 Wixey et al.
2019/0046181 A1 2/2019 McCuen
2019/0046187 A1 2/2019 Yates et al.
2019/0059886 A1 2/2019 Shelton, IV et al.
2019/0076143 A1 3/2019 Smith
2019/0090870 A1 3/2019 Shelton, IV et al.
2019/0090871 A1 3/2019 Shelton, IV et al.
2019/0091183 A1 3/2019 Tomat et al.
2019/0099177 A1 4/2019 Yates et al.
2019/0099179 A1 4/2019 Leimbach et al.
2019/0099181 A1 4/2019 Shelton, IV et al.
2019/0099182 A1 4/2019 Bakos et al.
2019/0099183 A1 4/2019 Leimbach et al.
2019/0099184 A1 4/2019 Setser et al.
2019/0099229 A1 4/2019 Spivey et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105038 A1 4/2019 Schmid et al.
2019/0105039 A1 4/2019 Morgan et al.
2019/0105043 A1 4/2019 Jaworek et al.
2019/0105044 A1 4/2019 Shelton, IV et al.
2019/0105049 A1 4/2019 Moore et al.
2019/0110791 A1 4/2019 Shelton, IV et al.
2019/0110792 A1 4/2019 Shelton, IV et al.
2019/0110793 A1 4/2019 Parihar et al.
2019/0117216 A1 4/2019 Overmyer et al.
2019/0117217 A1 4/2019 Overmyer et al.
2019/0117222 A1 4/2019 Shelton, IV et al.
2019/0117224 A1 4/2019 Setser et al.
2019/0117225 A1 4/2019 Moore et al.
2019/0125320 A1 5/2019 Shelton, IV et al.

(56) References Cited

U.S. PATENT DOCUMENTS

2019/0125321 A1 5/2019 Shelton, IV et al.
2019/0125324 A1 5/2019 Scheib et al.
2019/0125335 A1 5/2019 Shelton, IV et al.
2019/0125336 A1 5/2019 Deck et al.
2019/0125337 A1 5/2019 Shelton, IV et al.
2019/0125338 A1 5/2019 Shelton, IV et al.
2019/0125339 A1 5/2019 Shelton, IV et al.
2019/0125343 A1 5/2019 Wise et al.
2019/0125344 A1 5/2019 DiNardo et al.
2019/0125345 A1 5/2019 Baber et al.
2019/0125347 A1 5/2019 Stokes et al.
2019/0125348 A1 5/2019 Shelton, IV et al.
2019/0125352 A1 5/2019 Shelton, IV et al.
2019/0125353 A1 5/2019 Shelton, IV et al.
2019/0125354 A1 5/2019 Deck et al.
2019/0125355 A1 5/2019 Shelton, IV et al.
2019/0125356 A1 5/2019 Shelton, IV et al.
2019/0125357 A1 5/2019 Shelton, IV et al.
2019/0125358 A1 5/2019 Shelton, IV et al.
2019/0125359 A1 5/2019 Shelton, IV et al.
2019/0125360 A1 5/2019 Shelton, IV et al.
2019/0125361 A1 5/2019 Shelton, IV et al.
2019/0125377 A1 5/2019 Shelton, IV
2019/0125378 A1 5/2019 Shelton, IV et al.
2019/0125379 A1 5/2019 Shelton, IV et al.
2019/0125380 A1 5/2019 Hunter et al.
2019/0125384 A1 5/2019 Scheib et al.
2019/0125386 A1 5/2019 Shelton, IV et al.
2019/0125387 A1 5/2019 Parihar et al.
2019/0125388 A1 5/2019 Shelton, IV et al.
2019/0125389 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125455 A1 5/2019 Shelton, IV et al.
2019/0125456 A1 5/2019 Shelton, IV et al.
2019/0125457 A1 5/2019 Parihar et al.
2019/0125458 A1 5/2019 Shelton, IV et al.
2019/0125459 A1 5/2019 Shelton, IV et al.
2019/0125476 A1 5/2019 Shelton, IV et al.
2019/0133422 A1 5/2019 Nakamura
2019/0133585 A1 5/2019 Smith et al.
2019/0142421 A1 5/2019 Shelton, IV
2019/0142449 A1 5/2019 Shelton, IV et al.
2019/0150925 A1 5/2019 Marczyk et al.
2019/0159778 A1 5/2019 Shelton, IV et al.
2019/0183490 A1 6/2019 Shelton, IV et al.
2019/0183491 A1 6/2019 Shelton, IV et al.
2019/0183493 A1 6/2019 Shelton, IV et al.
2019/0183494 A1 6/2019 Shelton, IV et al.
2019/0183496 A1 6/2019 Shelton, IV et al.
2019/0183498 A1 6/2019 Shelton, IV et al.
2019/0183499 A1 6/2019 Shelton, IV et al.
2019/0183501 A1 6/2019 Shelton, IV et al.
2019/0183502 A1 6/2019 Shelton, IV et al.
2019/0183505 A1 6/2019 Vendely et al.
2019/0183592 A1 6/2019 Shelton, IV et al.
2019/0183594 A1 6/2019 Shelton, IV et al.
2019/0192138 A1 6/2019 Shelton, IV et al.
2019/0192141 A1 6/2019 Shelton, IV et al.
2019/0192144 A1 6/2019 Parfett et al.
2019/0192146 A1 6/2019 Widenhouse et al.
2019/0192147 A1 6/2019 Shelton, IV et al.
2019/0192148 A1 6/2019 Shelton, IV et al.
2019/0192149 A1 6/2019 Shelton, IV et al.
2019/0192150 A1 6/2019 Widenhouse et al.
2019/0192151 A1 6/2019 Shelton, IV et al.
2019/0192152 A1 6/2019 Morgan et al.
2019/0192153 A1 6/2019 Shelton, IV et al.
2019/0192154 A1 6/2019 Shelton, IV et al.
2019/0192155 A1 6/2019 Shelton, IV et al.
2019/0192156 A1 6/2019 Simms et al.
2019/0192157 A1 6/2019 Scott et al.
2019/0192158 A1 6/2019 Scott et al.
2019/0192159 A1 6/2019 Simms et al.
2019/0192227 A1 6/2019 Shelton, IV et al.
2019/0192235 A1 6/2019 Harris et al.
2019/0192236 A1 6/2019 Shelton, IV et al.
2019/0200844 A1 7/2019 Shelton, IV et al.
2019/0200863 A1 7/2019 Shelton, IV et al.
2019/0200895 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200991 A1 7/2019 Moore et al.
2019/0200992 A1 7/2019 Moore et al.
2019/0200993 A1 7/2019 Moore et al.
2019/0200994 A1 7/2019 Moore et al.
2019/0200998 A1 7/2019 Shelton, IV et al.
2019/0201023 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201028 A1 7/2019 Shelton, IV et al.
2019/0201029 A1 7/2019 Shelton, IV et al.
2019/0201030 A1 7/2019 Shelton, IV et al.
2019/0201033 A1 7/2019 Yates et al.
2019/0201034 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201104 A1 7/2019 Shelton, IV et al.
2019/0201105 A1 7/2019 Shelton, IV et al.
2019/0201111 A1 7/2019 Shelton, IV et al.
2019/0201112 A1 7/2019 Wiener et al.
2019/0201113 A1 7/2019 Shelton, IV et al.
2019/0201114 A1 7/2019 Shelton, IV et al.
2019/0201115 A1 7/2019 Shelton, IV et al.
2019/0201116 A1 7/2019 Shelton, IV et al.
2019/0201118 A1 7/2019 Shelton, IV et al.
2019/0201120 A1 7/2019 Shelton, IV et al.
2019/0201135 A1 7/2019 Shelton, IV et al.
2019/0201136 A1 7/2019 Shelton, IV et al.
2019/0201137 A1 7/2019 Shelton, IV et al.
2019/0201138 A1 7/2019 Yates et al.
2019/0201139 A1 7/2019 Shelton, IV et al.
2019/0201140 A1 7/2019 Yates et al.
2019/0201141 A1 7/2019 Shelton, IV et al.
2019/0201142 A1 7/2019 Shelton, IV et al.
2019/0201143 A1 7/2019 Shelton, IV et al.
2019/0201145 A1 7/2019 Shelton, IV et al.
2019/0201594 A1 7/2019 Shelton, IV et al.
2019/0205001 A1 7/2019 Messerly et al.
2019/0205566 A1 7/2019 Shelton, IV et al.
2019/0205567 A1 7/2019 Shelton, IV et al.
2019/0206003 A1 7/2019 Harris et al.
2019/0206004 A1 7/2019 Shelton, IV et al.
2019/0206050 A1 7/2019 Yates et al.
2019/0206551 A1 7/2019 Yates et al.
2019/0206555 A1 7/2019 Morgan et al.
2019/0206561 A1 7/2019 Shelton, IV et al.
2019/0206562 A1 7/2019 Shelton, IV et al.
2019/0206563 A1 7/2019 Shelton, IV et al.
2019/0206564 A1 7/2019 Shelton, IV et al.
2019/0206565 A1 7/2019 Shelton, IV
2019/0206569 A1 7/2019 Shelton, IV et al.
2019/0208641 A1 7/2019 Yates et al.
2019/0209164 A1 7/2019 Timm et al.
2019/0209165 A1 7/2019 Timm et al.
2019/0209171 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0216558 A1 7/2019 Giordano et al.
2019/0223865 A1 7/2019 Shelton, IV et al.
2019/0223871 A1 7/2019 Moore et al.
2019/0261984 A1 8/2019 Nelson et al.
2019/0261991 A1 8/2019 Beckman et al.
2019/0267403 A1 8/2019 Li et al.

(56) References Cited

U.S. PATENT DOCUMENTS

2019/0269400 A1 9/2019 Mandakolathur Vasudevan et al.
2019/0269402 A1 9/2019 Murray et al.
2019/0269403 A1 9/2019 Baxter, III et al.
2019/0269407 A1 9/2019 Swensgard et al.
2019/0269428 A1 9/2019 Allen et al.
2019/0274677 A1 9/2019 Shelton, IV
2019/0274678 A1 9/2019 Shelton, IV
2019/0274679 A1 9/2019 Shelton, IV
2019/0274680 A1 9/2019 Shelton, IV
2019/0274685 A1 9/2019 Olson et al.
2019/0290263 A1 9/2019 Morgan et al.
2019/0290264 A1 9/2019 Morgan et al.
2019/0290265 A1 9/2019 Shelton, IV et al.
2019/0290267 A1 9/2019 Baxter, III et al.
2019/0290274 A1 9/2019 Shelton, IV
2019/0290281 A1 9/2019 Aronhalt et al.
2019/0290297 A1 9/2019 Haider et al.
2019/0298340 A1 10/2019 Shelton, IV et al.
2019/0298341 A1 10/2019 Shelton, IV et al.
2019/0298342 A1 10/2019 Shelton, IV et al.
2019/0298343 A1 10/2019 Shelton, IV et al.
2019/0298346 A1 10/2019 Shelton, IV et al.
2019/0298347 A1 10/2019 Shelton, IV et al.
2019/0298348 A1 10/2019 Harris et al.
2019/0298350 A1 10/2019 Shelton, IV et al.
2019/0298352 A1 10/2019 Shelton, IV et al.
2019/0298353 A1 10/2019 Shelton, IV et al.
2019/0298354 A1 10/2019 Shelton, IV et al.
2019/0298355 A1 10/2019 Shelton, IV et al.
2019/0298356 A1 10/2019 Shelton, IV et al.
2019/0298357 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0307452 A1 10/2019 Shelton, IV et al.
2019/0307453 A1 10/2019 Shelton, IV et al.
2019/0307454 A1 10/2019 Shelton, IV et al.
2019/0307455 A1 10/2019 Shelton, IV et al.
2019/0307456 A1 10/2019 Shelton, IV et al.
2019/0307476 A1 10/2019 Shelton, IV et al.
2019/0307477 A1 10/2019 Shelton, IV et al.
2019/0307478 A1 10/2019 Shelton, IV et al.
2019/0307479 A1 10/2019 Shelton, IV et al.
2019/0314016 A1 10/2019 Huitema et al.
2019/0314017 A1 10/2019 Huitema et al.
2019/0314018 A1 10/2019 Huitema et al.
2019/0321039 A1 10/2019 Harris et al.
2019/0321040 A1 10/2019 Shelton, IV
2019/0321041 A1 10/2019 Shelton, IV
2019/0328386 A1 10/2019 Harris et al.
2019/0328387 A1 10/2019 Overmyer et al.
2019/0328390 A1 10/2019 Harris et al.
2019/0336128 A1 11/2019 Harris et al.
2019/0343514 A1 11/2019 Shelton, IV et al.
2019/0343515 A1 11/2019 Morgan et al.
2019/0343518 A1 11/2019 Shelton, IV
2019/0343525 A1 11/2019 Shelton, IV et al.
2019/0350581 A1 11/2019 Baxter, III et al.
2019/0350582 A1 11/2019 Shelton, IV et al.
2019/0357909 A1 11/2019 Huitema et al.
2019/0365384 A1 12/2019 Baxter, III et al.
2019/0374224 A1 12/2019 Huitema et al.
2020/0000461 A1 1/2020 Yates et al.
2020/0000468 A1 1/2020 Shelton, IV et al.
2020/0000469 A1 1/2020 Shelton, IV et al.
2020/0000471 A1 1/2020 Shelton, IV et al.
2020/0000531 A1 1/2020 Giordano et al.
2020/0008800 A1 1/2020 Shelton, IV et al.
2020/0008802 A1 1/2020 Aronhalt et al.
2020/0008809 A1 1/2020 Shelton, IV et al.
2020/0015815 A1 1/2020 Harris et al.
2020/0015819 A1 1/2020 Shelton, IV et al.
2020/0022702 A1 1/2020 Shelton, IV et al.
2020/0029964 A1 1/2020 Overmyer et al.
2020/0030050 A1 1/2020 Shelton, IV et al.
2020/0038016 A1 2/2020 Shelton, IV et al.
2020/0038018 A1 2/2020 Shelton, IV et al.
2020/0038020 A1 2/2020 Yates et al.
2020/0046348 A1 2/2020 Shelton, IV et al.
2020/0046893 A1 2/2020 Shelton, IV et al.
2020/0054320 A1 2/2020 Harris et al.
2020/0054321 A1 2/2020 Harris et al.
2020/0054322 A1 2/2020 Harris et al.
2020/0054323 A1 2/2020 Harris et al.
2020/0054324 A1 2/2020 Shelton, IV et al.
2020/0054326 A1 2/2020 Harris et al.
2020/0054327 A1 2/2020 Harris et al.
2020/0054328 A1 2/2020 Harris et al.
2020/0054329 A1 2/2020 Shelton, IV et al.
2020/0054330 A1 2/2020 Harris et al.
2020/0054331 A1 2/2020 Harris et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060680 A1 2/2020 Shelton, IV et al.
2020/0060681 A1 2/2020 Shelton, IV et al.
2020/0060713 A1 2/2020 Leimbach et al.
2020/0077994 A1 3/2020 Shelton, IV et al.
2020/0078015 A1 3/2020 Miller et al.
2020/0078016 A1 3/2020 Swayze et al.
2020/0085427 A1 3/2020 Giordano et al.
2020/0085431 A1 3/2020 Swayze et al.
2020/0085435 A1 3/2020 Shelton, IV et al.
2020/0085436 A1 3/2020 Beckman et al.
2020/0085518 A1 3/2020 Giordano et al.
2020/0093484 A1 3/2020 Shelton, IV et al.
2020/0093485 A1 3/2020 Shelton, IV et al.
2020/0093487 A1 3/2020 Baber et al.
2020/0093488 A1 3/2020 Baber et al.
2020/0093506 A1 3/2020 Leimbach et al.
2020/0093550 A1 3/2020 Spivey et al.
2020/0100699 A1 4/2020 Shelton, IV et al.
2020/0100783 A1 4/2020 Yates et al.
2020/0100787 A1 4/2020 Shelton, IV et al.
2020/0107829 A1 4/2020 Shelton, IV et al.
2020/0138434 A1 5/2020 Miller et al.
2020/0138435 A1 5/2020 Shelton, IV et al.
2020/0138436 A1 5/2020 Yates et al.
2020/0138437 A1 5/2020 Vendely et al.
2020/0138534 A1 5/2020 Garcia Kilroy et al.
2020/0146678 A1 5/2020 Leimbach et al.
2020/0146741 A1 5/2020 Long et al.
2020/0155151 A1 5/2020 Overmyer et al.
2020/0155155 A1 5/2020 Shelton, IV et al.
2020/0178958 A1 6/2020 Overmyer et al.
2020/0178960 A1 6/2020 Overmyer et al.
2020/0187943 A1 6/2020 Shelton, IV et al.
2020/0214706 A1 7/2020 Vendely et al.
2020/0214731 A1 7/2020 Shelton, IV et al.
2020/0222047 A1 7/2020 Shelton, IV et al.
2020/0229812 A1 7/2020 Parihar et al.
2020/0229816 A1 7/2020 Bakos et al.
2020/0237371 A1 7/2020 Huitema et al.
2020/0246001 A1 8/2020 Ming et al.
2020/0253605 A1 8/2020 Swayze et al.
2020/0261106 A1 8/2020 Hess et al.
2020/0268377 A1 8/2020 Schmid et al.
2020/0268394 A1 8/2020 Parfett et al.
2020/0275926 A1 9/2020 Shelton, IV et al.
2020/0275927 A1 9/2020 Shelton, IV et al.
2020/0275928 A1 9/2020 Shelton, IV et al.
2020/0275930 A1 9/2020 Harris et al.
2020/0281585 A1 9/2020 Timm et al.
2020/0281587 A1 9/2020 Schmid et al.
2020/0281590 A1 9/2020 Shelton, IV et al.
2020/0289112 A1 9/2020 Whitfield et al.
2020/0297340 A1 9/2020 Hess et al.
2020/0297341 A1 9/2020 Yates et al.
2020/0297346 A1 9/2020 Shelton, IV et al.
2020/0297438 A1 9/2020 Shelton, IV et al.
2020/0305862 A1 10/2020 Yates et al.
2020/0305863 A1 10/2020 Yates et al.
2020/0305864 A1 10/2020 Yates et al.

(56) References Cited

U.S. PATENT DOCUMENTS

| | | | |
|---|---|---|---|
| 2020/0305865 | A1 | 10/2020 | Shelton, IV |
| 2020/0305868 | A1 | 10/2020 | Shelton, IV |
| 2020/0305869 | A1 | 10/2020 | Shelton, IV |
| 2020/0305870 | A1 | 10/2020 | Shelton, IV |
| 2020/0305871 | A1 | 10/2020 | Shelton, IV et al. |
| 2020/0305874 | A1 | 10/2020 | Huitema et al. |
| 2020/0315612 | A1 | 10/2020 | Shelton, IV et al. |
| 2020/0315616 | A1 | 10/2020 | Yates et al. |
| 2020/0315625 | A1 | 10/2020 | Hall et al. |
| 2020/0315983 | A1 | 10/2020 | Widenhouse et al. |
| 2020/0323526 | A1 | 10/2020 | Huang et al. |
| 2020/0330092 | A1 | 10/2020 | Shelton, IV et al. |
| 2020/0330093 | A1 | 10/2020 | Shelton, IV et al. |
| 2020/0330094 | A1 | 10/2020 | Baxter, III et al. |
| 2020/0330096 | A1 | 10/2020 | Shelton, IV et al. |
| 2020/0337693 | A1 | 10/2020 | Shelton, IV et al. |
| 2020/0337702 | A1 | 10/2020 | Shelton, IV et al. |
| 2020/0337703 | A1 | 10/2020 | Shelton, IV et al. |
| 2020/0337791 | A1 | 10/2020 | Shelton, IV et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345354 | A1 | 11/2020 | Leimbach et al. |
| 2020/0345355 | A1 | 11/2020 | Baxter, III et al. |
| 2020/0345356 | A1 | 11/2020 | Leimbach et al. |
| 2020/0345357 | A1 | 11/2020 | Leimbach et al. |
| 2020/0345358 | A1 | 11/2020 | Jenkins |
| 2020/0345359 | A1 | 11/2020 | Baxter, III et al. |
| 2020/0345360 | A1 | 11/2020 | Leimbach et al. |
| 2020/0345446 | A1 | 11/2020 | Kimball et al. |
| 2020/0352562 | A1 | 11/2020 | Timm et al. |
| 2020/0367885 | A1 | 11/2020 | Yates et al. |
| 2020/0367886 | A1 | 11/2020 | Shelton, IV et al. |
| 2020/0375585 | A1 | 12/2020 | Swayze et al. |
| 2020/0375592 | A1 | 12/2020 | Hall et al. |
| 2020/0375593 | A1 | 12/2020 | Hunter et al. |
| 2020/0375597 | A1 | 12/2020 | Shelton, IV et al. |
| 2020/0390444 | A1 | 12/2020 | Harris et al. |
| 2020/0397433 | A1 | 12/2020 | Lytle, IV et al. |
| 2020/0397434 | A1 | 12/2020 | Overmyer et al. |
| 2020/0405290 | A1 | 12/2020 | Shelton, IV et al. |
| 2020/0405291 | A1 | 12/2020 | Shelton, IV et al. |
| 2020/0405292 | A1 | 12/2020 | Shelton, IV et al. |
| 2020/0405293 | A1 | 12/2020 | Shelton, IV et al. |
| 2020/0405294 | A1 | 12/2020 | Shelton, IV |
| 2020/0405295 | A1 | 12/2020 | Shelton, IV et al. |
| 2020/0405296 | A1 | 12/2020 | Shelton, IV et al. |
| 2020/0405297 | A1 | 12/2020 | Shelton, IV et al. |
| 2020/0405301 | A1 | 12/2020 | Shelton, IV et al. |
| 2020/0405302 | A1 | 12/2020 | Shelton, IV et al. |
| 2020/0405303 | A1 | 12/2020 | Shelton, IV |
| 2020/0405305 | A1 | 12/2020 | Shelton, IV et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405309 | A1 | 12/2020 | Shelton, IV et al. |
| 2020/0405311 | A1 | 12/2020 | Shelton, IV et al. |
| 2020/0405312 | A1 | 12/2020 | Shelton, IV et al. |
| 2020/0405313 | A1 | 12/2020 | Shelton, IV |
| 2020/0405314 | A1 | 12/2020 | Shelton, IV et al. |
| 2020/0405316 | A1 | 12/2020 | Shelton, IV et al. |
| 2020/0405341 | A1 | 12/2020 | Hess et al. |
| 2020/0405409 | A1 | 12/2020 | Shelton, IV et al. |
| 2020/0405410 | A1 | 12/2020 | Shelton, IV |
| 2020/0405436 | A1 | 12/2020 | Shelton, IV et al. |
| 2020/0405437 | A1 | 12/2020 | Shelton, IV et al. |
| 2020/0405438 | A1 | 12/2020 | Shelton, IV et al. |
| 2020/0405439 | A1 | 12/2020 | Shelton, IV et al. |
| 2020/0405440 | A1 | 12/2020 | Shelton, IV et al. |
| 2020/0405441 | A1 | 12/2020 | Shelton, IV et al. |
| 2020/0410177 | A1 | 12/2020 | Shelton, IV |
| 2020/0410180 | A1 | 12/2020 | Shelton, IV et al. |
| 2021/0000466 | A1 | 1/2021 | Leimbach et al. |
| 2021/0000467 | A1 | 1/2021 | Shelton, IV et al. |
| 2021/0000470 | A1 | 1/2021 | Leimbach et al. |
| 2021/0015480 | A1 | 1/2021 | Shelton, IV et al. |
| 2021/0022741 | A1 | 1/2021 | Baxter, III et al. |
| 2021/0030416 | A1 | 2/2021 | Shelton, IV et al. |
| 2021/0045742 | A1 | 2/2021 | Shelton, IV et al. |
| 2021/0052271 | A1 | 2/2021 | Harris et al. |
| 2021/0059661 | A1 | 3/2021 | Schmid et al. |
| 2021/0059662 | A1 | 3/2021 | Shelton, IV |
| 2021/0059666 | A1 | 3/2021 | Schmid et al. |
| 2021/0059669 | A1 | 3/2021 | Yates et al. |
| 2021/0059670 | A1 | 3/2021 | Overmyer et al. |
| 2021/0059671 | A1 | 3/2021 | Shelton, IV et al. |
| 2021/0059672 | A1 | 3/2021 | Giordano et al. |
| 2021/0059673 | A1 | 3/2021 | Shelton, IV et al. |
| 2021/0068817 | A1 | 3/2021 | Shelton, IV et al. |
| 2021/0068818 | A1 | 3/2021 | Overmyer et al. |
| 2021/0068820 | A1 | 3/2021 | Parihar et al. |
| 2021/0068830 | A1 | 3/2021 | Baber et al. |
| 2021/0068831 | A1 | 3/2021 | Baber et al. |
| 2021/0068832 | A1 | 3/2021 | Yates et al. |
| 2021/0068835 | A1 | 3/2021 | Shelton, IV et al. |
| 2021/0077092 | A1 | 3/2021 | Parihar et al. |
| 2021/0077099 | A1 | 3/2021 | Shelton, IV et al. |
| 2021/0077100 | A1 | 3/2021 | Shelton, IV et al. |
| 2021/0085313 | A1 | 3/2021 | Morgan et al. |
| 2021/0085314 | A1 | 3/2021 | Schmid et al. |
| 2021/0085315 | A1 | 3/2021 | Aronhalt et al. |
| 2021/0085316 | A1 | 3/2021 | Harris et al. |
| 2021/0085317 | A1 | 3/2021 | Miller et al. |
| 2021/0085318 | A1 | 3/2021 | Swayze et al. |
| 2021/0085319 | A1 | 3/2021 | Swayze et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0085326 | A1 | 3/2021 | Vendely et al. |
| 2021/0100541 | A1 | 4/2021 | Shelton, IV et al. |
| 2021/0100550 | A1 | 4/2021 | Shelton, IV et al. |

FOREIGN PATENT DOCUMENTS

| | | | |
|---|---|---|---|
| AU | 2012200594 | A1 | 2/2012 |
| AU | 2012203035 | A1 | 6/2012 |
| AU | 2011218702 | B2 | 6/2013 |
| AU | 2012200178 | B2 | 7/2013 |
| BR | 112013027777 | A2 | 1/2017 |
| CA | 1015829 | A | 8/1977 |
| CA | 1125615 | A | 6/1982 |
| CA | 2458946 | A1 | 3/2003 |
| CA | 2477181 | A1 | 4/2004 |
| CA | 2512960 | A1 | 1/2006 |
| CA | 2514274 | A1 | 1/2006 |
| CA | 2520413 | A1 | 3/2007 |
| CA | 2725181 | A1 | 11/2007 |
| CA | 2851239 | A1 | 11/2007 |
| CA | 2639177 | A1 | 2/2009 |
| CA | 2664874 | A1 | 11/2009 |
| CA | 2813230 | A1 | 4/2012 |
| CA | 2576347 | C | 8/2015 |
| CA | 2940510 | A1 | 8/2015 |
| CA | 2698728 | C | 8/2016 |
| CN | 86100996 | A | 9/1986 |
| CN | 1163558 | A | 10/1997 |
| CN | 2488482 | Y | 5/2002 |
| CN | 1424891 | A | 6/2003 |
| CN | 1523725 | A | 8/2004 |
| CN | 1545154 | A | 11/2004 |
| CN | 1634601 | A | 7/2005 |
| CN | 1636525 | A | 7/2005 |
| CN | 1636526 | A | 7/2005 |
| CN | 2716900 | Y | 8/2005 |
| CN | 2738962 | Y | 11/2005 |
| CN | 1726874 | A | 2/2006 |
| CN | 1726878 | A | 2/2006 |
| CN | 1777406 | A | 5/2006 |
| CN | 2796654 | Y | 7/2006 |
| CN | 1868411 | A | 11/2006 |
| CN | 1915180 | A | 2/2007 |
| CN | 2868212 | Y | 2/2007 |
| CN | 1960679 | A | 5/2007 |

(56) References Cited

FOREIGN PATENT DOCUMENTS

| | | | |
|---|---|---|---|
| CN | 101011286 | A | 8/2007 |
| CN | 200942099 | Y | 9/2007 |
| CN | 101073509 | A | 11/2007 |
| CN | 200984209 | Y | 12/2007 |
| CN | 200991269 | Y | 12/2007 |
| CN | 101095621 | A | 1/2008 |
| CN | 101111196 | A | 1/2008 |
| CN | 201001747 | Y | 1/2008 |
| CN | 101137402 | A | 3/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101224122 | A | 7/2008 |
| CN | 101224124 | A | 7/2008 |
| CN | 101254126 | A | 9/2008 |
| CN | 101378791 | A | 3/2009 |
| CN | 101507620 | A | 8/2009 |
| CN | 101507622 | A | 8/2009 |
| CN | 101507623 | A | 8/2009 |
| CN | 101507625 | A | 8/2009 |
| CN | 101507628 | A | 8/2009 |
| CN | 101507635 | A | 8/2009 |
| CN | 101522120 | A | 9/2009 |
| CN | 101534724 | A | 9/2009 |
| CN | 101541251 | A | 9/2009 |
| CN | 101626731 | A | 1/2010 |
| CN | 101669833 | A | 3/2010 |
| CN | 101675898 | A | 3/2010 |
| CN | 101683280 | A | 3/2010 |
| CN | 101721236 | A | 6/2010 |
| CN | 101801284 | A | 8/2010 |
| CN | 101828940 | A | 9/2010 |
| CN | 101868203 | A | 10/2010 |
| CN | 101873834 | A | 10/2010 |
| CN | 101912285 | A | 12/2010 |
| CN | 101028205 | B | 1/2011 |
| CN | 101933824 | A | 1/2011 |
| CN | 201719298 | U | 1/2011 |
| CN | 101934098 | A | 5/2011 |
| CN | 102038531 | A | 5/2011 |
| CN | 102038532 | A | 5/2011 |
| CN | 101534722 | B | 6/2011 |
| CN | 201879759 | U | 6/2011 |
| CN | 101361666 | B | 8/2011 |
| CN | 201949071 | U | 8/2011 |
| CN | 101224119 | B | 9/2011 |
| CN | 101336835 | B | 9/2011 |
| CN | 102188270 | A | 9/2011 |
| CN | 102217961 | A | 10/2011 |
| CN | 102217963 | A | 10/2011 |
| CN | 102243850 | A | 11/2011 |
| CN | 102247183 | A | 11/2011 |
| CN | 101779977 | B | 12/2011 |
| CN | 101534723 | B | 1/2012 |
| CN | 101310680 | B | 4/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 101317782 | B | 10/2012 |
| CN | 202489990 | U | 10/2012 |
| CN | 101507639 | B | 11/2012 |
| CN | 102228387 | B | 11/2012 |
| CN | 102835977 | A | 12/2012 |
| CN | 202568350 | U | 12/2012 |
| CN | 101507633 | B | 2/2013 |
| CN | 101023879 | B | 3/2013 |
| CN | 101507624 | B | 3/2013 |
| CN | 103037781 | A | 4/2013 |
| CN | 103083053 | A | 5/2013 |
| CN | 101327137 | B | 6/2013 |
| CN | 101401736 | B | 6/2013 |
| CN | 101332110 | B | 7/2013 |
| CN | 103391037 | A | 11/2013 |
| CN | 203328751 | U | 12/2013 |
| CN | 101683281 | B | 1/2014 |
| CN | 103505264 | A | 1/2014 |
| CN | 103584893 | A | 2/2014 |
| CN | 103648408 | A | 3/2014 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 203815517 | U | 9/2014 |
| CN | 102783741 | B | 10/2014 |
| CN | 102973300 | B | 10/2014 |
| CN | 102793571 | B | 12/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102166129 | B | 3/2015 |
| CN | 102469995 | B | 3/2015 |
| CN | 104422849 | A | 3/2015 |
| CN | 102113902 | A | 4/2015 |
| CN | 104586463 | A | 5/2015 |
| CN | 204520822 | U | 8/2015 |
| CN | 204636451 | U | 9/2015 |
| CN | 102247177 | B | 2/2016 |
| CN | 103860225 | B | 3/2016 |
| CN | 103750872 | B | 5/2016 |
| CN | 103648410 | B | 10/2016 |
| CN | 106344091 | A | 1/2017 |
| CN | 104349800 | B | 11/2017 |
| CN | 107635483 | A | 1/2018 |
| DE | 273689 | C | 5/1914 |
| DE | 1775926 | A | 1/1972 |
| DE | 3036217 | A1 | 4/1982 |
| DE | 3212828 | A1 | 11/1982 |
| DE | 3210466 | A1 | 9/1983 |
| DE | 3709067 | A1 | 9/1988 |
| DE | 4228909 | A1 | 3/1994 |
| DE | 9412228 | U1 | 9/1994 |
| DE | 19509116 | A1 | 9/1996 |
| DE | 19534043 | A1 | 3/1997 |
| DE | 19707373 | C1 | 2/1998 |
| DE | 19851291 | A1 | 1/2000 |
| DE | 19924311 | A1 | 11/2000 |
| DE | 69328576 | T2 | 1/2001 |
| DE | 20016423 | U1 | 2/2001 |
| DE | 10052679 | A1 | 5/2001 |
| DE | 20112837 | U1 | 10/2001 |
| DE | 20121753 | U1 | 4/2003 |
| DE | 10314827 | B3 | 4/2004 |
| DE | 10314072 | A1 | 10/2004 |
| DE | 202004012389 | U1 | 11/2004 |
| DE | 102004014011 | A1 | 10/2005 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0070230 | B1 | 10/1985 |
| EP | 0156774 | A2 | 10/1985 |
| EP | 0072754 | B1 | 4/1986 |
| EP | 0033548 | B1 | 5/1986 |
| EP | 0077262 | B1 | 8/1986 |
| EP | 0189807 | A2 | 8/1986 |
| EP | 0212278 | A2 | 3/1987 |
| EP | 0129442 | B1 | 11/1987 |
| EP | 0255631 | A1 | 2/1988 |
| EP | 0276104 | A2 | 7/1988 |
| EP | 0379721 | B1 | 8/1990 |

(56) References Cited

FOREIGN PATENT DOCUMENTS

| | | | |
|---|---|---|---|
| EP | 0178940 | B1 | 1/1991 |
| EP | 0178941 | B1 | 1/1991 |
| EP | 0169044 | B1 | 6/1991 |
| EP | 0248844 | B1 | 1/1993 |
| EP | 0539762 | A1 | 5/1993 |
| EP | 0541950 | A1 | 5/1993 |
| EP | 0545029 | A1 | 6/1993 |
| EP | 0548998 | A1 | 6/1993 |
| EP | 0277959 | B1 | 10/1993 |
| EP | 0591946 | A1 | 10/1993 |
| EP | 0233940 | B1 | 11/1993 |
| EP | 0261230 | B1 | 11/1993 |
| EP | 0639349 | A2 | 2/1994 |
| EP | 0324636 | B1 | 3/1994 |
| EP | 0593920 | A1 | 4/1994 |
| EP | 0594148 | A1 | 4/1994 |
| EP | 0427949 | B1 | 6/1994 |
| EP | 0523174 | B1 | 6/1994 |
| EP | 0600182 | A2 | 6/1994 |
| EP | 0310431 | B1 | 11/1994 |
| EP | 0375302 | B1 | 11/1994 |
| EP | 0376562 | B1 | 11/1994 |
| EP | 0623311 | A2 | 11/1994 |
| EP | 0630612 | A1 | 12/1994 |
| EP | 0630614 | A1 | 12/1994 |
| EP | 0634144 | A1 | 1/1995 |
| EP | 0646356 | A2 | 4/1995 |
| EP | 0646357 | A1 | 4/1995 |
| EP | 0505036 | B1 | 5/1995 |
| EP | 0653189 | A2 | 5/1995 |
| EP | 0669104 | A1 | 8/1995 |
| EP | 0387980 | B1 | 10/1995 |
| EP | 0511470 | B1 | 10/1995 |
| EP | 0674876 | A2 | 10/1995 |
| EP | 0679367 | A2 | 11/1995 |
| EP | 0392547 | B1 | 12/1995 |
| EP | 0685204 | A1 | 12/1995 |
| EP | 0686374 | A2 | 12/1995 |
| EP | 0364216 | B1 | 1/1996 |
| EP | 0699418 | A1 | 3/1996 |
| EP | 0702937 | A1 | 3/1996 |
| EP | 0488768 | B1 | 4/1996 |
| EP | 0705571 | A1 | 4/1996 |
| EP | 0528478 | B1 | 5/1996 |
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0737446 | A1 | 10/1996 |
| EP | 0748614 | A1 | 12/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0621009 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0623312 | B1 | 9/1997 |
| EP | 0621006 | B1 | 10/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0869104 | A1 | 10/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0640317 | B1 | 9/1999 |
| EP | 0843906 | B1 | 3/2000 |
| EP | 0552050 | B1 | 5/2000 |
| EP | 0833592 | B1 | 5/2000 |
| EP | 0832605 | B1 | 6/2000 |
| EP | 0830094 | B1 | 9/2000 |
| EP | 1034747 | A1 | 9/2000 |
| EP | 1034748 | A1 | 9/2000 |
| EP | 0726632 | B1 | 10/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1058177 | A1 | 12/2000 |
| EP | EU-1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 0768840 | B1 | 12/2001 |
| EP | 0908152 | B1 | 1/2002 |
| EP | 0717959 | B1 | 2/2002 |
| EP | 0872213 | B1 | 5/2002 |
| EP | 0862386 | B1 | 6/2002 |
| EP | 1234587 | A1 | 8/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0717967 | B1 | 5/2003 |
| EP | 0869742 | B1 | 5/2003 |
| EP | 0829235 | B1 | 6/2003 |
| EP | 0887046 | B1 | 7/2003 |
| EP | 1323384 | A2 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1411626 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1453432 | A2 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1496805 | A2 | 1/2005 |
| EP | 1256318 | B1 | 2/2005 |

(56) References Cited

FOREIGN PATENT DOCUMENTS

| | | | |
|---|---|---|---|
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | EU-1558161 | A1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621143 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1676539 | A1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1723914 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1791473 | A2 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1980214 | A2 | 10/2008 |
| EP | 1759645 | B1 | 11/2008 |
| EP | 1987780 | A2 | 11/2008 |
| EP | 1990014 | A2 | 11/2008 |
| EP | 1992296 | A1 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 2025293 | A1 | 2/2009 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | B1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2100562 | A2 | 9/2009 |
| EP | 2110082 | A1 | 10/2009 |
| EP | 2110084 | A2 | 10/2009 |

(56) References Cited

FOREIGN PATENT DOCUMENTS

EP 2111803 A2 10/2009
EP 1762190 B8 11/2009
EP 1813208 B1 11/2009
EP 1908426 B1 11/2009
EP 2116195 A1 11/2009
EP 2116196 A2 11/2009
EP 2116197 A2 11/2009
EP 1607050 B1 12/2009
EP 1815804 B1 12/2009
EP 1875870 B1 12/2009
EP 1878395 B1 1/2010
EP 2151204 A1 2/2010
EP 1813211 B1 3/2010
EP 2165654 A1 3/2010
EP 2165656 A2 3/2010
EP 2165660 A2 3/2010
EP 2165663 A2 3/2010
EP 2165664 A2 3/2010
EP 1566150 B1 4/2010
EP 1813206 B1 4/2010
EP 2184014 A2 5/2010
EP 1769754 B1 6/2010
EP 1854416 B1 6/2010
EP 1911408 B1 6/2010
EP 2198787 A1 6/2010
EP 2214610 A1 8/2010
EP 2218409 A1 8/2010
EP 1647286 B1 9/2010
EP 1825821 B1 9/2010
EP 1535565 B1 10/2010
EP 1702570 B1 10/2010
EP 1785098 B1 10/2010
EP 2005896 B1 10/2010
EP 2030578 B1 11/2010
EP 2036505 B1 11/2010
EP 2245993 A2 11/2010
EP 2245994 A1 11/2010
EP 2253280 A1 11/2010
EP 1627605 B1 12/2010
EP 2027811 B1 12/2010
EP 2130498 B1 12/2010
EP 2258282 A2 12/2010
EP 2263568 A2 12/2010
EP 1994890 B1 1/2011
EP 2005900 B1 1/2011
EP 2277667 A1 1/2011
EP 2283780 A2 2/2011
EP 2286738 A2 2/2011
EP 1494595 B1 3/2011
EP 1690502 B1 3/2011
EP 1884201 B1 3/2011
EP 2292153 A1 3/2011
EP 1769755 B1 4/2011
EP 2090240 B1 4/2011
EP 2305135 A1 4/2011
EP 2308388 A1 4/2011
EP 2314254 A2 4/2011
EP 2316345 A1 5/2011
EP 2316366 A2 5/2011
EP 2319443 A1 5/2011
EP 2324776 A2 5/2011
EP 1813205 B1 6/2011
EP 2042107 B1 6/2011
EP 2090243 B1 6/2011
EP 2329773 A1 6/2011
EP 2090239 B1 7/2011
EP 2340771 A2 7/2011
EP 2353545 A1 8/2011
EP 2361562 A1 8/2011
EP 2377472 A1 10/2011
EP 1836986 B1 11/2011
EP 1908414 B1 11/2011
EP 2153781 B1 11/2011
EP 2387943 A2 11/2011
EP 2389928 A2 11/2011
EP 1847225 B1 12/2011
EP 2397079 A1 12/2011
EP 2399538 A2 12/2011
EP 1785102 B1 1/2012
EP 1316290 B1 2/2012
EP 1962711 B1 2/2012
EP 2415416 A1 2/2012
EP 2090253 B1 3/2012
EP 2430986 A2 3/2012
EP 1347638 B1 5/2012
EP 1943956 B1 5/2012
EP 2446834 A1 5/2012
EP 2455007 A2 5/2012
EP 2457519 A1 5/2012
EP 2462878 A1 6/2012
EP 2462880 A2 6/2012
EP 1813204 B1 7/2012
EP 2189121 B1 7/2012
EP 2248475 B1 7/2012
EP 2478845 A2 7/2012
EP 2005895 B1 8/2012
EP 2090248 B1 8/2012
EP 2481359 A1 8/2012
EP 2484304 A2 8/2012
EP 2486860 A2 8/2012
EP 2486862 A2 8/2012
EP 2486868 A2 8/2012
EP 1908412 B1 9/2012
EP 1935351 B1 9/2012
EP 2497431 A1 9/2012
EP 1550412 B2 10/2012
EP 1616549 B1 10/2012
EP 2030579 B1 10/2012
EP 2090252 B1 10/2012
EP 2517637 A1 10/2012
EP 2517638 A1 10/2012
EP 2517642 A2 10/2012
EP 2517645 A2 10/2012
EP 2517649 A2 10/2012
EP 2517651 A2 10/2012
EP 2526877 A1 11/2012
EP 2526883 A1 11/2012
EP 1884206 B1 3/2013
EP 2286735 B1 3/2013
EP 2090238 B1 4/2013
EP 2586380 A1 5/2013
EP 2586383 A2 5/2013
EP 2606812 A1 6/2013
EP 2606834 A2 6/2013
EP 1982657 B1 7/2013
EP 2614782 A2 7/2013
EP 2617369 A1 7/2013
EP 2090234 B1 9/2013
EP 2633830 A1 9/2013
EP 2644124 A1 10/2013
EP 2644209 A2 10/2013
EP 2649948 A1 10/2013
EP 2649949 A1 10/2013
EP 1997438 B1 11/2013
EP 2668910 A2 12/2013
EP 2684529 A2 1/2014
EP 2687164 A2 1/2014
EP 2700367 A1 2/2014
EP 2713902 A1 4/2014
EP 1772105 B1 5/2014
EP 2743042 A2 6/2014
EP 2759267 A2 7/2014
EP 2764826 A1 8/2014
EP 2764827 A2 8/2014
EP 2767243 A3 8/2014
EP 2772206 A2 9/2014
EP 2772209 A1 9/2014
EP 2777520 A1 9/2014
EP 2777524 A2 9/2014
EP 2777528 A2 9/2014
EP 2777537 A1 9/2014
EP 2777538 A2 9/2014
EP 2786714 A2 10/2014
EP 2792313 A2 10/2014

(56) References Cited

FOREIGN PATENT DOCUMENTS

| | | | |
|---|---|---|---|
| EP | 2803324 | A2 | 11/2014 |
| EP | 2815704 | A1 | 12/2014 |
| EP | 2446835 | B1 | 1/2015 |
| EP | 2842500 | A1 | 3/2015 |
| EP | 2845545 | A1 | 3/2015 |
| EP | 1943960 | B1 | 4/2015 |
| EP | 2090255 | B1 | 4/2015 |
| EP | 2853220 | A1 | 4/2015 |
| EP | 2923647 | A2 | 9/2015 |
| EP | 2923653 | A2 | 9/2015 |
| EP | 2923660 | A2 | 9/2015 |
| EP | 2944270 | A1 | 11/2015 |
| EP | 1774914 | B1 | 12/2015 |
| EP | 2090235 | B1 | 4/2016 |
| EP | 2823773 | B1 | 4/2016 |
| EP | 2131750 | B1 | 5/2016 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 1915957 | B1 | 8/2016 |
| EP | 2296559 | B1 | 8/2016 |
| EP | 2586379 | B1 | 8/2016 |
| EP | 2777533 | B1 | 10/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 2116192 | B1 | 3/2017 |
| EP | 3135225 | A2 | 3/2017 |
| EP | 2789299 | B1 | 5/2017 |
| EP | 2311386 | B1 | 6/2017 |
| EP | 2839787 | B1 | 6/2017 |
| EP | 2745782 | B1 | 10/2017 |
| EP | 3225190 | A2 | 10/2017 |
| EP | EU-3326548 | A1 | 5/2018 |
| EP | 3363378 | A1 | 8/2018 |
| EP | 3275378 | B1 | 7/2019 |
| ES | 2396594 | T3 | 2/2013 |
| FR | 459743 | A | 11/1913 |
| FR | 999646 | A | 2/1952 |
| FR | 1112936 | A | 3/1956 |
| FR | 2452275 | B1 | 4/1983 |
| FR | 2598905 | A1 | 11/1987 |
| FR | 2689749 | B1 | 7/1994 |
| FR | 2765794 | A1 | 1/1999 |
| FR | 2815842 | A1 | 10/2000 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2284242 | A | 5/1995 |
| GB | 2286435 | A | 8/1995 |
| GB | 2336214 | A | 10/1999 |
| GB | 2425903 | A | 11/2006 |
| GB | 2423199 | B | 5/2009 |
| GB | 2509523 | A | 7/2014 |
| GR | 930100110 | A | 11/1993 |
| JP | S 47-11908 | Y1 | 5/1972 |
| JP | S 50-33988 | U | 4/1975 |
| JP | S5367286 | A | 6/1978 |
| JP | S 56-112235 | A | 9/1981 |
| JP | S 58500053 | A | 1/1983 |
| JP | S 58-501360 | A | 8/1983 |
| JP | S 59-174920 | A | 3/1984 |
| JP | S 60-100955 | A | 6/1985 |
| JP | S60113007 | A | 6/1985 |
| JP | S 60-212152 | A | 10/1985 |
| JP | S 61-98249 | A | 5/1986 |
| JP | S 61502036 | A | 9/1986 |
| JP | S 62-170011 | U | 10/1987 |
| JP | S 63-59764 | A | 3/1988 |
| JP | S 63-147449 | A | 6/1988 |
| JP | S 63-203149 | A | 8/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H 02-279149 | A | 11/1990 |
| JP | H 03-12126 | A | 1/1991 |
| JP | H 03-18354 | A | 1/1991 |
| JP | H 03-78514 | U | 8/1991 |
| JP | H 03-85009 | U | 8/1991 |
| JP | H 04-215747 | A | 8/1992 |
| JP | H 04-131860 | U | 12/1992 |
| JP | H 05-84252 | A | 4/1993 |
| JP | H 05-123325 | A | 5/1993 |
| JP | H05226945 | A | 9/1993 |
| JP | H 06-7357 | | 1/1994 |
| JP | H 06-30945 | A | 2/1994 |
| JP | H 06-54857 | A | 3/1994 |
| JP | H 06-63054 | A | 3/1994 |
| JP | H 06-26812 | U | 4/1994 |
| JP | H 06-121798 | A | 5/1994 |
| JP | H 06-125913 | A | 5/1994 |
| JP | H 06-197901 | A | 7/1994 |
| JP | H 06-237937 | A | 8/1994 |
| JP | H 06-327684 | A | 11/1994 |
| JP | H 07-31623 | A | 2/1995 |
| JP | H 07-47070 | A | 2/1995 |
| JP | H 07-51273 | A | 2/1995 |
| JP | H 079622 | U | 2/1995 |
| JP | H 07-124166 | A | 5/1995 |
| JP | H 07-163573 | A | 6/1995 |
| JP | H 07-163574 | A | 6/1995 |
| JP | H 07-171163 | A | 7/1995 |
| JP | H 07-255735 | A | 10/1995 |
| JP | H 07-285089 | A | 10/1995 |
| JP | H 07-299074 | A | 11/1995 |
| JP | H 08-33641 | A | 2/1996 |
| JP | H 08-33642 | A | 2/1996 |
| JP | H 08-164141 | A | 6/1996 |
| JP | H 08-173437 | A | 7/1996 |
| JP | H 08-182684 | A | 7/1996 |
| JP | H 08-215201 | A | 8/1996 |
| JP | H 08-507708 | A | 8/1996 |
| JP | H 08-229050 | A | 9/1996 |
| JP | H 08-289895 | A | 11/1996 |
| JP | H 08-336540 | A | 12/1996 |
| JP | H 08-336544 | A | 12/1996 |
| JP | H 09-501081 | A | 2/1997 |
| JP | H 09-501577 | A | 2/1997 |
| JP | H 09-164144 | A | 6/1997 |
| JP | H09-323068 | A | 12/1997 |
| JP | H 10-113352 | A | 5/1998 |
| JP | H 10-118090 | A | 5/1998 |
| JP | H10-200699 | A | 7/1998 |
| JP | H 10-296660 | A | 11/1998 |
| JP | H 10-512465 | A | 12/1998 |
| JP | H 10-512469 | A | 12/1998 |
| JP | 2000-014632 | A | 1/2000 |
| JP | 2000-033071 | A | 2/2000 |
| JP | 2000-112002 | A | 4/2000 |
| JP | 2000-166932 | A | 6/2000 |
| JP | 2000-171730 | A | 6/2000 |
| JP | 3056672 | B2 | 6/2000 |
| JP | 2000210299 | A | 8/2000 |
| JP | 2000-287987 | A | 10/2000 |
| JP | 2000271141 | A | 10/2000 |
| JP | 2000-325303 | A | 11/2000 |
| JP | 2001-037763 | A | 2/2001 |
| JP | 2001-046384 | A | 2/2001 |
| JP | 2001-69758 | A | 3/2001 |
| JP | 2001-087272 | A | 4/2001 |
| JP | 2001208655 | A | 8/2001 |
| JP | 2001-514541 | A | 9/2001 |
| JP | 2001-276091 | A | 10/2001 |
| JP | 2001-286477 | A | 10/2001 |
| JP | 2001-517473 | A | 10/2001 |

(56) References Cited

FOREIGN PATENT DOCUMENTS

| | | | |
|---|---|---|---|
| JP | 2002-051974 | A | 2/2002 |
| JP | 2002054903 | A | 2/2002 |
| JP | 2002-085415 | A | 3/2002 |
| JP | 2002-143078 | A | 5/2002 |
| JP | 2002153481 | A | 5/2002 |
| JP | 2002-204801 | A | 7/2002 |
| JP | 2002-528161 | A | 9/2002 |
| JP | 2002-314298 | A | 10/2002 |
| JP | 2002-369820 | A | 12/2002 |
| JP | 2002-542186 | A | 12/2002 |
| JP | 2003-000603 | A | 1/2003 |
| JP | 2003-500153 | A | 1/2003 |
| JP | 2003-504104 | A | 2/2003 |
| JP | 2003-135473 | A | 5/2003 |
| JP | 2003-148903 | A | 5/2003 |
| JP | 2003-164066 | A | 6/2003 |
| JP | 2003-521301 | A | 7/2003 |
| JP | 2003-521304 | A | 7/2003 |
| JP | 2003-523251 | A | 8/2003 |
| JP | 2003-523254 | A | 8/2003 |
| JP | 2003-524431 | A | 8/2003 |
| JP | 3442423 | B2 | 9/2003 |
| JP | 2003-300416 | A | 10/2003 |
| JP | 2004-147701 | A | 5/2004 |
| JP | 2004-162035 | A | 6/2004 |
| JP | 2004-229976 | A | 8/2004 |
| JP | 2004-524076 | A | 8/2004 |
| JP | 2004-531280 | A | 10/2004 |
| JP | 2004-532084 | A | 10/2004 |
| JP | 2004-532676 | A | 10/2004 |
| JP | 2004-329624 | A | 11/2004 |
| JP | 2004-535217 | A | 11/2004 |
| JP | 2004-337617 | A | 12/2004 |
| JP | 2004-344662 | A | 12/2004 |
| JP | 2004-344663 | A | 12/2004 |
| JP | 2005-013573 | A | 1/2005 |
| JP | 2005-028147 | A | 2/2005 |
| JP | 2005-028148 | A | 2/2005 |
| JP | 2005-028149 | A | 2/2005 |
| JP | 2005-505309 | A | 2/2005 |
| JP | 2005-505322 | A | 2/2005 |
| JP | 2005-505334 | A | 2/2005 |
| JP | 2005-080702 | A | 3/2005 |
| JP | 2005-103280 | A | 4/2005 |
| JP | 2005-103281 | A | 4/2005 |
| JP | 2005-103293 | A | 4/2005 |
| JP | 2005-511131 | A | 4/2005 |
| JP | 2005-511137 | A | 4/2005 |
| JP | 2005-131163 | A | 5/2005 |
| JP | 2005-131164 | A | 5/2005 |
| JP | 2005-131173 | A | 5/2005 |
| JP | 2005-131211 | A | 5/2005 |
| JP | 2005-131212 | A | 5/2005 |
| JP | 2005-137423 | A | 6/2005 |
| JP | 2005-137919 | A | 6/2005 |
| JP | 2005-144183 | A | 6/2005 |
| JP | 2005-152416 | A | 6/2005 |
| JP | 2005-516714 | A | 6/2005 |
| JP | 2005-187954 | A | 7/2005 |
| JP | 2005-521109 | A | 7/2005 |
| JP | 2005-523105 | A | 8/2005 |
| JP | 2005-524474 | A | 8/2005 |
| JP | 4461008 | B2 | 8/2005 |
| JP | 2005211455 | A | 8/2005 |
| JP | 2005-296412 | A | 10/2005 |
| JP | 2005-529675 | A | 10/2005 |
| JP | 2005-529677 | A | 11/2005 |
| JP | 2005-328882 | A | 12/2005 |
| JP | 2005-335432 | A | 12/2005 |
| JP | 2005-342267 | A | 12/2005 |
| JP | 2006-034975 | A | 2/2006 |
| JP | 2006-034977 | A | 2/2006 |
| JP | 2006-034978 | A | 2/2006 |
| JP | 2006-034980 | A | 2/2006 |
| JP | 2006-043451 | A | 2/2006 |
| JP | 2006-506106 | A | 2/2006 |
| JP | 2006-510879 | A | 3/2006 |
| JP | 3791856 | B2 | 6/2006 |
| JP | 2006-187649 | A | 7/2006 |
| JP | 2006-218228 | A | 8/2006 |
| JP | 2006-218297 | A | 8/2006 |
| JP | 2006-223872 | A | 8/2006 |
| JP | 2006-281405 | A | 10/2006 |
| JP | 2006-289064 | A | 10/2006 |
| JP | 2006291180 | A | 10/2006 |
| JP | 2006-334412 | A | 12/2006 |
| JP | 2006-334417 | A | 12/2006 |
| JP | 2006-346445 | A | 12/2006 |
| JP | 2007-000634 | A | 1/2007 |
| JP | 2007-050253 | A | 3/2007 |
| JP | 2007-061628 | A | 3/2007 |
| JP | 2007-083051 | A | 4/2007 |
| JP | 2007-97252 | A | 4/2007 |
| JP | 2007-098130 | A | 4/2007 |
| JP | 2007-105481 | A | 4/2007 |
| JP | 3906843 | B2 | 4/2007 |
| JP | 2007-117725 | A | 5/2007 |
| JP | 2007-130471 | A | 5/2007 |
| JP | 2007-130479 | A | 5/2007 |
| JP | 2007-222615 | A | 6/2007 |
| JP | 3934161 | B2 | 6/2007 |
| JP | 2007-203047 | A | 8/2007 |
| JP | 2007-203049 | A | 8/2007 |
| JP | 2007-203051 | A | 8/2007 |
| JP | 2007-203055 | A | 8/2007 |
| JP | 2007-203057 | A | 8/2007 |
| JP | 2007-524435 | A | 8/2007 |
| JP | 2007-229448 | A | 9/2007 |
| JP | 2007-526026 | A | 9/2007 |
| JP | 2007-252916 | A | 10/2007 |
| JP | 4001860 | B2 | 10/2007 |
| JP | 2007-307373 | A | 11/2007 |
| JP | 2007289715 | A | 11/2007 |
| JP | 2007304057 | A | 11/2007 |
| JP | 2007306710 | A | 11/2007 |
| JP | 2007-325922 | A | 12/2007 |
| JP | D1322057 | | 2/2008 |
| JP | 2008-068073 | A | 3/2008 |
| JP | 2008-510515 | A | 4/2008 |
| JP | 2008-516669 | A | 5/2008 |
| JP | 2008-528203 | A | 7/2008 |
| JP | 2008-206967 | A | 9/2008 |
| JP | 2008-212637 | A | 9/2008 |
| JP | 2008-212638 | A | 9/2008 |
| JP | 2008-212640 | A | 9/2008 |
| JP | 2008-220956 | A | 9/2008 |
| JP | 2008220032 | A | 9/2008 |
| JP | 2008-237881 | A | 10/2008 |
| JP | 2008-259860 | A | 10/2008 |
| JP | 2008-264535 | A | 11/2008 |
| JP | 2008-283459 | A | 11/2008 |
| JP | 2008-307393 | A | 12/2008 |
| JP | 2009-000531 | A | 1/2009 |
| JP | 2009-006137 | A | 1/2009 |
| JP | 2009-502351 | A | 1/2009 |
| JP | 2009-502352 | A | 1/2009 |
| JP | 2009-022742 | A | 2/2009 |
| JP | 2009-506799 | A | 2/2009 |
| JP | 2009-507526 | A | 2/2009 |
| JP | 2009-072595 | A | 4/2009 |
| JP | 2009-072599 | A | 4/2009 |
| JP | 2009-090113 | A | 4/2009 |
| JP | 2009-106752 | A | 5/2009 |
| JP | 2009-189821 | A | 8/2009 |
| JP | 2009-189823 | A | 8/2009 |
| JP | 2009-189836 | A | 8/2009 |
| JP | 2009-189837 | A | 8/2009 |
| JP | 2009-189838 | A | 8/2009 |
| JP | 2009-189846 | A | 8/2009 |
| JP | 2009-189847 | A | 8/2009 |
| JP | 2009-201998 | A | 9/2009 |
| JP | 2009207260 | A | 9/2009 |
| JP | 2009-536082 | A | 10/2009 |
| JP | 2009226028 | A | 10/2009 |

(56) References Cited

FOREIGN PATENT DOCUMENTS

| | | | |
|---|---|---|---|
| JP | 2009-261944 | A | 11/2009 |
| JP | 2009-268908 | A | 11/2009 |
| JP | 2009-538684 | A | 11/2009 |
| JP | 2009-539420 | A | 11/2009 |
| JP | 2009-291604 | A | 12/2009 |
| JP | 2010-504808 | A | 2/2010 |
| JP | 2010-504809 | A | 2/2010 |
| JP | 2010-504813 | A | 2/2010 |
| JP | 2010-504846 | A | 2/2010 |
| JP | 2010-505524 | A | 2/2010 |
| JP | D1383743 | | 2/2010 |
| JP | 2010065594 | A | 3/2010 |
| JP | 2010-069307 | A | 4/2010 |
| JP | 2010-069310 | A | 4/2010 |
| JP | 2010-075694 | A | 4/2010 |
| JP | 2010-075695 | A | 4/2010 |
| JP | 2010-088876 | A | 4/2010 |
| JP | 2010-094514 | A | 4/2010 |
| JP | 2010-098844 | A | 4/2010 |
| JP | 2010-520025 | A | 6/2010 |
| JP | 2010-142636 | A | 7/2010 |
| JP | 2010-148879 | A | 7/2010 |
| JP | 2010-214166 | A | 9/2010 |
| JP | 4549018 | B2 | 9/2010 |
| JP | 2010214128 | A | 9/2010 |
| JP | 2010-240411 | A | 10/2010 |
| JP | 2010-240429 | A | 10/2010 |
| JP | 2010-246948 | A | 11/2010 |
| JP | 2010-279690 | A | 12/2010 |
| JP | 2010-540041 | A | 12/2010 |
| JP | 2010-540192 | A | 12/2010 |
| JP | 2011-005260 | A | 1/2011 |
| JP | 2011-504391 | A | 2/2011 |
| JP | 2011-509786 | A | 3/2011 |
| JP | 2011-072797 | A | 4/2011 |
| JP | 2011-078763 | A | 4/2011 |
| JP | 2011072574 | A | 4/2011 |
| JP | 2011-115594 | A | 6/2011 |
| JP | 2011-520564 | A | 7/2011 |
| JP | 4722849 | B2 | 7/2011 |
| JP | 4728996 | B2 | 7/2011 |
| JP | 2011-524199 | A | 9/2011 |
| JP | 4783373 | B2 | 9/2011 |
| JP | 2011-251156 | A | 12/2011 |
| JP | D1432094 | | 12/2011 |
| JP | 2012-040398 | A | 3/2012 |
| JP | 2012-507356 | A | 3/2012 |
| JP | 2012115542 | A | 6/2012 |
| JP | 2012-517289 | A | 8/2012 |
| JP | 2012143283 | A | 8/2012 |
| JP | 5140421 | B2 | 2/2013 |
| JP | 5154710 | B1 | 2/2013 |
| JP | 5162595 | B2 | 3/2013 |
| JP | 2013-517891 | A | 5/2013 |
| JP | 2013099551 | A | 5/2013 |
| JP | 2013-526342 | A | 6/2013 |
| JP | 2013126430 | A | 6/2013 |
| JP | 2013-128791 | A | 7/2013 |
| JP | H 05-212039 | A | 8/2013 |
| JP | D1481426 | | 9/2013 |
| JP | 5333899 | B2 | 11/2013 |
| JP | 2013541983 | A | 11/2013 |
| JP | 2013541997 | A | 11/2013 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015521525 | A | 7/2015 |
| JP | 2016007800 | A | 1/2016 |
| JP | 2016512057 | A | 4/2016 |
| JP | 2016530949 | A | 10/2016 |
| JP | 1601498 | S | 4/2018 |
| KR | 20100110134 | A | 10/2010 |
| KR | 20110003229 | A | 1/2011 |
| KR | 300631507 | | 3/2012 |
| KR | 300747646 | | 6/2014 |
| RU | 1814161 | A1 | 5/1993 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 2189091 | C2 | 9/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2007-103563 | A | 8/2008 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 886900 | A1 | 12/1981 |
| SU | 1009439 | A | 4/1983 |
| SU | 1022703 | A1 | 6/1983 |
| SU | 1271497 | A1 | 11/1986 |
| SU | 1333319 | A2 | 8/1987 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1377052 | A1 | 2/1998 |
| WO | WO 82/02824 | A1 | 9/1982 |
| WO | WO 86/02254 | A1 | 4/1986 |
| WO | WO 91/15157 | A1 | 10/1991 |
| WO | WO 92/20295 | A1 | 11/1992 |
| WO | WO 92/21300 | A1 | 12/1992 |
| WO | WO 93/08755 | A1 | 5/1993 |
| WO | WO-9308754 | A1 | 5/1993 |
| WO | WO 93/13718 | A1 | 7/1993 |
| WO | WO 93/14690 | A1 | 8/1993 |
| WO | WO 93/15648 | A1 | 8/1993 |
| WO | WO 93/15850 | A1 | 8/1993 |
| WO | WO 93/19681 | A1 | 10/1993 |
| WO | WO 94/00060 | A1 | 1/1994 |
| WO | WO 94/11057 | A1 | 5/1994 |
| WO | WO 94/12108 | A1 | 6/1994 |
| WO | WO 94/14129 | A1 | 6/1994 |
| WO | WO 94/17737 | A1 | 8/1994 |
| WO | WO 94/18893 | A1 | 9/1994 |
| WO | WO 94/20030 | A1 | 9/1994 |
| WO | WO 94/22378 | A1 | 10/1994 |
| WO | WO 94/23659 | A1 | 10/1994 |
| WO | WO 94/24943 | A1 | 11/1994 |
| WO | WO 94/24947 | A1 | 11/1994 |
| WO | WO 95/02369 | A1 | 1/1995 |
| WO | WO 95/03743 | A1 | 2/1995 |
| WO | WO 95/06817 | A1 | 3/1995 |
| WO | WO 95/09576 | A1 | 4/1995 |
| WO | WO 95/09577 | A1 | 4/1995 |
| WO | WO 95/14436 | A1 | 6/1995 |
| WO | WO 95/17855 | A1 | 7/1995 |
| WO | WO 95/18383 | A1 | 7/1995 |
| WO | WO 95/18572 | A1 | 7/1995 |
| WO | WO 95/19739 | A1 | 7/1995 |

(56) References Cited

FOREIGN PATENT DOCUMENTS

| | | | |
|---|---|---|---|
| WO | WO 95/20360 | A1 | 8/1995 |
| WO | WO 95/23557 | A1 | 9/1995 |
| WO | WO 95/24865 | A1 | 9/1995 |
| WO | WO 95/25471 | A3 | 9/1995 |
| WO | WO 95/26562 | A1 | 10/1995 |
| WO | WO 95/29639 | A1 | 11/1995 |
| WO | WO 96/04858 | A1 | 2/1996 |
| WO | WO 96/18344 | A2 | 6/1996 |
| WO | WO 96/19151 | A1 | 6/1996 |
| WO | WO 96/19152 | A1 | 6/1996 |
| WO | WO 96/20652 | A1 | 7/1996 |
| WO | WO 96/21119 | A1 | 7/1996 |
| WO | WO 96/22055 | A1 | 7/1996 |
| WO | WO 96/23448 | A1 | 8/1996 |
| WO | WO 96/24301 | A1 | 8/1996 |
| WO | WO 96/27337 | A1 | 9/1996 |
| WO | WO 96/31155 | A1 | 10/1996 |
| WO | WO 96/35464 | A1 | 11/1996 |
| WO | WO 96/39085 | A1 | 12/1996 |
| WO | WO 96/39086 | A1 | 12/1996 |
| WO | WO 96/39087 | A1 | 12/1996 |
| WO | WO 96/39088 | A1 | 12/1996 |
| WO | WO 96/39089 | A1 | 12/1996 |
| WO | WO 97/00646 | A1 | 1/1997 |
| WO | WO 97/00647 | A1 | 1/1997 |
| WO | WO 97/01989 | A1 | 1/1997 |
| WO | WO 97/06582 | A1 | 2/1997 |
| WO | WO 97/10763 | A1 | 3/1997 |
| WO | WO 97/10764 | A1 | 3/1997 |
| WO | WO 97/11648 | A2 | 4/1997 |
| WO | WO 97/11649 | A1 | 4/1997 |
| WO | WO 97/15237 | A1 | 5/1997 |
| WO | WO 97/24073 | A1 | 7/1997 |
| WO | WO 97/24993 | A1 | 7/1997 |
| WO | WO 97/30644 | A1 | 8/1997 |
| WO | WO 97/30659 | A1 | 8/1997 |
| WO | WO 97/34533 | A1 | 9/1997 |
| WO | WO 97/37598 | A1 | 10/1997 |
| WO | WO 97/39688 | A2 | 10/1997 |
| WO | WO 97/41767 | A2 | 11/1997 |
| WO | WO 98/01080 | A1 | 1/1998 |
| WO | WO 98/17180 | A1 | 4/1998 |
| WO | WO 98/22154 | A2 | 5/1998 |
| WO | WO 98/27880 | A1 | 7/1998 |
| WO | WO 98/30153 | A1 | 7/1998 |
| WO | WO-9827870 | A1 | 7/1998 |
| WO | WO 98/47436 | A1 | 10/1998 |
| WO | WO 98/58589 | A1 | 12/1998 |
| WO | WO 99/02090 | A1 | 1/1999 |
| WO | WO 99/03407 | A1 | 1/1999 |
| WO | WO 99/03408 | A1 | 1/1999 |
| WO | WO 99/03409 | A1 | 1/1999 |
| WO | WO 99/12483 | A1 | 3/1999 |
| WO | WO 99/12487 | A1 | 3/1999 |
| WO | WO 99/12488 | A1 | 3/1999 |
| WO | WO 99/15086 | A1 | 4/1999 |
| WO | WO 99/15091 | A1 | 4/1999 |
| WO | WO 99/23933 | A2 | 5/1999 |
| WO | WO 99/23959 | A1 | 5/1999 |
| WO | WO 99/25261 | A1 | 5/1999 |
| WO | WO 99/29244 | A1 | 6/1999 |
| WO | WO 99/34744 | A1 | 7/1999 |
| WO | WO 99/45849 | A1 | 9/1999 |
| WO | WO 99/48430 | A1 | 9/1999 |
| WO | WO 99/51158 | A1 | 10/1999 |
| WO | WO 00/24322 | A1 | 5/2000 |
| WO | WO 00/24330 | A1 | 5/2000 |
| WO | WO 00/33755 | A1 | 6/2000 |
| WO | WO 00/41638 | A1 | 7/2000 |
| WO | WO 00/48506 | A1 | 8/2000 |
| WO | WO 00/53112 | A2 | 9/2000 |
| WO | WO 00/54653 | A1 | 9/2000 |
| WO | WO 00/057796 | A1 | 10/2000 |
| WO | WO-0024448 | A2 | 10/2000 |
| WO | WO 00/64365 | A1 | 11/2000 |
| WO | WO 00/72762 | A1 | 12/2000 |
| WO | WO 00/72765 | A1 | 12/2000 |
| WO | WO 00/78222 | A1 | 12/2000 |
| WO | WO 01/03587 | A1 | 1/2001 |
| WO | WO 01/05702 | A1 | 1/2001 |
| WO | WO 01/010482 | A1 | 2/2001 |
| WO | WO 01/35845 | A1 | 5/2001 |
| WO | WO 01/54594 | A1 | 8/2001 |
| WO | WO 01/58371 | A1 | 8/2001 |
| WO | WO 01/62158 | A2 | 8/2001 |
| WO | WO 01/62161 | A1 | 8/2001 |
| WO | WO 01/62162 | A1 | 8/2001 |
| WO | WO 01/62163 | A1 | 8/2001 |
| WO | WO 01/62164 | A2 | 8/2001 |
| WO | WO 01/62169 | A2 | 8/2001 |
| WO | WO 01/78605 | A2 | 10/2001 |
| WO | WO 01/80757 | A2 | 11/2001 |
| WO | WO 01/91646 | A1 | 12/2001 |
| WO | WO 02/00121 | A1 | 1/2002 |
| WO | WO 02/07608 | A2 | 1/2002 |
| WO | WO 02/07618 | A1 | 1/2002 |
| WO | WO 02/17799 | A1 | 3/2002 |
| WO | WO 02/19920 | A1 | 3/2002 |
| WO | WO 02/19932 | A1 | 3/2002 |
| WO | WO 02/26143 | A1 | 4/2002 |
| WO | WO 02/30297 | A2 | 4/2002 |
| WO | WO 02/32322 | A2 | 4/2002 |
| WO | WO 02/36028 | A1 | 5/2002 |
| WO | WO 02/43571 | A2 | 6/2002 |
| WO | WO 02/058568 | A1 | 8/2002 |
| WO | WO 02/060328 | A1 | 8/2002 |
| WO | WO 02/065933 | A2 | 8/2002 |
| WO | WO 02/067785 | A2 | 9/2002 |
| WO | WO 02/080781 | A2 | 10/2002 |
| WO | WO 02/085218 | A2 | 10/2002 |
| WO | WO 02/087586 | A1 | 11/2002 |
| WO | WO 02/098302 | A1 | 12/2002 |
| WO | WO 03/000138 | A2 | 1/2003 |
| WO | WO 03/001329 | A2 | 1/2003 |
| WO | WO 03/001986 | A2 | 1/2003 |
| WO | WO 03/013363 | A1 | 2/2003 |
| WO | WO 03/013372 | A2 | 2/2003 |
| WO | WO 03/015604 | A2 | 2/2003 |
| WO | WO 03/020106 | A2 | 3/2003 |
| WO | WO 03/020139 | A2 | 3/2003 |
| WO | WO 03/024339 | A1 | 3/2003 |
| WO | WO 2003/079909 | A3 | 3/2003 |
| WO | WO 03/030743 | A2 | 4/2003 |
| WO | WO 03/037193 | A1 | 5/2003 |
| WO | WO 2003/047436 | A3 | 6/2003 |
| WO | WO 03/055402 | A1 | 7/2003 |
| WO | WO 03/057048 | A1 | 7/2003 |
| WO | WO 03/057058 | A1 | 7/2003 |
| WO | WO 2003/063694 | A1 | 8/2003 |
| WO | WO 03/077769 | A1 | 9/2003 |
| WO | WO 03/079911 | A1 | 10/2003 |
| WO | WO 03/082126 | A1 | 10/2003 |
| WO | WO 03/086206 | A1 | 10/2003 |
| WO | WO 03/088845 | A2 | 10/2003 |
| WO | WO 03/090630 | A2 | 11/2003 |
| WO | WO 03/094743 | A1 | 11/2003 |
| WO | WO 03/094745 | A1 | 11/2003 |
| WO | WO 2003/094746 | A1 | 11/2003 |
| WO | WO 2003/094747 | A1 | 11/2003 |
| WO | WO 03/101313 | A1 | 12/2003 |
| WO | WO 03/105698 | A2 | 12/2003 |
| WO | WO 03/105702 | A2 | 12/2003 |
| WO | WO 2004/004578 | A1 | 1/2004 |
| WO | WO 2004/006980 | A2 | 1/2004 |
| WO | WO 2004/011037 | A2 | 2/2004 |
| WO | WO 2004/014238 | A2 | 2/2004 |
| WO | WO 2004/019769 | A1 | 3/2004 |
| WO | WO 2004/019803 | A1 | 3/2004 |
| WO | WO 2004/021868 | A2 | 3/2004 |
| WO | WO 2004/028585 | A2 | 4/2004 |
| WO | WO 2004/030554 | A1 | 4/2004 |
| WO | WO 2004/032754 | A2 | 4/2004 |
| WO | WO 2004/032760 | A2 | 4/2004 |
| WO | WO 2004/032762 | A1 | 4/2004 |

(56) References Cited

FOREIGN PATENT DOCUMENTS

WO WO 2004/032763 A2 4/2004
WO WO 2004/032783 A1 4/2004
WO WO 2004/034875 A2 4/2004
WO WO 2004/047626 A1 6/2004
WO WO 2004/047653 A2 6/2004
WO WO 2004/049956 A2 6/2004
WO WO 2004/050971 A2 6/2004
WO WO 2004/052426 A2 6/2004
WO WO 2004/056276 A1 7/2004
WO WO 2004/056277 A1 7/2004
WO WO 2004/062516 A1 7/2004
WO WO 2004/064600 A2 8/2004
WO WO 2004/078050 A2 9/2004
WO WO 2004/078051 A2 9/2004
WO WO 2004/078236 A2 9/2004
WO WO 2004/086987 A1 10/2004
WO WO 2004/096015 A2 11/2004
WO WO 2004/096057 A2 11/2004
WO WO 2004/103157 A2 12/2004
WO WO 2004/105593 A1 12/2004
WO WO 2004/105621 A1 12/2004
WO WO 2004/112618 A2 12/2004
WO WO 2004/112652 A2 12/2004
WO WO 2005/027983 A2 3/2005
WO WO 2005/037329 A2 4/2005
WO WO 2005/042041 A1 5/2005
WO WO 2005/044078 A2 5/2005
WO WO 2005/048809 A1 6/2005
WO WO 2005/055846 A1 6/2005
WO WO 2005/072634 A2 8/2005
WO WO 2005/078892 A1 8/2005
WO WO 2005/079675 A2 9/2005
WO WO 2005/087128 A1 9/2005
WO WO 2005/096954 A2 10/2005
WO WO 2005/110243 A2 11/2005
WO WO 2005/112806 A2 12/2005
WO WO 2005/112808 A1 12/2005
WO WO 2005/115251 A1 12/2005
WO WO 2005/115253 A2 12/2005
WO WO 2005/117735 A1 12/2005
WO WO 2005/122936 A1 12/2005
WO WO 2006/023486 A1 3/2006
WO WO 2006/023578 A2 3/2006
WO WO 2006/026520 A2 3/2006
WO WO 2006/027014 A1 3/2006
WO WO 2006/028314 A1 3/2006
WO WO 2006/044490 A2 4/2006
WO WO 2006/044581 A2 4/2006
WO WO 2006/044810 A2 4/2006
WO WO 2006/049852 A2 5/2006
WO WO 2006/050360 A1 5/2006
WO WO 2006/051252 A1 5/2006
WO WO 2006/057702 A2 6/2006
WO WO 2006/059067 A1 6/2006
WO WO 2006/073581 A2 7/2006
WO WO 2006/083748 A1 8/2006
WO WO 2006/085389 A1 8/2006
WO WO 2006/092563 A1 9/2006
WO WO 2006/092565 A1 9/2006
WO WO 2006/115958 A1 11/2006
WO WO 2006/125940 A1 11/2006
WO WO 2006/132992 A2 12/2006
WO WO 2007/002180 A2 1/2007
WO WO 2007/016290 A2 2/2007
WO WO 2007/018898 A2 2/2007
WO WO-2007015971 A2 2/2007
WO WO 2007/034161 A2 3/2007
WO WO 2007/051000 A2 5/2007
WO WO 2007/059233 A2 5/2007
WO WO 2007/074430 A1 7/2007
WO WO 2007/089603 A2 8/2007
WO WO 2007/098220 A2 8/2007
WO WO 2007/121579 A1 11/2007
WO WO 2007/129121 A1 11/2007
WO WO 2007/131110 A2 11/2007
WO WO 2007/137304 A2 11/2007
WO WO 2007/139734 A2 12/2007
WO WO 2007/142625 A2 12/2007
WO WO 2007/145825 A2 12/2007
WO WO 2007/146987 A2 12/2007
WO WO 2007/147439 A1 12/2007
WO WO 2008/020964 A2 2/2008
WO WO 2008/021687 A1 2/2008
WO WO 2008/021969 A2 2/2008
WO WO 2008/027972 A1 3/2008
WO WO 2008/039237 A1 4/2008
WO WO 2008/039249 A1 4/2008
WO WO 2008/039270 A1 4/2008
WO WO 2008/045383 A2 4/2008
WO WO 2008/057281 A2 5/2008
WO WO-2008061566 A1 5/2008
WO WO 2008/070763 A1 6/2008
WO WO 2008/080148 A2 7/2008
WO WO 2008/089404 A2 7/2008
WO WO 2008/101080 A1 8/2008
WO WO 2008/101228 A2 8/2008
WO WO 2008/103797 A2 8/2008
WO WO 2008/109123 A2 9/2008
WO WO 2008/109125 A1 9/2008
WO WO 2008/112912 A2 9/2008
WO WO 2008/118728 A1 10/2008
WO WO 2008/118928 A2 10/2008
WO WO 2008/124748 A1 10/2008
WO WO 2008/131357 A1 10/2008
WO WO 2009/005969 A2 1/2009
WO WO 2009/022614 A1 2/2009
WO WO 2009/023851 A1 2/2009
WO WO 2009/033057 A2 3/2009
WO WO 2009/039506 A1 3/2009
WO WO 2009/046394 A1 4/2009
WO WO 2009/066105 A1 5/2009
WO WO 2009/067649 A2 5/2009
WO WO 2009/091497 A2 7/2009
WO WO 2009/120944 A2 10/2009
WO WO 2009/137761 A2 11/2009
WO WO 2009/143092 A1 11/2009
WO WO 2009/143331 A1 11/2009
WO WO 2009/150650 A2 12/2009
WO WO 2009/152307 A1 12/2009
WO WO 2010/028332 A2 3/2010
WO WO 2010/030434 A1 3/2010
WO WO 2010/045425 A1 4/2010
WO WO 2010/050771 A2 5/2010
WO WO 2010/054404 A1 5/2010
WO WO 2010/056714 A1 5/2010
WO WO 2010/063795 A1 6/2010
WO WO 2010/090940 A1 8/2010
WO WO 2010/093333 A1 8/2010
WO WO 2010/098871 A2 9/2010
WO WO-2010126129 A1 11/2010
WO WO-2010134913 A1 11/2010
WO WO 2011/008672 A2 1/2011
WO WO 2011/013103 A1 2/2011
WO WO 2011/044343 A2 4/2011
WO WO 2011/060311 A2 5/2011
WO WO 2011/084969 A1 7/2011
WO WO 2011/127137 A1 10/2011
WO WO 2012/006306 A2 1/2012
WO WO 2012/009431 A2 1/2012
WO WO 2012/021671 A1 2/2012
WO WO-2012013577 A1 2/2012
WO WO 2012/040438 A1 3/2012
WO WO 2012/044551 A1 4/2012
WO WO 2012/044554 A1 4/2012
WO WO 2012/044597 A1 4/2012
WO WO 2012/044606 A2 4/2012
WO WO 2012/044820 A1 4/2012
WO WO 2012/044844 A2 4/2012
WO WO 2012/044853 A1 4/2012
WO WO 2012/044854 A1 4/2012
WO WO 2012/058213 A2 5/2012
WO WO 2012/068156 A2 5/2012
WO WO-2012061725 A1 5/2012
WO WO-2012072133 A1 6/2012

(56) References Cited

FOREIGN PATENT DOCUMENTS

WO WO 2012/109760 A1 8/2012
WO WO 2012/127462 A1 9/2012
WO WO 2012/135705 A1 10/2012
WO WO 2012/143913 A2 10/2012
WO WO 2012/148667 A2 11/2012
WO WO 2012/148668 A2 11/2012
WO WO 2012/148703 A2 11/2012
WO WO 2012/160163 A1 11/2012
WO WO 2012/166503 A1 12/2012
WO WO 2013/009252 A2 1/2013
WO WO 2013/009699 A2 1/2013
WO WO 2013/023114 A1 2/2013
WO WO 2013/036409 A1 3/2013
WO WO 2013/043707 A2 3/2013
WO WO 2013/043717 A1 3/2013
WO WO 2013/043721 A2 3/2013
WO WO 2013/062978 A2 5/2013
WO WO-2013087092 A1 6/2013
WO WO 2013/116869 A1 8/2013
WO WO 2013/148762 A2 10/2013
WO WO-2013151888 A1 10/2013
WO WO 2013/167427 A1 11/2013
WO WO 2013/188130 A1 12/2013
WO WO 2014/004199 A1 1/2014
WO WO 2014/004294 A2 1/2014
WO WO 2014/008289 A2 1/2014
WO WO-2014004209 A2 1/2014
WO WO-2014113438 A1 7/2014
WO WO 2014/134034 A2 9/2014
WO WO 2014/172213 A2 10/2014
WO WO-2014175894 A1 10/2014
WO WO 2015/032797 A1 3/2015
WO WO-2015076780 A1 5/2015
WO WO-2015137040 A1 9/2015
WO WO-2015138760 A1 9/2015
WO WO 2015/148136 A1 10/2015
WO WO 2015/148141 A1 10/2015
WO WO 2015/153642 A1 10/2015
WO WO-2015187107 A1 12/2015
WO WO-2016100682 A1 6/2016
WO WO-2016107448 A1 7/2016
WO WO 2007/014355 A2 2/2017
WO WO-2019036490 A1 2/2019

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

Matsuda, "Thermodynamics of Formation of Porous Polymeric Membrane from Solutions," Polymer Journal, vol. 23, No. 5, pp. 435-444 (1991).

Young, "Microcellular foams via phase separation," Journal of Vacuum Science & Technology A 4(3), (May/Jun. 1986).

Chen et al., "Elastomeric Biomaterials for Tissue Engineering," Progress in Polymer Science 38 (2013), pp. 584-671.

Pitt et al., "Attachment of Hyaluronan to Metallic Surfaces," J. Biomed. Mater. Res. 68A: pp. 95-106, 2004.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Solorio et al., "Gelatin Microspheres Crosslinked with Genipin for Local Delivery of Growth Factors," J. Tissue Eng. Regen. Med. (2010), 4(7): pp. 514-523.

http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.

Covidien iDrive™ Ultra in Service Reference Card, "iDrive™ Ultra Powered Stapling Device," (4 pages).

Covidien iDrive™ Ultra Powered Stapling System ibrochure, "The Power of iDrive™ Ultra Powered Stapling System and Tri-Staple™ Technology," (23 pages).

Seils et al., Covidien Summary: Clinical Study "UCONN Biodynamics: Final Report on Results," (2 pages).

Covidien "iDrive™ Ultra Powered Stapling System, A Guide for Surgeons," (6 pages).

Covidien "iDrive™ Ultra Powered Stapling System, Cleaning and Sterilization Guide," (2 pages).

Covidien brochure "iDrive™ Ultra Powered Stapling System," (6 pages).

"Indian Standard: Automotive Vehicles—Brakes and Braking Systems (IS 11852-1:2001)", Mar. 1, 2001.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

(56) References Cited

OTHER PUBLICATIONS

Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheetashx?la=en.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry—II: Second Year Diploma in Pharmacy, Nirali Prakashan, p. 339, 2007.
Forum discussion regarding "Speed Is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power

(56) References Cited

OTHER PUBLICATIONS

Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).

* cited by examiner 1104
1126
1130
1131
127
1138
1149
1138
1138
1138
1125
990
990
123
1149
1138
121
1122

1320
1395p
1398c
1326
1340a
1395h
1398a
1395n
1340c
1346
1399
1340d
1254
1395v
1398b
1340b
1398d 1517
1516
1556
1550
1556
112
1556
1500
1516
1504
130

130
1516
1517
1556
1517
1550
112
1517
1556
52
52
1517
1517
1556
1504
1516

130
1516
112
1504
1550
1517

SURGICAL STAPLING SYSTEM

CROSS REFERENCE TO RELATED APPLICATIONS

This application is a continuation application claiming priority under 35 U.S.C. § 120 to U.S. patent application Ser. No. 13/835,592, entitled SURGICAL STAPLING INSTRUMENT COMPRISING A MAGNETIC ELEMENT DRIVER, filed Mar. 15, 2013, now U.S. Patent Application Publication No. 2013/0270322, which is a continuation application claiming priority under 35 U.S.C. § 120 to U.S. patent application Ser. No. 12/366,538, entitled SURGICAL STAPLING INSTRUMENT COMPRISING A MAGNETIC ELEMENT DRIVER, filed Feb. 5, 2009, which issued on Aug. 27, 2013 as U.S. Pat. No. 8,517,239, the entire disclosures of which are hereby incorporated by reference herein.

BACKGROUND i. Technical Field

The present invention relates, in general, to surgical instruments and, more particularly, to surgical stapling instruments.

ii. Background of the Related Art

Surgical stapling instruments have been used to simultaneously make an incision in tissue and apply lines of staples on opposing sides of the incision. Such instruments commonly include a pair of cooperating jaw members that, if the instrument is intended for endoscopic or laparoscopic applications, are capable of passing through a cannula passageway. In various embodiments, one of the jaw members can receive a staple cartridge having at least two laterally spaced rows of staples. The other jaw member can define an anvil having staple-forming pockets aligned with the rows of staples in the cartridge. The instrument can further include a plurality of wedges, or a staple sled, which, when driven distally, passes through openings in the staple cartridge and engages drivers supporting the staples in order to effect the firing of the staples toward the anvil. The simultaneous severing of tissue while forming rows of staples on each side of the cut can reduce bleeding and simplify various surgical procedures. In certain circumstances, however, the force required to form the staples and incise the tissue simultaneously may be significant.

Previous surgical stapling instruments have included a handle assembly, an elongate shaft extending from the handle assembly, and an end effector movably mounted to the elongate shaft, wherein the end effector can be articulated relative to the elongate shaft. Often, a surgeon is required to use both hands in order to articulate the end effector relative to the shaft, i.e., the surgeon is often required to use one hand to hold the handle assembly of the surgical instrument, for example, and use their other hand to operate a lever, for example, which articulates the end effector. While such surgical instruments can be suitable in many circumstances, a surgeon may not have a hand free to perform another step in the surgical procedure. The foregoing discussion is intended only to illustrate some of the shortcomings present in the field of the invention at the time, and should not be taken as a disavowal of claim scope.

SUMMARY

In one general aspect, a surgical instrument can comprise a plurality of magnetic elements configured to articulate an end effector of the surgical instrument. The surgical instrument can comprise at least one electromagnet which can be selectively activated, or polarized, to generate a magnetic field sufficient to motivate at least one second magnetic element, such as a permanent magnet and/or an iron core, for example, mounted to the end effector. In various embodiments, a surgical instrument can comprise a first electromagnet configured to generate a first magnetic field which rotates an end effector in a first direction and, in addition, a second electromagnet configured to generate a second magnetic field which rotates the end effector in a second direction. In certain embodiments, a surgical instrument can comprise at least one solenoid which can be configured to pivot an end effector of the surgical instrument.

In one general aspect, a surgical instrument can comprise a motor which can be configured to pivot an end effector of the surgical instrument. In certain embodiments, the motor can comprise windings which can be selectively energized to rotate an iron core. In at least one embodiment, the motor can comprise at least one electromagnet which can be configured to rotate a shaft having at least one magnetic element mounted thereto. In various embodiments, a surgical instrument can further comprise a lock and/or brake which can be configured to prevent, or at least inhibit, the articulation of the end effector of the surgical instrument. In certain embodiments, a lock can comprise at least one solenoid, motor, and/or electromagnet which can be configured to move a locking element between locked and unlocked positions in order to engage and disengage the locking element with the end effector.

In one general aspect, a surgical instrument can comprise a plurality of magnetic elements configured to open and close an end effector of the surgical instrument. In certain embodiments, the surgical instrument can comprise at least one electromagnet which can be selectively activated, or polarized, to generate a magnetic field sufficient to motivate at least one second magnetic element, such as a permanent magnet and/or an iron core, for example, mounted to an anvil of the end effector. In another general aspect, a surgical stapling instrument can comprise a plurality of magnetic elements configured to advance and/or retract a firing bar, cutting member, and/or staple sled within the surgical instrument in order to incise and/or staple tissue positioned within an end effector of the surgical instrument. In certain embodiments, the cutting element can comprise at least one electromagnet mounted thereto which can be configured to generate a magnetic field configured to interact with one or more permanent magnets, for example, mounted to the end effector.

In various embodiments, a surgical stapling system comprising a stapling assembly, a firing member, a shaft, an articulation joint, and a handle is disclosed. The stapling assembly comprises a distal end, a staple cartridge, and an anvil. The staple cartridge comprises a plurality of staples removably stored therein. The anvil is configured to deform the staples. The stapling assembly is configurable in an open configuration and a closed configuration by a closure member. The firing member is movable toward the distal end to eject the staples from the staple cartridge. The shaft is rotatable in a first rotation direction and a second rotation direction. The stapling assembly is articulatable about the articulation joint in a first articulation direction and a second articulation direction. The shaft extends from the handle. The handle comprises a firing actuator configured to move the firing member toward the distal end, and a rotation actuator comprising a first initial position. The rotation actuator is configured to rotate the shaft in the first rotation direction when the rotation actuator is rotated in a first rotation actuator direction, and rotate the shaft in the second rotation direction when the rotation actuator is rotated in a second rotation actuator direction which is opposite the first rotation actuator direction. The handle further comprises an articulation actuator comprising a second initial position. The articulation actuator is rotatable about a longitudinal axis extending toward the distal end. The articulation actuator is configured to rotate the stapling assembly in the first articulation direction when the articulation actuator is rotated in a first articulation actuator direction, and rotate the stapling assembly in the second articulation direction when the articulation actuator is rotated in a second articulation actuator direction which is opposite the first articulation actuator direction. The handle further comprises means for preventing the articulation of the stapling assembly and the rotation of the shaft when the firing actuator is being actuated. The means is independent from the closure member.

This Summary is intended to briefly outline certain embodiments of the subject application. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 51A is a cross-sectional view of the distal portion of the elongate shaft and the movable firing bar illustrating an array of electromagnets positioned within the elongate shaft;

FIG. 51B is a cross-sectional view of the middle portion of the elongate shaft and the movable firing bar of FIG. 51A illustrating permanent magnets mounted to the firing bar and electromagnets positioned within the shaft;

FIG. 51C is a cross-sectional view of the proximal portion of the elongate shaft and the movable firing bar of FIG. 51A;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The disclosures of the following commonly-owned, U.S. Patent Applications filed on Feb. 5, 2009, are incorporated herein by reference in their entirety:

(1) U.S. patent application Ser. No. 12/366,514, entitled SURGICAL STAPLING INSTRUMENT COMPRISING AN ARTICULATION JOINT, now U.S. Pat. No. 8,485,413; and (2) U.S. patent application Ser. No. 12/366,539, entitled SURGICAL STAPLING INSTRUMENT, now U.S. Patent Application Publication No. 2010/0193566.

Figure 1A:
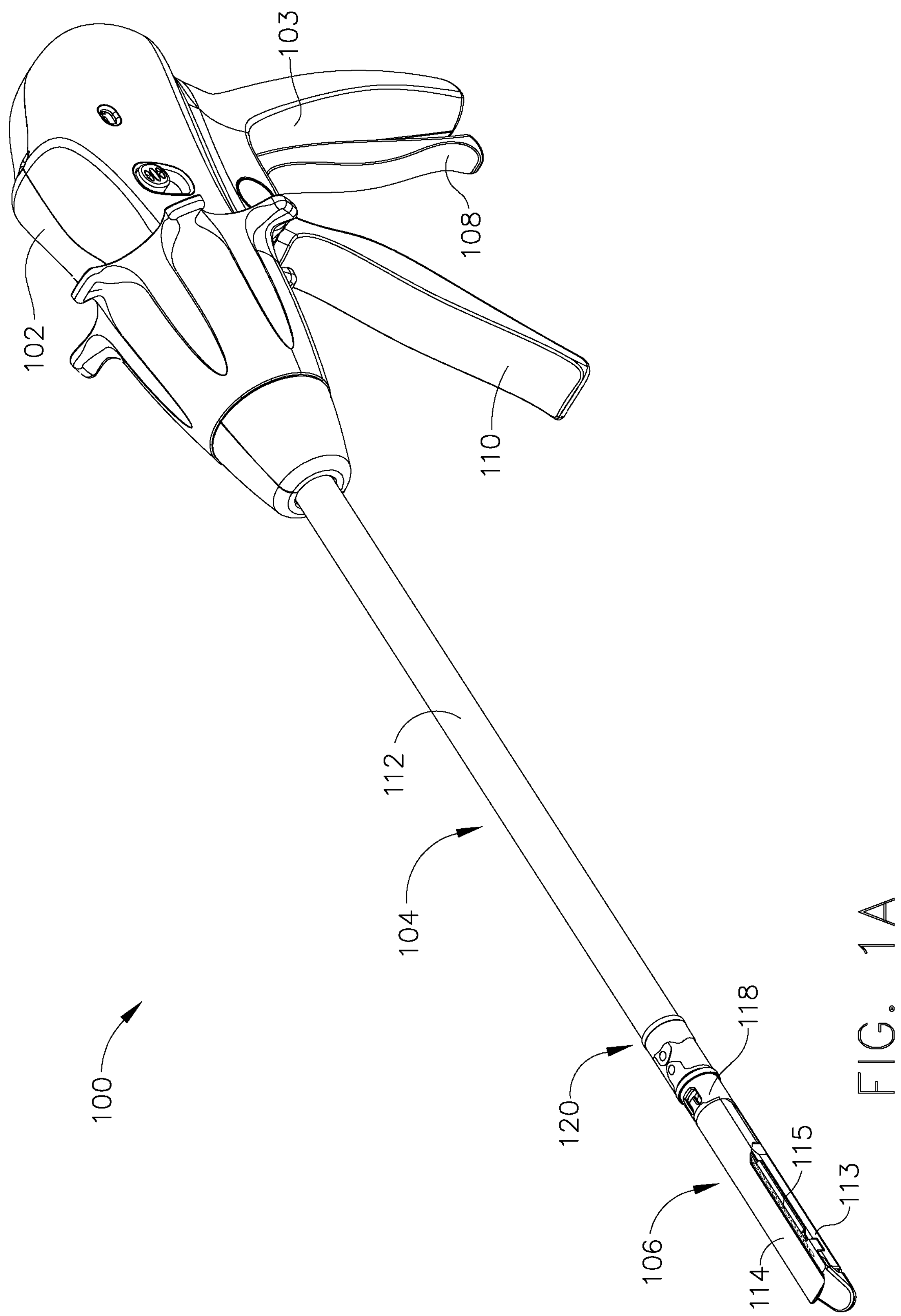
FIG. 1A is a perspective view of a surgical stapling instrument comprising a handle assembly, an elongate shaft extending from the handle assembly, and an articulatable end effector extending from the elongate shaft.
Figure 1B:
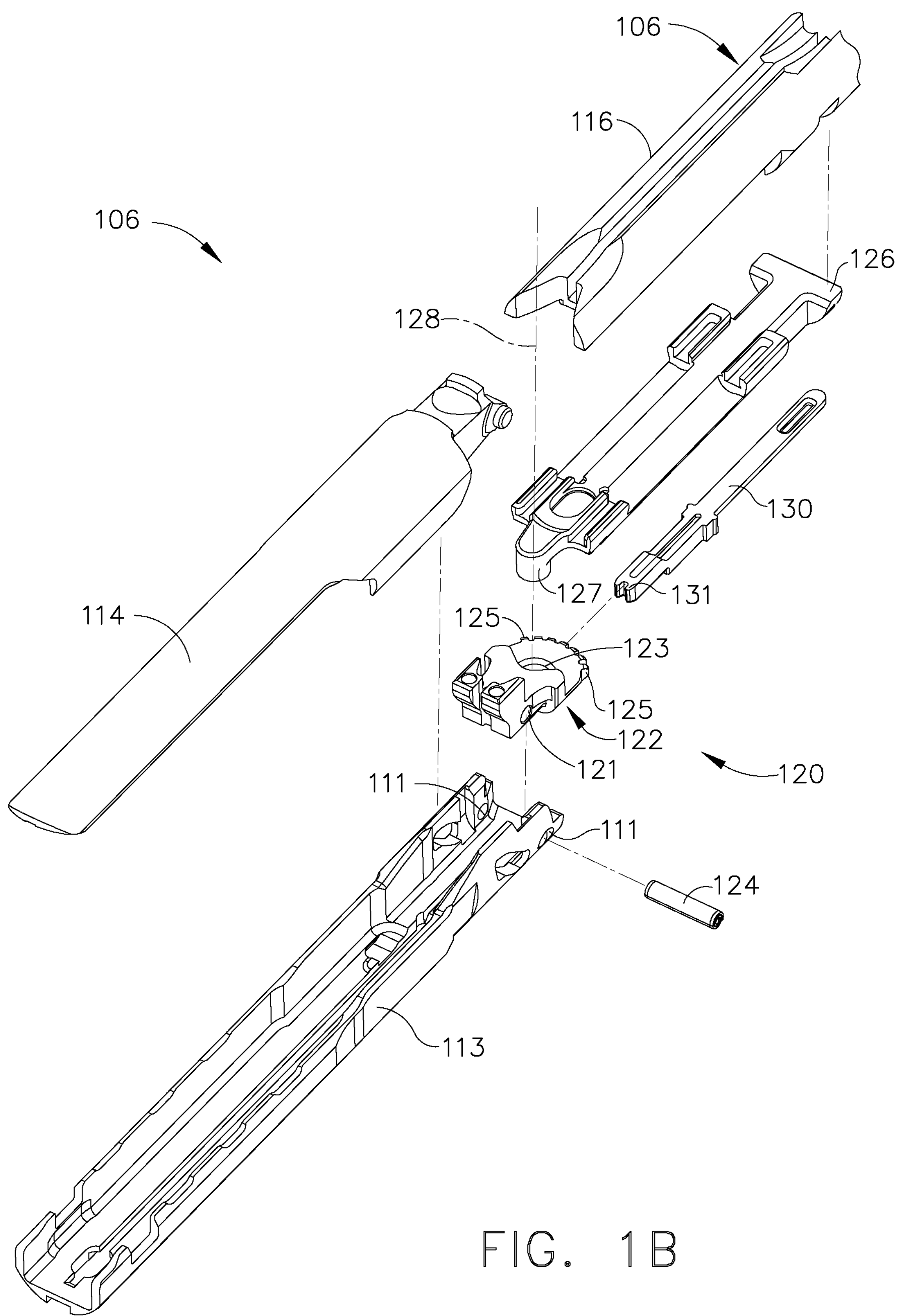
FIG. 1B is an exploded view of the end effector of the surgical instrument of FIG. 1.

In various embodiments, referring to FIGS. 1A and 1B, a surgical instrument, such as surgical instrument 100, for example, can comprise a handle assembly 102, an elongate shaft 104 extending from handle assembly 102, and an end effector 106 which can be moved, or articulated, relative to elongate shaft 104 as described in greater detail further below. In at least one embodiment, handle assembly 102 can comprise a closure trigger 108 which can be configured to open and close end effector 106. More particularly, end effector 106 can comprise anvil 114 and, in addition, elongate shaft 104 can comprise closure tube 112 wherein the actuation of closure trigger 108 can displace closure tube 112 longitudinally in order to rotate anvil 114 between opened and closed positions relative to staple cartridge channel 113 and staple cartridge 115. In at least one embodiment, closure tube 112 can be configured to slide relative to a stationary portion of elongate shaft 104, such as spine 116 (FIG. 1B), for example. In certain embodiments, end effector 106 can further comprise a tube portion, such as distal tube portion 118, for example, which can be displaced by closure tube 112 in order open and/or close anvil 114. In at least one embodiment, surgical instrument 100 can further comprise one or more pivot links 211 (FIGS. 2 and 3) which can be configured to connect closure tube 112 to distal tube portion 118 and permit distal tube portion 118 to articulate relative to closure tube 112 when end effector 106 articulates relative to elongate shaft 104. In any event, once anvil 114 has been closed, firing trigger 110 of handle assembly 112 can be actuated to move a cutting and/or stapling member through end effector 106 in order to incise and/or staple tissue captured within end effector 106. After the tissue has been sufficiently incised and/or stapled, closure trigger 108 can be released in order to move closure tube 112 in an opposite longitudinal direction and open anvil 114. Other surgical instruments are disclosed in U.S. Pat. No. 7,441,685, entitled SURGICAL STAPLING INSTRUMENT WITH A RETURN MECHANISM, which issued on Oct. 28, 2008, the entire disclosure of which is hereby incorporated by reference herein. Further surgical instruments are disclosed in U.S. patent application Ser. No. 12/008,303, entitled SURGICAL STAPLING INSTRUMENT WITH A GEARED RETURN MECHANISM, which was filed on Jan. 10, 2008, now U.S. Pat. No. 7,658,311, and U.S. patent application Ser. No. 12/008,266, entitled SURGICAL STAPLING INSTRUMENT WITH A FIRING MEMBER RETURN MECHANISM, which was filed on Jan. 10, 2008, now U.S. Pat. No. 7,954,684, the entire disclosures of which are hereby incorporated by reference herein.

In various embodiments, referring once again to FIGS. 1A and 1B, a surgical instrument can further comprise an articulation joint, such as articulation joint 120, for example, which can be configured to permit end effector 106 to move relative to elongate shaft 104. In at least one embodiment, end effector 106 can further comprise a pivot plate 122 which can be retained within staple cartridge channel 113 by channel pin 124. As illustrated in FIG. 1B, channel pin 124 can be inserted, press-fit, and/or snap-fit into and/or through apertures 111 in cartridge channel 113 and aperture 121 in pivot plate 122 in order to secure pivot plate 122 to cartridge channel 113. In certain embodiments, pivot plate 122 can be immovably retained within staple cartridge channel 113. Further to the above, elongate shaft 104 can further comprise pin insert plate 126 which can be secured in position by spine 116 wherein, in at least one embodiment, pin insert plate 126 can be immovably retained within elongate shaft 104. Referring primarily to FIG. 1B, pivot plate 122 can further comprise pin aperture 123 which can be configured to receive articulation pin 127 extending from pin insert plate 126. In various embodiments, pin 127 and pin aperture 123 can be sized and configured to define an axis, such as axis 128, for example, about which staple cartridge channel 113 and pivot plate 122 can rotate relative to pin insert plate 126. As a result of the above, end effector 106 can be articulated relative to elongate shaft 104 in order to suitably position end effector 106 within a surgical site, for example. Once suitably positioned, end effector 106 can be locked in position relative to shaft 104. In certain embodiments, elongate shaft 104 can further comprise a lock or brake, such as lock 130, for example, which can be configured to selectively engage pivot plate 122, for example, and hold it in position relative to pin insert plate 126. In at least one such embodiment, pivot plate 122 can include one or more teeth 125 which can be captured within, or meshed with, one or more grooves 131 in the distal end of lock 130 such that relative movement between teeth 125 and grooves 131 is prevented, or at least limited.

In use, lock 130 can be disengaged from pivot plate 122 such that end effector 106 can be rotated relative to elongate shaft 104. Once lock 130 has been disengaged from pivot plate 122, in at least one such embodiment, end effector 106 can be placed against a cavity wall within a surgical site, such as the peritoneal cavity wall, for example, and a longitudinal force can be applied to shaft 104 via handle assembly 102 in order to rotate end effector 106 relative to elongate shaft 104. In certain circumstances, such articulation can be referred to as passive articulation. In any event, once end effector 106 has been suitably articulated, lock 130 can be re-engaged with pivot plate 122 and closure tube 112 can be advanced longitudinally by trigger 108 in order to close anvil 114 as described above. The reader will note that, when end effector 106 is moved between a straight position, i.e., a position in which it is aligned or at least substantially aligned with elongate shaft 104, and an articulated position, distal tube portion 118 can be moved between a first angle with respect to closure tube 112 and a second, or different, angle with respect to closure tube 112. In order to accommodate such relative movement, referring to FIGS. 2 and 3, pivot links 211 can be pivotably connected to distal tube portion 118 and closure tube 112 via pin projections 109 extending from pivot links 211 and via apertures 107 within tube portion 118 and closure tube 112. Pin projections 109 and pin apertures 107 can be configured such that pivot links 211 can provide at least one degree of freedom between distal tube portion 118 and closure tube 112. In such embodiments, pivot links 211 can permit distal tube 118 to articulate relative to closure tube 112 eventhough at least a portion of closure tube 112 has been advanced distally past articulation joint 120. In any event, once anvil 114 has been suitably closed, trigger 110 can be actuated to advance a firing bar distally into end effector 106. Although a firing bar is not illustrated in FIGS. 1A and 1B, surgical instrument 200, referring to FIGS. 2-4, includes a suitable firing bar 250 and cutting member 252 which can be configured to be advanced into and/or within end effector 106. In at least one embodiment, the elongate shaft and/or end effector of surgical instrument 100, for example, can include one or more slots configured for receiving and/or guiding firing bar 250 and/or cutting member 252 when they are advanced and/or retracted within the shaft and/or end effector of surgical instrument 100.

Figure 2:
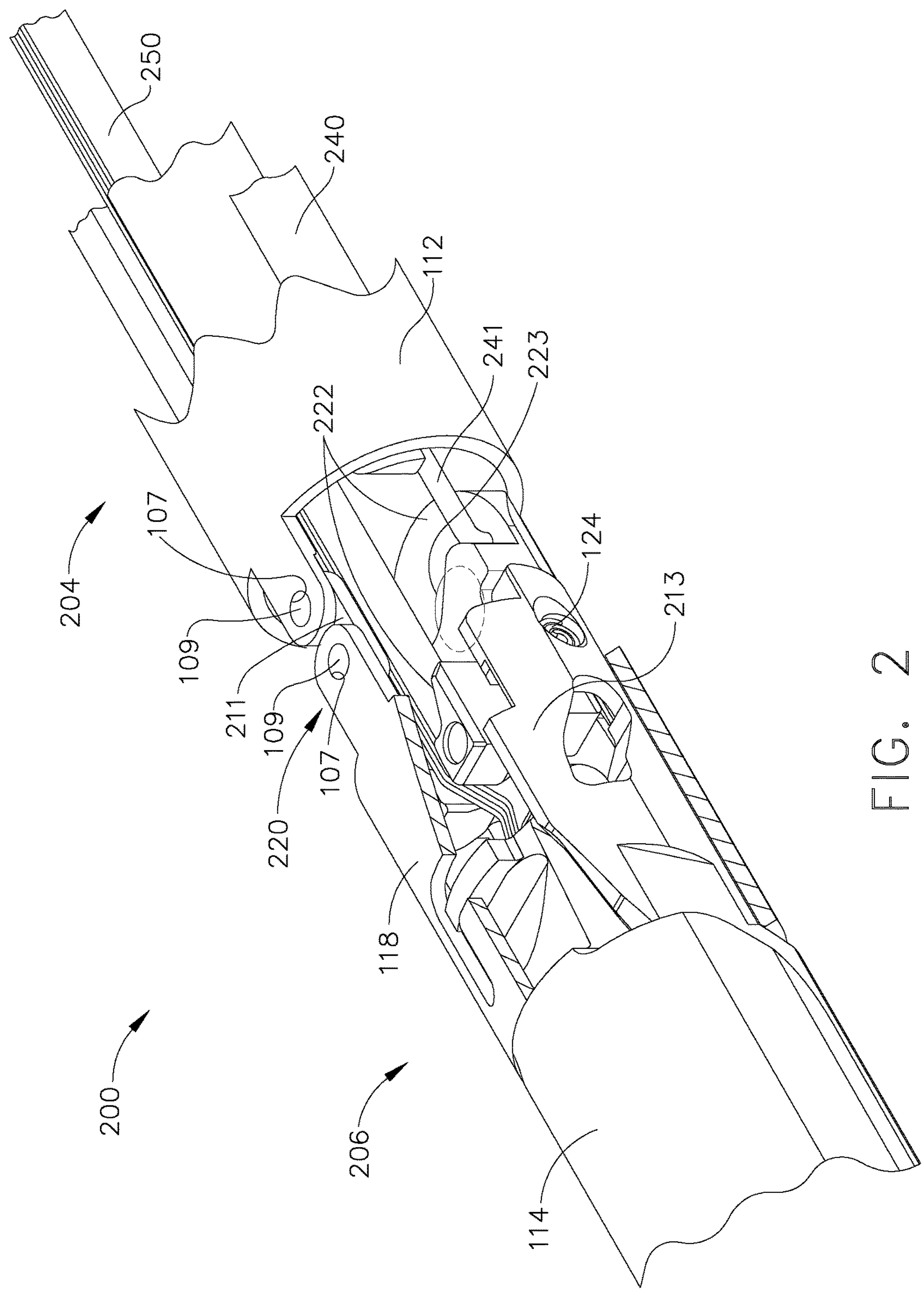
FIG. 2 is a perspective view of an articulation joint connecting an end effector and an elongate shaft of a surgical instrument in accordance with at least one embodiment of the present invention, the articulation joint being illustrated with some components removed.
Figure 3:
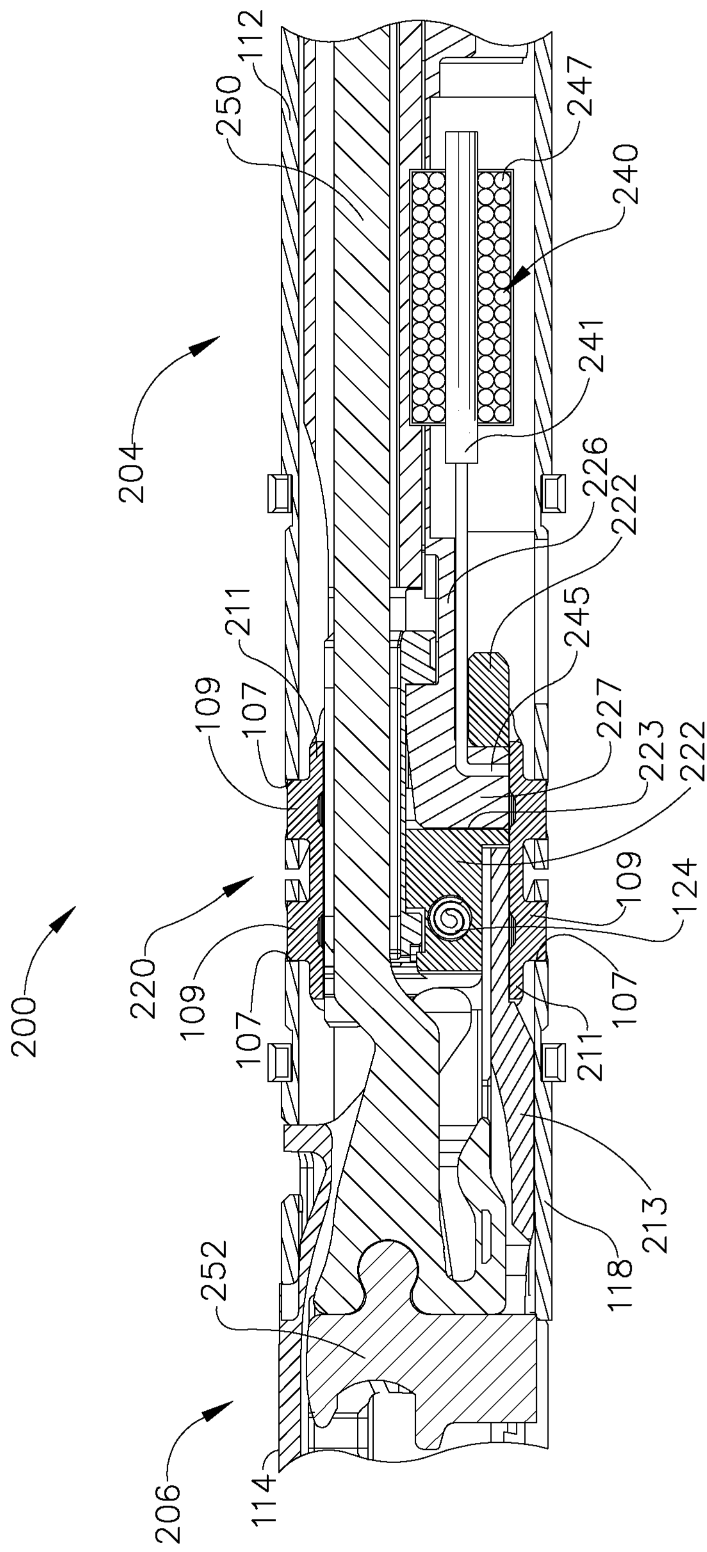
FIG. 3 is across-sectional view of the end effector of FIG. 2 illustrating a solenoid positioned within the elongate shaft of the surgical instrument, wherein the solenoid is configured to articulate the end effector.
Figure 4:
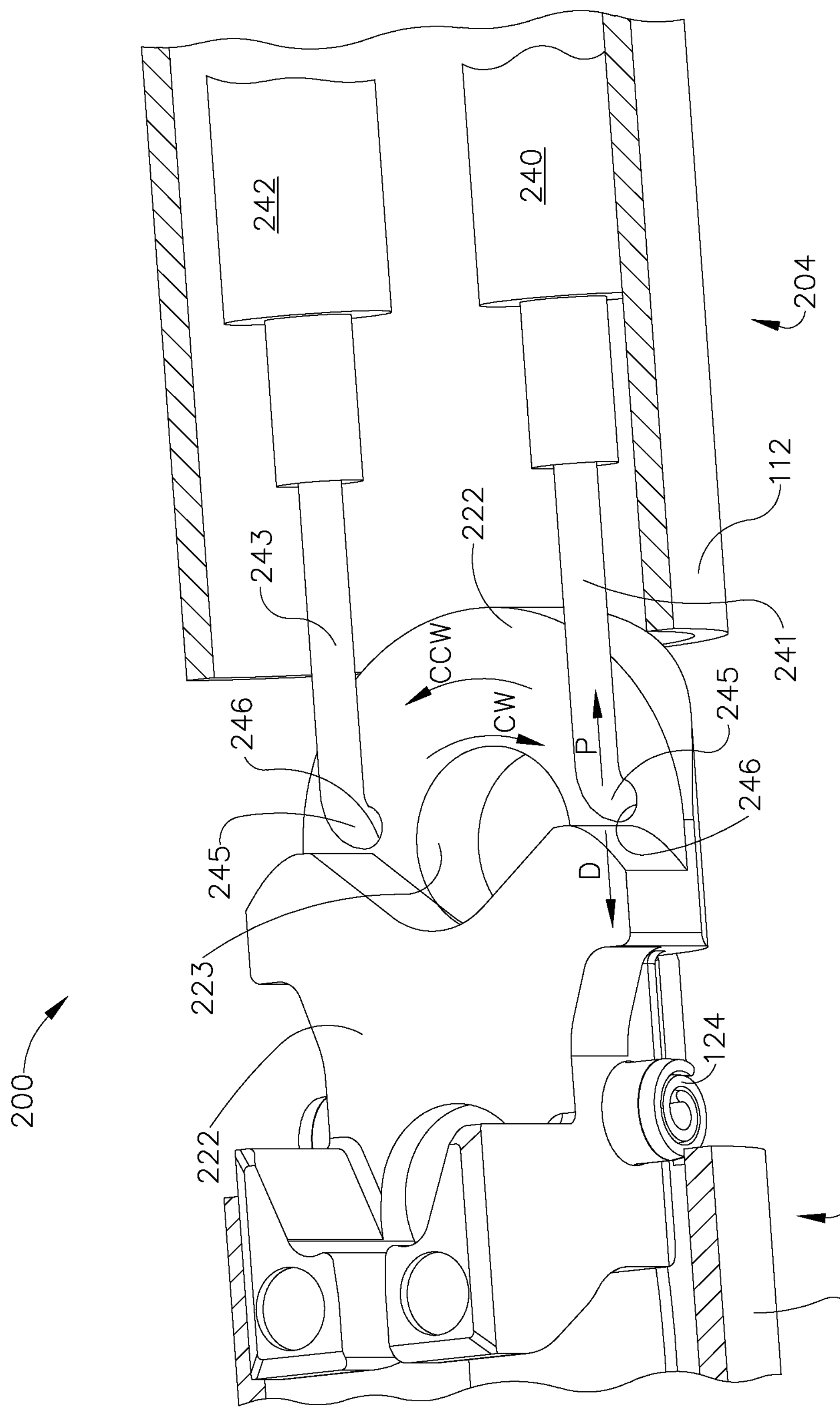
FIG. 4 is a partial perspective view of the end effector, articulation joint, and elongate shaft of FIG. 2 illustrated with some components removed.

In various embodiments, referring to FIGS. 2-4, a surgical instrument, such as surgical instrument 200, for example, can include an elongate shaft 204 and an end effector 206, wherein end effector 206 can be configured to articulate relative to elongate shaft 204 about articulation joint 220. Similar to surgical instrument 100, end effector 206 can comprise a pivot plate 222 retained within a staple cartridge channel 213, wherein pivot plate 222 can comprise a pin aperture 223 configured to receive articulation pin 227 extending from pin insert plate 226. In various embodiments, referring primarily to FIG. 4, elongate shaft 204 can further comprise one or more actuators which can be configured to rotate, or pivot, end effector 206 relative to shaft 204. In at least one such embodiment, elongate shaft 204 can further comprise first solenoid 240 and second solenoid 242 mounted therein which can be operably engaged with pivot plate 222 such that the actuation of first solenoid 240 and/or second solenoid 242 can rotate pivot plate 222 about an axis, for example. In certain embodiments, first solenoid 240 can comprise a piston and/or rod 241 sufficiently mounted to pivot plate 222 such that pivot plate 222 can be pushed distally and/or pulled proximally by first solenoid 240 in order to rotate end effector 206 in clockwise (CW) and/or counter-clockwise (CCW) directions. In certain circumstances, such articulation can be referred to as active articulation.

In various embodiments, further to the above, rod 241 can be advanced distally in a direction indicated by arrow "D" in order to rotate end effector 206 in a clockwise direction indicated by arrow "CW". In order to rotate end effector 206 in a counter-clockwise direction indicated by arrow "CCW", rod 241 can be retracted proximally in a direction indicated by arrow "P". In certain embodiments, rod 241 can include a distal end 245 which can be positioned within an aperture 246 in pivot plate 222 such that rod 241 can pivot relative pivot plate 222. In at least one embodiment, rod 241 can be suitably flexible to accommodate relative movement between pivot plate 222 and solenoid 240. In certain embodiments, solenoid 240 can be slidably and/or rotatably mounted within elongate shaft 204 such that rod 241 does not unsuitably bend or bind when it is extended or retracted to drive pivot plate 222 about an axis. In any event, referring to FIG. 3, solenoid 240 can include coils or windings 247 which can be energized by an electrical current and/or voltage in order to create a sufficient magnetic field to move rod 241 in a distal and/or proximal direction, depending on the direction in which the current is flowing through, and/or the polarity of the voltage applied to, the windings. In at least one such embodiment, piston and/or rod 241 can comprise an iron core, for example, which can be configured to interact with the magnetic field produced by the solenoid windings 247.

In certain embodiments, further to the above, elongate shaft 204 can include at least one additional solenoid, such as solenoid 242, for example, which can be configured to rotate pivot plate 222 contemporaneously with, and/or independently of, solenoid 240. In at least one such embodiment, solenoid 242 can comprise a piston and/or rod 243 which can be advanced distally and/or proximally in order to rotate end effector 206 in a clockwise and/or clockwise direction. Conversely to solenoid 240, rod 243 can be extended distally to rotate pivot plate 222 in a counter-clockwise direction and/or retracted proximally to rotate pivot plate 222 in a clockwise direction. Similar to solenoid 240, rod 243 can include a distal end 245 which can be pivotably mounted within an aperture 246 in pivot plate 222. Also similar to solenoid 240, solenoid 242 can be rotatably and/or slidably mounted within elongate shaft 204 in order to add at least one degree of freedom to a system of linkages comprising pivot plate 222, pin insert plate 226, solenoid 242, and rod 243 in order to permit articulation between end effector 206 and shaft 204.

Figure 5:
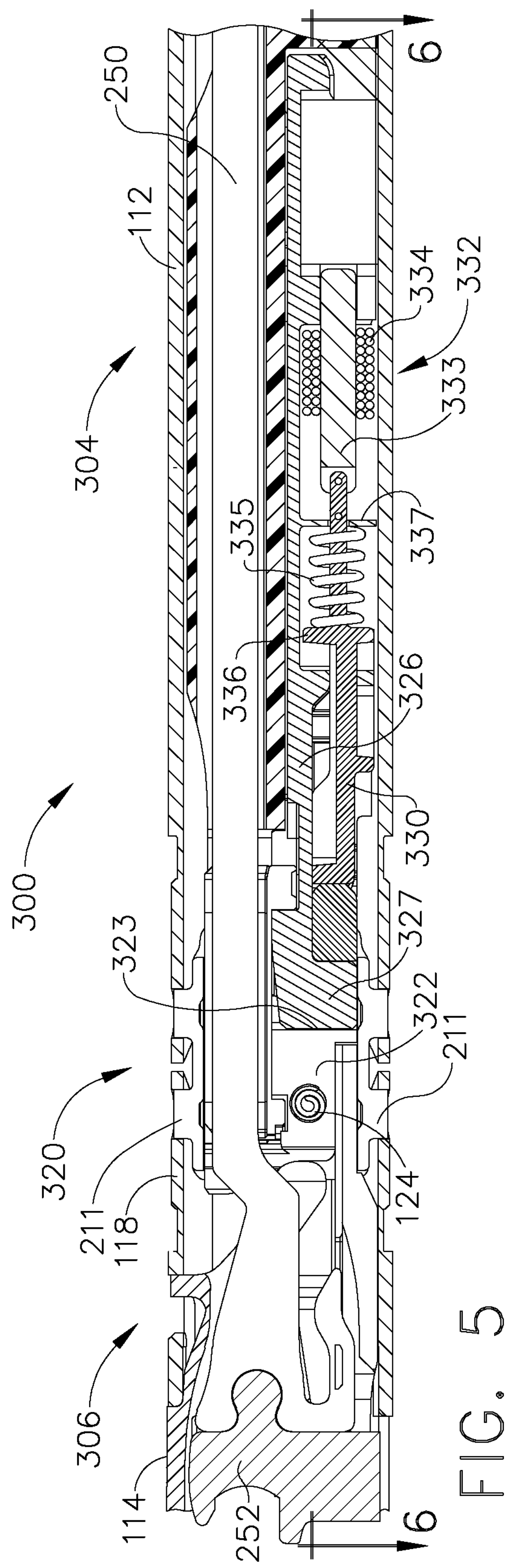
FIG. 5 is a side cross-sectional view of an articulation joint connecting an end effector and an elongate shaft of a surgical instrument in accordance with at least one embodiment of the present invention.
Figure 6:
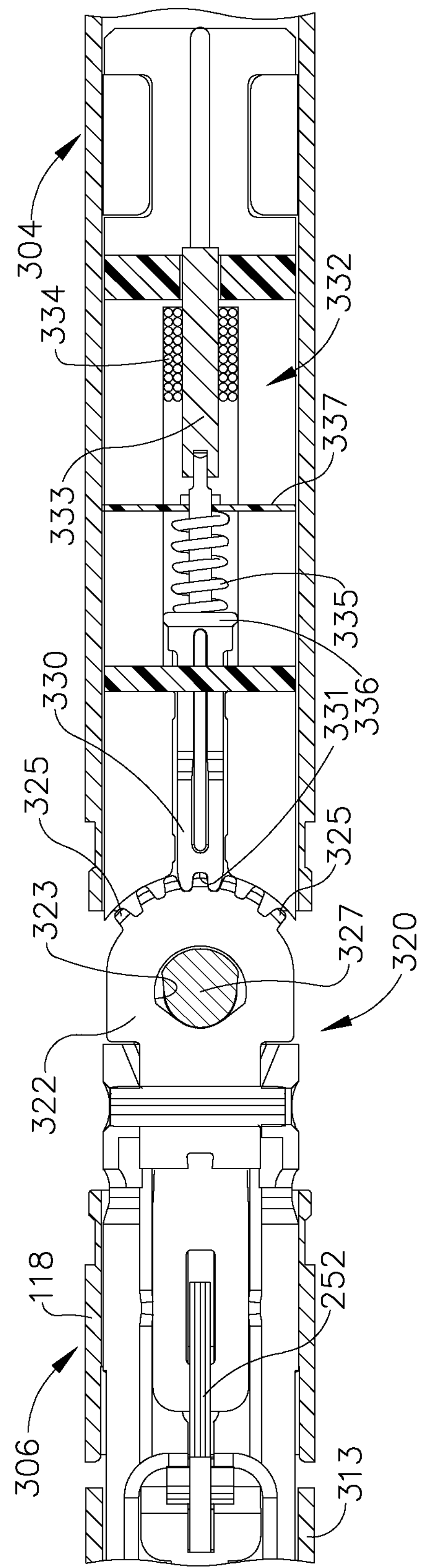
FIG. 6 is a bottom cross-sectional view of the surgical instrument of FIG. 5 taken along line 6-6 in FIG. 5 illustrating a solenoid-driven articulation lock.

As described above, an end effector of a surgical instrument can be locked into position once the end effector has been suitably articulated. In various embodiments, referring to FIGS. 5 and 6, a surgical instrument, such as surgical instrument 300, for example, can include an elongate shaft 304 and an end effector 306, wherein end effector 306 can be configured to articulate relative to elongate shaft 304 about articulation joint 320. Similar to surgical instrument 100, end effector 306 can comprise a pivot plate 322 retained within a staple cartridge channel 313, wherein pivot plate 322 can comprise a pin aperture 323 configured to receive articulation pin 327 extending from a pin insert plate 326 retained within elongate shaft 304. In certain embodiments, elongate shaft 304 can further comprise a lock, or brake, and a lock actuator which can be configured to engage the lock with pivot plate 322 and, as a result, hold pivot plate 322 in position relative to elongate shaft 304. In at least one embodiment, elongate shaft 304 can comprise lock actuator 332 which can be configured to move lock 330 distally to engage lock 330 with plate 322 and/or move lock 330 proximally to disengage lock 330 from plate 322. In at least one such embodiment, lock actuator 332 can comprise a solenoid mounted within elongate shaft 304 wherein the solenoid can comprise a piston and/or rod 333 which can be extended distally and/or retracted proximally by coils or windings 334. In certain embodiments, lock 330 can be mounted to rod 333 such that the displacement of rod 333 can displace lock 330 toward and/or away from pivot plate 322. Similar to the above, lock 330 can be biased into contact with pivot plate 322 such that groove 331 in the distal end of lock 330 can engage, or mesh with, a projection, or tooth, 325 extending from pivot plate 322. In at least one embodiment, lock actuator 332 can further comprise a biasing element, such as spring 335, for example, which can be configured to bias lock 330 into engagement with pivot plate 322. In at least one such embodiment, the solenoid of lock actuator 332 can overcome the biasing force applied by spring 335 in order to disengage lock 330 from pivot plate 322. In certain embodiments, spring 335 can be compressed between a flange 336 extending from lock 330 and a stationary, or at least substantially stationary, flange 337 in elongate shaft 306 such that spring 335 can apply a biasing force to lock 330. In at least one embodiment, spring 335 can comprise a linear spring wherein the force in which it applies can be proportional to the distance in which it is compressed.

Figure 7:
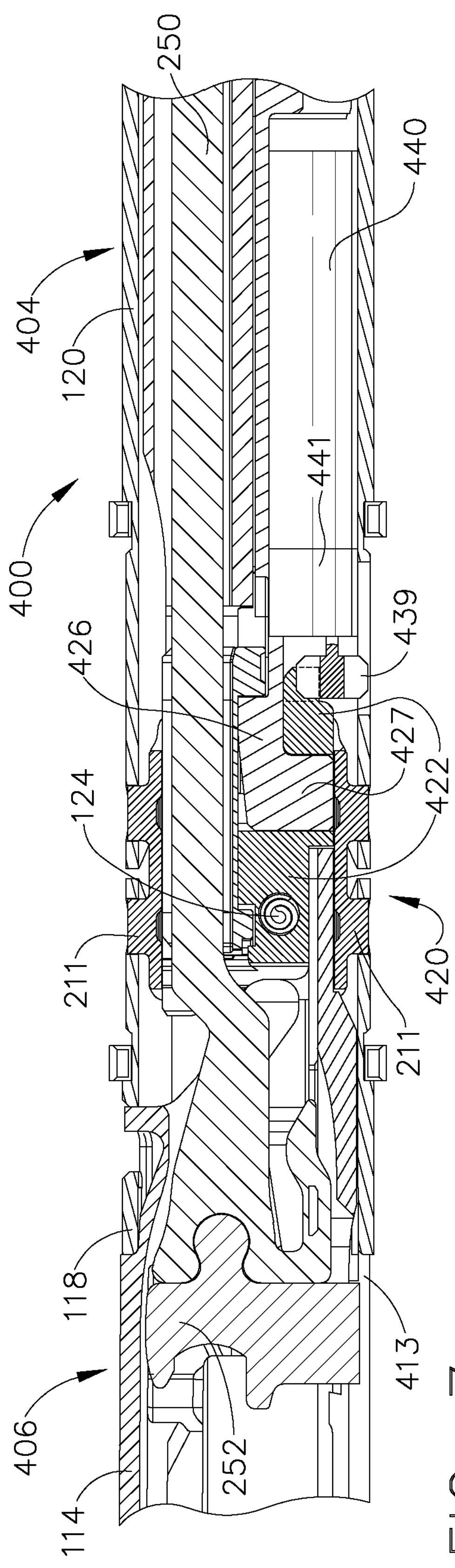
FIG. 7 is a cross-sectional view of an articulation joint connecting an end effector and an elongate shaft of a surgical instrument in accordance with at least one embodiment of the present invention.
Figure 8:
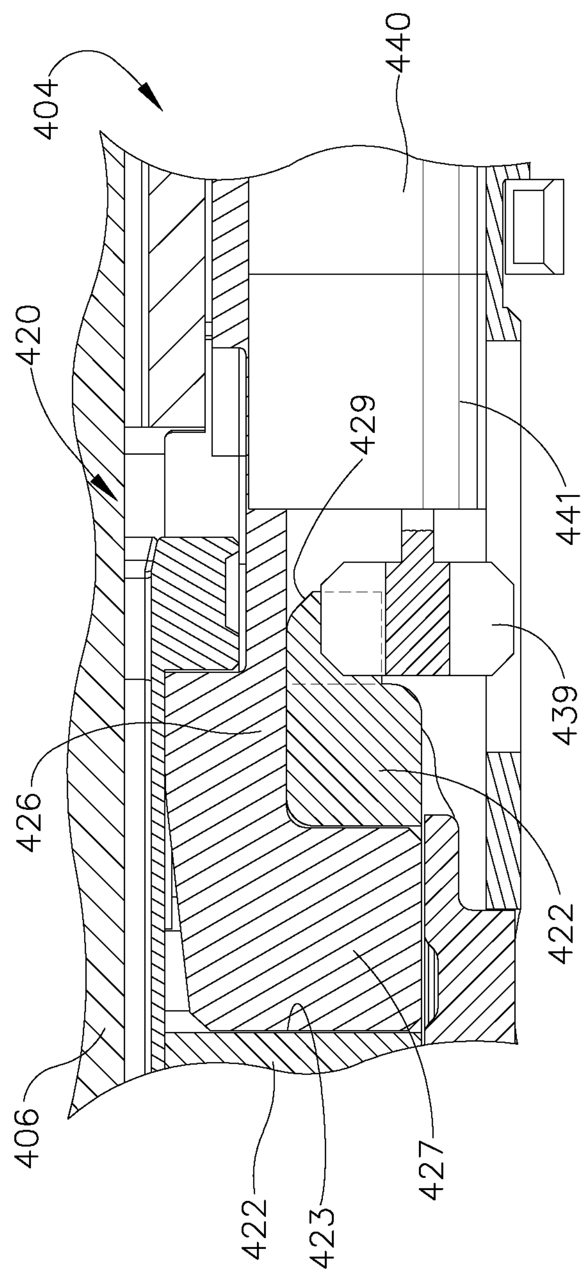
FIG. 8 is a detail view of the articulation joint of FIG. 7 illustrating a motor configured to articulate the end effector.
Figure 9:
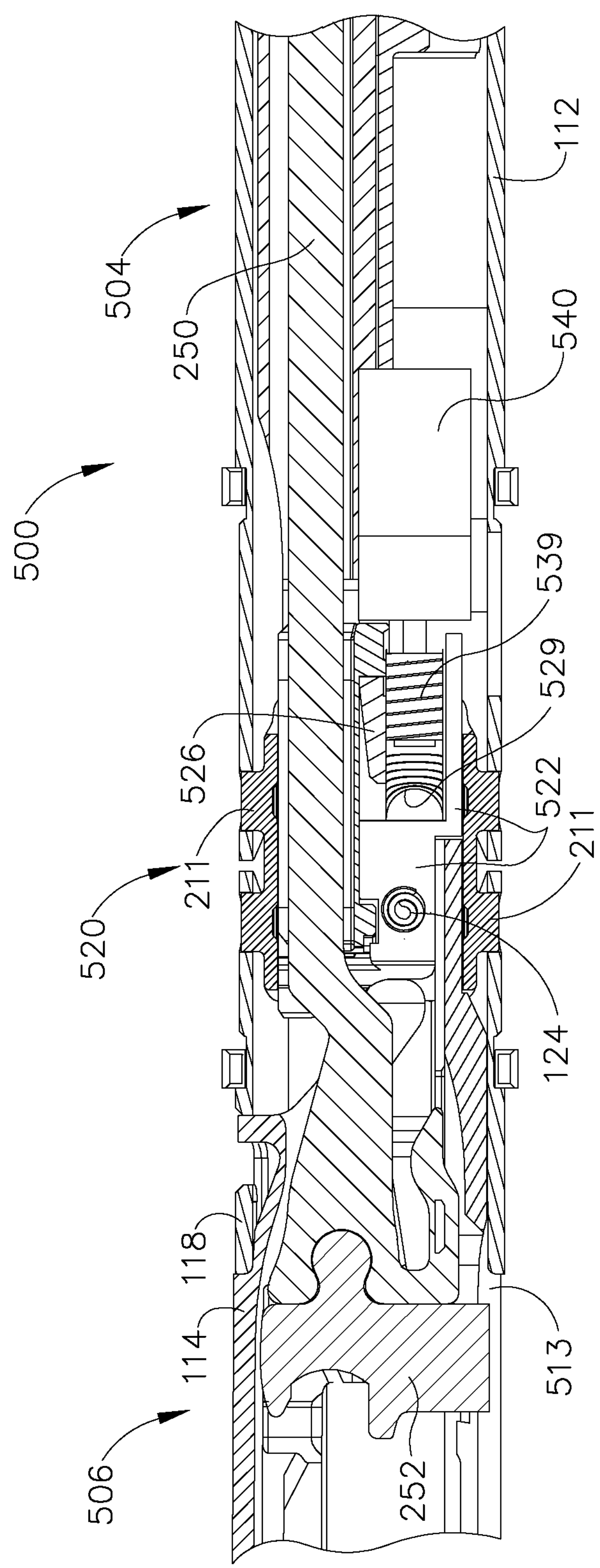
FIG. 9 is a cross-sectional view of an articulation joint connecting an end effector and an elongate shaft of a surgical instrument in accordance with at least one embodiment of the present invention.
Figure 10:
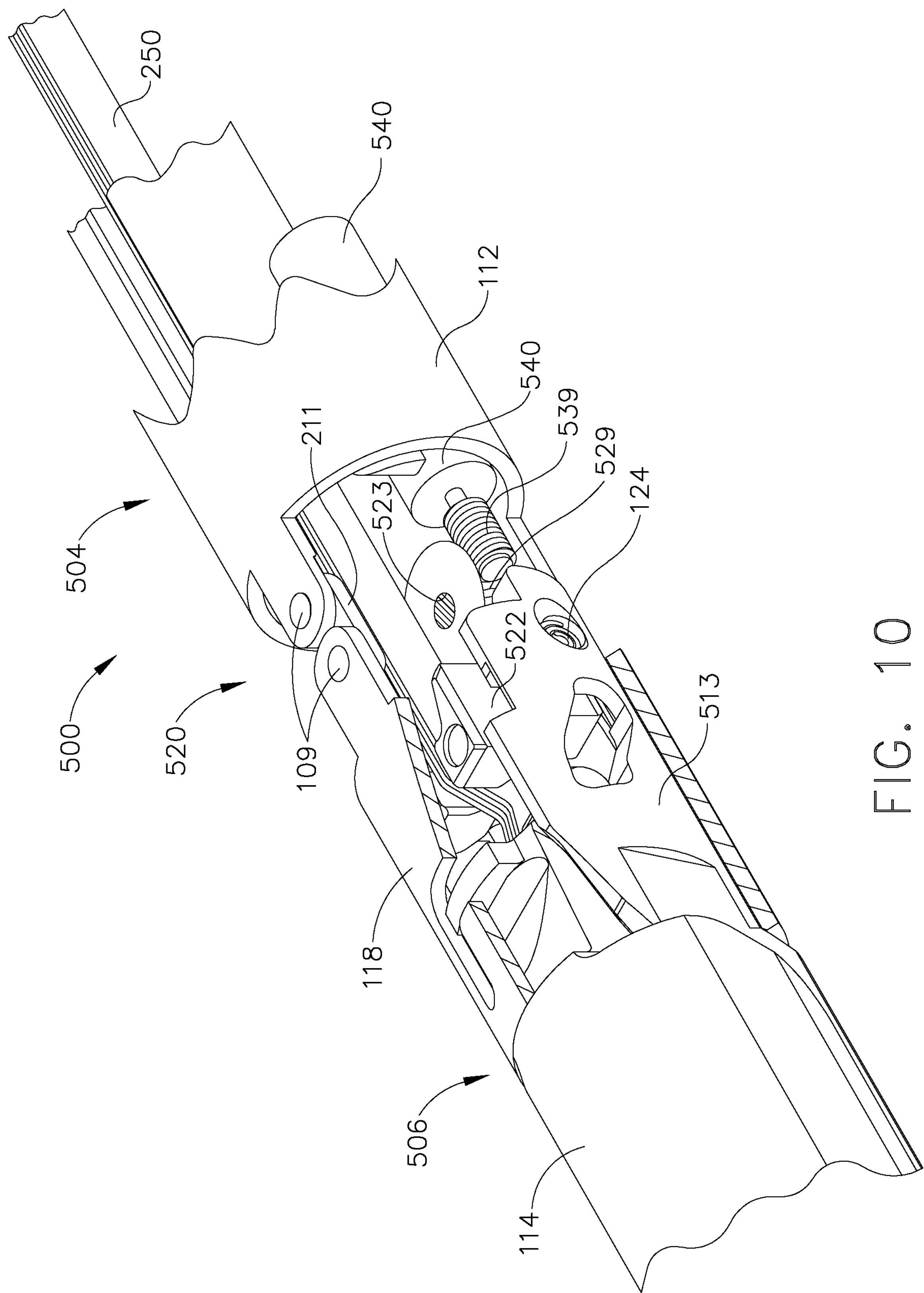
FIG. 10 is a partial perspective view of the end effector, the articulation joint, and the elongate shaft of FIG. 9 illustrating a motor operably engaged with a worm gear configured to articulate the end effector.
Figure 11:
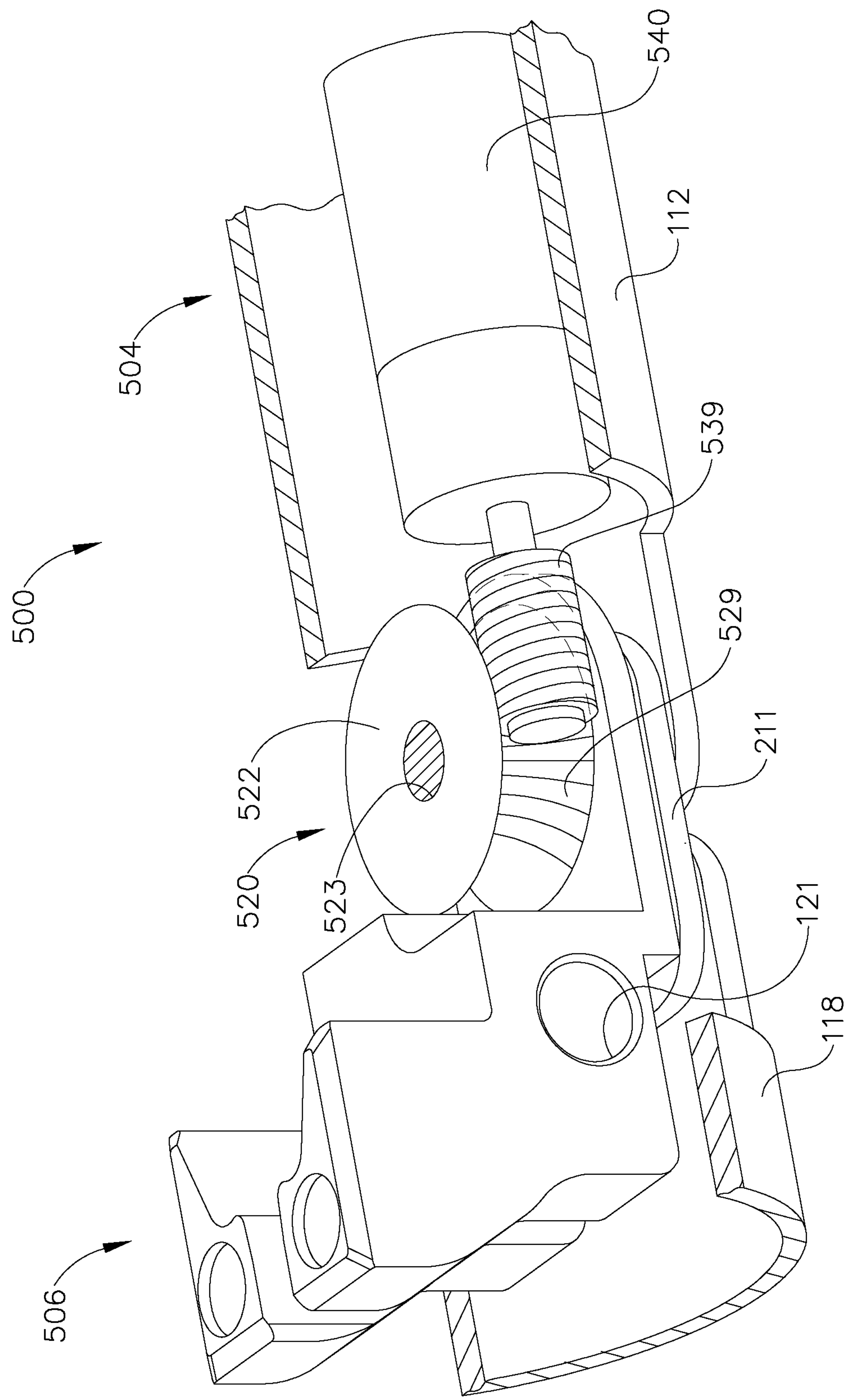
FIG. 11 is another partial perspective view of the end effector, the articulation joint, and the elongate shaft of FIG. 9 illustrated with some components removed.
Figure 12:
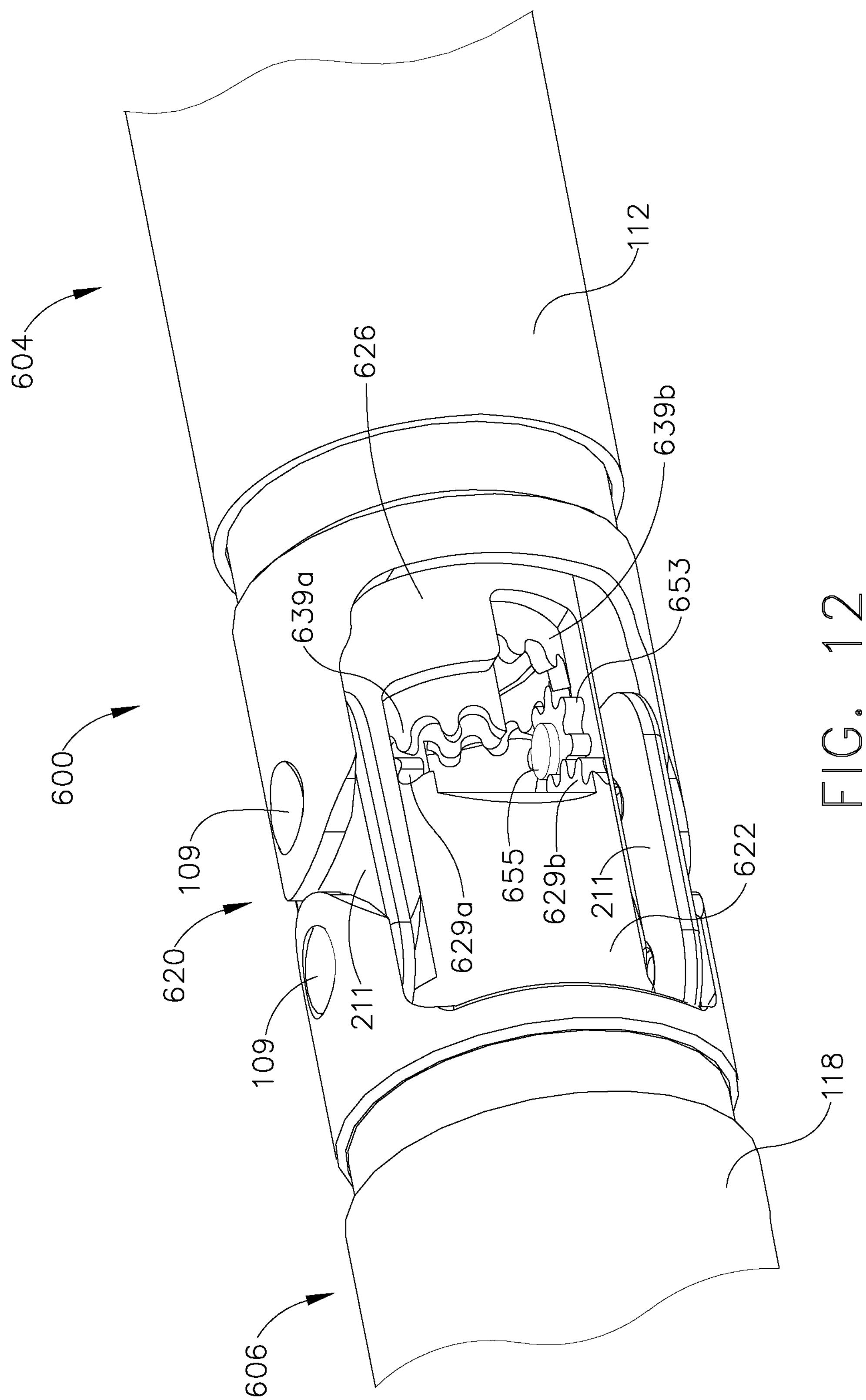
FIG. 12 is a partial perspective view of an articulation joint connecting an end effector and an elongate shaft of a surgical instrument in accordance with at least one embodiment of the present invention.
Figure 13:
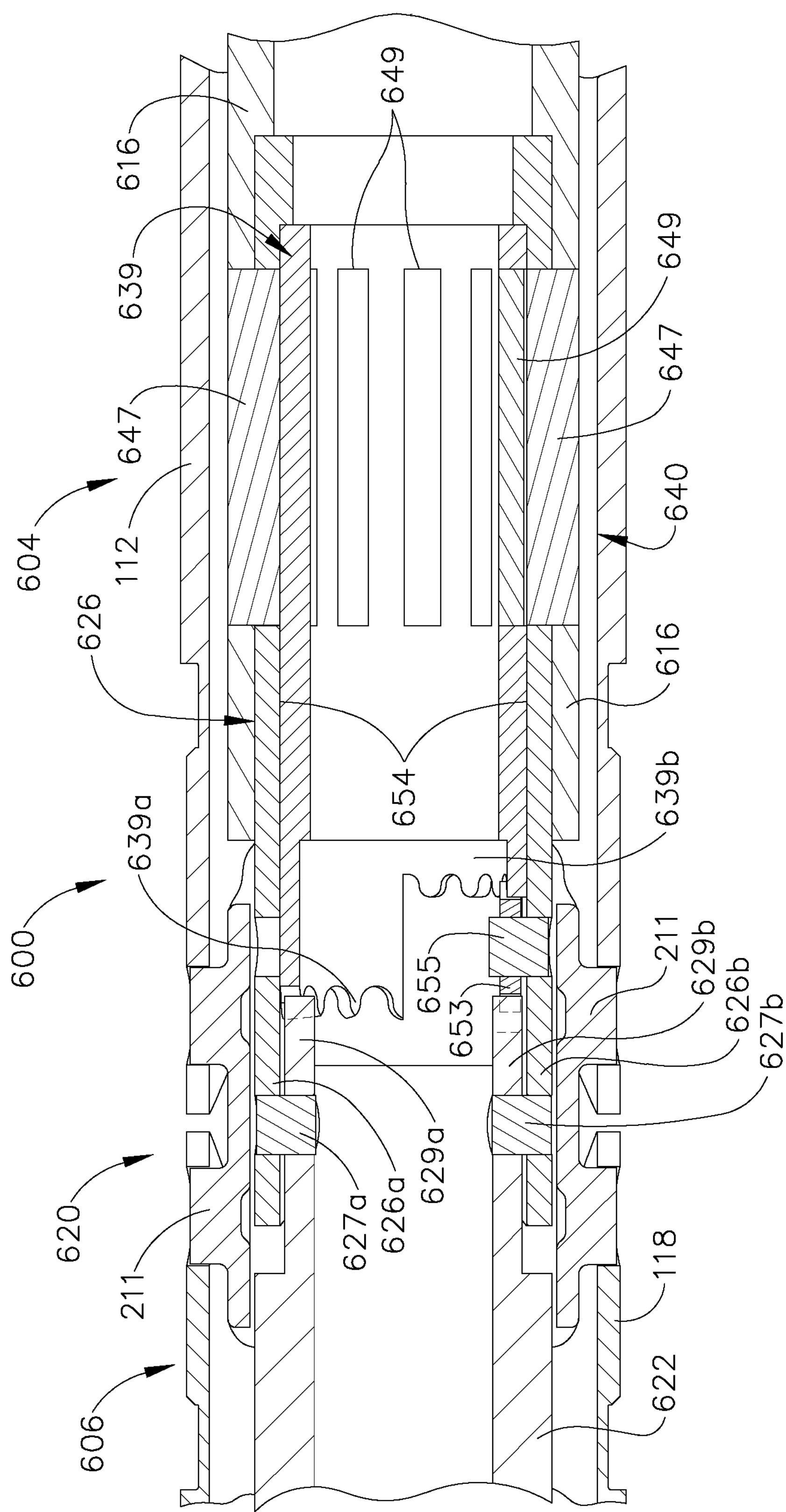
FIG. 13 is a cross-sectional view of the end effector, the articulation joint, and the elongate shaft of FIG. 12 illustrating a motor driven tube configured to articulate the end effector.
Figure 14:
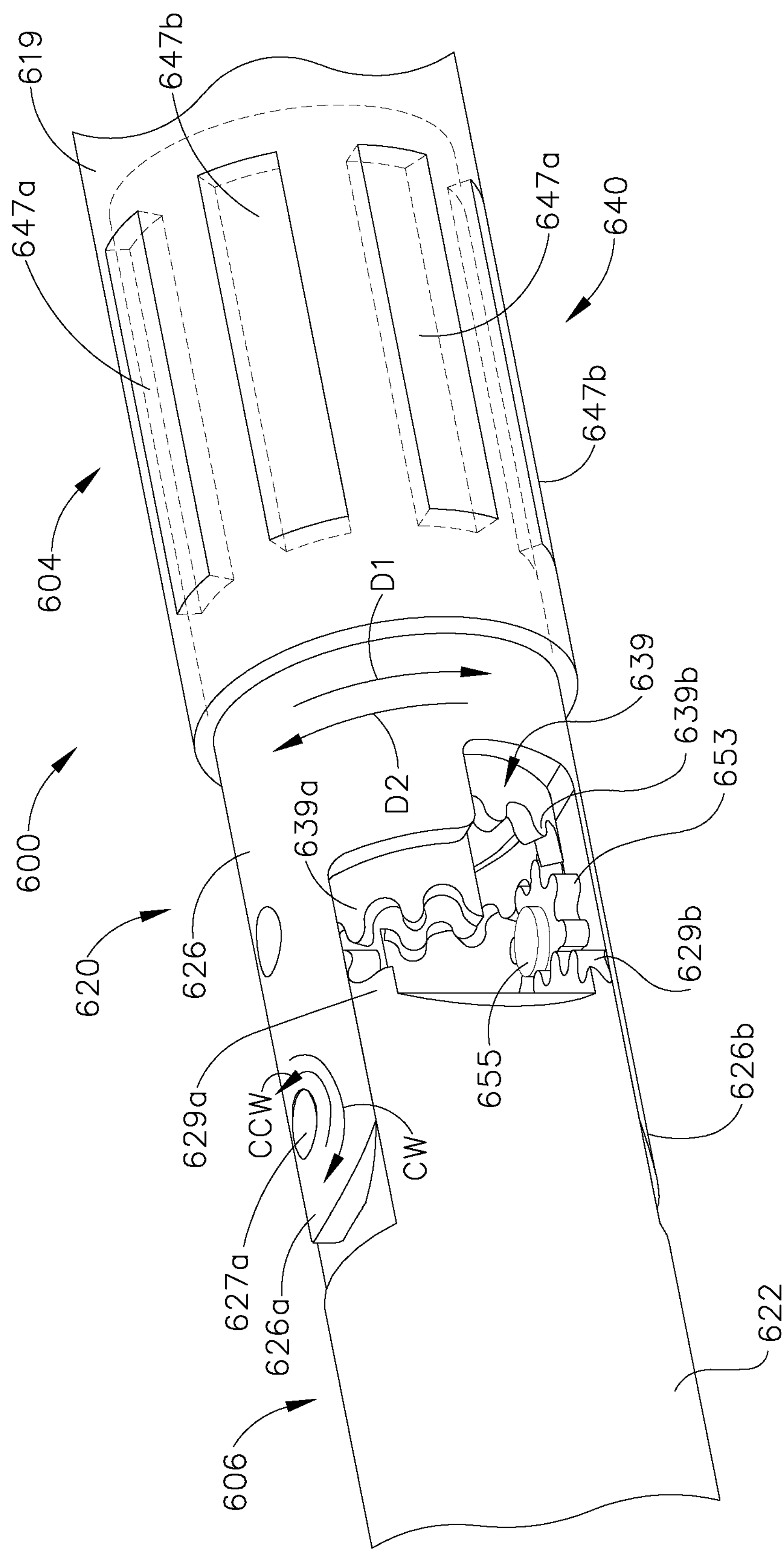
FIG. 14 is another partial perspective view of the end effector, the articulation joint, and the elongate shaft of FIG. 12 with some components removed and others illustrated in phantom lines.

In various embodiments, referring to FIGS. 7 and 8, a surgical instrument, such as surgical instrument 400, for example, can include one or more motors configured to articulate an end effector of the surgical instrument. In such embodiments, a motor can comprise an induction motor, a brushless DC motor, a stepper motor, and/or a synchronous motor, for example. In certain embodiments, surgical instrument 400 can comprise an elongate shaft 404 and an end effector 406, wherein end effector 406 can be configured to articulate relative to elongate shaft 404 about articulation joint 420. Similar to surgical instrument 100, end effector 406 can comprise a pivot plate 422 retained within a staple cartridge channel 413, wherein pivot plate 422 can comprise a pin aperture 423 configured to receive articulation pin 427 extending from a pin insert plate 426 retained within elongate shaft 404. In at least one embodiment, elongate shaft 404 can further comprise a motor, such as motor 440, for example, mounted therein which can be operably engaged with pivot plate 422 in order to rotate, or articulate, end effector 406 relative to shaft 404. More particularly, in at least one such embodiment, motor 440 can be configured to rotate a gear, such as spur gear 439, for example, which can be meshingly engaged with one or more teeth, such as teeth 429, for example, on pivot plate 422 such that the rotation of spur gear 439 can be transmitted to pivot plate 422. In at least one such embodiment, teeth 429 can be arranged in an at least partially annular array around the perimeter of pivot plate 422. In various embodiments, elongate shaft 404 can further comprise a gear box, such as gear box 441, for example, for reducing, and/or increasing, the gear ratio between an input shaft driven by motor 440 and an output shaft which drives spur gear 439.

Similar to the above, a surgical instrument, such as surgical instrument 500, for example, can include one or more motors configured to articulate an end effector of the surgical instrument using a worm drive arrangement. In various embodiments, surgical instrument 500 can comprise an elongate shaft 504 and an end effector 506, wherein end effector 506 can be configured to articulate relative to elongate shaft 504 about articulation joint 520. Similar to surgical instrument 400, end effector 506 can comprise a pivot plate 522 retained within a staple cartridge channel 513, wherein pivot plate 522 can comprise a pin aperture 523 configured to receive an articulation pin extending from a pin insert plate 526 retained within elongate shaft 504. In at least one embodiment, elongate shaft 504 can further comprise a motor, such as motor 540, for example, mounted therein which can be operably engaged with pivot plate 522 in order to rotate, or articulate, end effector 506 relative to shaft 504. More particularly, in at least one such embodiment, motor 540 can be configured to rotate a worm, such as worm 539, for example, which can be meshingly engaged with a worm gear, or concave worm wheel portion, 529 on pivot plate 522 such that the rotation of worm 539 can be transmitted to pivot plate 522. A worm drive arrangement, such as the one described above, for example, can provide a very large gear ratio such that a gear box is not required to reduce the speed of the motor, although a gear box can be used. In certain embodiments, a worm drive arrangement can be self-locking. More particularly, the lead angle of the helical thread on worm 539 can be such that end effector 506 and worm gear portion 529 cannot be rotated in order to drive worm 539 and motor 540 in reverse. Stated another way, worm gear portion 529 and worm 539 can be configured such that they are friction-locked together if a rotational force is applied to end effector 506. In certain embodiments, as a result, the articulation of end effector 506 relative to elongate shaft 504 can only be controlled by the selective rotation of worm 539 by motor 540 in clockwise and counter-clockwise directions in order to rotate end effector 506 in left and right directions, for example, about articulation joint 520. In at least one such embodiment, a separate articulation lock, such as those described above, for example, may not be required, although they can be used.

Figure 15:
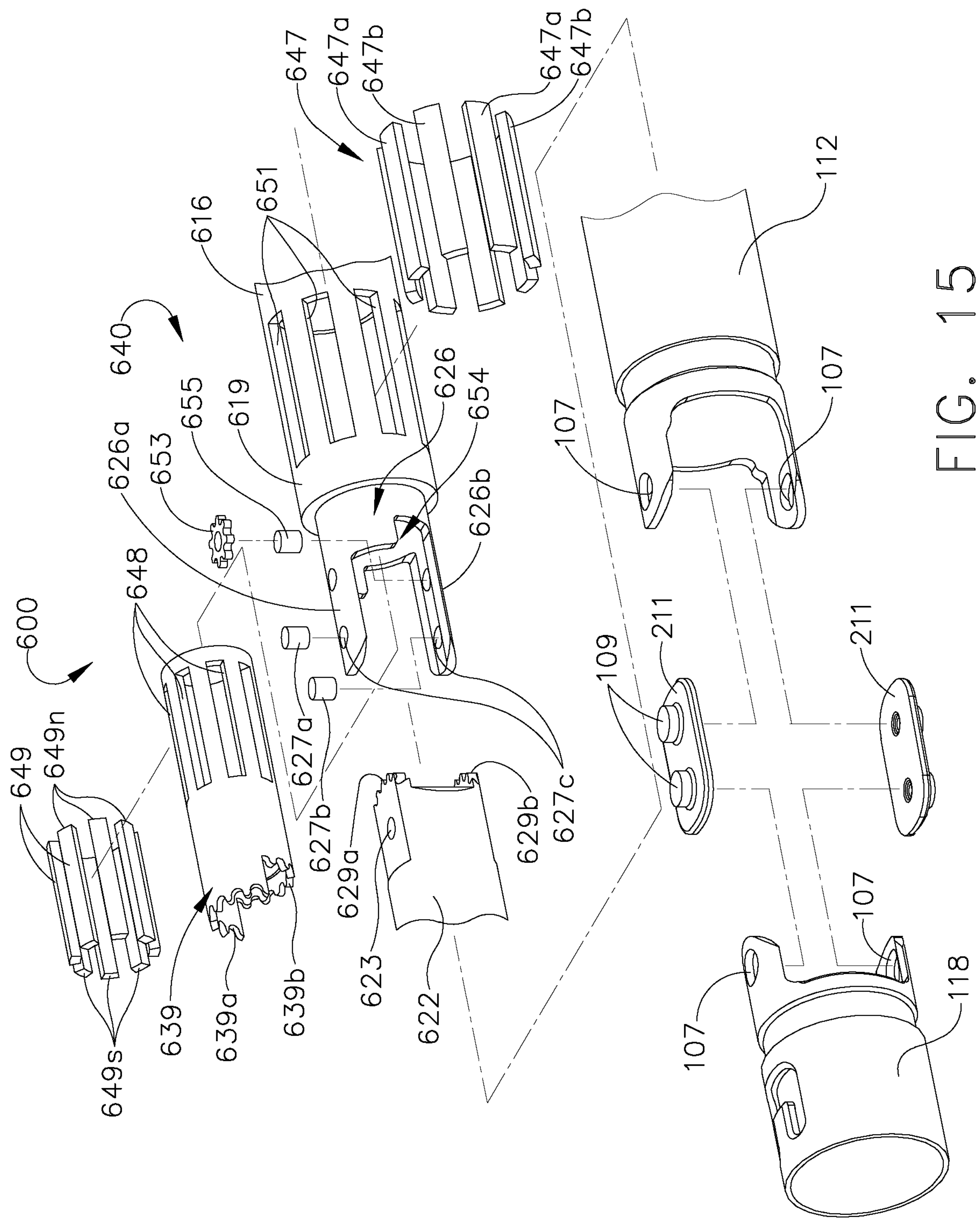
FIG. 15 is an exploded view of the articulation joint of FIG. 12.

In various embodiments, at least a portion of an elongate shaft of a surgical instrument, such as surgical instrument 600, for example, can comprise a motor configured to articulate an end effector of a surgical instrument. In various embodiments, referring to FIGS. 12-15, surgical instrument 600 can comprise an elongate shaft 604 and an end effector 606, wherein end effector 606 can be configured to articulate relative to elongate shaft 604 about articulation joint 620. In various embodiments, end effector 606 can further comprise a pivot member 622 mounted therein wherein, in at least some embodiments, pivot member 622 can be immovably mounted within end effector 606. In addition, elongate shaft 604 can comprise one or more motors, such as motor 640, for example, which can be configured to rotate pivot member 622 about an axis defined by pivot pins 627*a* and 627*b*. In at least one embodiment, motor 640 can comprise a spine portion 616 mounted within elongate shaft 604 and, in addition, a pivot pin member 626 mounted to spine portion 616, wherein spine portion 616 and pivot pin member 626 can be immovably mounted within elongate shaft 604. Referring to FIG. 15, pivot pin member 626 can comprise upper and lower tines 626*a*, 626*b* extending therefrom, wherein pivot pins 627*a* and 627*b* can extend from tines 626*a* and 626*b*, respectively, and can be mounted within apertures 627*c* within tines 626*a* and 626*b* in any suitable manner such as by a press-fit relationship and/or an adhesive, for example. In various embodiments, pivot member 622 can include one or more apertures, such as aperture 623, for example, configured to closely receive pivot pins 627*a* and 627*b* such that pivot member 622 and end effector 606 can be rotated or articulated about an axis as described above.

In various embodiments, further to the above, spine portion 616 and/or pivot pin member 626 can include one or more apertures or recesses, such as apertures 651, for example, which can be configured to receive one or more electromagnets, such as electromagnets 647, for example, mounted therein. Although not illustrated, surgical instrument 600 can further comprise one or more conductors, such as insulated wires, for example, which can be configured to conduct an electrical current therethrough when a current source and/or voltage source, such as a battery, for example, is operably coupled with the conductors. In at least one such embodiment, the conductors can extend from a handle assembly of the surgical instrument, such as handle assembly 102, for example, to the distal end of elongate shaft 604, wherein the conductors can be wrapped or coiled around ferromagnetic cores, which can be comprised of iron and/or cobalt, for example, to comprise electromagnets 647*a* and 647*b*. In use, in at least one embodiment, a surgical instrument can further include a switch, or actuator, which can be operated to selectively couple the current source and/or voltage source to the conductors. In certain embodiments, when electrical current is not flowing through the conductors, electromagnets 647*a*, 647*b* may not generate a magnetic field and, when sufficient electrical current is flowing through the conductors, the electrical current can generate one or more magnetic fields which can be utilized to rotate driver 639. Referring primarily to FIG. 15, driver 639 can include one or more magnetic elements mounted thereto which, when exposed to the magnetic field, or fields, created by electromagnets 647, can interact with the magnetic field, or fields, and cause driver 639 to rotate. In at least one such embodiment, driver 639 can comprise one or more apertures ore recesses, such as apertures 648, for example, which can be configured to receive one or more permanent magnets 649 therein.

In various embodiments, further to the above, permanent magnets 649 can comprise a magnetic polarity regardless of whether they are present in a magnetic field. In at least one embodiment, each permanent magnet 649 can comprise a positive, or north, pole 649*n* and a negative, or south, pole 649*s*, wherein poles 649*n* and 649*s* can be arranged such that, when the magnetic field, or fields, produced by the electromagnets 647*a* and 647*b* are selectively produced, such magnetic fields can interact with magnetic fields produced by permanent magnets 649 and, as a result, rotate driver 639. In various embodiments, driver 639 can be closely received and rotatably supported within aperture 654 in spine 616 such that driver 639 can be rotated about an axis when permanent magnets 649 are displaced within the magnetic field produced by electromagnets 647*a*, 647*b*. As outlined above, electromagnets 647*a* and 647*b* can be selectively energized to create a magnetic field which, owing to the polarity of permanent magnets 649, causes permanent magnets 649 to be displaced within the magnetic field(s). In various embodiments, electromagnets 647*a* and 647*b* can be energized such that electromagnets 647*a* have a different polarity than the polarity of electromagnets 647*b*. In at least one embodiment, electromagnets 647*a* and 647*b* can be energized such that they have opposite polarities, or different positive (north) and negative (south) poles, and such that the poles of electromagnets 647*a* and 647*b* are arranged in an alternating fashion. In various embodiments, the direction of current flowing through the conductors wrapped around the cores of electromagnets 647*a*, 647*b* can determine the polarity of the magnetic field(s) generated by the electromagnets. In use, the direction of the current flowing through the conductors as described above can be repeatedly switched, or alternated, such that the polarities of one or more of the electromagnets 647*a* and 647*b* can be repeatedly switched, or alternated, in order to attract and/or repel permanent magnets 649 in a manner such that driver 639 can be continuously rotated in clockwise and/or counter-clockwise directions, for example.

As described above, the operation of permanent magnets 647*a*, 647*b* can rotate driver 639 in a clockwise and/or counter-clockwise direction. In various embodiments, driver 639 can further comprise one or more gear portions, or drive teeth, which can be configured to engage or mate with a corresponding gear portion, or drive teeth, on pivot member 622. More particularly, in at least one embodiment, driver 639 can include a first gear portion 639*a* extending therefrom which can be configured to engage a first gear portion 629*a* extending from pivot member 622 such that, when driver 639 is rotated as described above, first gear portion 639*a* can drive first gear portion 629*a* to pivot or articulate pivot member 622 and, correspondingly, end effector 606 about pivot pins 627*a* and 627*b*. In at least one such embodiment, referring primarily to FIG. 14, driver 639 can be rotated in a first direction indicated by arrow D1 in order to rotate end effector 606 in a clockwise direction indicated by arrow CW and, in addition, driver 639 can be rotated in a second direction indicated by arrow D2 in order to rotate end effector 606 in a counter-clockwise direction indicated by arrow CCW. In at least one embodiment, as a result, driver 639 can be rotated about a first axis and end effector 606 can be rotated about a second axis, wherein the first axis and the second axis can be perpendicular, or at least substantially perpendicular, to each other. In other embodiments, the first and second axes may be non-parallel, transverse, and/or skew to one another. In various embodiments, referring again to FIG. 14, driver 639 can further include a second gear portion 639*b* which can be operably engaged with a second gear portion 629*b* of pivot member 622 via a transmission gear 653. In at least one such embodiment, transmission gear 653 can be rotatably mounted to pivot pin member 626 by a pin, such as pin 655, for example, such that, when driver 639 is rotated in direction D1 as described above, second gear portion 639*b* can assist first gear portion 639*a* in rotating pivot member 622 in a clockwise direction CW, for example.

Figure 16:
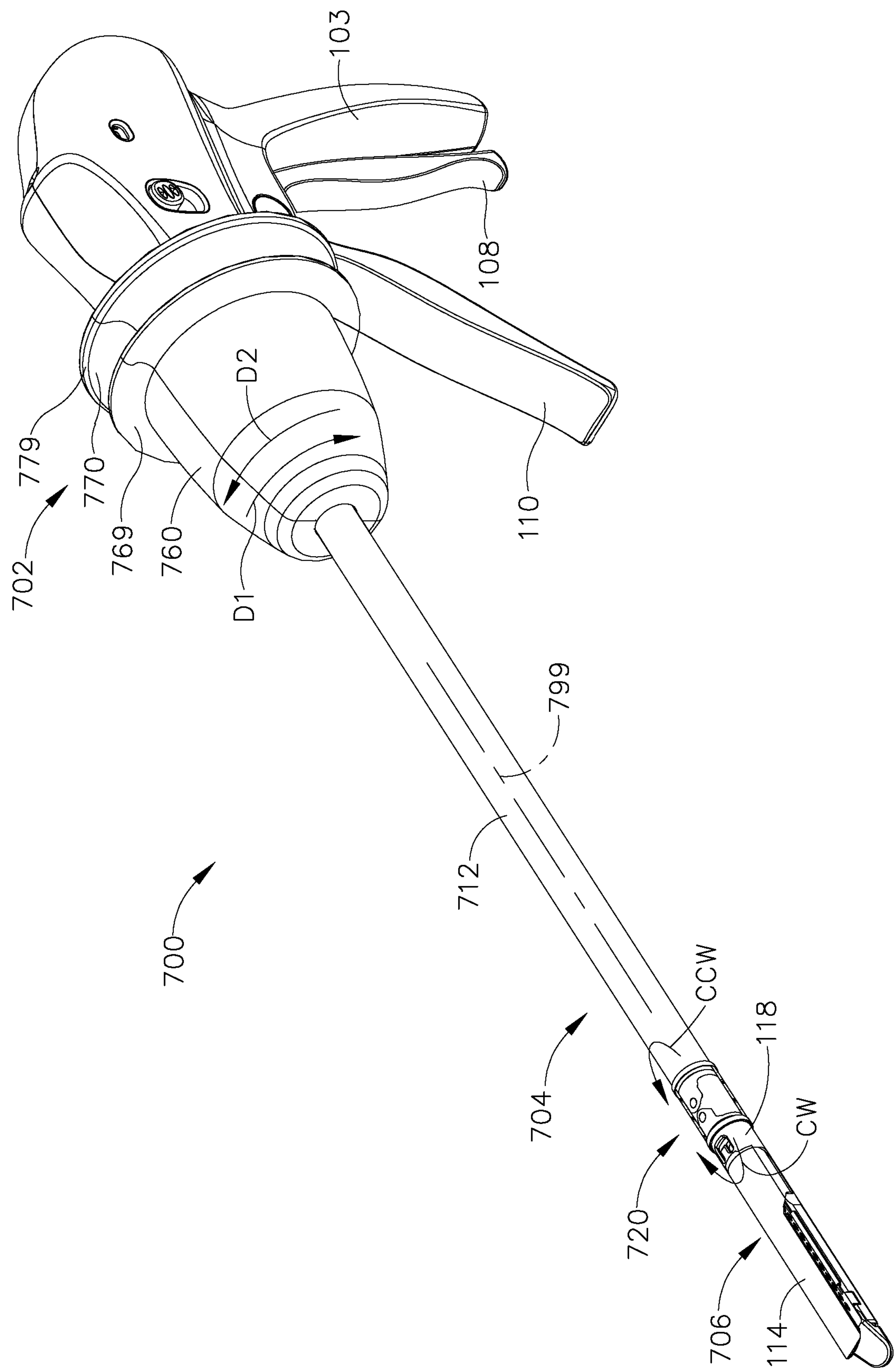
FIG. 16 is a perspective view of a surgical instrument having an articulation knob for articulating an end effector of the surgical instrument and a rotation knob for rotating the end effector.

As outlined above, a surgical instrument can include a handle assembly for operating the surgical instrument. In various embodiments, referring now to FIGS. 16 and 17, a surgical instrument, such as surgical instrument 700, for example, can comprise a frame 701, a closure trigger 108 pivotably mounted to frame 701, and, in addition, a firing trigger 110 also pivotably mounted to frame 701. Similar to surgical instrument 100, the operation of closure trigger 108, and the closure drive associated therewith, can displace closure tube 712 longitudinally along elongate shaft 704 in order to open and close anvil 114. In certain embodiments, referring primarily now to FIG. 17, the closure drive can comprise a retaining collar 108*b* slidably positioned within frame 701 and, in addition, a closure link 108*a* pivotably mounted to retaining collar 108*b* and trigger 108. In at least one such embodiment, at least a portion of closure tube 712 can be retained within retaining collar 108*b* such that the rotation of closure trigger 108 toward pistol grip 103 can displace closure link 108*a*, retaining collar 108*b*, and closure tube 712 distally, i.e., in a direction indicated by arrow D.

Figure 19:
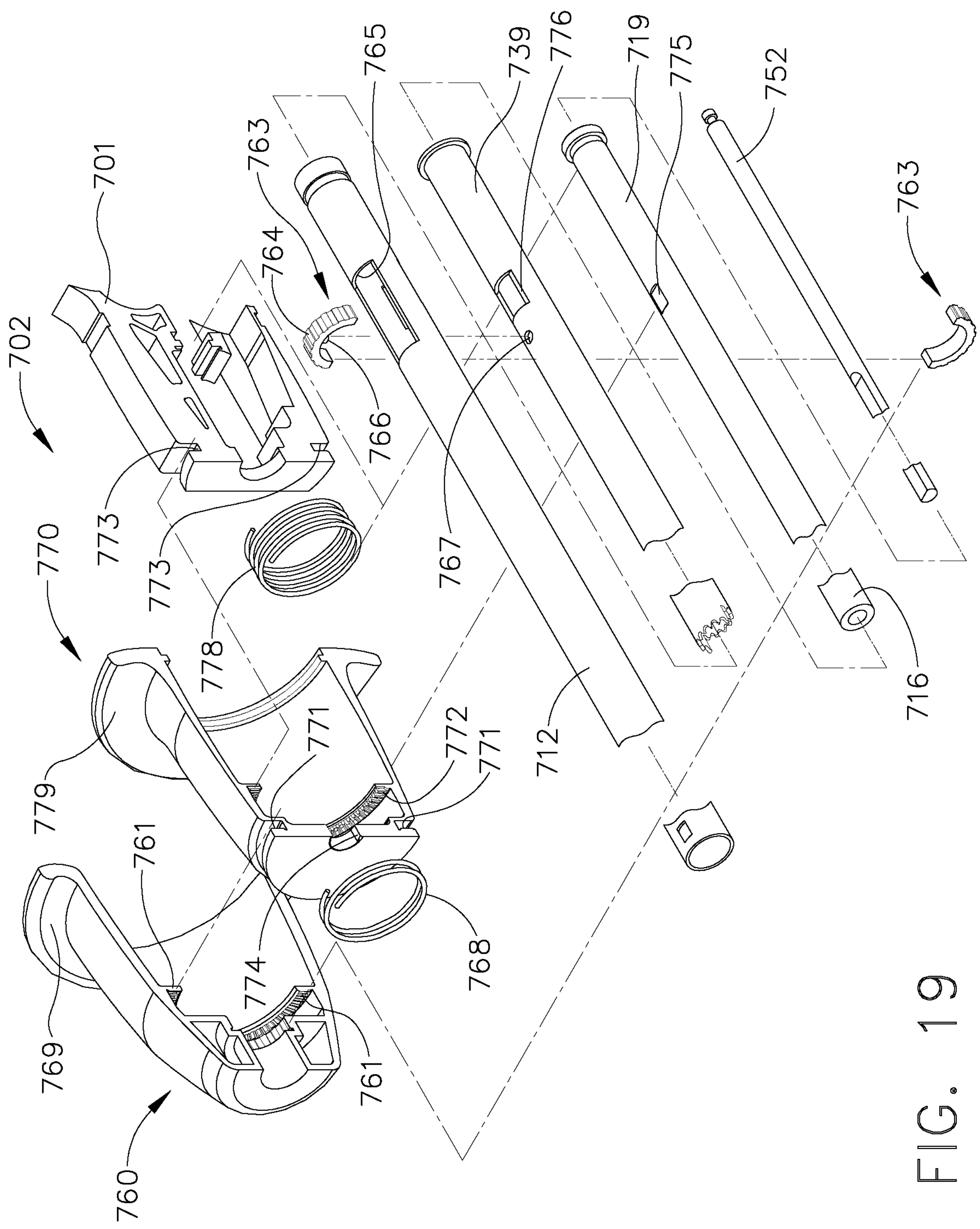
FIG. 19 is an exploded view of the handle portion of FIG. 17.

In addition to the closure drive described above, handle assembly 702 can further comprise an articulation system configured to rotate a driver, such as driver 739, for example, in order to articulate end effector 706 relative to elongate shaft 704. In at least one such embodiment, handle assembly 702 can further comprise articulation knob 760 which can be moved between locked and unlocked positions wherein, in certain embodiments, referring primarily to FIG. 17, articulation knob 760 can be slid between a first, or distal, position in which it is locked to rotation knob 770 and a second, or proximal, position in which it is unlocked from rotation knob 770. Referring primarily to FIG. 19, articulation knob 760 can comprise one or more locking teeth, or projections, 761 which can be configured to be engaged with one or more locking teeth, or projections, 771 on rotation knob 770 such that articulation knob 760 cannot be rotated relative to rotation knob 770 when articulation knob 760 is positioned in its locked, or distal, position. In at least one such embodiment, as a result, articulation knob 760 cannot be utilized to rotate driver 739 and articulate end effector 706 when articulation knob 760 is in its locked position.

Figure 18:
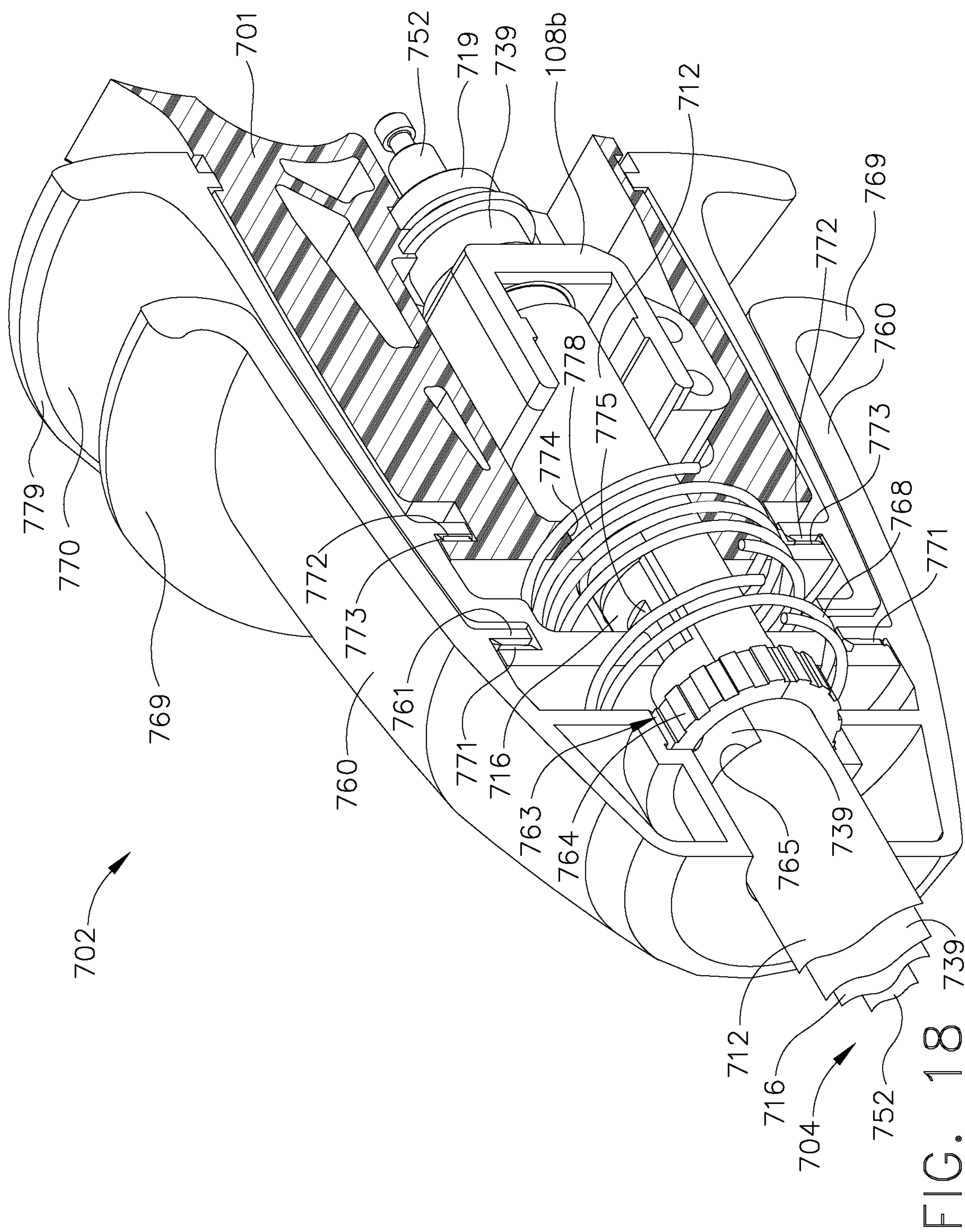
FIG. 18 is a perspective cross-sectional view of the handle portion of FIG. 17.

Further to the above, when articulation knob 760 is moved into its unlocked, or proximal, position, locking teeth 761 can be sufficiently disengaged from locking teeth 771 such that articulation knob 760 can be rotated relative to rotation knob 770. In at least one such embodiment, referring again to FIG. 16, articulation knob 760 can be rotated in a first direction indicated by arrow D1 in order to rotate end effector 706 in a clockwise direction indicated by arrow CW and, correspondingly, articulation knob 760 can be rotated in a second direction indicated by arrow D2 in order to rotate end effector 706 in a counter-clockwise direction indicated by arrow CCW, for example. Referring primarily to FIG. 18, articulation knob 760 can be operably engaged with spline ring 763 such that, when articulation knob 760 is rotated, spline ring 763 can be rotated by articulation knob 760. In at least one such embodiment, referring to FIG. 18, spline ring 763 can include one or more splines 764 which can be configured to permit articulation knob 760 to be slid between its locked and unlocked positions, yet transmit rotational motion to spline ring 763. In various embodiments, referring now to FIG. 19, spline ring 763 can comprise two or more portions which can be assembled together such that spline ring 763 encompasses at least a portion of closure tube 712. In at least one such embodiment, closure tube 712 can include an aperture, or window, 765 which can be configured to permit at least a portion of spline ring 763 to extend through closure tube 712 and operably engage driver 739. More particularly, spline ring 763 can further comprise one or more projections, or keys, 766 extending therefrom which can be received within one or more apertures 767 in driver 739 such that, when spline ring 763 is rotated by articulation knob 760, spline ring 763 can rotate driver 739. In various embodiments, as a result, articulation knob 760 and driver 739 can be rotated relative to closure tube 712 and spine member 716 when articulation knob 760 is in its unlocked position.

In use, as outlined above, articulation knob 760 can be pulled proximally to disengage locking teeth 761 from locking teeth 771 of rotation knob 770. In various embodiments, referring generally to FIG. 16, articulation knob 760 can further comprise lip 769 extending therefrom wherein, in at least one embodiment, lip 769 can be configured to allow a surgeon to grasp lip 769 with one or more fingers and pull articulation knob 760 proximally. In such circumstances, referring to FIG. 17, articulation knob 760 can compress a biasing member, such as spring 768, for example, positioned intermediate articulation knob 760 and rotation knob 770. In certain embodiments, articulation knob 760, driver 739, and end effector 706 can be configured such that, when articulation knob 760 is rotated substantially 10 degrees in direction D1, for example, end effector 706 can be rotated substantially 10 degrees in direction CW. Such embodiments can be referred to as having a 1:1 gear ratio, although other embodiments are envisioned which can have a smaller gear ratio or a larger gear ratio. In any event, once end effector 706 has been satisfactorily articulated, the surgeon can release articulation knob 760 such that spring 768 can move articulation knob 760 from its unlocked position into its locked position once again. Referring to FIG. 19, lock teeth 761 and/or lock teeth 771 can each comprise an array of teeth which can be configured such that at least some of lock teeth 761 and 771 can intermesh, or be interlocked, regardless of the degree in which articulation knob 760 is rotated relative to rotation knob 770. In the illustrated embodiment, teeth 761 and teeth 771 are each arranged in an annular, or at least substantially annular, and a concentric, or at least substantially concentric, array.

In various embodiments, further to the above, rotation knob 770 can be configured to rotate end effector 706 about a longitudinal axis, such as longitudinal axis 799, for example. In at least one such embodiment, referring primarily to FIG. 17, rotation knob 770 can be moved between a locked, distal, position in which it is locked to frame 701 and an unlocked, proximal, position in which it is unlocked from frame 701. In various embodiments, referring to FIG. 17 once again, rotation knob 770 can further comprise lip 779 extending therefrom wherein, in at least one embodiment, lip 779 can be configured to allow a surgeon to grasp lip 779 with one or more fingers and pull rotation knob 770 proximally. Similar to the above, referring primarily to FIG. 19, rotation knob 770 can comprise one or more locking teeth, or projections, 772 which can be configured to be engaged with one or more locking teeth 773, or projections, on frame 701 such that rotation knob 770 cannot be rotated relative to frame 701 when rotation knob 770 is positioned in its locked, or distal, position. When rotation knob 770 is unlocked from frame 701, however, rotation knob 770 can be rotated relative to frame 701 in order to rotate end effector 706 about longitudinal axis 799. More particularly, in at least one embodiment, rotation knob 770 can further include one or more driver portions, such as flat driver portions 774, for example, which can be configured to transmit the rotation of rotation knob 770 to spine portion 716 via corresponding flat portions 775 on spine portion 716. In at least one such embodiment, referring primarily to FIG. 19, flat driver portions 774 can be configured to extend through window 765 in closure tube 712 and, in addition, window 776 in driver 739 such that flat driver portions 774 can directly engage flat portions 775 on spine 716.

Figure 17:
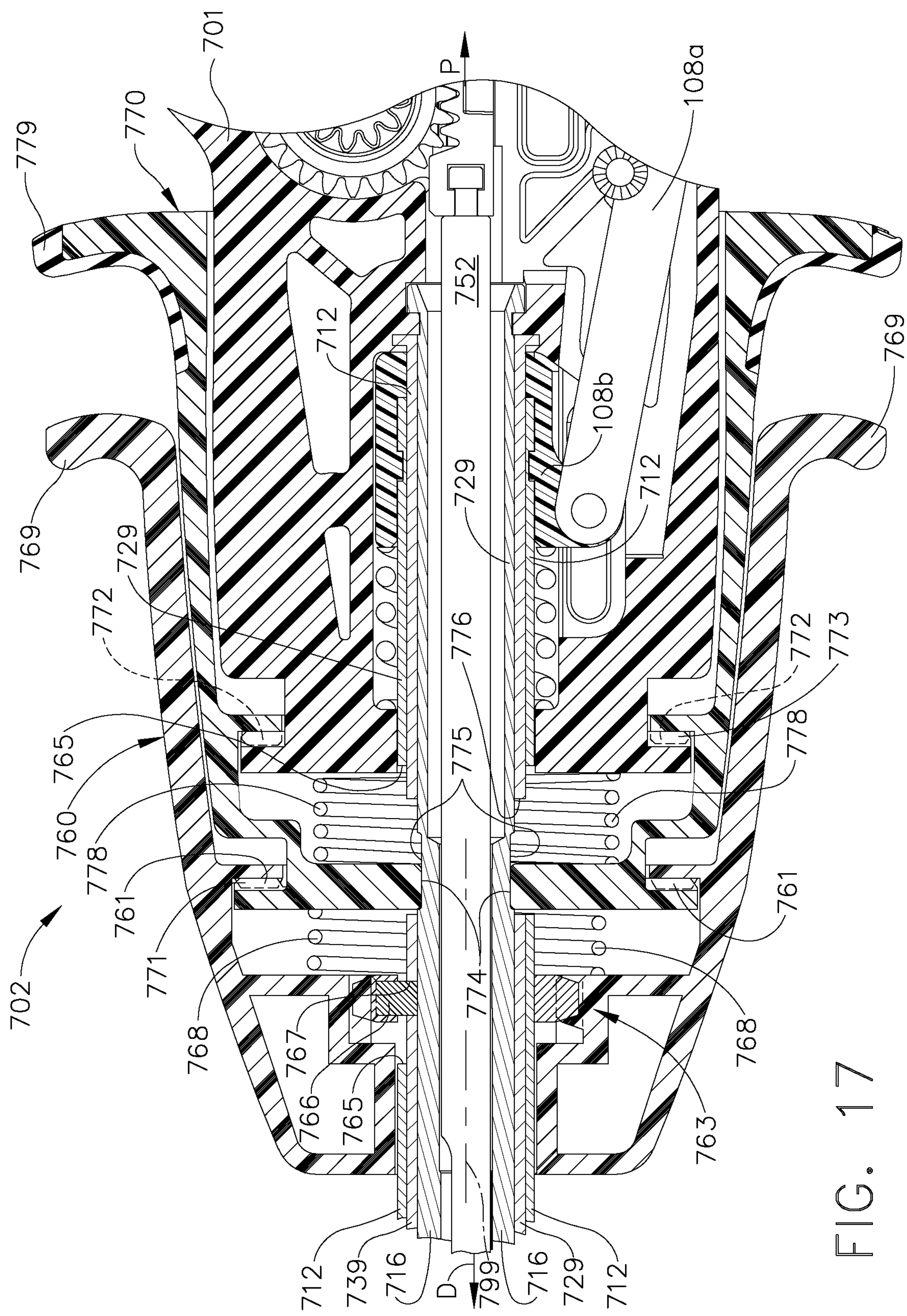
FIG. 17 is a side cross-sectional view of a handle portion of the surgical instrument of FIG. 16.

In addition to the above, referring to FIG. 17, rotation knob 770 can be configured such that, when it is pulled proximally into its unlocked position as described above, locking teeth 771 can transmit the rotation of rotation knob 770 to articulation knob 760 via locking teeth 761. In at least one such embodiment, as a result, articulation knob 760 can turn synchronously with rotation knob 770 such that spine member 716 can turn synchronously with driver 739 when rotation knob 770 is in its unlocked position. In at least one embodiment, owing to the synchronous rotation of spine member 716 and driver 739, end effector 706 may not articulate relative to elongate shaft 704 when rotation knob 770 is rotated relative to handle frame 701. Stated another way, as rotation knob 770 is not being rotated relative to articulation knob 760 and driver 739 is not being rotated relative to spine 716, driver 739 may not be able to articulate end effector 706 relative to shaft 704. In any event, once end effector 706 has been properly rotated about axis 799, rotation knob 770 can be released in order to re-engage locking teeth 772 of rotation knob 770 with locking teeth 773 of handle frame 701. In at least one embodiment, referring to FIGS. 17-19, handle assembly 702 can further comprise a biasing member, such as spring 778, for example, positioned intermediate rotation knob 770 and frame 701, wherein spring 778 can be compressed between rotation knob 770 and frame 701 when rotation knob 770 is moved from its locked, distal, position into its unlocked, proximal, position and, when rotation knob 770 is released, as described above, spring 778 can bias rotation knob 770 away from frame 701 such that lock teeth 772 are re-engaged with lock teeth 773. Referring again to FIG. 19, lock teeth 772 and/or lock teeth 773 can each comprise an array of teeth which can be configured such that at least some of lock teeth 772 and 773 can intermesh, or be interlocked, regardless of the degree in which rotation knob 770 is rotated relative to frame 701. In the illustrated embodiment, lock teeth 772 and lock teeth 773 are each arranged in an annular, or at least substantially annular, and a concentric, or at least substantially concentric, array.

In various embodiments, further to the above, a surgeon can hold handle assembly 702 in one hand, such as their right hand, for example, and operate surgical instrument 700. In at least one embodiment, as outlined above, the surgeon can retract triggers 108 and 110 toward pistol grip 103 by positioning their thumb, for example, on the proximal side of pistol grip 103 and positioning one or more fingers of the same hand on the distal side of triggers 108 and 110 in order to apply a force thereto and pull them toward pistol grip 103. As also outlined above, a surgeon can extend one or more of their fingers of the same hand distally in order to grasp lip 769 of articulation knob 760 and/or lip 779 of rotation knob 770 and pull them proximally. Stated another way, a surgeon can open and close anvil 114 via closure trigger 108, incise and staple tissue via firing trigger 110, articulate end effector 706 relative to elongate shaft 704 about articulation joint 720, and, in addition, rotate end effector 706 about longitudinal axis 799 all with one hand. As a result, the surgeon can have their other hand available to perform other tasks during a surgery. In various circumstances, however, the operation of knobs 760 and 770 and triggers 108 and 110 may require a surgeon to use two hands to operate the surgical instrument, especially if the surgeon's hands are too small or are otherwise unable to perform the tasks set forth above, thereby defeating one or more possible advantages. In various alternative embodiments, referring now to FIGS. 20 and 21, a surgical instrument, such as surgical instrument 800, for example, may include a system of magnetic elements for articulating end effector 706 relative to elongate shaft 704 and, in addition, a system of magnetic elements for rotating end effector 706 about longitudinal axis 799. In various embodiments, surgical instrument 800 can further comprise additional systems of magnetic elements for moving articulation knob 760 and rotation knob 770 between their locked and unlocked positions. In any event, surgical instrument 800 can be similar to surgical instrument 700 in many respects although various differences are discussed in greater detail further below.

Figure 20:
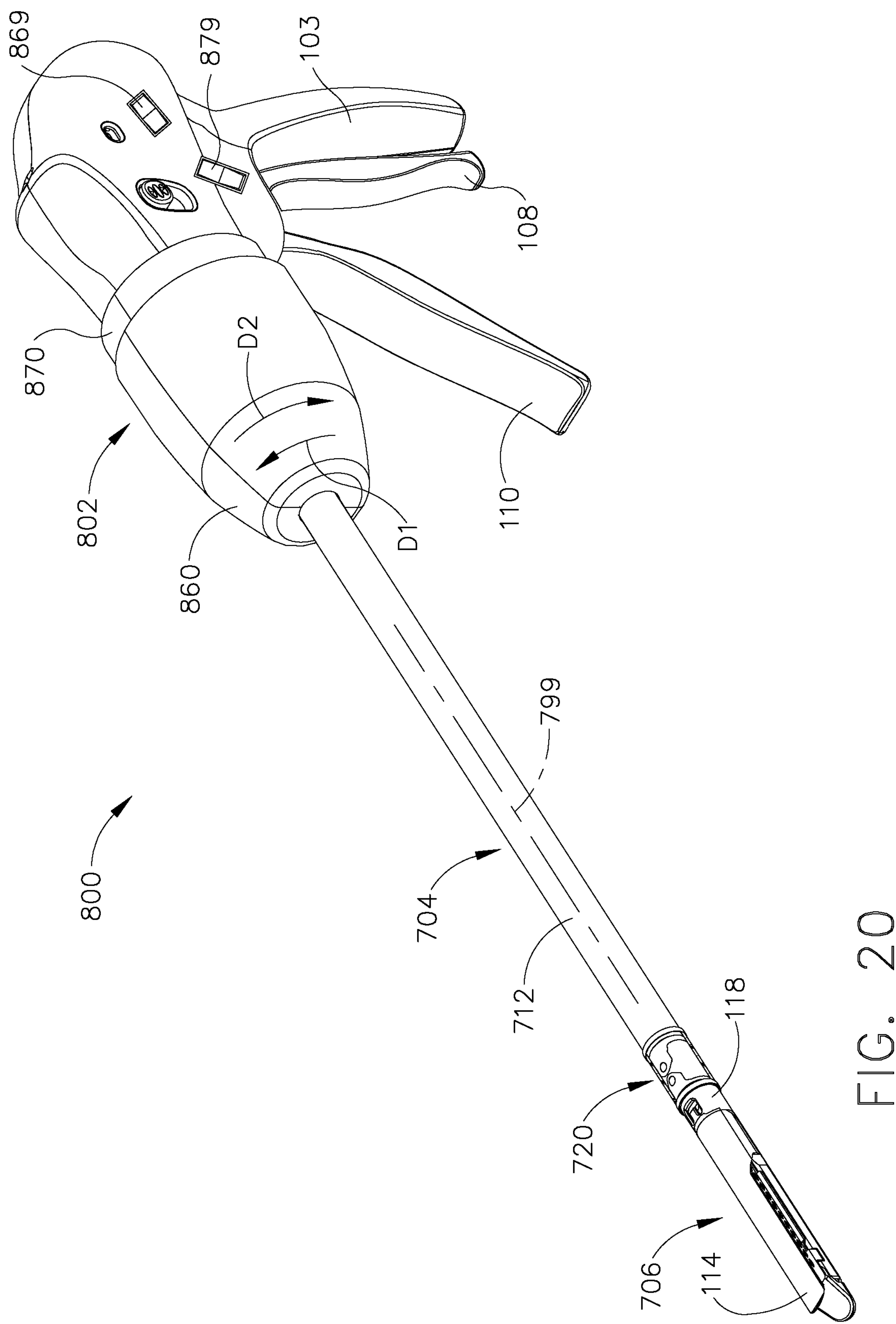
FIG. 20 is a perspective view of a surgical instrument in accordance with at least one embodiment of the present invention comprising an articulation switch and a rotation switch.
Figure 21:
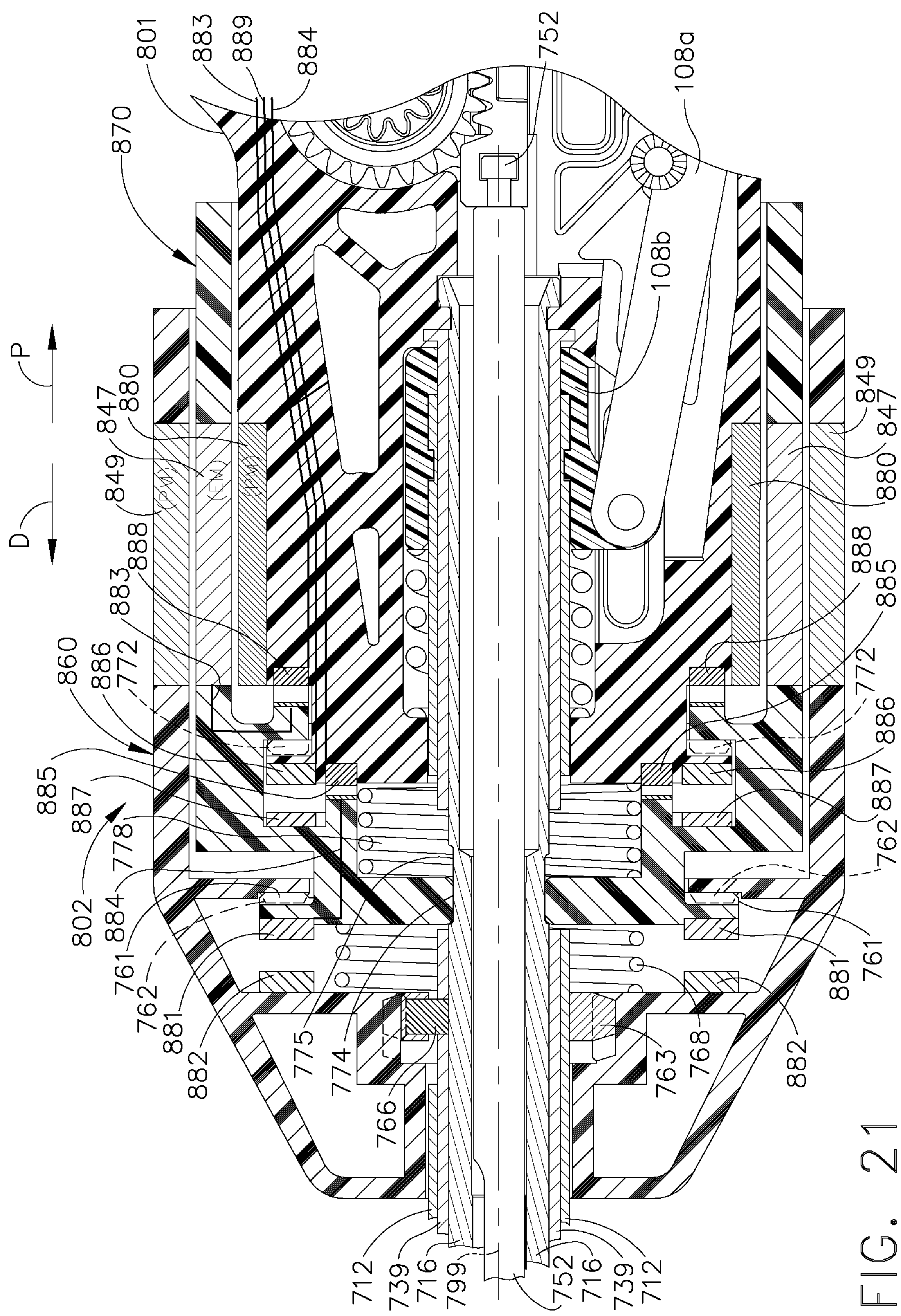
FIG. 21 is a cross-sectional view of a handle portion of the surgical instrument of FIG. 20.

Similar to articulation knob 760 of surgical instrument 700, referring now to FIG. 20, articulation knob 860 of surgical instrument 800 can be moved between a locked, distal, position and an unlocked, proximal, position. Also similar to articulation knob 760, referring to FIG. 21, articulation knob 860 can include lock teeth 761 which can be engaged and disengaged from lock teeth 762 on rotation knob 870 when articulation knob 860 is moved between its locked and unlocked positions, respectively. In various embodiments, articulation knob 860 can be pulled back, or proximally, by a system of electromagnets 881 and magnetic elements 882, for example. In at least one embodiment, referring again to FIG. 21, electromagnets 881 can be mounted to rotation knob 870 in a circular, or at least substantially circular array, which can be concentric, or at least substantially concentric, with a circular, or at least substantially circular, array of magnetic elements 882 mounted to articulation knob 860. In various embodiments, a surgeon can operate a switch on handle assembly 802, for example, in order to place a current source and/or voltage source in communication with electromagnets 881 such that electromagnets 881 can be sufficiently energized, or polarized, in order to attract magnetic elements 882 toward electromagnets 881 and, correspondingly, move articulation knob 860 proximally. In at least one such embodiment, electromagnets 881 can apply a sufficient magnetomotive force (mmf) to magnetic elements 882 in order to sufficiently displace articulation knob 860 and disengage lock teeth 761 from lock teeth 762 such that articulation knob 860 can be rotated relative to rotation knob 870, as described in greater detail further below. In various embodiments, similar to the above, a biasing member, such as spring 768, for example, can be positioned intermediate articulation knob 860 and rotation knob 870 such that spring 768 is compressed when articulation knob 860 is moved into, and held in, its proximal, unlocked position by electromagnets 881. After electromagnets 881 have been sufficiently de-energized, or depolarized, spring 768 can be configured to bias articulation knob 860 back into its locked, distal position. In various embodiments, further to the above, magnetic elements 882 can be comprised of iron, and/or any suitable ferromagnetic material, for example, which can interact with a magnetic field. In at least some embodiments, magnetic elements 882 can comprise permanent magnets, such as neodymium magnets, samarium-cobalt magnets, and/or any suitable rare earth magnets, for example. In at least one such embodiment, magnetic elements 882 can be arranged and configured to attract, or repel, at least a portion of electromagnets 881 such that the mmf applied to electromagnets 881 can preload spring 768 and/or provide a resistive force to the proximal movement of articulation knob 860.

Once articulation knob 860 has been sufficiently unlocked, as described above, articulation knob 860 can be rotated relative to rotation knob 870 in order to articulate end effector 706 relative to elongate shaft 704. In various embodiments, articulation knob 860 can include one or more magnetic elements 849 which can be configured to interact with a magnetic field, or fields, produced by one or more electromagnets 847 mounted to rotation knob 870. In at least one such embodiment, magnetic elements 849 can be comprised of iron, and/or any other suitable ferromagnetic material, for example, and can be embedded within and/or otherwise suitably mounted to articulation knob 860. In various embodiments, electromagnets 847 can apply a magnetomotive force (mmf) to magnetic elements 849 in order to displace magnetic elements 849, and articulation knob 860, relative to electromagnets 847 and rotation knob 870. In at least one embodiment, the polarity of electromagnets 847 can be switched between first and second polarities in order to drive articulation knob 860 in a first direction indicated by arrow D1 (FIG. 20) and/or a second direction indicated by arrow D2. In use, referring to FIG. 20, a surgeon can actuate switch 869 to place a current source and/or voltage source in communication with electromagnets 847 such that electromagnets 847 can produce a magnetic field sufficient to displace articulation knob 860 relative to rotation knob 870 in a desired direction and, accordingly, articulate end effector 706 relative to elongate shaft 704 in the same manner, or an at least similar manner, as described above in connection with surgical instrument 700, for example.

Similar to rotation knob 770 of surgical instrument 700, rotation knob 870 of surgical instrument 800 can be moved between a distal position in which it is locked to frame 801 and a proximal position in which it is unlocked from frame 801. In various embodiments, further to the above, a system of electromagnets and magnetic elements, for example, can be utilized to move rotation knob 870 between its locked and unlocked positions. In at least one such embodiment, referring to FIG. 21, frame 801 can include a plurality or electromagnets 886 mounted thereto which are arranged in a circular, or at least substantially circular, array, wherein electromagnets 886 can be configured to generate a magnetic field, or fields, configured to attract and/or repel magnetic elements 887 mounted to rotation knob 870. Similar to the above, electromagnets 886 can be sufficiently energized, or polarized, in order to pull magnetic elements 887, and rotation knob 870, toward electromagnets 886 in order to disengage lock teeth 772 from lock teeth on frame 701. Once rotation knob 870 is in its unlocked position, rotation knob 870 can be rotated relative to frame 801 by another system of electromagnets and magnetic elements. In at least one such embodiment, referring again to FIG. 21, frame 801 can include a plurality of magnetic elements 880 mounted thereto which can be configured to interact with a magnetic field, or fields, produced by electromagnets 847. Similar to the above, referring to FIG. 20, a surgeon can operate a switch 879 in order to selectively energize, or polarize, magnetic elements 847 in order to produce a first magnetic field for rotating rotation knob 870 in a first direction and a second magnetic field for rotating rotation knob 870 in a second direction. In such embodiments, when rotation knob 870 is rotated, rotation knob 870 can rotate end effector 706 about longitudinal axis 799 in the same manner, or an at least similar manner, as described above in connection with surgical instrument 700, for example.

Although not illustrated, the reader will appreciate that the electromagnets of surgical instrument 800 can be powered by a common power source, such as a battery, for example, and/or different power sources. Referring once again to FIG. 21, surgical instrument 800 may further include one or more conductors, or wires, for placing the power source, or sources, in communication with the electromagnets of surgical instrument 800. In various embodiments, handle assembly 802 can further comprise one or more conductors, or wires, 883 which can supply current and/or apply voltage to electromagnets 847. In some embodiments, although not illustrated, conductors 883 can have sufficient flexibility and/or slack in order to accommodate relative movement between rotation knob 870 and frame 801. In other embodiments, referring to FIG. 21, handle assembly 802 can comprise one or more brushes 888 positioned intermediate frame 801 and rotation knob 870 which can be configured to conduct current between a power source and electromagnets 847 regardless of whether rotation knob 870 is moving relative to frame 801 and/or regardless of the degree of rotation between rotation knob 870 and frame 801. In at least one such embodiment, brushes 888 can be positioned in an annular, or at least substantially annular, array around frame 801 and rotation knob 870. In various embodiments, brushes 888 can comprise metal fiber brushes, such as braided copper brushes, for example, carbon brushes, and/or any other suitable brush. In at least one embodiment, a "brush" can comprise one or more blocks of material, such as a carbon block, for example, which can be configured to conduct current and permit relative sliding contact of an opposing "brush" across a face thereof. In certain embodiments, a "brush" can comprise any suitable compliant member. In any event, brushes 888 can be sufficiently resilient such that they can flex, or compress, when rotation knob 870 is pulled distally and re-expand when rotation knob 870 is moved back into its locked position.

In various embodiments, similar to the above, handle assembly 802 can further comprise one or more conductors, or wires, 884 which can supply current and/or apply voltage to electromagnets 881. In some embodiments, although not illustrated, conductors 884 can have sufficient flexibility and/or slack in order to accommodate relative movement between rotation knob 870 and frame 801. In other embodiments, similar to the above, handle assembly 802 can comprise one or more brushes 885 positioned intermediate rotation knob 870 and frame 801 which can be configured to conduct current between a power source and electromagnets 881 regardless of whether rotation knob 860 is moving relative to frame 801 and/or regardless of the degree of rotation between rotation knob 870 and frame 801. Similar to the above, brushes 885 comprise metal fiber brushes, such as braided copper brushes, for example, carbon brushes, and/or any other suitable brush which can be sufficiently resilient such that they can flex, or compress, when rotation knob 870 is pulled distally and re-expand when rotation knob 870 is moved back into its locked position. In addition to the above, brushes 885, and/or brushes 888, can permit relative sliding movement between two halves of the brush. More particularly, in at least one embodiment, a brush 885, for example, can comprise a first half mounted to rotation knob 870 having bristles extending therefrom, wherein the second half of brush 885 can comprise a contact plate, or plates, mounted to frame 801 against which the bristles can contact and slide thereover. In other various embodiments, a brush 885, for example, can comprise first and second halves each having bristles extending therefrom, wherein the first and second halves can be mounted to rotation knob 870 and frame 801 and can contact and slide over one another. In any event, brushes 885 can be positioned in an annular, or at least substantially annular, array around frame 801 and rotation knob 870. In various embodiments, referring once again to FIG. 21, handle assembly 802 can include one or more conductors, or wires, 889 which can supply current and/or apply voltage to electromagnets 886.

Figure 22:
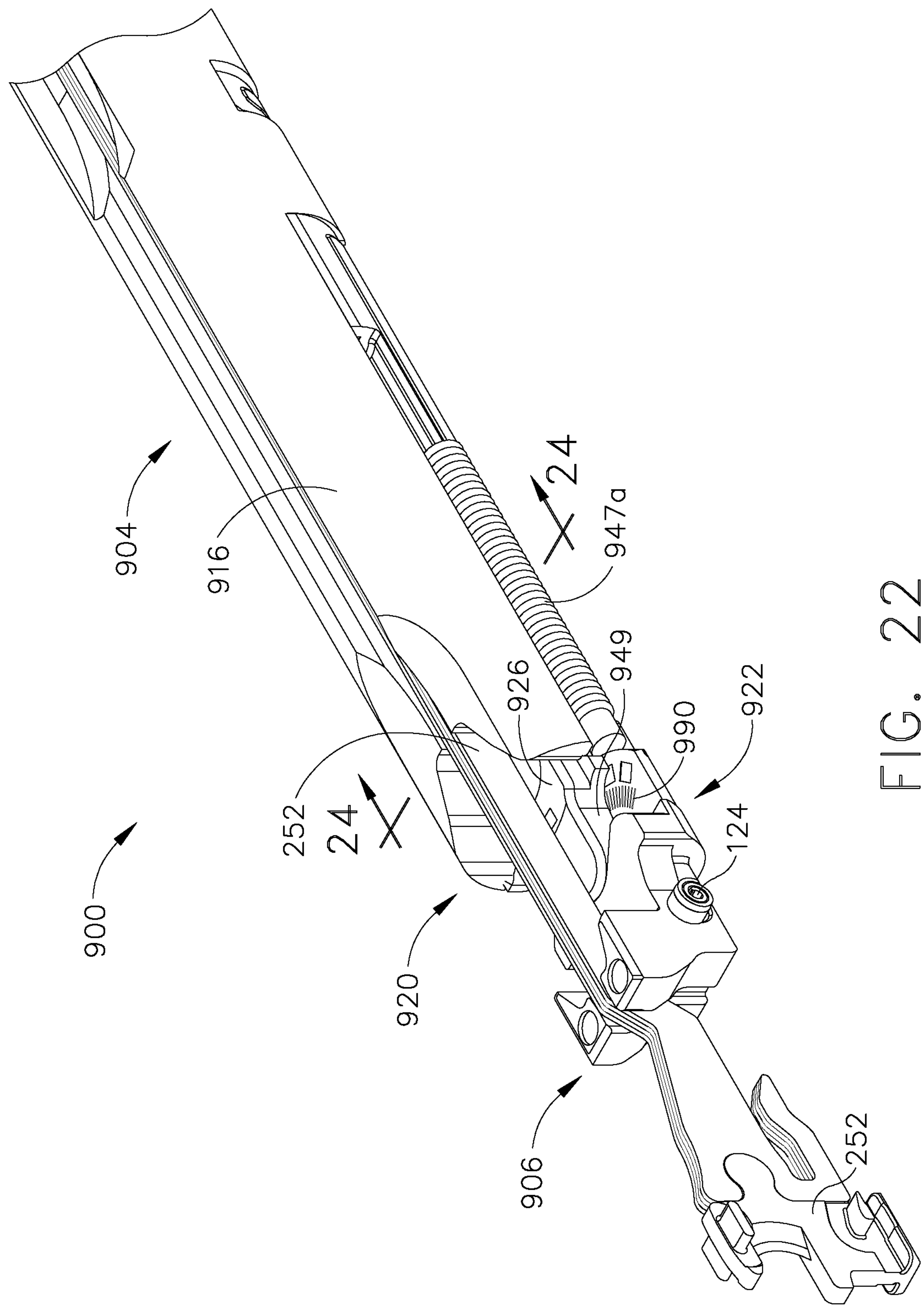
FIG. 22 is a perspective view of an articulation joint connecting an end effector and an elongate shaft of a surgical instrument in accordance with at least one embodiment of the present invention illustrated with some components removed.

In various embodiments, a surgical instrument can include one or more electromagnets positioned within an elongate shaft, wherein the electromagnets can be configured to articulate an end effector of the surgical instrument relative to the elongate shaft. In at least one embodiment, referring to FIGS. 22-24, surgical instrument 900 can comprise an elongate shaft 904 and an end effector 906 (shown with portions removed), wherein end effector 906 can be pivotably connected to elongate shaft 904 by articulation joint 920. Similar to the above, end effector 906 can comprise a pivot plate 922 and, in addition, elongate shaft 904 can comprise a pin insert plate 926 which can be secured within elongate shaft 904 by spine 916. Also similar to the above, pin insert plate 926 can include a pin extending therefrom which can be configured to be closely received within pin aperture 123 in pivot plate 922. In certain embodiments, referring primarily to FIG. 23, elongate shaft 904 can further comprise electromagnets **940*a* and 940*b* mounted therein and, in addition, pivot plate 922 can further comprise magnetic elements 949 mounted thereto wherein electromagnets 940*a*, 940*b* can be configured to generate a magnetic field, or fields, which can be configured to interact with magnetic elements 949 and rotate pivot plate 922, and end effector 906, about an axis defined by pin insert plate 926. In various embodiments, magnetic elements 949 can comprise magnets, such as rare earth magnets, for example, which can be positioned and arranged on pivot plate 922 such that the poles of the magnets are aligned in a predetermined orientation. In at least one embodiment, magnetic elements 949 can be arranged such that the poles of each magnet are arranged in an end-to-end configuration such that the positive, or north, pole of each magnet is positioned next to the negative, or south, pole of the adjacent magnet, for example. Other embodiments are envisioned in which the positive poles of magnets 949** are positioned radially outwardly with respect to their negative poles, for example.

In use, in at least one embodiment, electromagnet **940*b*, for example, can be energized, or polarized, such that the distal end of electromagnet 940*b* comprises a positive, or north, magnetic pole of a magnetic field. In such circumstances, the positive poles of magnetic elements 949 can be repulsed away from electromagnet 940*b* and the negative poles of magnetic elements 949 can be attracted toward electromagnet 940*b*. In various embodiments, as a result, the magnetic field produced by electromagnet 940*b*, for example, can be sufficient to displace, or rotate, pivot plate 922, and end effector 906, in a counter-clockwise direction indicated by arrow CCW, for example. In at least one such embodiment, referring to FIG. 23, the intensity of the magnetic field produced by electromagnet 940*b* can be controlled by controlling the magnitude of current flowing through conductor 947*b*, wherein a larger current can produce a more intense magnetic field and a smaller current can produce a less intense magnetic field. In certain embodiments, similar to the above, the direction in which current is supplied, or the polarity in which voltage is applied, to conductor 947*b* can control the polarity of the magnetic pole generated at the distal end of electromagnet 940*b*. More particularly, if the current flowing through conductor 947*b* is flowing in a first direction, the current can generate a positive pole at the distal end of core 941*b* whereas, if the current flowing through conductor 947*b* flows in the opposite direction, the current can generate a negative pole at the distal end of core 941*b*. In various embodiments, as a result, the direction of the current flowing through conductor 947*b*** can be selectively changed in order to selectively change the polarity of the magnetic field produced by electromagnet 940*b*, for example. In at least one such embodiment, the initial polarity of the distal end of electromagnet 940*b* can be positive, for example, in order to repel a first magnet 949 wherein the polarity of the distal end of electromagnet 940*b* can then be changed from positive to negative so as to draw the next permanent magnet 949 toward electromagnet 940*b* in order to continue to rotate pivot plate 922 and end effector 906. Once the second permanent magnet 949 has been sufficiently positioned, the polarity of electromagnet 940*b* can be switched once again, i.e., from negative to positive, and repel the second electromagnet 949 away from electromagnet 940*b* and, again, continue to rotate pivot plate 922 and end effector 906.

In various embodiments, it may be desirable to limit the range in which end effector 906 can be rotated relative to elongate shaft 904. In certain embodiments, although not illustrated, elongate shaft 904 can include one or more stops which can be configured to stop the rotation of end effector 906 when it is moved in a clockwise direction and/or a counter-clockwise direction. In at least one such embodiment, the stops can limit the maximum rotation of end effector 906 in the clockwise and/or counter-clockwise directions. In some embodiments, referring to FIG. 23, a surgical instrument can further comprise means for detecting the position, or relative angle, between end effector 906 and elongate shaft 904 and, in addition, means for stopping the rotation of end effector 906 once end effector 906 has been sufficiently displaced. In at least one such embodiment, elongate shaft 904 can further include one or more sensors which can be configured to detect one or more markings on end effector 906 in order to determine the amount, or degree, in which end effector 906 has been rotated relative to shaft 904. More particularly, in at least one embodiment, elongate shaft 904 can further comprise at least one photosensor, such as photosensor 991, for example, which can be configured to detect encoder markings 990 as they pass under photosensor 991 when end effector 906 is rotated. In various embodiments, photosensor 991 can further comprise a light emitter and, in addition, encoder markings 990 can comprise at least partially reflective surfaces on pivot plate 922 which can be configured to reflect light produced by the light emitter in order to facilitate the detection of encoder markings 990. In certain embodiments, encoder markings 990 can be etched into a surface on pivot plate 922. In at least one embodiment, although not illustrated, end effector 906 can comprise a plurality of slits, or apertures, arranged in a suitable array similar to the arrangement of encoder markings 990, wherein the apertures can be configured to allow light to pass therethrough from a light source positioned on the opposite, or bottom, side of pivot plate 922. In at least one such embodiment, the light source can comprise one or more light emitting diodes. In certain other embodiments, although not illustrated, an end effector and elongate shaft can comprise a mechanical encoder which is indexed as the end effector is rotated.

Figure 23:
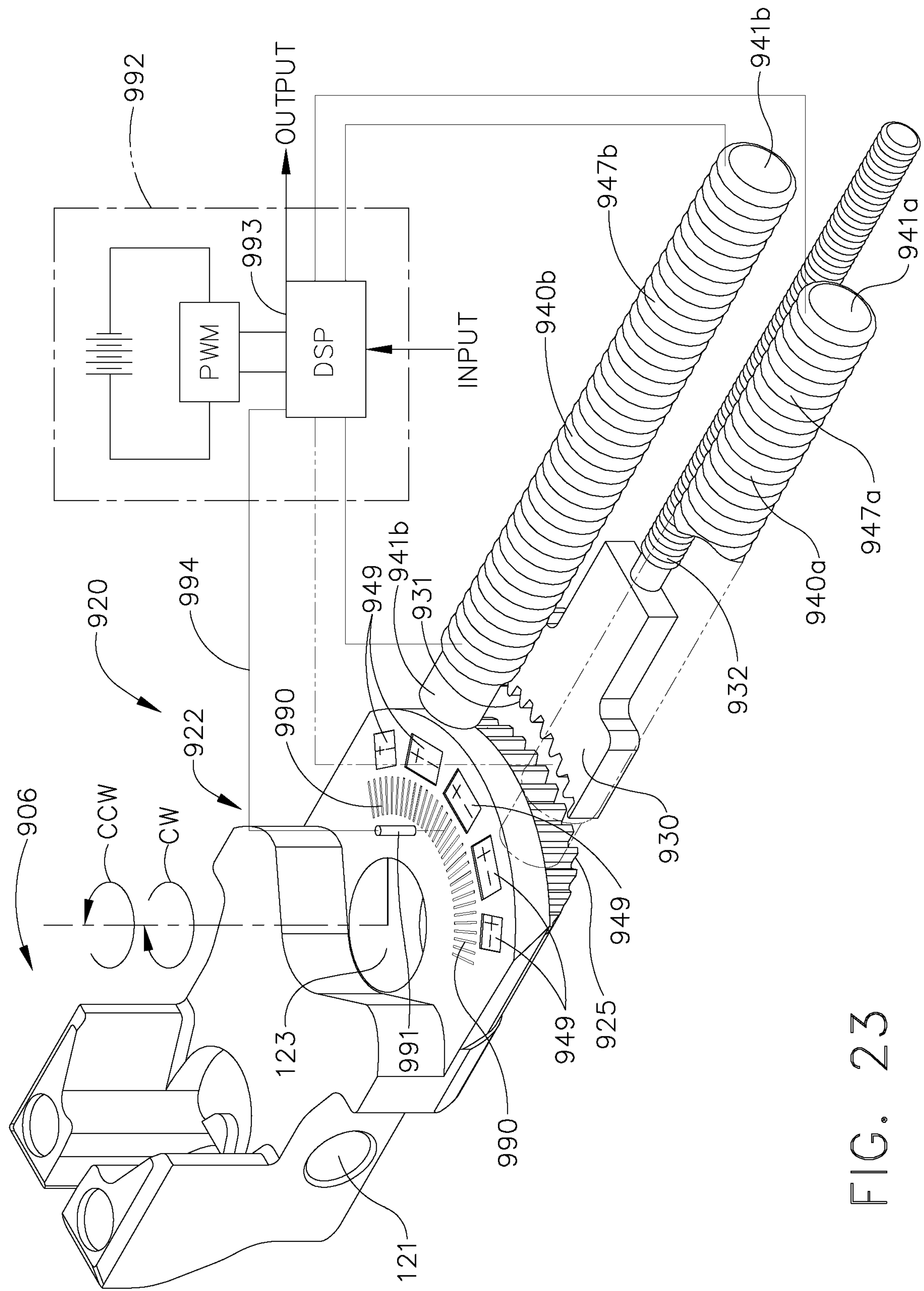
FIG. 23 is a schematic illustrating electromagnets positioned within the elongate shaft of FIG. 22 configured to apply a magnetic force to permanent magnets mounted to the end effector of FIG. 22.
Figure 24:
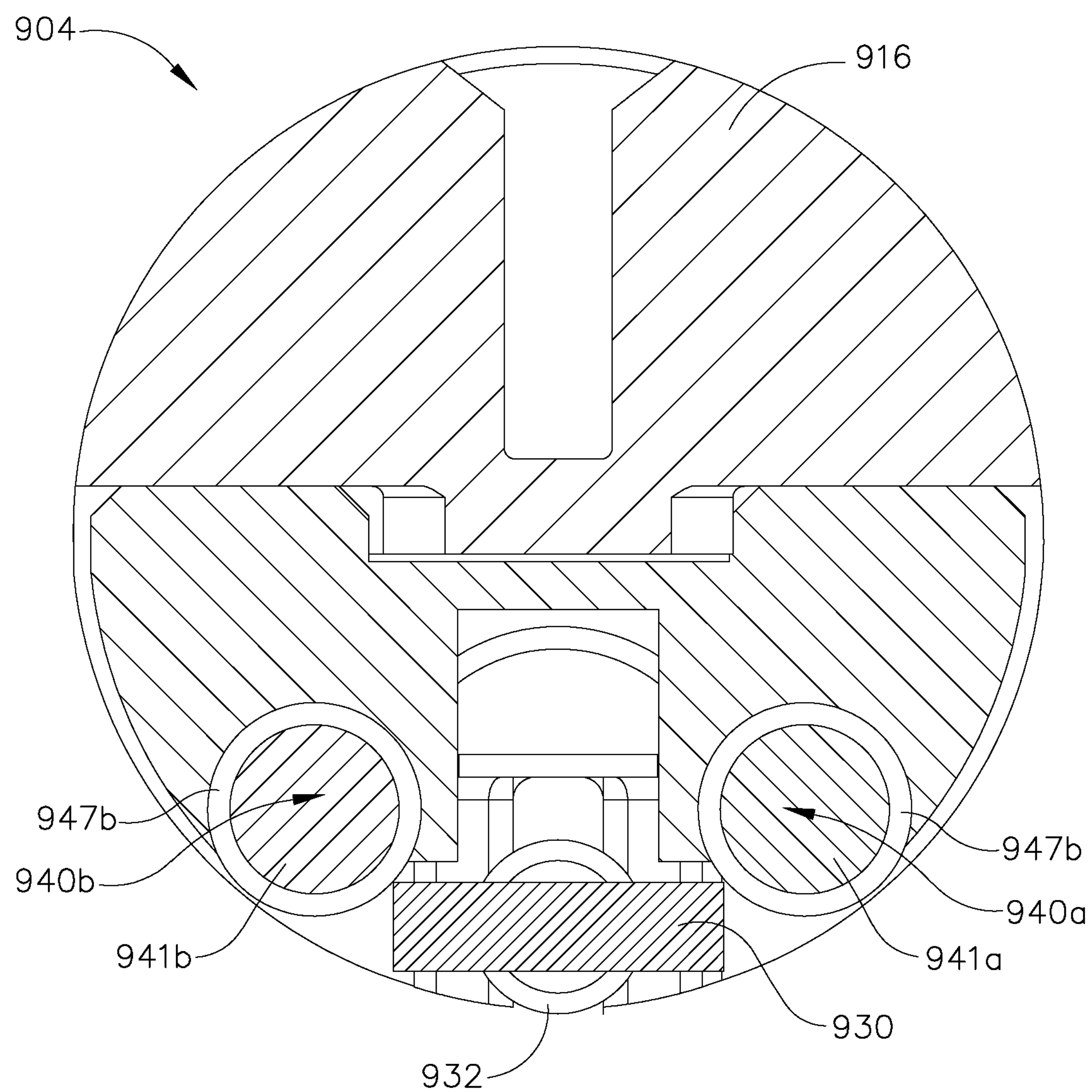
FIG. 24 is a cross-sectional view of the elongate shaft of FIG. 22.

In various embodiments, referring primarily to FIG. 23, photosensor 991, for example, can be placed in signal communication with a control unit, such as control unit 992, for example, such that data regarding the number of encoder markings 990 that pass under photosensor 991 can be transmitted to control unit 992. More particularly, in at least one embodiment, control unit 992 can comprise at least one digital signal processor, such as DSP 993, for example, which can be configured to receive signal pulses from photosensor 991 which correspond to the passing of encoder markings 990 under photosensor 991. For example, if five markings 990 pass under sensor 991, sensor 991 can transmit five signal pulses to DSP 993 via conductor 994, although such communication can be wireless via a wireless transmitter (not illustrated). In any event, DSP 993 can be configured to process such signal pulses, calculate the amount in which end effector 906 has rotated relative to end effector 904, and output such information to the surgeon. In at least one embodiment, further to the above, the detection of one encoder marking 990 can represent one degree of articulation of end effector 906, wherein DSP 993 can be configured to transmit the degree in which end effector 906 has been rotated to an LCD display on the handle assembly of the surgical instrument. In various embodiments, the LCD display can comprise a screen, wherein data can be displayed in the form of numerals, text, and/or a graphical form such as an increasing or decreasing bar scale, for example. In various embodiments, further to the above, control unit 992 can further include a pulse width modulator (PWM) which can be configured to modify and control the output signals or power supplied to electromagnets 940*a* and 940*b*.

Figure 25:
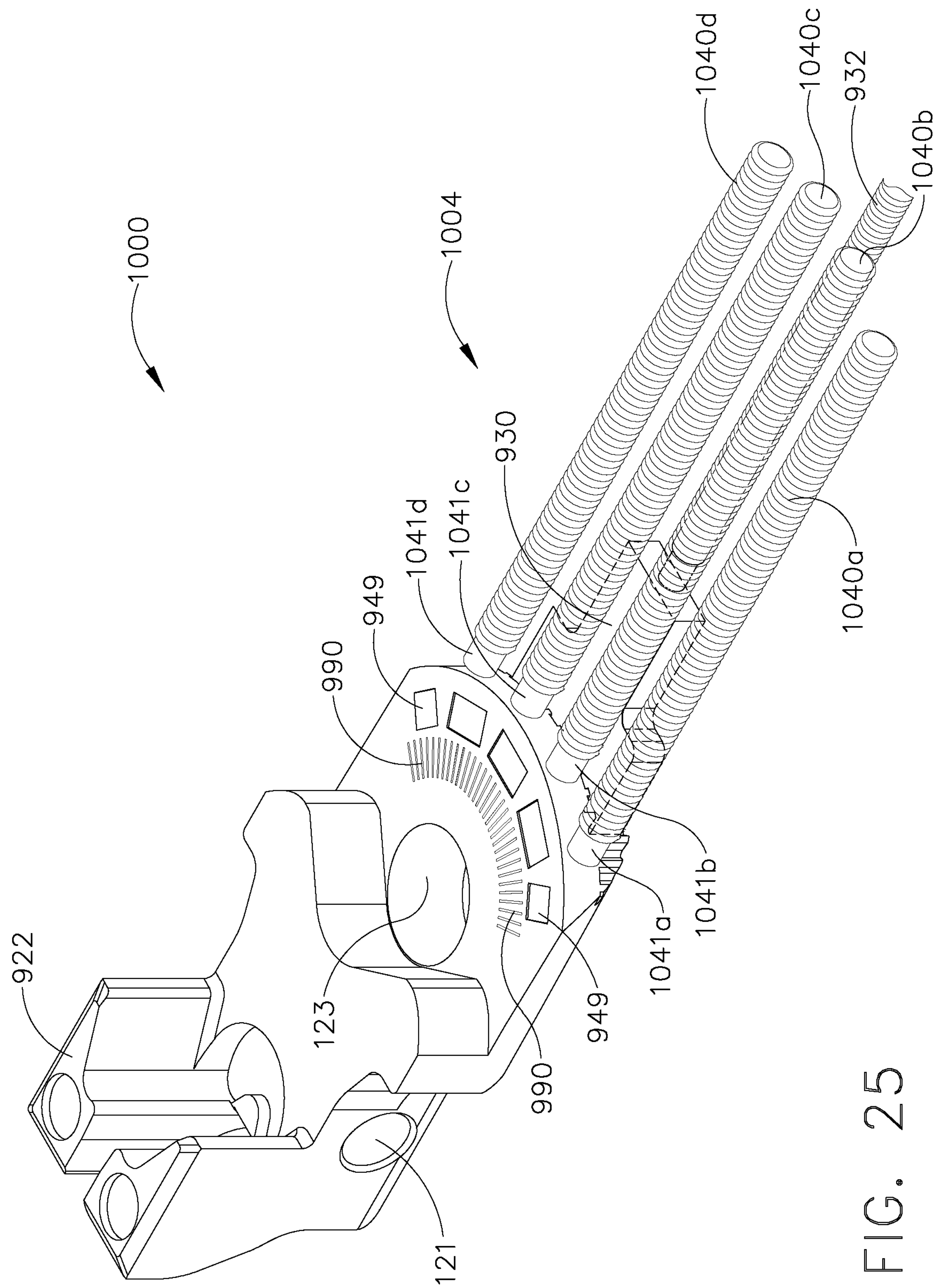
FIG. 25 is a perspective view of an articulation joint connecting an end effector and an elongate shaft of a surgical instrument in accordance with at least one embodiment of the present invention with some components removed.
Figure 26:
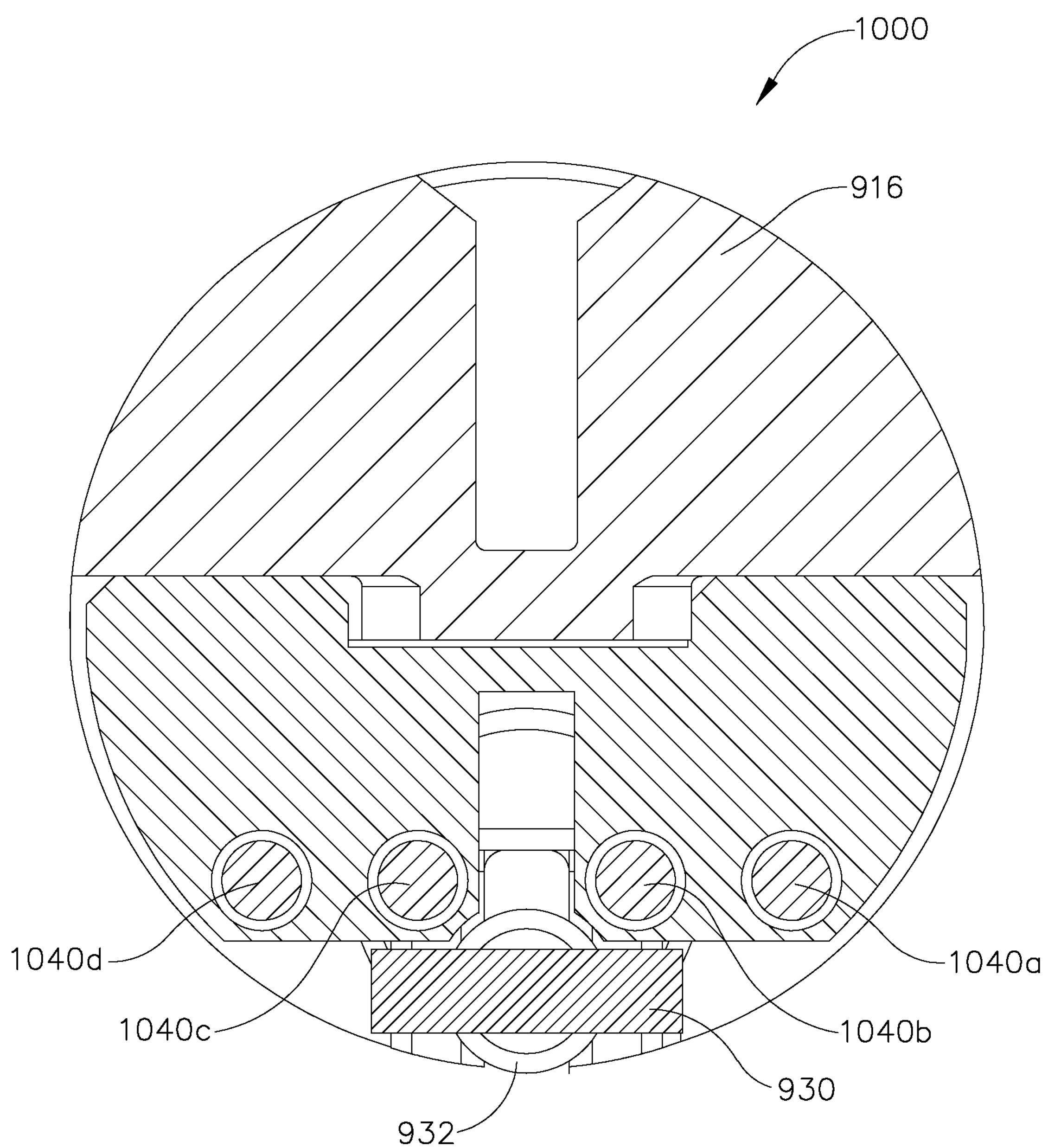
FIG. 26 is a cross-sectional view of the end effector of FIG. 25 illustrating a plurality of electromagnets.
Figure 27:
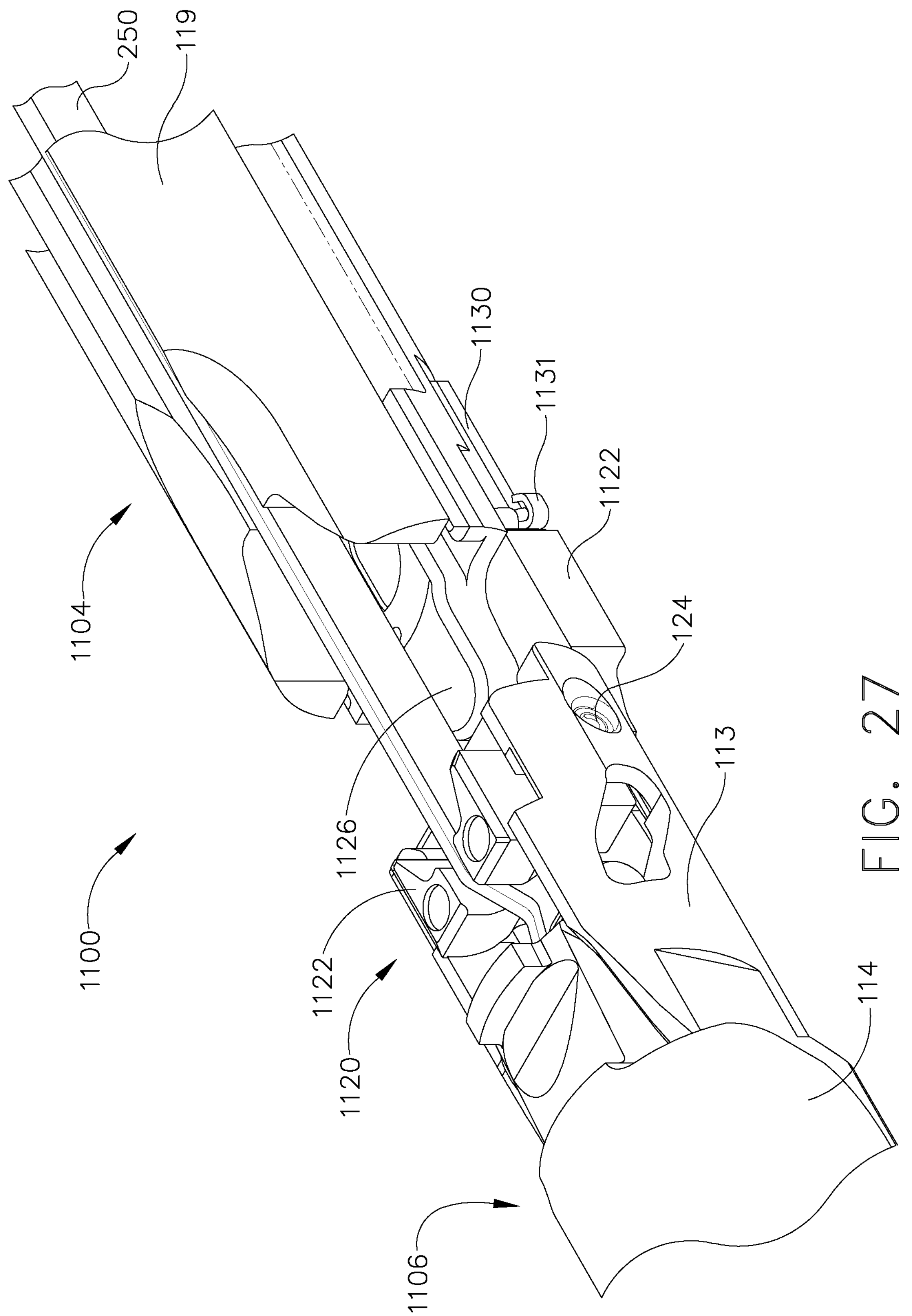
FIG. 27 is a perspective view of an articulation joint connecting an end effector and an elongate shaft of a surgical instrument in accordance with at least one embodiment of the present invention illustrated with some components removed.
Figure 28:
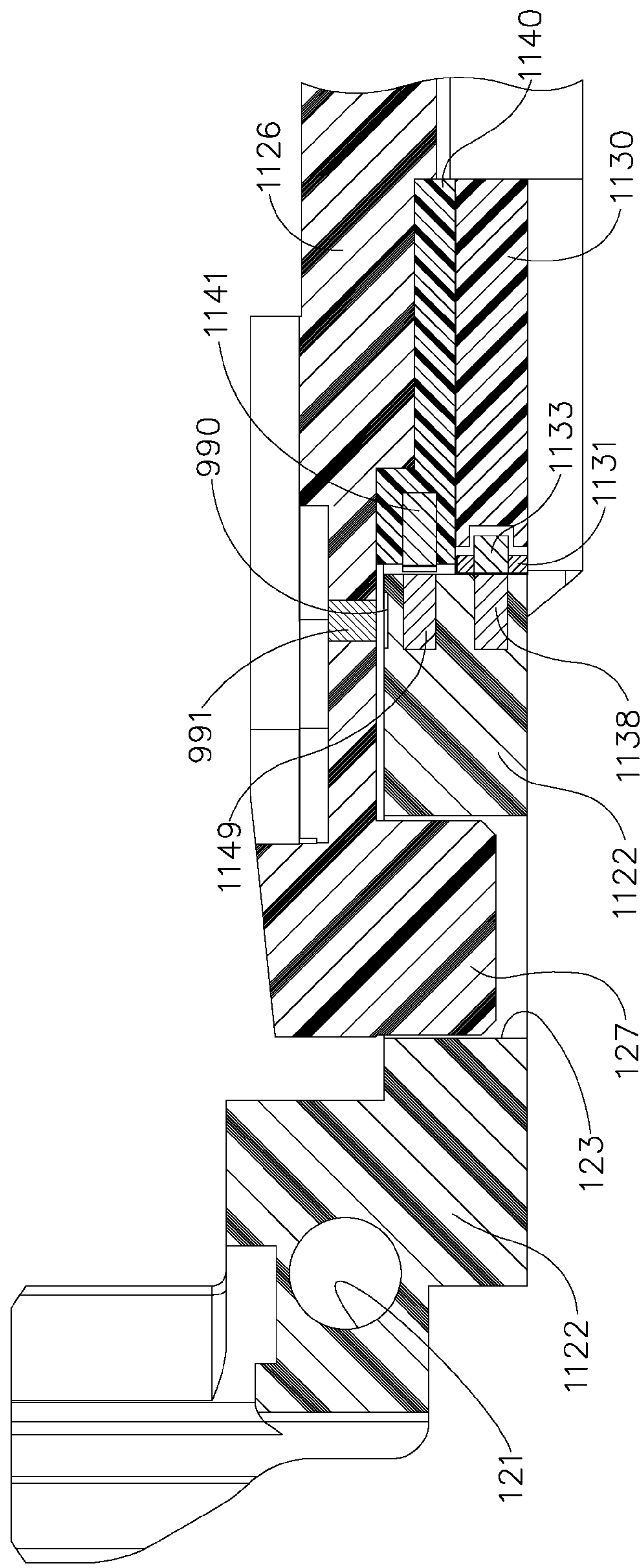
FIG. 28 is a cross-sectional view of the articulation joint of FIG. 27 illustrating a system of permanent magnets and electromagnets configured to articulate the end effector of the surgical instrument and another system of permanent magnets and electromagnets configured to lock the end effector in position relative to the elongate shaft of the surgical instrument.
Figure 29:
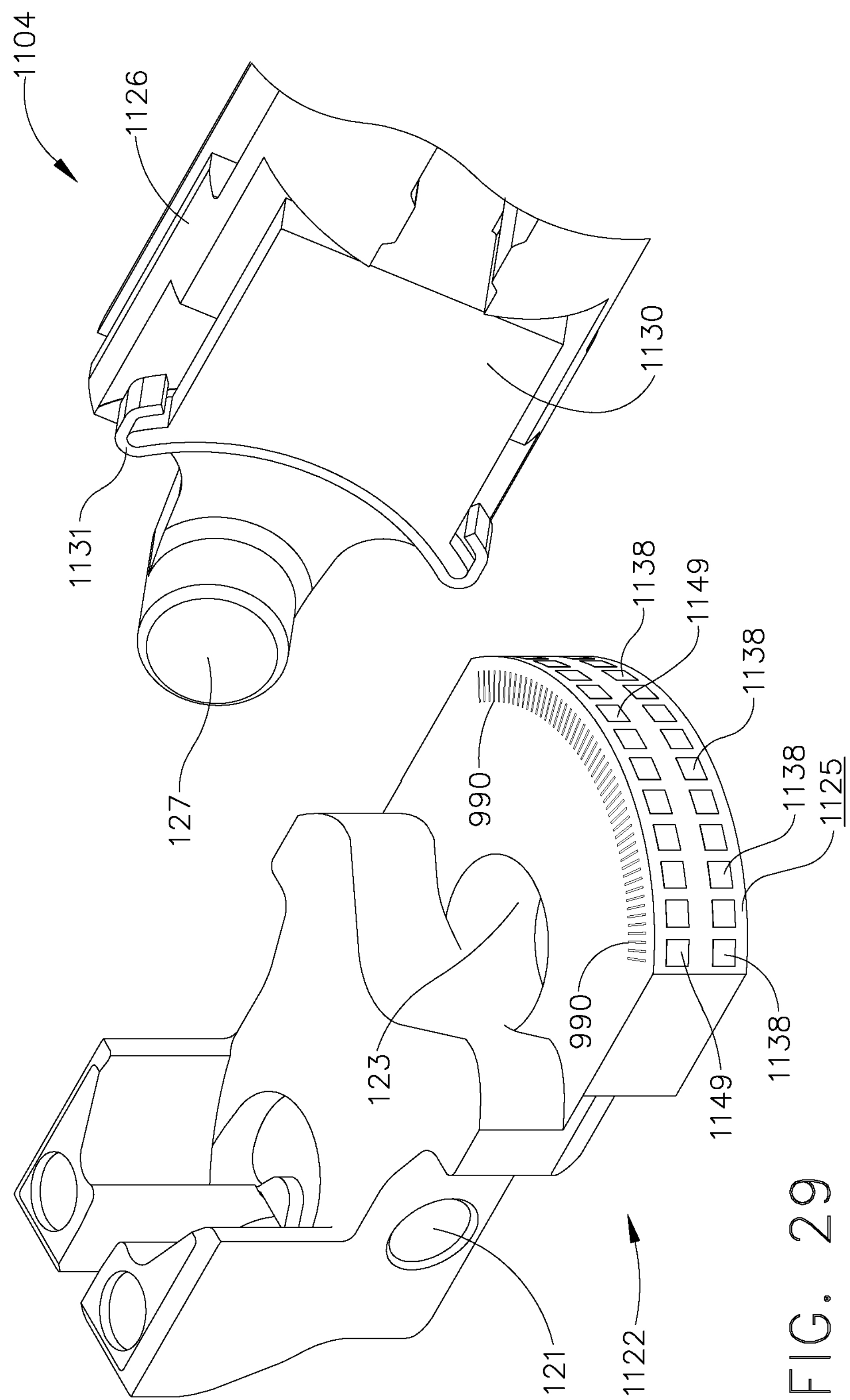
FIG. 29 is a disassembled view of the articulation joint of FIG. 27 illustrated with some components removed.
Figure 30:
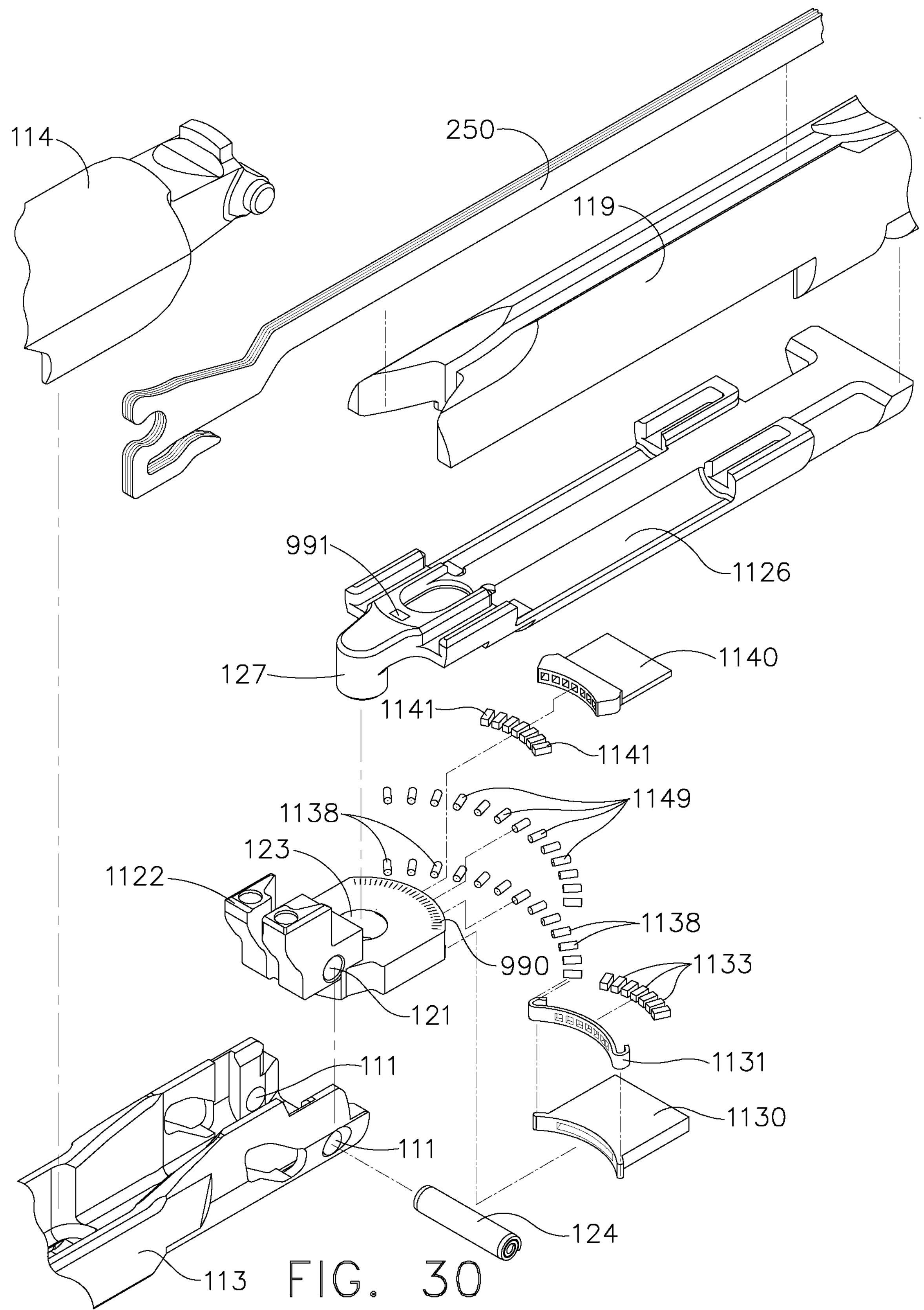
FIG. 30 is an exploded view of the articulation joint of FIG. 27.
Figure 31:
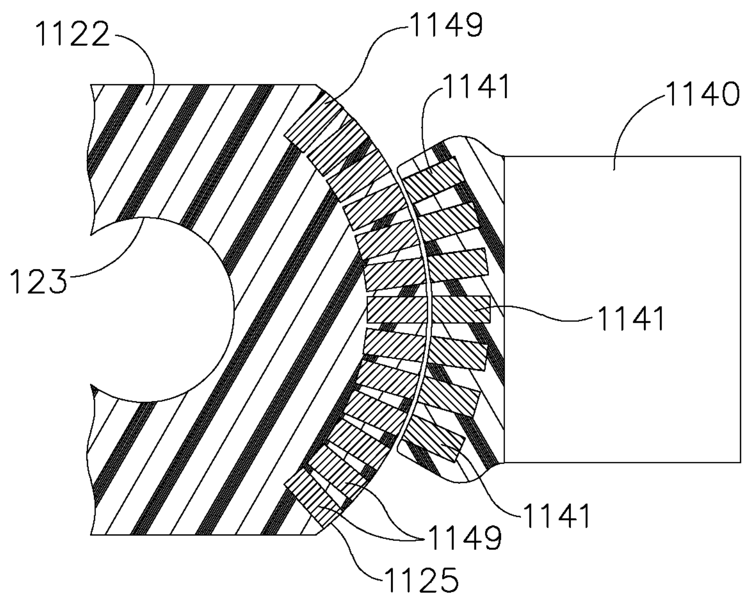
FIG. 31 is a cross-sectional view of the articulation joint of FIG. 27 illustrating the system of permanent magnets and electromagnets for articulating the end effector of the surgical instrument.
Figure 32:
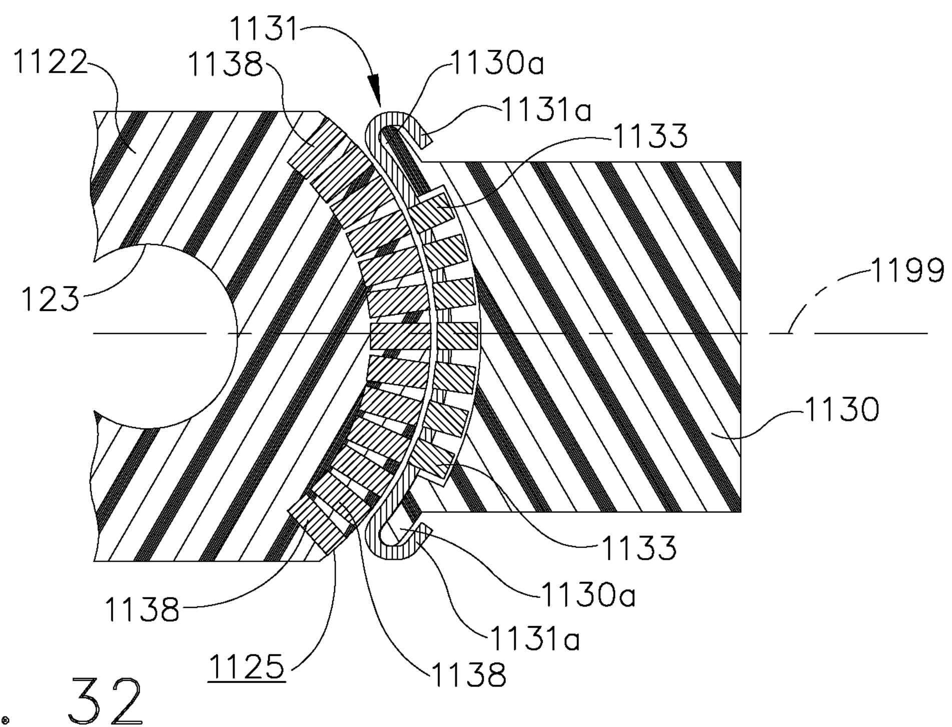
FIG. 32 is a cross-sectional view of the articulation joint of FIG. 27 illustrating the system of permanent magnets and electromagnets for locking the end effector in position.

As described above, elongate shaft 904 can comprise two electromagnets, i.e., electromagnets 940*a* and 940*b*, which can be configured to emit a magnetic field, or fields, which can interact with magnetic elements 949. As illustrated in FIG. 23, pivot plate 922 includes five magnetic elements 949 embedded therein; however, other embodiments may have less than five magnetic elements 949 or more than five magnetic elements. Similarly, other surgical instruments can comprise any suitable number of electromagnets. In at least one embodiment, referring now to FIG. 25, an elongate shaft 1004 of surgical instrument 1000 can comprise four electromagnets, i.e., electromagnets 1040*a*, 1040*b*, 1040*c*, and 1040*d* which can each be configured to independently generate a magnetic field and polarity at the distal ends of cores 1041*a*-1041*d*, respectively. Similar to the above, the strength and polarity of the magnetic felids produced by electromagnets 1040*a*-1040*d* can be determined by the direction and magnitude of the current flowing through conductors, or wires, 1041*a*-1041*d*, respectively. In any event, once end effector 906 has been sufficiently articulated, similar to the above, end effector 106 can be locked into position. In various embodiments, referring to FIG. 23, elongate shaft 904 can further comprise lock 930 which can be moved between a proximal, unlocked position and a distal, locked position in which lock 930 is engaged with teeth 925 on pivot plate 922. In at least one embodiment, lock 930 can include a plurality of recesses 931 which can be configured to receive one or more teeth 925 such that pivot plate 922 cannot rotate, or at least substantially rotate, relative to lock 930 and, correspondingly, elongate shaft 904. Similarly, lock 930 can comprise a plurality of teeth positioned intermediate recesses 931 which can be configured to be received within recesses positioned intermediate teeth 925 on pivot plate 922, for example. In various embodiments, also similar to the above, elongate shaft 904 can further comprise lock actuator 932 which can be configured to move lock 930 between its locked and unlocked positions. In at least one such embodiment, lock actuator 932 can comprise a solenoid, for example.

In various embodiments, referring now to FIGS. 27-32, a surgical instrument, such as surgical instrument 1100, for example, can comprise an elongate shaft 1104 and an end effector 1106, wherein end effector 1106 can be configured to articulate relative to elongate shaft 1104 about articulation joint 1120. In at least one embodiment, similar to the above, end effector 1106 can comprise pivot plate 1122 mounted thereto and, in addition, elongate shaft 1104 can comprise pin plate member 1126 mounted therein, wherein pin 127 extending from pin plate member 1126 can be closely received within pin aperture 123 in pivot plate 1122 in order to define an axis about which pivot plate 1122, and end effector 1106, can articulate relative to elongate shaft 1104. Also similar to the above, elongate shaft 1104 can further comprise one or more electromagnets which can be configured to generate a magnetic field, or fields, which can be configured to interact with one or more magnetic elements mounted to end effector 1106. In at least one such embodiment, referring primarily to FIGS. 28-31, pivot plate 1122 of end effector 1106 can have a plurality of permanent magnets 1149 mounted thereto wherein, in at least one embodiment, permanent magnets 1149 can be embedded within one or more cavities within pivot plate 1122. In certain embodiments, similar to the above, permanent magnets 1149 can have positive and negative poles which can be arranged in a suitable manner such that, when electromagnets 1141 mounted within elongate shaft 1104 are sufficiently energized, or polarized, permanent magnets 1149 can interact with the magnetic field, or fields, generated by electromagnets 1141. In at least one such embodiment, the positive poles of permanent magnets 1149 can be arranged such that their positive poles are positioned radially outwardly with respect to their negative poles. Stated another way, in at least one embodiment, the positive poles of permanent magnets 1149 can be positioned adjacent to surface 1125 whereas the negative poles of magnets 1149 can be positioned distally, or at least somewhat distally, with respect to the positive poles. In certain other embodiments, permanent magnets 1141 can be arranged such that their poles alternate. For example, permanent magnets 1141 can be arranged such that the radially outward end of a first magnet 1141 is positive, for example, the radially outward end of a second magnet 1141 is negative, and the radially outward end of a third magnet is positive, and so forth.

In various embodiments, further to the above, electromagnets 1141 can be selectively energized, or polarized, in order to retract or repel permanent magnets 1149 and rotate end effector 1106 in a desired direction. In certain embodiments, referring to FIGS. 28 and 30, electromagnets 1141 can be embedded in or positioned within one or more cavities in actuator member 1140. In at least one embodiment, a first group of electromagnets 1141 can be energized, or polarized, such that their distal ends, i.e., their ends positioned adjacent to permanent magnets 1149, generate negative poles, for example, while a second group of electromagnets 1141 can remain unenergized, or unpolarized, or at least substantially unenergized, or unpolarized. In at least one such embodiment, as a result, the negative polarity of the distal ends of electromagnets 1141 can attract the positive poles of permanent magnets 1149 and move permanent magnets 1149 toward the negative poles electromagnets 1141. In various circumstances, the selective energization, or polarization, of the first group of electromagnets 1141 can displace permanent magnets 1149 such that end effector 1106 is rotated in a counter-clockwise direction, for example. In certain circumstances, the first group of electromagnets 1141 can be subsequently de-energized, or depolarized, or at least substantially de-energized, or depolarized, and the second group of electromagnets 1141 can be energized, or polarized, such that their distal ends generate a negative polarity which, similar to the above, attracts the positive poles of permanent magnets 1149 in order to continue the rotation of end effector 1106 in a counter-clockwise direction, for example. In certain other embodiments, the first group of electromagnets 1141 can be energized such that their distal ends generate a negative polarity, for example, while the second group of electromagnets 1141 can be energized such that their distal ends generate a positive polarity, for example. In various embodiments, the first and second groups can be energized such that they have different polarities simultaneously or in a suitable alternating sequence.

Once end effector 1106 has been sufficiently articulated, further to the above, end effector 1106 can be locked into position. In various embodiments, referring to FIGS. 28-30 and 32, elongate shaft 1104 can further comprise lock 1130, wherein at least a portion of lock 1130 can be moved between a distal, locked position, in which it is engaged with pivot plate 1122, for example, and a proximal, unlocked position in which it is sufficiently disengaged from pivot plate 1122 to allow end effector 1106 to rotate about an axis defined by pin aperture 123 and pin 127. In at least one embodiment, lock 1130 can comprise a movable brake shoe, such as brake shoe 1131, for example, which can be moved between proximal and distal positions. More particularly, in at least one embodiment, pivot plate 1122 can include one or more permanent magnets 1138 mounted thereto, wherein permanent magnets 1138 can be configured and arranged such that their positive, or north, poles, for example, are positioned radially outwardly with respect to their negative, or south, poles, and wherein permanent magnets 1138 can be configured to attract brake shoe 1131 toward pivot plate 1122 such that brake shoe 1131 contacts brake surface 1125. In various embodiments, brake shoe 1131 can include one or more magnetic elements 1133 mounted thereto which can interact with the magnetic field, or fields, produced by permanent magnets 1138, wherein the magnetic field, or fields, can apply a sufficient magnetomotive force (mmf) to magnetic elements 1133 such that the bearing force, or braking force, between brake shoe 1131 and brake surface 1125 is sufficient to prevent, or at least inhibit, relative movement between pivot plate 1122 and pivot pin member 1126.

In order to disengage brake shoe 1131 from pivot plate 1122, in various embodiments, magnetic elements 1133 can comprise electromagnets which can be selectively energized to order to create a magnetic field, or fields, which can move brake shoe 1131 away from pivot plate 1122. In at least one circumstance, electromagnets 1133 can be energized in order to generate positive poles at their distal ends, i.e., their ends closest to pivot plate 122, such that the positive poles generated by electromagnets 1133 are repelled by the positive poles of permanent magnets 1138. In various embodiments, electromagnets 1133 can be mounted to brake shoe 1131 such that, when a sufficient magnetomotive force is generated, brake shoe 1131 can be displaced proximally. Brake shoe 1131 can be displaced proximally such that brake shoe 1131 is no longer engaged with brake surface 1125 and/or such that brake shoe 1131 is otherwise unable to apply a sufficient braking force to pivot plate 1122 in order to hold end effector 1106 in position. In certain other embodiments, the negative poles of permanent magnets 1138 can be positioned radially outwardly such that, when electromagnets 1133 are energized, negative poles generated at the distal ends of electromagnets 1133 can be repelled by the negative poles of permanent magnets 1138. In at least one embodiment, referring primarily to FIGS. 29 and 32, lock 1130 can comprise one or more features for limiting the displacement of brake shoe 1131 such that brake shoe 1131 travels along a predetermined path, such as axis 1199, for example. In at least one such embodiment, lock 1130 can further comprise one or more projections, or travel limiters 1130*a*, and brake shoe 1131 can further comprise stop arms 1131*a*, wherein travel limiters 1130*a* and stop arms 1131*a* can be configured to prevent, or at least inhibit, relative movement between brake shoe 1131 and lock 1130 which is transverse to axis 1199.

Figure 38:
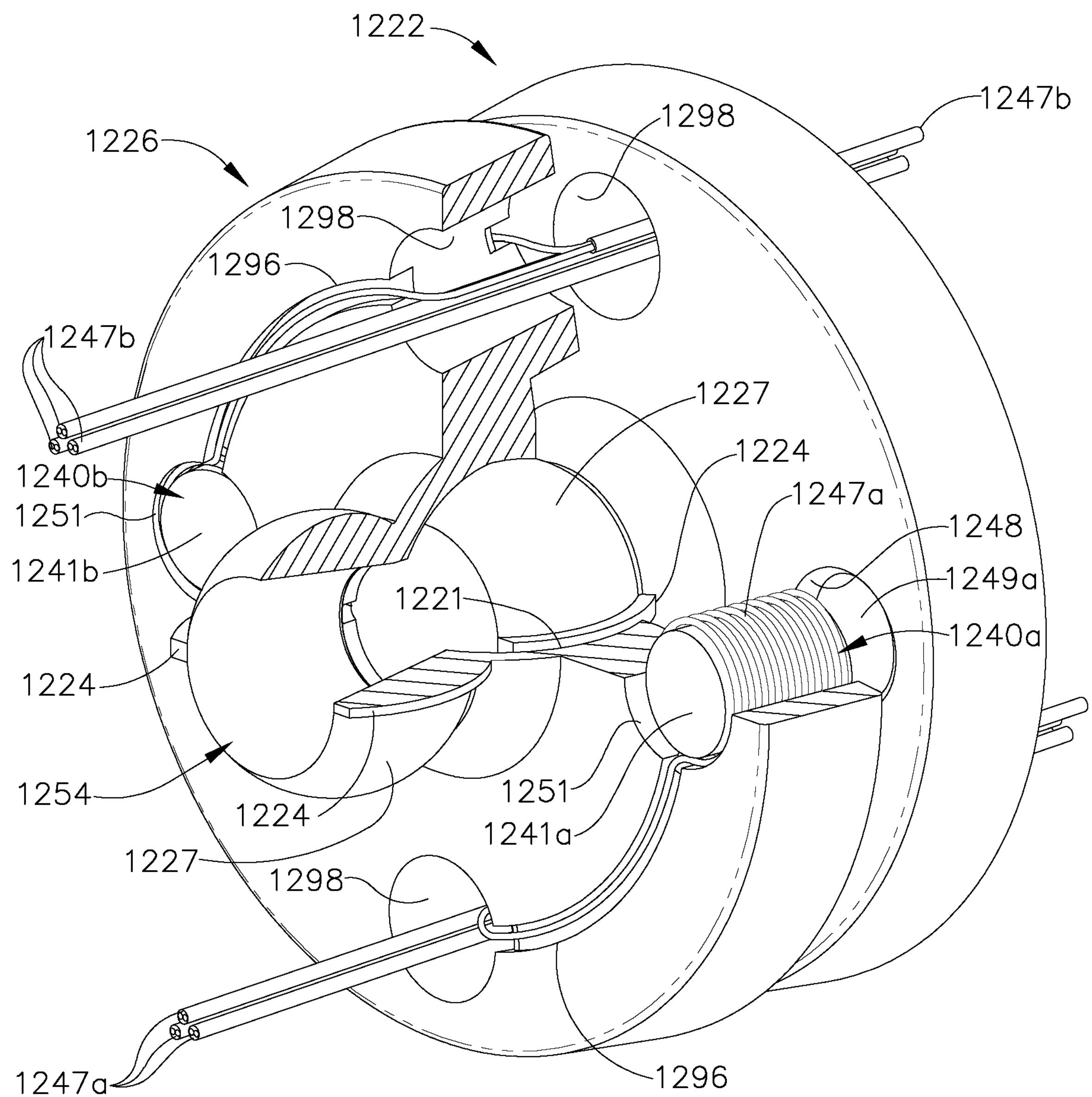
FIG. 38 is an assembly view of the disc of FIG. 36 and a second disc positioned adjacent thereto, wherein the second disc comprises a plurality of permanent magnets positioned within a first set of apertures and another set of apertures configured to permit the wires of FIG. 36 to extend therethrough.
Figure 39:
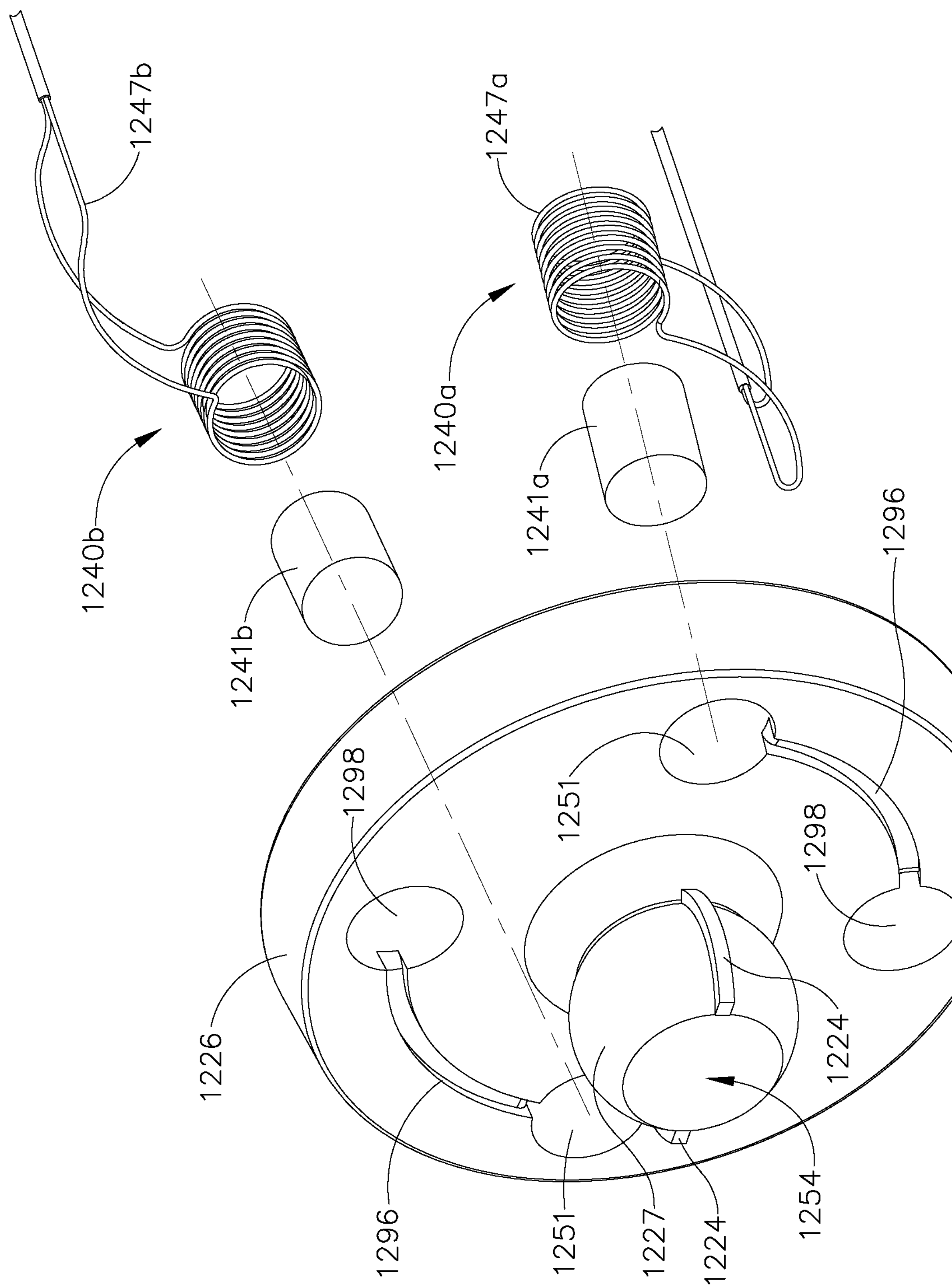
FIG. 39 is an exploded view of the disc of FIG. 36.
Figure 40:
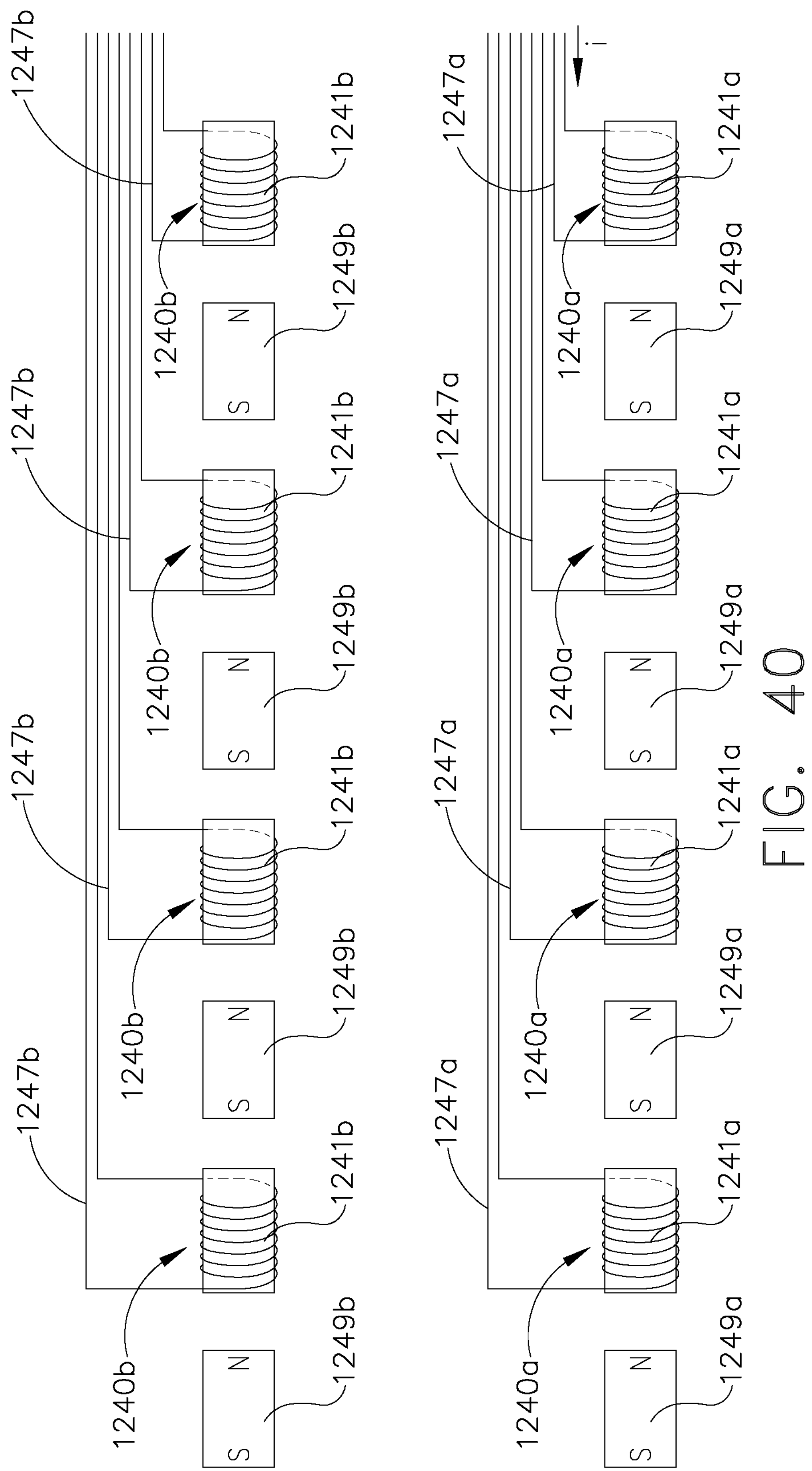
FIG. 40 is an electrical schematic of the permanent magnets and electromagnets of the articulation joint of FIG. 34.

In various embodiments, further to the above, an articulation joint can comprise first and second portions which can be configured to articulate relative to one another. In various other embodiments, an articulation joint can comprise more than two portions which can articulate relative to one another. In at least one such embodiment, referring to FIGS. 33-40, a surgical instrument, such as surgical instrument 1200, for example, can comprise a handle assembly 1202, an elongate shaft 1204, and an end effector 1206, wherein articulation joint 1220 can be configured to permit end effector 1206 to rotate relative to elongate shaft 1204, and wherein articulation joint 1220 can comprise a plurality of first joint members 1222 and a plurality of second joint members 1226, for example. In certain embodiments, referring primarily to FIGS. 34 and 35, first joint members 1222 and second joint members 1226 can be arranged in an alternating arrangement wherein, in at least one embodiment, first joint members 1222 can each include one or more permanent magnets mounted thereto and second joint members 1226 can each include one or more electromagnets mounted thereto. Referring now to FIGS. 38 and 40, each first joint member 1222 can include a first permanent magnet 1249*a* positioned within an aperture therein, such as an aperture 1248, for example, and, in addition, a second permanent magnet 1249*b* positioned within another aperture 1248 on the opposite, or at least substantially opposite, side of the first joint member 1222. Similarly, referring to FIGS. 36-40, each second joint member 1226 can include a first electromagnet 1240*a* positioned within an aperture therein, such as an aperture 1251, for example, and, in addition, a second electromagnet 1240*b* positioned within another aperture 1251 on the opposite, or at least substantially opposite, side of second joint member 1226. In various embodiments, referring again to FIGS. 34 and 35, joint members 1222 and 1226 can be arranged such that permanent magnets 1249*a* are aligned, or at least substantially aligned, with electromagnets 1240*a* and, in addition, permanent magnets 1249*b* are aligned, or at least substantially aligned, with electromagnets 1240*b*.

Figure 33:
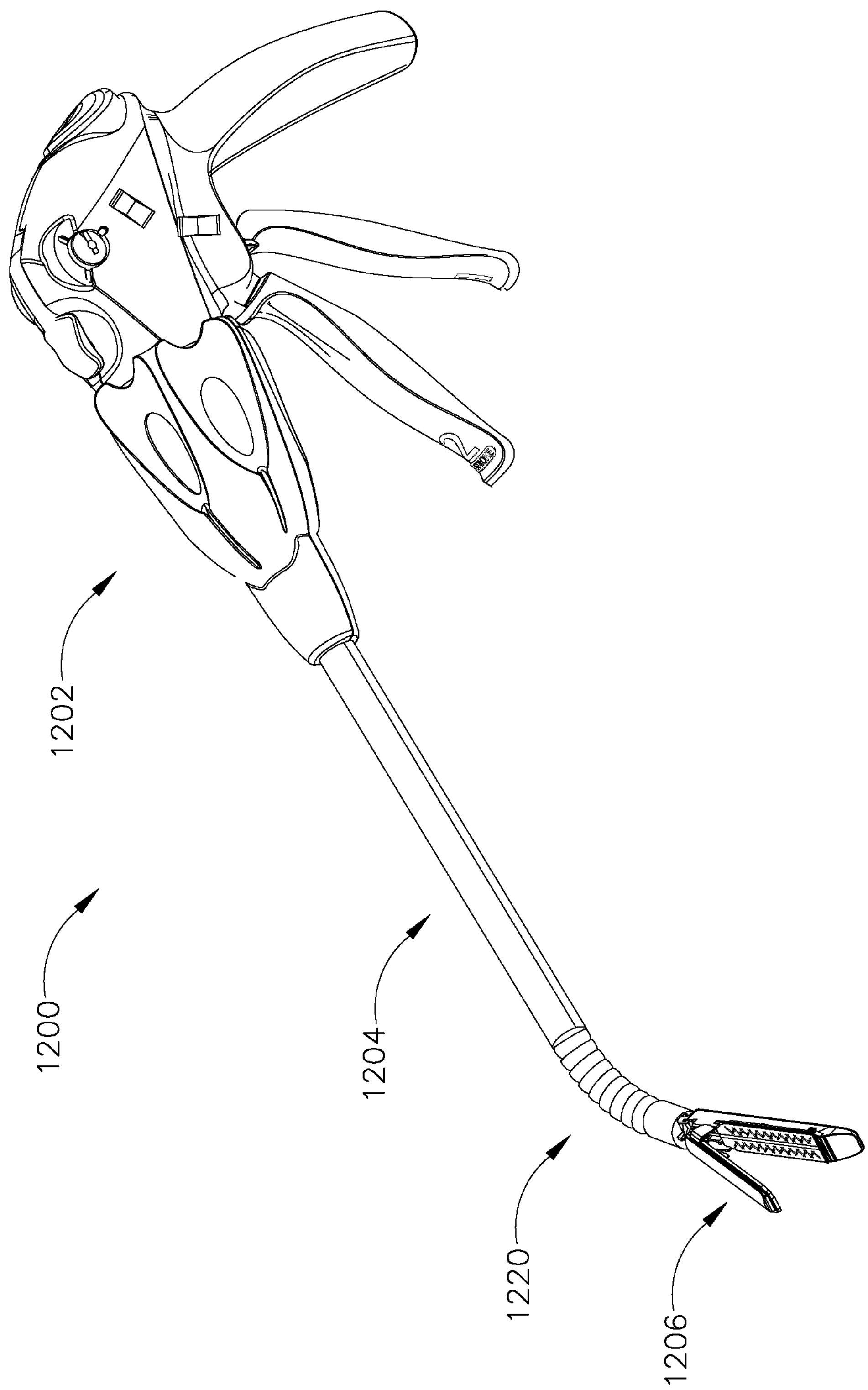
FIG. 33 is a perspective view of a surgical instrument comprising a handle assembly, an elongate shaft, and an end effector articulatable relative to the elongate shaft in accordance with at least one embodiment of the present invention.
Figure 34:
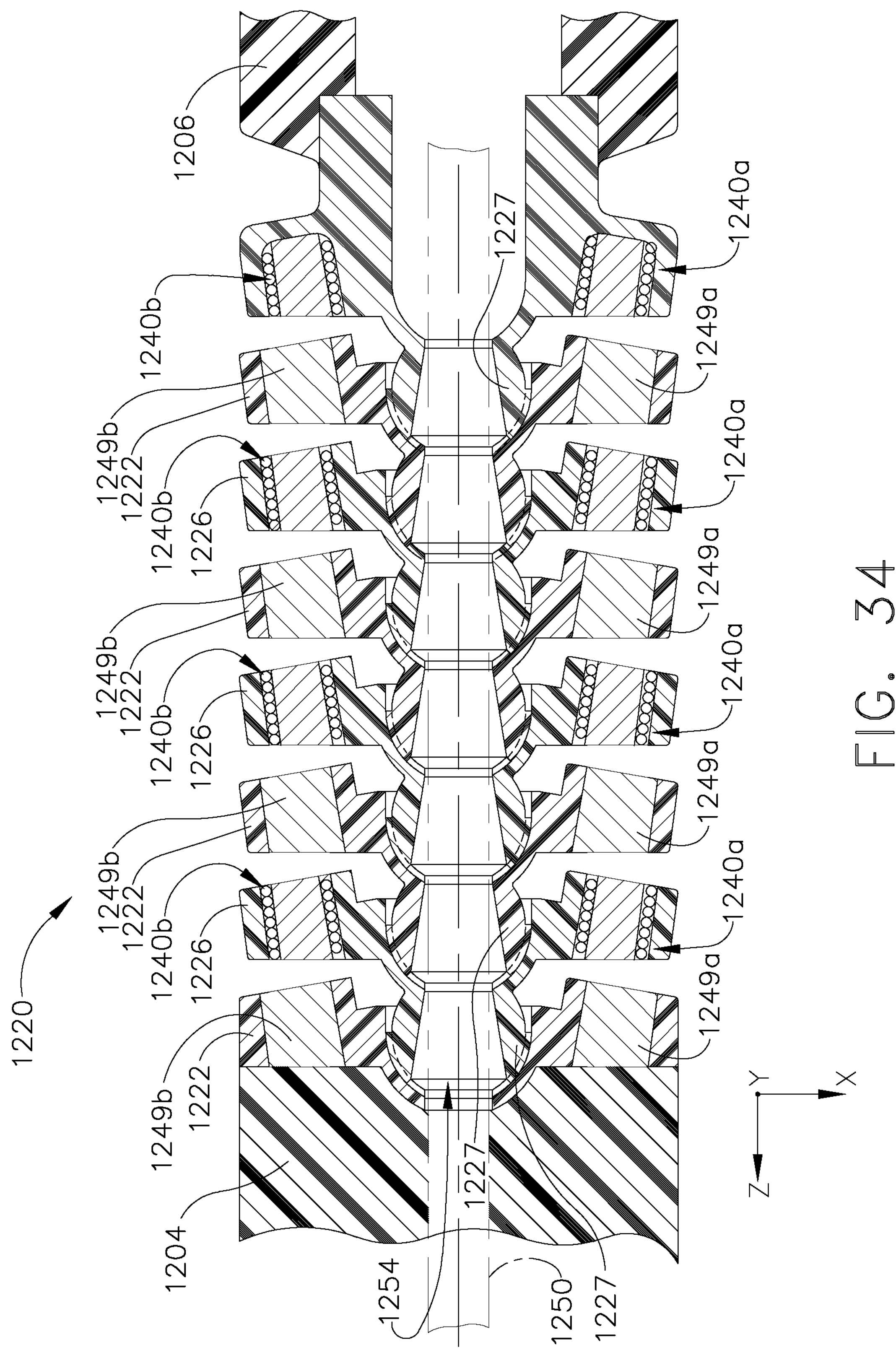
FIG. 34 is a cross-sectional view of an articulation joint connecting the elongate shaft and the end effector of FIG. 33, wherein the articulation joint comprises a plurality of discs.
Figure 35:
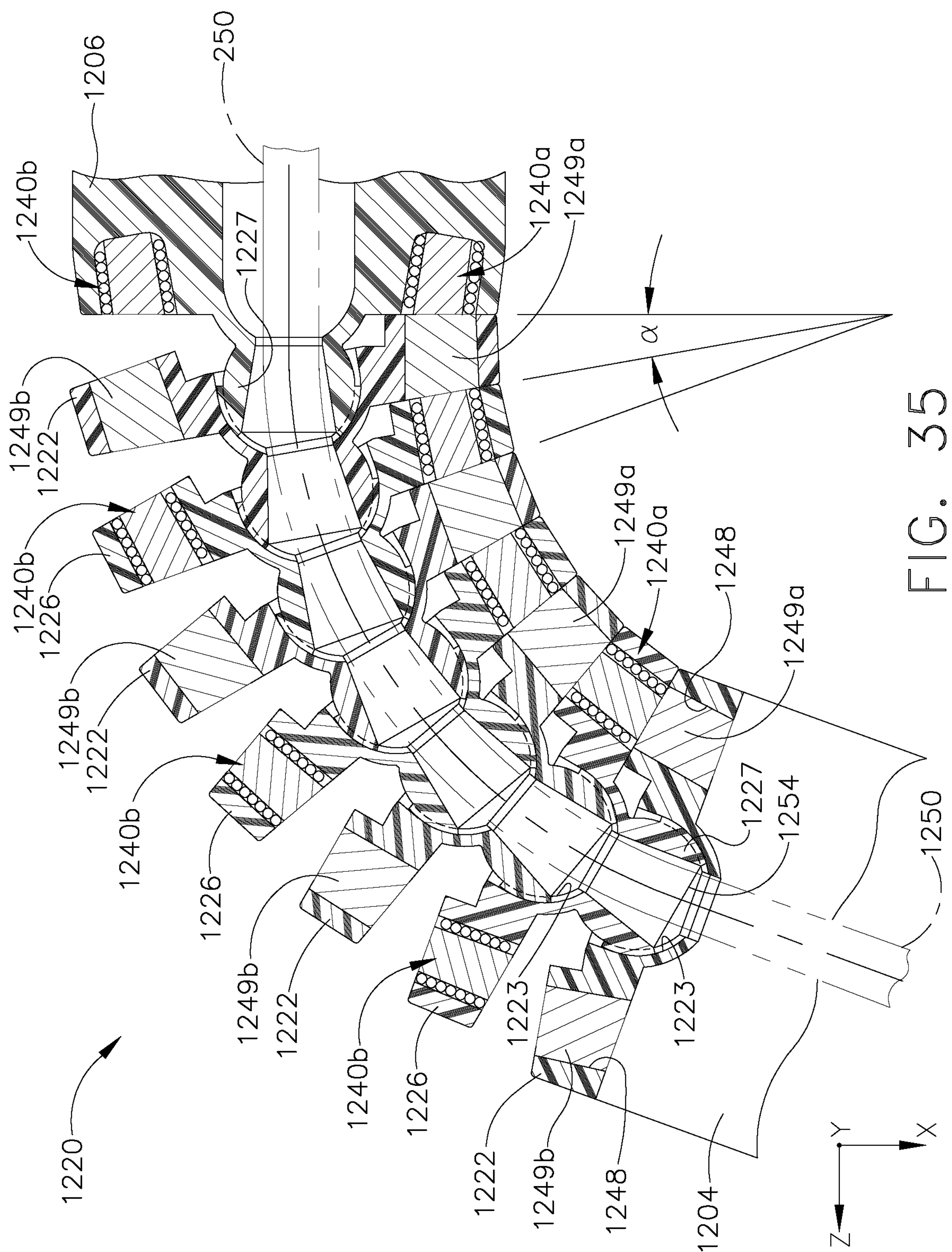
FIG. 35 is a cross-sectional view of the articulation joint of FIG. 34 illustrating the articulation joint in an articulated configuration.
Figure 36:
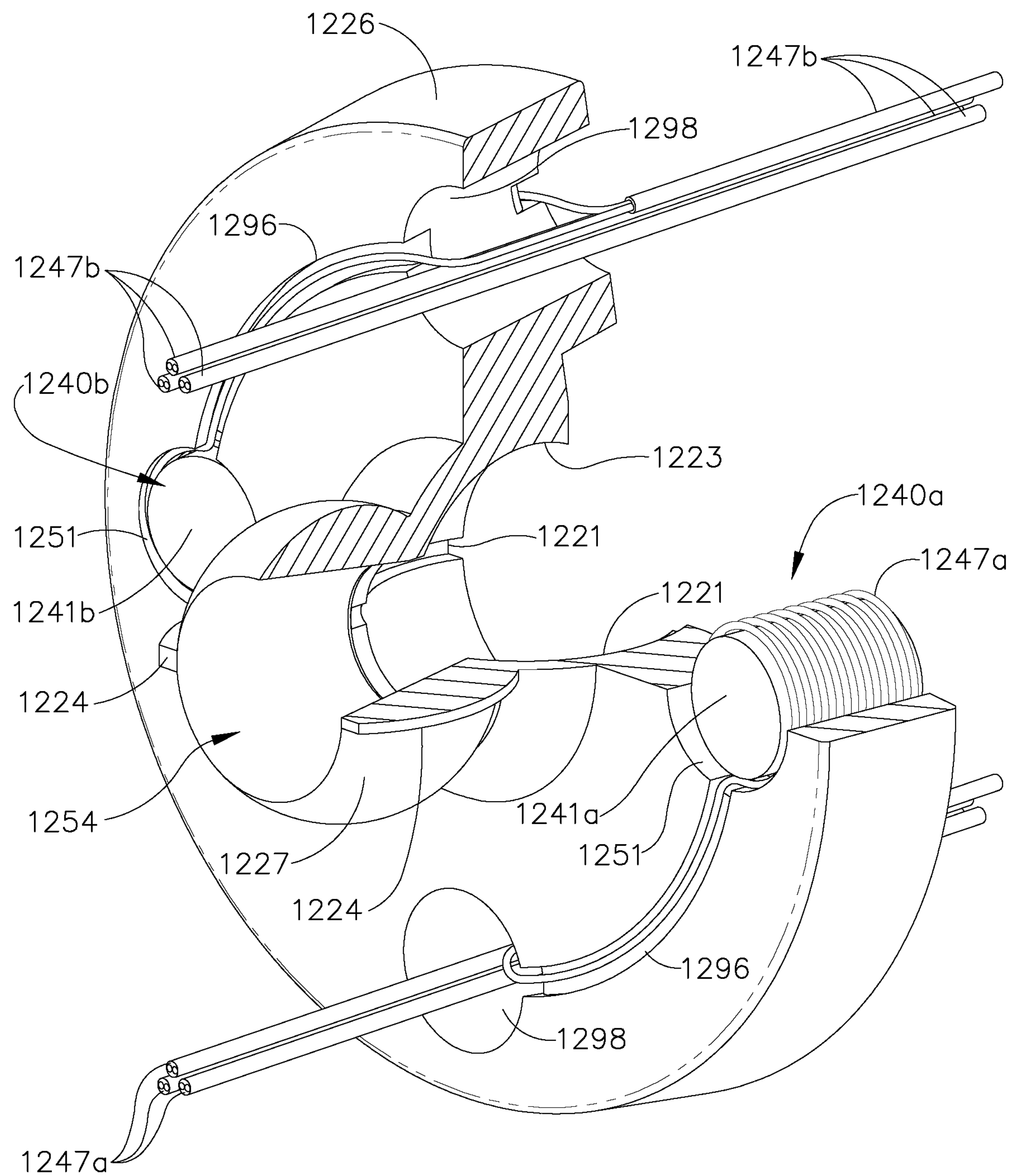
FIG. 36 is a cross-sectional perspective view of a disc of the articulation joint of FIG. 34 illustrating electromagnets positioned within a first set of apertures and wires extending through another set of apertures, the wires electrically coupling the electromagnets with a power source.
Figure 37:
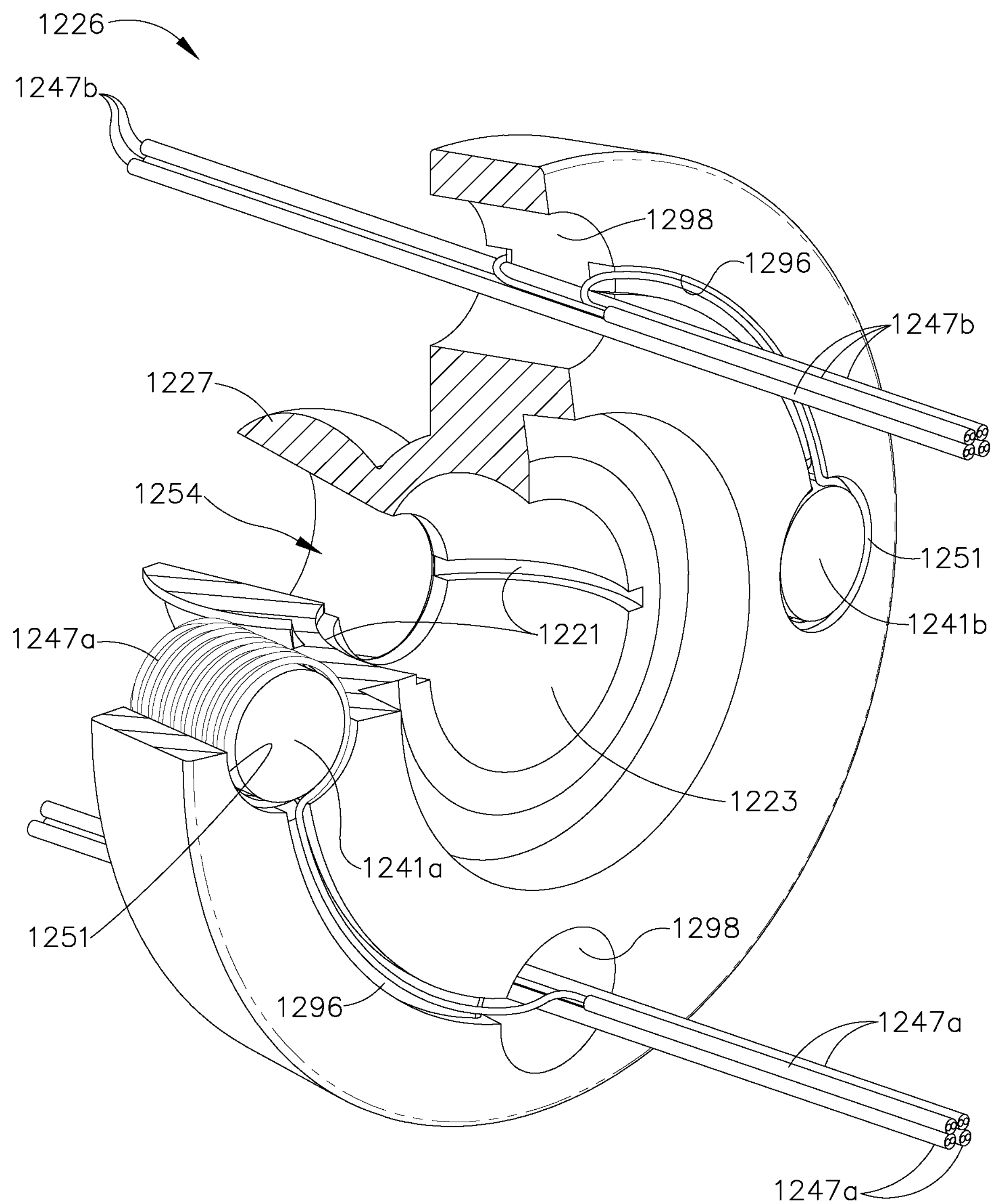
FIG. 37 is another cross-sectional perspective view of the disc of FIG. 36.

In various embodiments, further to the above, each electromagnet 1240*a* can comprise a core, such as core 1241*a*, for example, and a conductor, such as conductor 1247*a*, for example, wherein conductors 1247*a* can be configured to conduct current when a current source and/or voltage source is supplied to conductors 1247*a*, and wherein at least a portion of conductors 1247*a* can be wrapped around cores 1241*a* in order to generate a magnetic field having a polarity. As outlined above, the polarity of such magnetic fields may depend on the direction in which current is flowing through conductors 1247*a*. Similar to the above, each permanent magnet 1240*b* can comprise a core, such as core 1241*b*, for example, and a conductor, such as conductor 1247*b*, for example, wherein conductors 1247*b* can be configured to conduct current when a current source and/or voltage source is supplied to conductors 1247*b*. In use, in at least one embodiment, end effector 1206 can be articulated to the right, or in a clockwise direction, for example, as illustrated in FIG. 35, when current is supplied to, and/or voltage is applied to, conductors 1247*a* such that current flows through conductors 1247*a* in a first direction. More particularly, referring again to FIG. 40, electromagnets 1240*a* can be energized, or polarized, such that the negative, or south, poles of permanent magnets 1249*a*, marked with an "S", are attracted to positive, or north, poles generated by electromagnets 1240*a* and, in addition, the positive poles of permanent magnets 1249*a*, marked with an "N", are attracted to negative poles generated by electromagnets 1240*a*. In such circumstances, referring again to FIG. 35, the magnetomotive forces (mmf) between electromagnets 1240*a* and permanent magnets 1249*a* can be sufficient to cause first joint members 1222 and second joint members 1226 to articulate relative to each other. In certain embodiments, the joint members 1222 and 1226 can articulate relative to each other until they abut one another. In certain embodiments, end effector 1206 can be articulated to the left, or in a counter-clockwise direction, as illustrated in FIG. 33, when current is supplied to, and/or voltage is applied to, conductors 1247*a* such that current flows through conductors 1247*a* in a second, or opposite, direction. In such embodiments, referring again to FIG. 40, electromagnets 1240*a* can be energized, or polarized, such that the negative poles of permanent magnets 1249 are repelled by negative poles generated by electromagnets 1240*a* and, in addition, the positive poles of permanent magnets 1249*a* are repelled by poles generated by electromagnets 1240*a*.

In various embodiments, similar to the above, end effector 1206 can be articulated to the left, or in a counter-clockwise direction, for example, when current is supplied to, and/or voltage is applied to, conductors 1247*b* such that current flows through conductors 1247*b* in a first direction. More particularly, referring again to FIG. 40, electromagnets 1240*b* can be energized, or polarized, such that the negative, or south, poles of permanent magnets 1249*b*, marked with an "S", are attracted to positive, or north, poles generated by electromagnets 1240*b* and, in addition, the positive poles of permanent magnets 1249*b*, marked with an "N", are attracted to negative poles generated by electromagnets 1240*b*. In such circumstances, referring again to FIG. 33, the magnetomotive forces (mmf) between electromagnets 1240*b* and permanent magnets 1249*b* can be sufficient to cause first joint members 1222 and second joint members 1226 to articulate relative to each other. In certain embodiments, the joint members 1222 and 1226 can articulate relative to each other until they abut one another. Also similar to the above, end effector 1206 can be articulated to the right, or in a clockwise direction, as illustrated in FIG. 35, when current is supplied to, and/or voltage is applied to, conductors 1247*b* such that current flows through conductors 1247*b* in a second, or opposite, direction. In such embodiments, referring again to FIG. 40, electromagnets 1240*b* can be energized, or polarized, such that the negative poles of permanent magnets 1249*b* are repelled by negative poles generated by electromagnets 1240*b* and, in addition, the positive poles of permanent magnets 1249*b* are repelled by positive poles generated by electromagnets 1240*b*. In various embodiments, further to the above, end effector 1206 and/or elongate shaft 1204 can include one or more permanent magnets and/or electromagnets which can be configured to articulate one or more of joint members 1222 and/or 1226.

In various embodiments, also further to the above, every electromagnet 1240*a*, for example, in articulation joint 1220 can be energized simultaneously in order to achieve a maximum rightward articulation of end effector 1206. Similarly, every electromagnet 1240*b*, for example, can be energized simultaneously in order to achieve a maximum leftward articulation of end effector 1206. In at least one embodiment, referring to FIG. 35, articulation joint 1220 can comprise three movable first joint members 1222 and three movable second joint members 1226, for example. In at least one such embodiment, each of the six joint members can be configured to articulate approximately 10 degrees relative to an adjacent joint member, for example, resulting in approximately 70 degrees of total articulation, for example. In certain embodiments, although not illustrated, a single conductor can be utilized to energize, or polarize, each of the electromagnets 1240*a* and, in addition, a single conductor can be utilized to energize, or polarize, each of the electromagnets 1240*b*. In effect, electromagnets 1240*a* can be placed in series with one another and, similarly, electromagnets 1240*b* can be placed in series with one another. In certain other embodiments, as illustrated in FIG. 40, for example, each electromagnet 1240*a* can be activated independently of the other electromagnets 1240*a* and, similarly, each electromagnet 1240*b* can be activated independently of the other electromagnets 1240*b*. In at least one such embodiment, the electromagnets 1240*a*, 1240*b* can be selectively actuated such that end effector 1206 can be articulated less than its maximum articulation. For example, only one electromagnet 1240*a* may be energized, or polarized, in order to articulate end effector 1206 approximately 20 degrees; two electromagnets 1240*a* may be energized, or polarized, to articulate end effector 1206 approximately 40 degrees; and three electromagnets 1240*a* may be energized, or polarized, to articulate end effector 1206 approximately 70 degrees. In certain embodiments, end effector 1206 and/or elongate shaft 1204 can include one or more electromagnets which can be actuated to articulate end effector 1206 more than 70 degrees, such as approximately 80 degrees, for example, or less than 20 degrees.

As described above, each electromagnet 1240*a*, 1240*b* can include a conductor 1247*a*, 1247*b*, respectively, which can be configured to conduct current. In various embodiments, conductors 1247*a* and 1247*b* can comprise wires, for example, which can be sufficiently flexible to accommodate relative movement between first joint members 1222 and second joint members 1226. In at least one embodiment, conductors 1247*a* and 1247*b* can extend through one or more throughholes 1298 in joint members 1222 and 1226, wherein conductors 1247*a* and 1247*b* can have sufficient slack such that they are not damaged when end effector 1206 is articulated. In at least some embodiments, referring again to FIG. 36, first joint members 1222 and/or second joint members 1226 can further comprise one or more channels 1296, for example, which can be configured to receive one or more conductors 1247*a* and/or 1247*b* such that the conductors can be seated flush with and/or below the faces of joint members 1222 and 1226. In various embodiments, one or more conductors, such as conductors 1247*a* and 1247*b*, for example, can extend through passages 1250 of joint members 1222 and 1226. In at least one such embodiment, passages 1250 can lie along a neutral axis of the articulation joint such that the stress and strain applied to conductors 1247*a* and 1247*b* can be minimized Stated another way, in at least one embodiment, a path extending through passages 1250 may define a length through the articulation joint wherein the length does not change, or at least substantially change, when the end effector is articulated such that the conductors are not subjected to large deformations.

In various embodiments, as described above, first joint members 1222 can be configured to articulate relative to second joint members 1226 and, correspondingly, second joint members 1226 can be configured to articulate relative to first joint members 1222. In at least one embodiment, referring again to FIGS. 36-39, joint members 1222 and 1226 can be coupled together by one or more ball and socket arrangements, or joints. More particularly, each first joint member 1222 can include a ball member 1227 which can be configured to be received within a socket 1223 of an adjacent second joint member 1226. Similarly, each second joint member 1226 can also include a ball member 1227 which can be configured to be received within a socket 1223 of an adjacent first joint member 1222. In at least one such embodiment, ball members 1227 can be spherical, or at least substantially spherical, and sockets 1223 can comprise a semispherical, or an at least partially spherical, pocket. In various embodiments, the ball and socket joints can be configured to permit the first and second joint members 1222 and 1226 to move in a side-to-side direction, an up-and-down direction, and/or any other suitable direction. In various embodiments, ball members 1227 and sockets 1223 can define a passage 1254 which can be configured to slidably receive firing member 1250 (FIG. 35) and define a path for firing member 1250, especially when end effector 1206 is in an articulated position. In certain embodiments, one or more of the ball and socket joints can be configured to limit the relative movement between joint members 1222 and 1226. In at least one such embodiment, one or more of the ball and socket joints can be configured to limit the relative movement between the first and second joint members such that the joint members can only move relative to each other along a plane, for example. Referring once again to FIG. 36, ball members 1227 can include one or more alignment flanges 1224, for example, extending therefrom which, referring now to FIGS. 37 and 38, can be configured to be received within alignment grooves 1221, for example, defined within sockets 1223. In at least one such embodiment, alignment ridges 1224 and alignment grooves 1221 can be sized and configured to limit the relative movement between first joint members 1222 and second joint members 1226 along a plane defined by alignment flanges 1224, for example.

In any event, further to the above, one or more first joint members 1222 and one or more second joint members 1226 can be realigned along an axis after they have been moved or articulated relative to one other. In at least one embodiment, electromagnets 1240*a* and 1240*b*, for example, can be energized in order to straighten out articulation joint 1220 and, in addition, realign end effector 1206 with shaft 1204. More particularly, in at least one embodiment, electromagnets 1240*a* and electromagnets 1240*b* can be energized simultaneously such that first joint members 1222 and second joint members 1226 are positioned along a central axis defined by shaft 1204. In certain embodiments, the magnitude of current, and/or power, supplied to electromagnets 1240*a* and 1240*b* can be different, at least initially, in order to move joint members 1222 and 1226 into substantial alignment with one another wherein, thereafter, the magnitude of the current and/or power supplied to electromagnets 1240*a* and 1240*b* can be equalized, or at least substantially equalized, such that joint members 1222 and 1226 can be more precisely aligned. In certain embodiments, the magnitude of the current and/or power supplied to electromagnets 1240*a* and 1240*b* can be the same, or at least substantially the same, initially, especially when end effector 1206 has not been significantly articulated.

Figure 41:
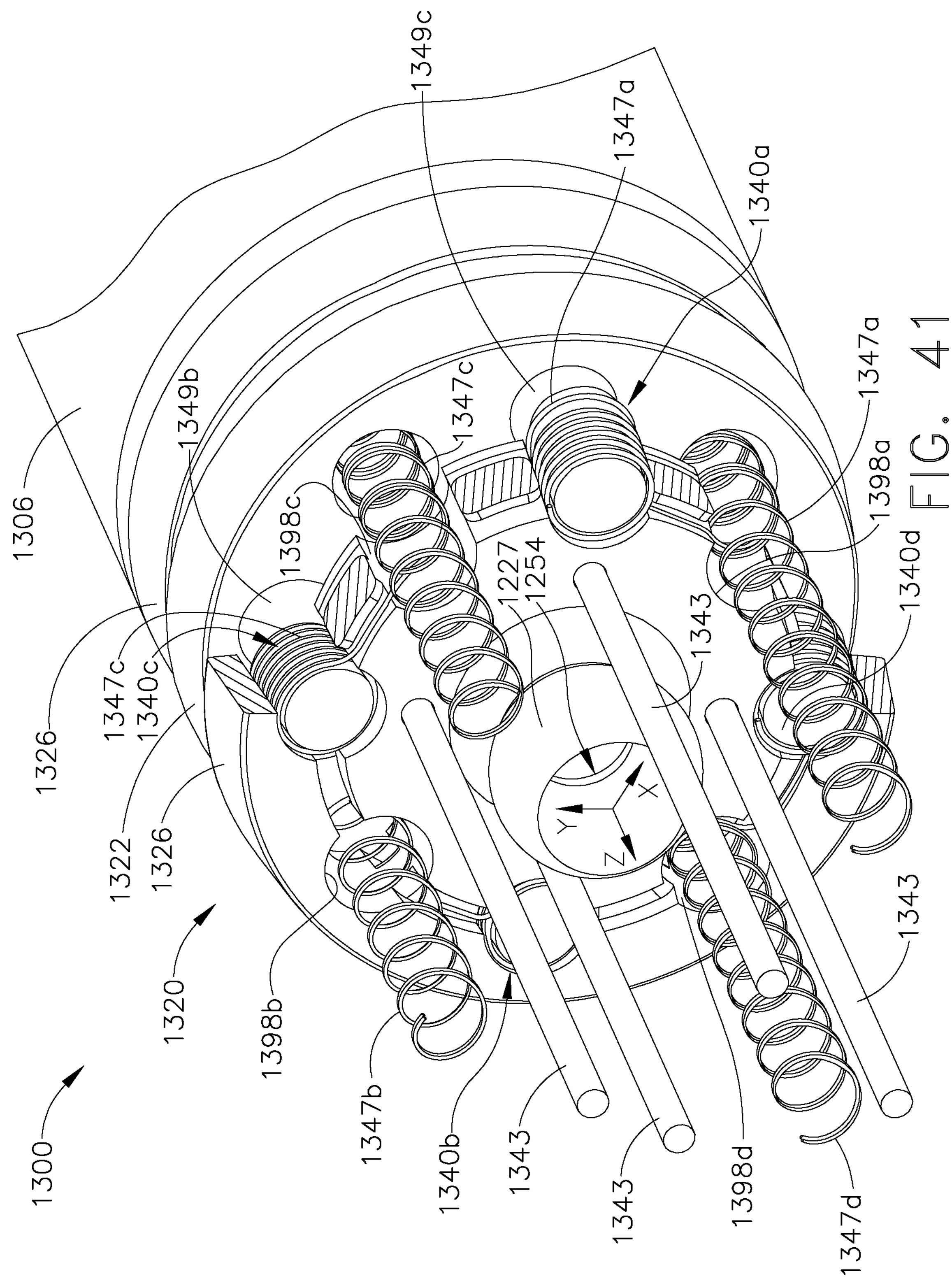
FIG. 41 is a partial perspective view of an articulation joint of a surgical instrument in accordance with at least one alternative embodiment of the present invention illustrated with some components removed and others shown in cross-section.
Figure 42:
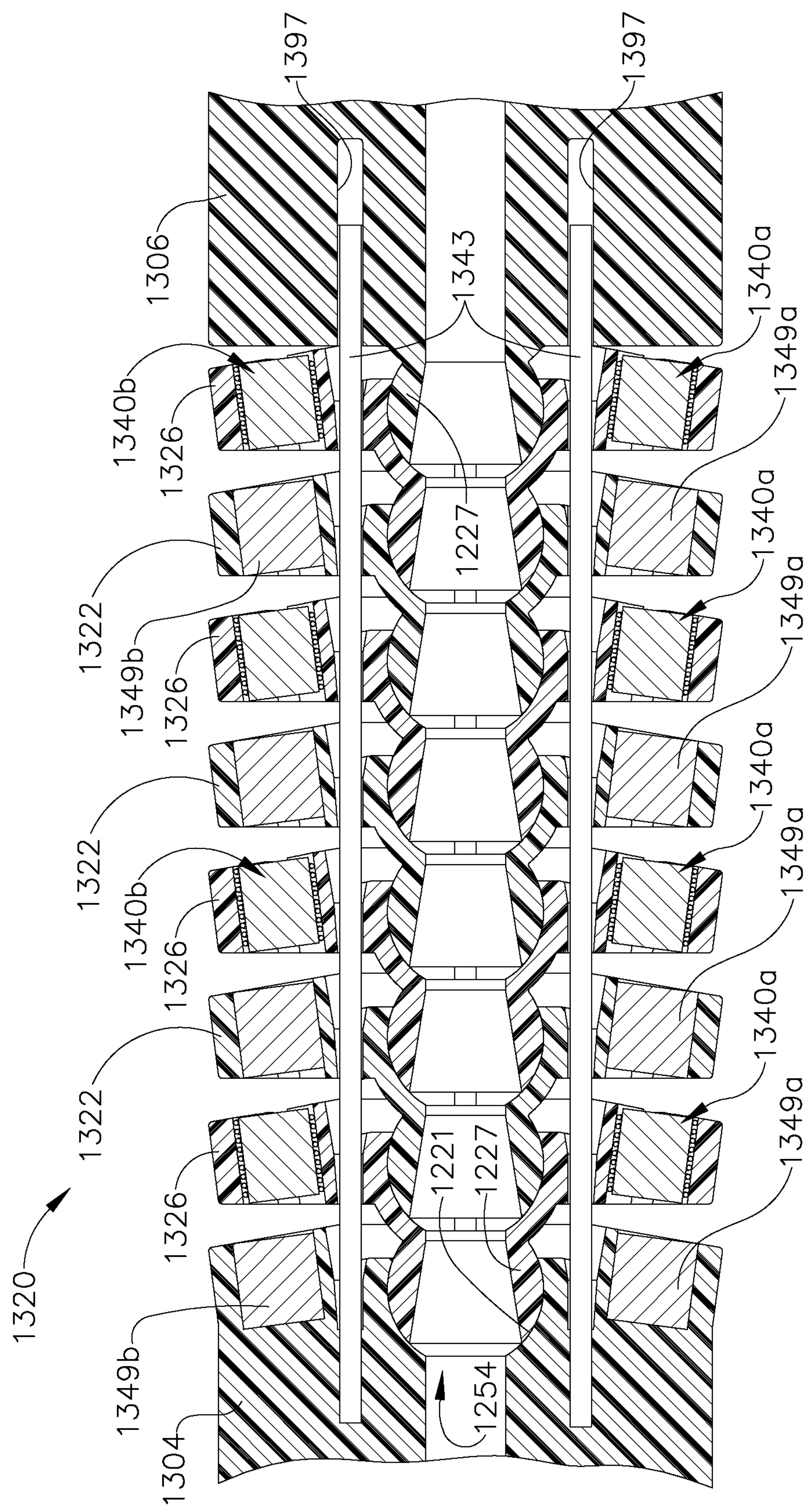
FIG. 42 is a cross-sectional view of the articulation joint of FIG. 41 illustrating alternating first and second discs of the articulation joint.

In various embodiments, further to the above, an end effector of a surgical instrument can be articulated in more than one plane. In at least one embodiment, referring now to FIGS. 41-45, a surgical instrument 1300 can comprise an elongate shaft 1304, an end effector 1306, and an articulation joint 1320 which can be configured to permit end effector 1306 to articulate relative to shaft 1304. Similar to articulation joint 1220, articulation joint 1320 can comprise a plurality of first joint members 1322 and a plurality of second joint members 1326 which can be configured to articulate relative to one another. Unlike joint members 1222 and 1226, though, joint members 1322 and 1326 do not include alignment features 1221 and 1224 which limit relative movement therebetween. In at least one embodiment, as a result, end effector 1306 can be articulated in a plurality of directions and/or planes. In certain embodiments, referring primarily to FIG. 41, each second joint member 1326 can include four electromagnets, such as electromagnets 1340*a*, 1340*b*, 1340*c*, and 1340*d*, for example, which can be mounted to second joint member 1326 within apertures in joint member 1326. In at least one such embodiment, electromagnets 1340*a*-1340*d* can be positioned equidistantly with respect to each other and with respect to the center of joint member 1326. Correspondingly, each first joint member 1322 can include four permanent magnets comprising, referring to FIG. 42, permanent magnets 1349*a*, 1349*b*, 1349*c* (FIG. 41), and a fourth permanent magnet not illustrated, wherein each permanent magnet 1349*a* can be aligned with one or more electromagnets 1340*a*, wherein each permanent magnet 1349*b* can be aligned with one or more electromagnets 1340*b*, wherein each permanent magnet 1349*c* can be aligned with one or more electromagnets 1340*c*, and wherein each fourth permanent magnet can be aligned with one or more electromagnets 1340*d*.

Figure 43:
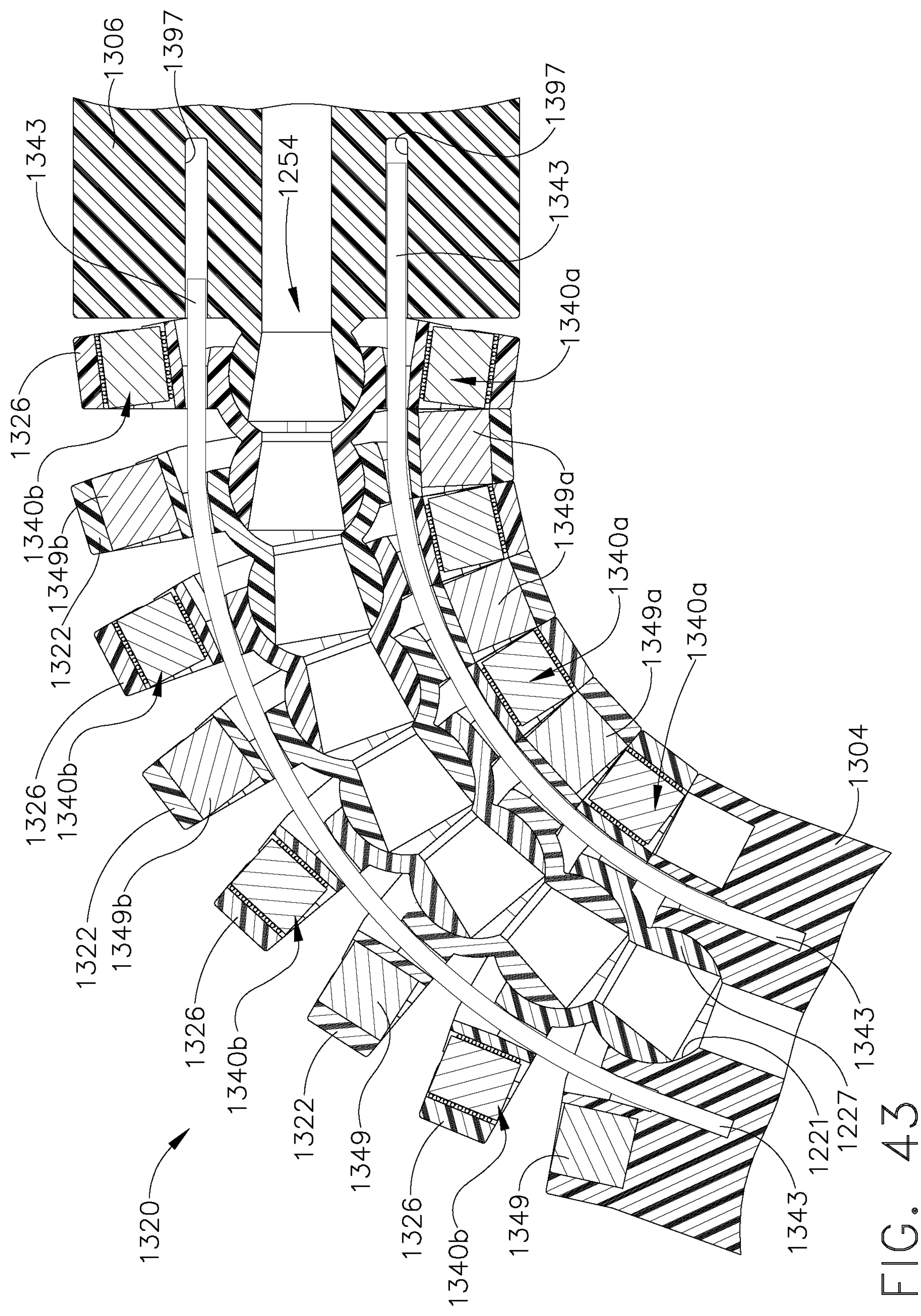
FIG. 43 is a cross-sectional view of the articulation joint of FIG. 41 illustrated in an articulated configuration.
Figure 44:
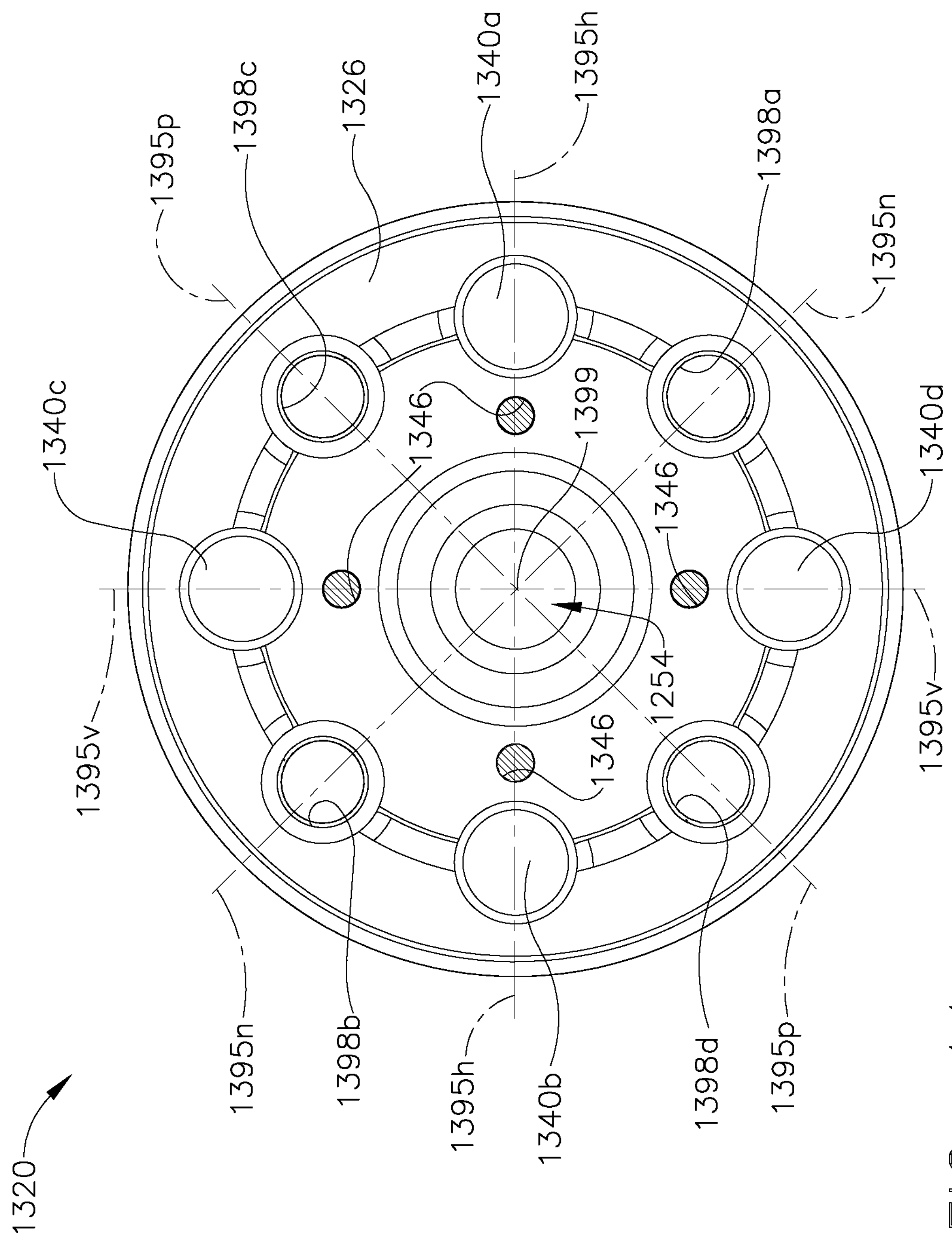
FIG. 44 is an end view of the articulation joint of FIG. 41.
Figure 45:
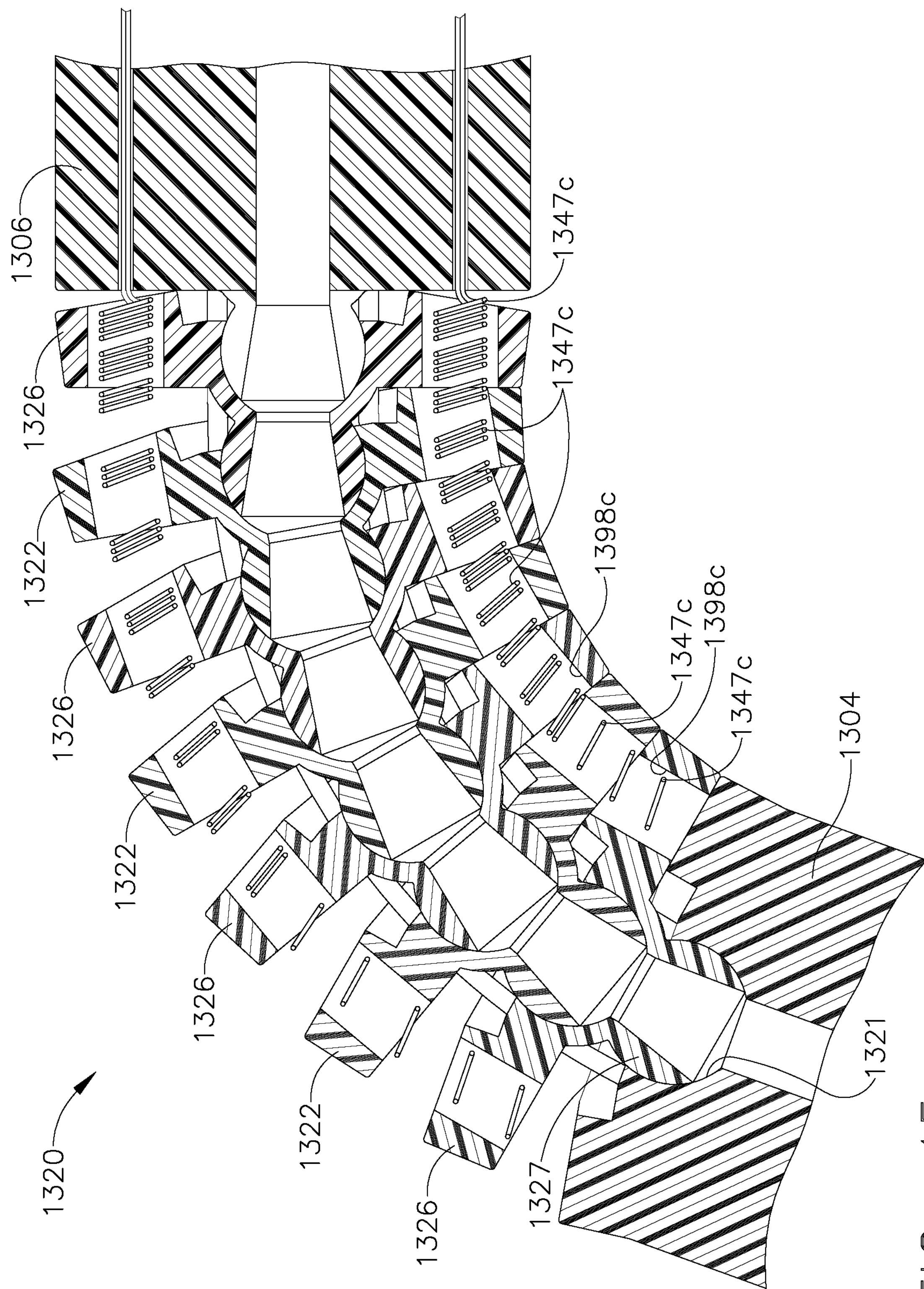
FIG. 45 is another cross-sectional view of the articulation joint of FIG. 41 illustrating the expanded and contracted configurations of electromagnet wires positioned within the discs of the articulation joint.

In use, similar to the above and referring to FIG. 43, electromagnets 1340*a* and/or electromagnets 1340*b* can be selectively actuated in order to articulate end effector 1306 relative to elongate shaft 1304 in left and right directions. Stated another way, referring to FIG. 44, end effector 1306 can be articulated in left and right directions with respect to axis 1395*v*, wherein, in some embodiments, axis 1395*v* can extend through electromagnets 1340*c* and 1340*d* and can intersect, and extend transversely to, longitudinal axis 1399. In addition to the above, electromagnets 1340*c* and/or electromagnets 1340*d* can be selectively actuated in order to articulate end effector 1306 relative to elongate shaft 1304 in up and down directions. Stated another way, end effector 1306 can be articulated in up and down directions with respect to axis 1395*h*, wherein, in some embodiments, axis 1395*h* can extend through electromagnets 1340*a* and 1340*b* and can intersect, and extend transversely to, longitudinal axis 1399. In various embodiments, any suitable combination of electromagnets 1390*a*, 1390*b*, 1390*c*, and 1390*d* can be actuated in order to articulate end effector 1306 relative to elongate shaft 1304 in any suitable direction. For example, referring again to FIG. 44, electromagnets 1340*b* and 1340*c* can be actuated in order to articulate end effector 1306 in a direction along axis 1395*n*. In such an embodiment, the magnitude of the current flowing through conductors 1347*b* can be the same, or at least substantially the same, as the magnitude of the current flowing through conductors 1347*c* such that the intensities of the magnetic fields generated by electromagnets 1340*b* and 1340*c* can be the same, or at least substantially the same, such that they apply equal, or at least substantially equal, magnetomotive forces to their respectfully-aligned permanent magnets. Electromagnets 1340*a* and 1340*d* can be actuated in order to articulate end effector 1306 in an opposite direction along 1395*n*. Similarly, electromagnets 1340*a* and 1340*c* can be actuated in order to articulate end effector 1306 in a direction along axis 1395*p* and, in addition, electromagnets 1340*b* and 1340*d* can be actuated in order to articulate end effector 1306 in an opposite direction along axis 1395*p*.

In various embodiments, as outlined above, electromagnets 1340*b* and 1340*c* can be actuated in order to articulate end effector 1306 in a direction along axis 1395*n*, for example. In at least one such embodiment, electromagnets 1340*b* and 1340*c* can be actuated in order to attract permanent magnets 1349*b* and 1349*c*, respectively, thereto. Contemporaneously, in certain embodiments, electromagnets 1340*a* and 1340*d* can be actuated in order to repel permanent magnets 1349*a* and 1349*d*, respectively, in order to assist in the articulation of end effector 1306. In various embodiments, in view of the above, any suitable combination of electromagnets can be actuated such that they can attract and/or repel the various permanent magnets associated therewith, for example, at the same time and/or in any suitable order.

As outlined above, various combinations of electromagnets 1340*a*, 1340*b*, 1340*c*, and 1340*d* can be actuated in order to articulate end effector 1306 wherein, in some embodiments, the same magnitude of current can be supplied to the actuated electromagnets in order to articulate end effector 1306 along axes 1395*n* and 1395*p*, i.e., along approximately 45 degree angles with respect to axes 1395*v* and 1395*h*, for example. In other embodiments, different magnitudes of current can be supplied to various electromagnets such that end effector 1306 is articulated in other directions. For example, conductors 1347*c* of electromagnets 1340*c* can be supplied with a current which has approximately twice the magnitude of the current supplied to conductors 1347*b* of electromagnets 1340*b* so as to articulate end effector 1306 in a direction which is intermediate axes 1395*n* and 1395*v*. In any event, electromagnets 1340*a*, 1340*b*, 1340*c*, and 1340*d* can all be actuated simultaneously in order to re-straighten articulation joint 1320 along longitudinal axis 1399, for example. In certain embodiments, referring once again to FIGS. 41 and 43, articulation joint 1320 can further comprise one or more flexible straightening and alignment rods, such as rods 1343, for example, which can be configured to straighten articulation joint 1320. In at least one such embodiment, the proximal ends of rods 1343 can be mounted to elongate shaft 1304 wherein rods 1343 can extend through apertures 1346 in joint members 1322 and 1326 and extend into apertures 1397 in end effector 1306. When end effector 1306 is articulated as described above, rods 1343 can be sufficiently flexible to permit such articulation but can be sufficiently resilient to return back to their original shape once electromagnets 1340*a*, 1340*b*, 1340*c*, and 1340*d* have been sufficiently deenergized. In at least one embodiment, rods 1343 can be configured to slide within apertures 1346 and apertures 1397 in order to accommodate the various configurations of articulation joint 1320. Similar to the above, referring to FIGS. 41 and 45, joint members 1322 and 1326 can include one or more through-holes 1398*a*-1398*d* which can be configured to slidably receive conductors 1347*a*-1347*d* therein, wherein conductors 1347*a*-1347*d* can also be sufficiently flexible to accommodate the various configurations of articulation joint 1320.

Figure 46:
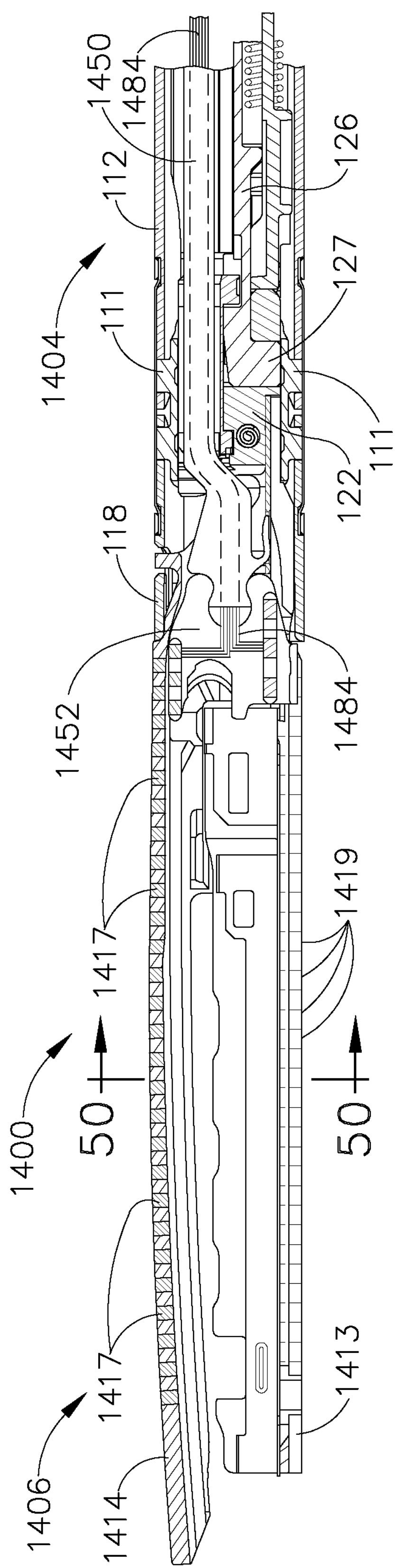
FIG. 46 is a cross-sectional view of an end effector of a surgical instrument in accordance with at least one embodiment of the present invention illustrating a plurality of permanent magnets positioned within an anvil of the end effector.
Figure 47:
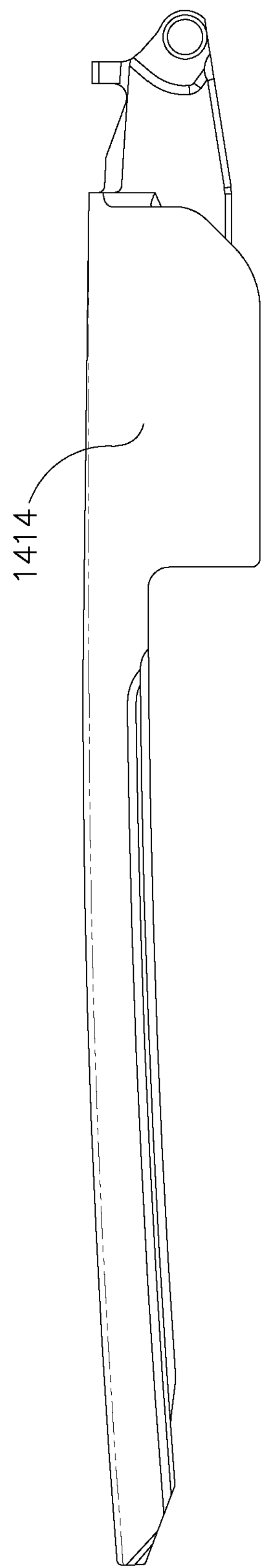
FIG. 47 is an elevational view of the anvil of FIG. 46.
Figure 48:
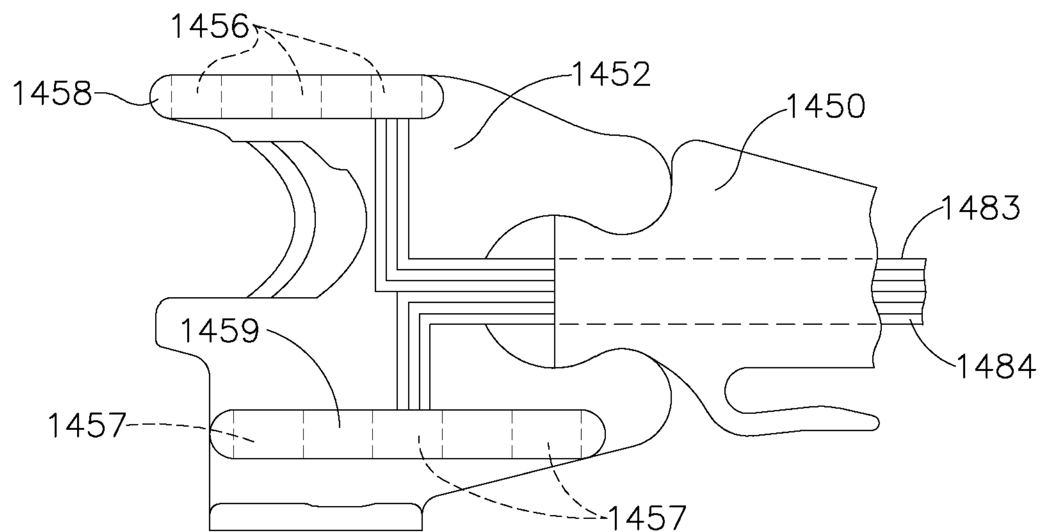
FIG. 48 is an elevational view of a cutting member of the end effector of FIG. 46 comprising a plurality of electromagnets configured to cooperate with permanent magnets positioned in the end effector of the surgical instrument and advance and/or retract the cutting member within the end effector.
Figure 49:
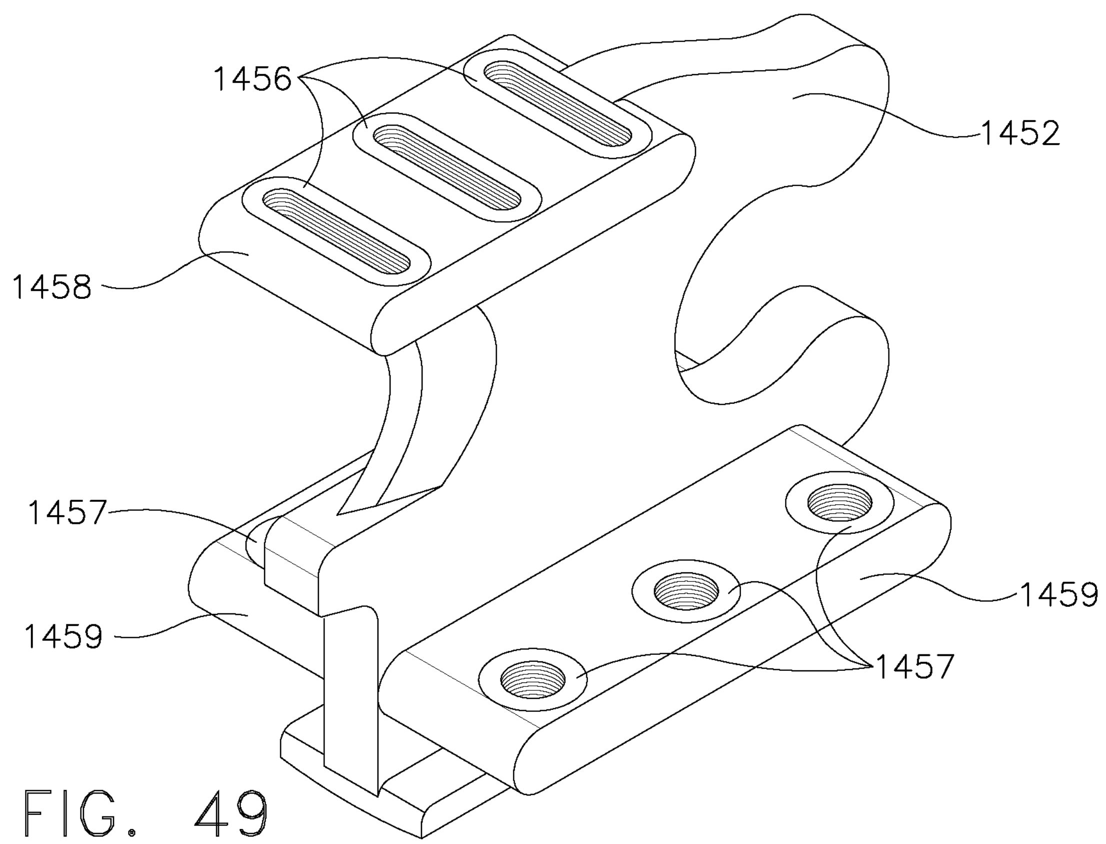
FIG. 49 is a perspective view of the cutting member of FIG. 48.
Figure 50:
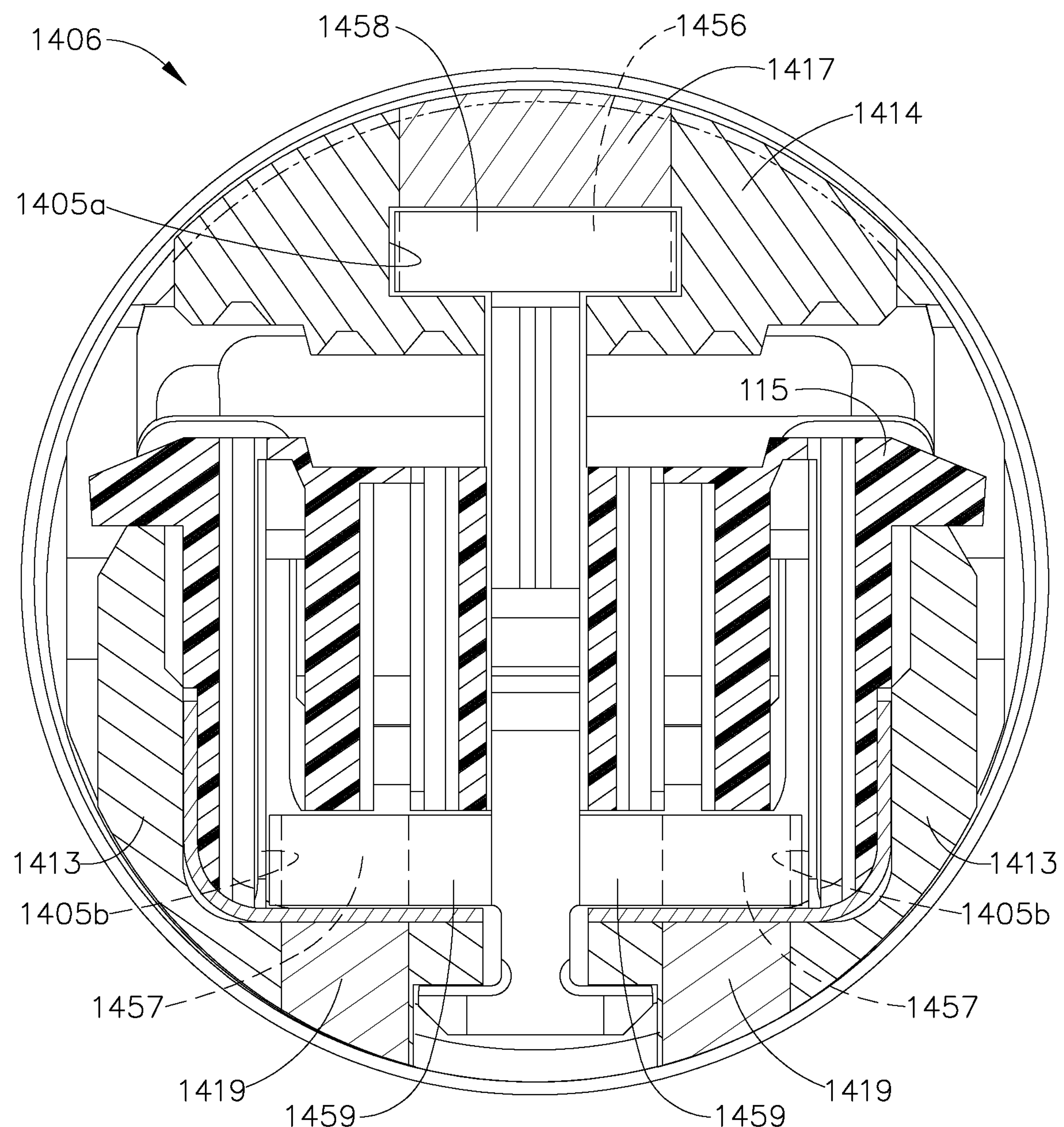
FIG. 50 is another cross-sectional view of the end effector of FIG. 46.
Figure 51A:
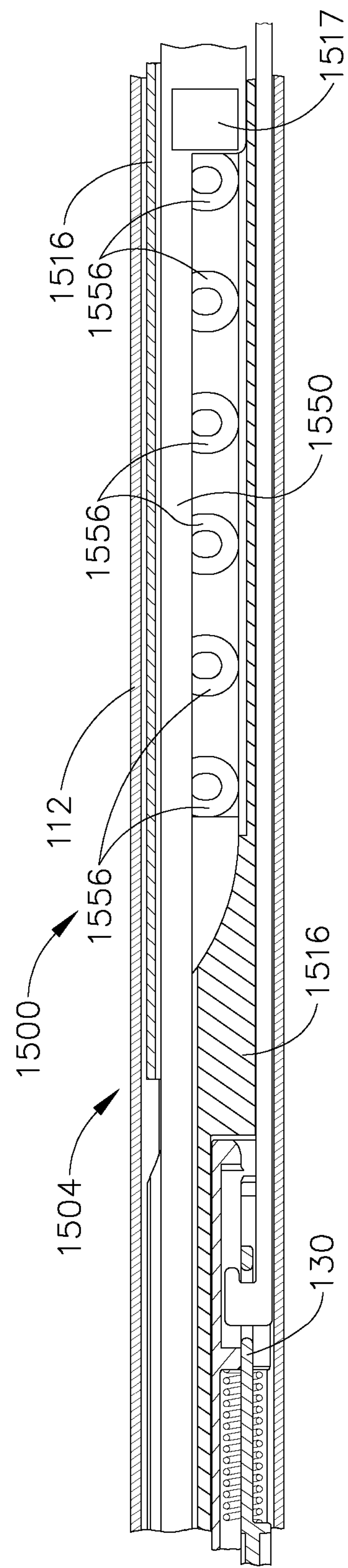
FIGS. 51A-51C illustrate distal, middle, and proximal portions of an elongate shaft of a surgical instrument and a movable firing bar positioned within the elongate shaft in accordance with at least one embodiment of the present invention.
Figure 51B:
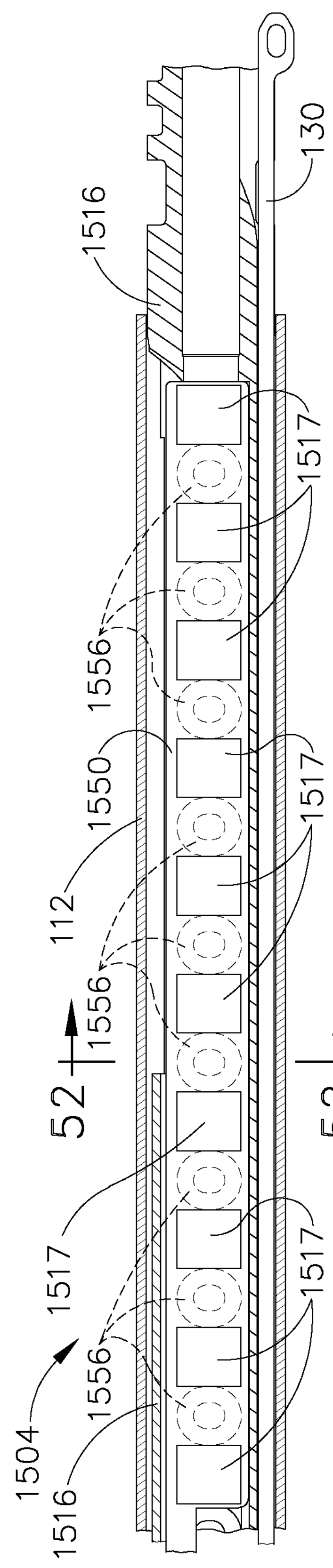
Figure 51C:
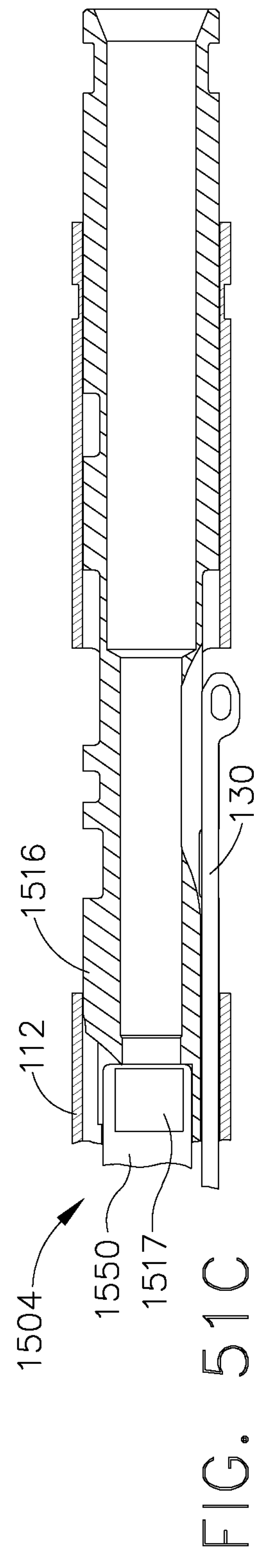

As described above, a system of permanent magnets and electromagnets can be utilized to articulate an end effector relative to an elongate shaft of a surgical instrument. In various embodiments, a surgical instrument can include a system of permanent magnets and electromagnets configured to drive a cutting member and/or staple driver through an end effector of the surgical instrument. In at least one embodiment, referring to FIGS. 46-50, a surgical instrument, such as surgical instrument 1400, for example, can include an end effector 1406, an elongate shaft 1404, and a cutting member 1452 configured to be advanced and/or retracted within end effector 1406. Referring primarily to FIGS. 46 and 50, end effector 1406 can comprise a staple cartridge channel 1413 configured to support and/or retain staple cartridge 115, for example, therein. End effector 1406 can further comprise an anvil 1414 which can be rotatably coupled to staple cartridge channel 1413 such that anvil 1414 can be rotated between open and closed positions. As best illustrated in FIG. 46, anvil 1414 can further include a plurality of permanent magnets 1417 mounted thereto wherein, when anvil 1414 is in its closed position, for example, permanent magnets 1417 can be configured to advance or retract cutting member 1452. More particularly, in at least one embodiment, cutting member 1452 can comprise one or more electromagnets 1456 (FIGS. 48-50) which can be energized, or polarized, in order to create a magnetic field, or fields, which can interact with permanent magnets 1417 and generate a magnetomotive force therebetween. In various embodiments, such forces can displace cutting member 1452 proximally and/or distally within end effector 1406. In at least one embodiment, permanent magnets 1417 can be secured within equidistant, or at least substantially equidistant, apertures in anvil 1414 and, in addition, electromagnets 1456 can be mounted within upper shoe 1458. In various embodiments, referring to FIG. 50, upper shoe 1458 can be configured to be received within channel 1405*a* in anvil 1414 such that, when cutting member 1452 traverses anvil 1414, upper shoe 1458 can bias anvil 1414 downwardly to compress tissue positioned intermediate anvil 1414 and staple cartridge 115, for example.

In various embodiments, similar to the above, staple cartridge channel 1413 can further include a plurality of permanent magnets 1419 mounted thereto wherein permanent magnets 1419 can be configured to advance or retract cutting member 1452. More particularly, in at least one embodiment, cutting member 1452 can comprise one or more electromagnets 1457 which can be energized, or polarized, in order to create a magnetic field, or fields, which can interact with permanent magnets 1419 and generate a magnetomotive force therebetween. In various embodiments, such forces can displace cutting member 1452 proximally and/or distally within end effector 1406. In at least one embodiment, permanent magnets 1419 can be secured within equidistant, or at least substantially equidistant, apertures in staple cartridge channel 1413 and, in addition, electromagnets 1457 can be mounted within lower shoe 1459. In various embodiments, referring to FIG. 50, lower shoe 1459 can be configured to be received within channel 1405*b* in staple cartridge 115 such that, when cutting member 1452 traverses staple cartridge 115, lower shoe 1459 can co-operate with upper shoe 1458 to compress tissue positioned intermediate anvil 1414 and staple cartridge 115, for example. In certain embodiments, various portions of staple cartridge 115, staple cartridge channel 1413, and/or anvil 1414 can be comprised of a non-conductive material, or materials, which can have a sufficient dielectric strength to prevent current from flowing between electromagnets and/or between electromagnets and permanent magnets, yet be sufficiently transmissive to magnetic fields. In any event, similar to the above, surgical instrument 1400 can further comprise one or more conductors, such as wires 1484, for example, which can be configured to supply electromagnets 1456 and/or 1457 with a flow of current in order to selectively polarize electromagnets 1456 and 1457. In at least one such embodiment, similar to the above once again, the direction of current flowing through conductors 1484 can be selectively alternated in order to control the poles generated by electromagnets 1456 and/or 1457. In various embodiments, at least a portion of conductors 1484 can be embedded within firing bar 1450. In certain embodiments, firing bar 1450 can comprise two or more laminated layers, wherein, although not illustrated, at least a portion of conductors 1484 can be positioned intermediate the layers, and wherein the layers can be configured to protect and/or electrically insulate conductors 1484 from unintentionally grounding to one another and/or any other portion of surgical instrument 1400. In various embodiments, although not illustrated, conductors 1484 can comprise a flexible ribbon cable which can comprise a plurality of conductors 1484 arranged in parallel and electrically insulated from one another. In any event, the system of permanent magnets and electromagnets within end effector 1406 may be sufficient to advance and retract cutting member 1452 without an additional firing force being transmitted to cutting member 1452 via firing bar 1450, although firing bar 1450 can be configured to transmit an additional firing force to cutting member 1452.

In various embodiments, as outlined above, electromagnets can be positioned on and/or within a cutting member movable within an end effector. In use, the electromagnets can be actuated, or energized, such that they can produce a polarized magnetic field. In at least one such embodiment, each electromagnet can include at least one conductor arranged in a wrapped configuration wherein, when current is supplied to the conductor, the current can generate a field having positive and negative poles. In certain embodiments, as also outlined above, iron cores positioned within the wrapped conductor can amplify the magnetic field produced by the current. Although electromagnets are entirely suitable in various embodiments, any device capable of selectively generating one or more magnetic fields can be used. In at least one embodiment, for example, a polarizable device can include an annular, or toroidal, permanent magnet, and/or iron core, wherein a conductor can extend through an aperture therein, and wherein a magnetic field produced by current flowing through the conductor can be amplified by the annular iron core surrounding the conductor. In various circumstances, the magnetic field produced by such a device may be sufficient to create a usable magnetomotive force as described herein. In certain embodiments, fields produced by a Hall Effect device, or coil, can be utilized to move a cutting member, for example, within an end effector.

In various embodiments, either in addition to or in lieu of the above, a surgical instrument can comprise a system of permanent magnets and electromagnets configured to advance and/or retract a firing bar within an elongate shaft of a surgical instrument. Referring now to FIGS. 51A-51C and 53, surgical instrument 1500 can comprise an elongate shaft 1504 and a firing bar 1550, wherein firing bar 1550 can be advanced distally (FIG. 53) and/or retracted proximally (FIGS. 51A-51C) in order to move a cutting member and/or staple driver, such as cutting member 1452, for example, within an end effector in order to incise tissue and/or deploy staples into the tissue, for example. In certain embodiments, shaft 1504 can comprise spine 1516 which can comprise one or more slots configured to permit firing bar 1550 to slide therein. In at least one such embodiment, elongate shaft 1504 can further comprise one or more electromagnets 1556 mounted to spine 1516 which can be configured to selectively generate one or more magnetic fields. Similar to the above, such magnetic fields can interact with permanent magnets 1517 mounted to drive bar 1550 such that the magnetomotive force generated between electromagnets

Figure 52:
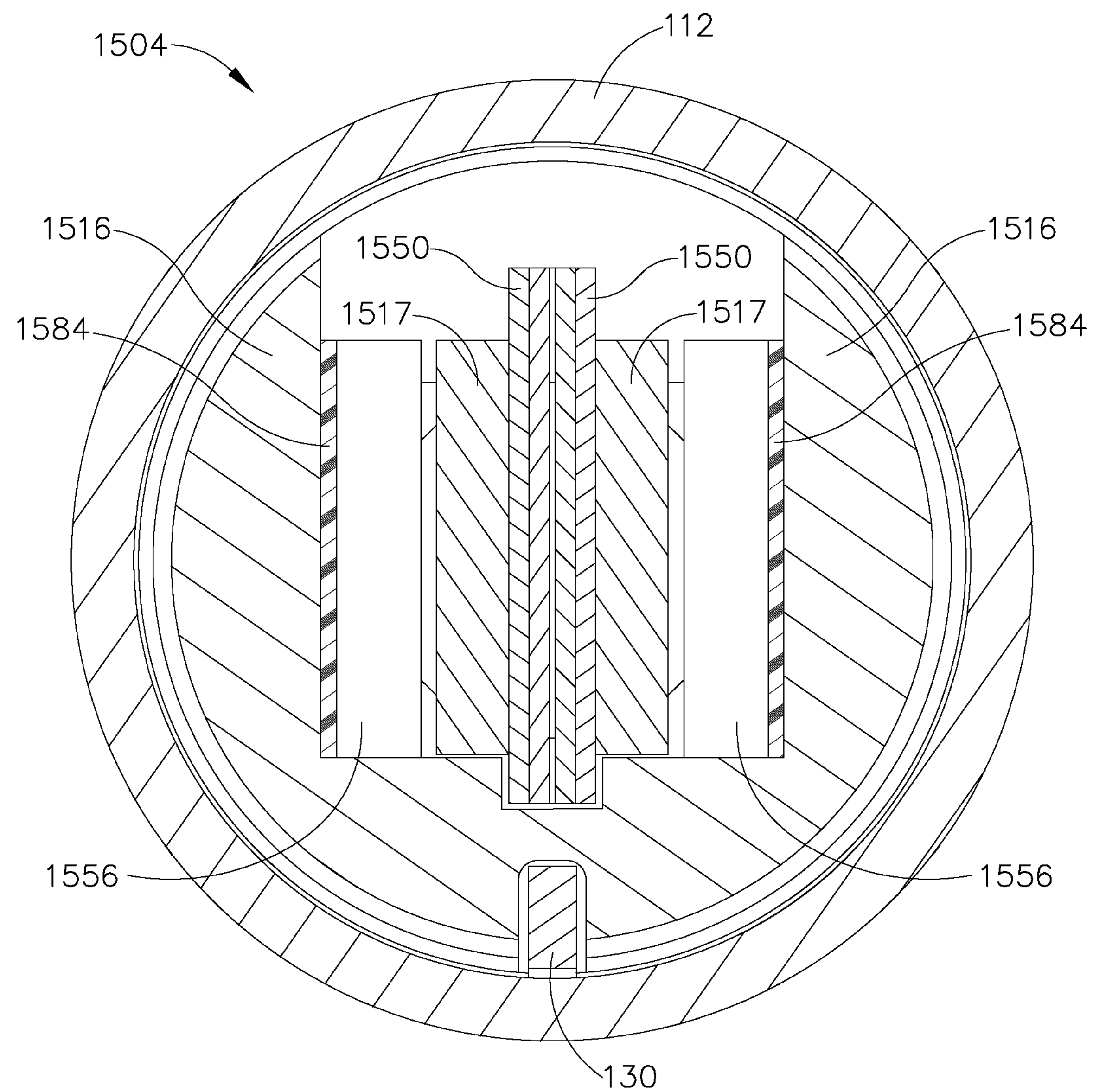
FIG. 52 is a cross-sectional view of the elongate shaft and the movable firing bar of FIGS. 51A-C.
Figure 53:
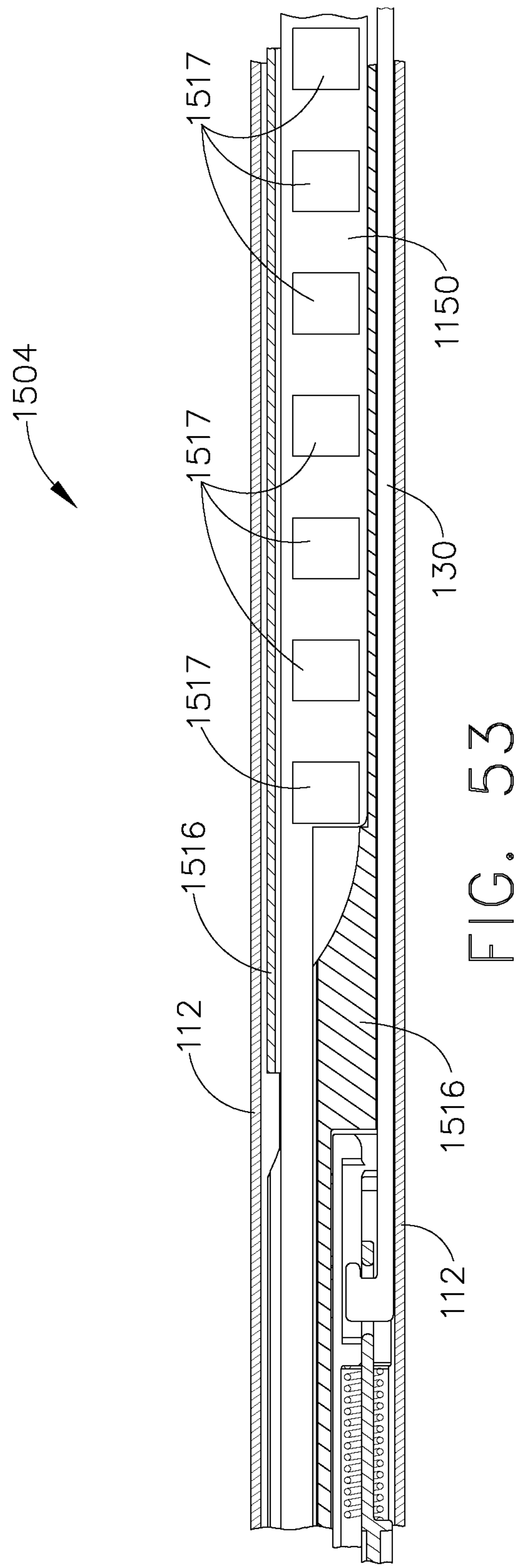
FIG. 53 is another cross-sectional view of the distal portion of the elongate shaft and the movable firing bar of FIG. 51A illustrating the firing bar in a fired position.

1556 and permanent magnets 1517 can move permanent magnets 1517, and drive bar 1550, relative to electromagnets 1556, and spine 1516. In at least one embodiment, referring now to FIG. 52, elongate shaft 1504 can include a first set of electromagnets 1556 positioned on one side of firing bar 1550 and a second set of electromagnets 1556 positioned on the opposite side of firing bar 1550. Correspondingly, a first set of permanent magnets 1517 can be positioned on a first side of firing bar 1550 and a second set of permanent magnets 1517 can be positioned on the opposite side of firing bar 1550. Also similar to the above, the current supplied to electromagnets 1556 can be selectively supplied in order to generate positive poles, negative poles, and/or no polarity within electromagnets 1556, as needed, in order to sufficiently attract and repel the positive and negative poles of permanent magnets 1517. In certain embodiments, referring again to FIG. 52, elongate shaft 1504 can further comprise one or more conductors 1584 which can be configured to supply current to electromagnets 1556. In certain embodiments, conductors 1584 can comprise a ribbon cable positioned intermediate spine 1516 and electromagnets 1556, wherein spine 1516 can be comprised of an electrically non-conductive material, for example.

In various embodiments, further to the above, a surgical instrument can comprise a system including magnetic elements, such as iron cores and/or permanent magnets, for example, and selectively actuatable electromagnets, wherein the system can comprise a linear motor configured to move a firing bar and/or cutting member along a predetermined path, and wherein the path can comprise linear portions and/or curved portions in one or more directions. In various embodiments, the surgical instrument can further comprise a computer, or processor, which can be configured to calculate the appropriate magnitude, duration, and/or direction of the current to be supplied to the electromagnets. In certain embodiments, the surgical instrument can further comprise one or more switches which can be operated by the computer in order to selectively supply current to one or more electromagnets. In certain embodiments, although not illustrated, a surgical instrument can include a handle, an elongate shaft extending from the handle, and an end effector operably coupled to the shaft, wherein the shaft can include one or more conductors wound about an axis or predetermined path within the shaft. In at least one such embodiment, a firing bar, or rod, having an iron portion, for example, can be positioned within an aperture defined by the wound conductors such that, when current is supplied to the conductors, the magnetic field, or fields, generated by the flow of current can move the iron firing bar along the predetermined path. In at least one embodiment, similar to the above, current flowing through the conductors in a first direction can move the firing bar distally within the shaft, for example, and, in addition, current flowing through the conductors in an opposite direction can move the firing bar in an opposite, or proximal, direction.

Figure 54:
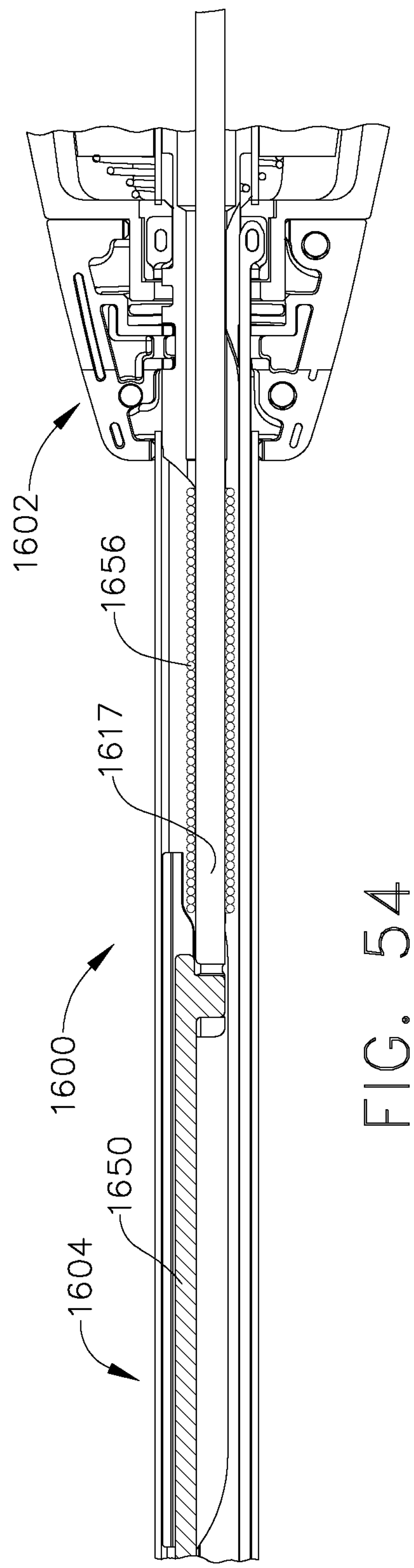
FIG. 54 is a cross-sectional view of an elongate shaft of a surgical instrument according to at least one embodiment of the present invention illustrating a firing bar in an unfired position.
Figure 55:
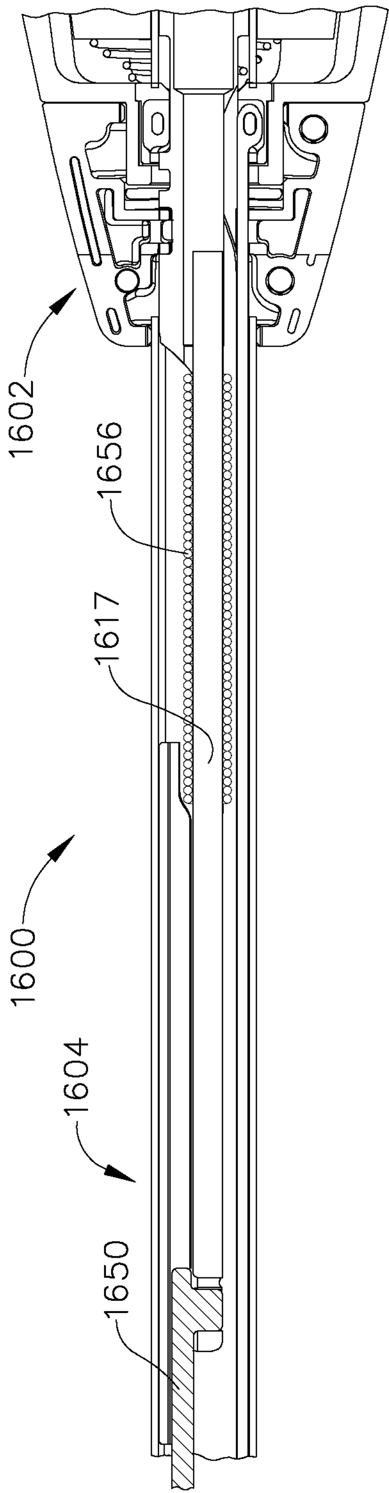
FIG. 55 is a cross-sectional view of the surgical instrument of FIG. 54 illustrating the firing bar moved into a fired position by an electromagnetic coil.

In various embodiments, an elongate shaft of a surgical instrument can include a solenoid configured to advance and/or retract a firing bar, cutting member, and/or staple driver. In at least one embodiment, referring to FIGS. 54 and 55, surgical instrument 1600 can comprise a handle assembly 1602, an elongate shaft 1604, and a firing bar 1650. Similar to handle assembly 102, handle assembly 1602 can further comprise a trigger (not illustrated) configured to advance and/or retract firing bar 1650. In at least one embodiment, the trigger of handle assembly 1602 can be configured to close, or complete, a circuit when actuated, wherein the closed circuit can be configured to supply current to a solenoid operably engaged with firing bar 1650. In certain embodiments, although not illustrated, handle assembly 1602, for example, can include one or more batteries positioned therein, wherein the batteries, and one or more conductors, can be configured to supply the current to the solenoid. In at least one embodiment, the solenoid can comprise windings 1656 which can be energized by the current in order to generate a polarized magnetic field. Similar to the above, the solenoid can further comprise a magnetic element 1617, which can be comprised of iron, for example, which can be configured to interact with the magnetic field. In use, current flowing in a first direction can be supplied to windings 1656 such that the magnetic field produced by windings 1656 can advance magnetic element 1617, and drive bar 1650 mounted thereto, distally within elongate shaft 1604 as illustrated in FIG. 55. In certain embodiments, the trigger can be released in order to disconnect the supply of current to windings 1656 and stop the advancement of firing bar 1650. In at least one such embodiment, handle assembly 1602 and/or elongate shaft 1604 can include one or more springs (not illustrated) which can be configured to bias magnetic element 1617 and firing bar 1650 back into their starting positions which are illustrated in FIG. 54. In other embodiments, the current flowing within windings 1656 can be reversed when the firing trigger is released such that the polarity of the magnetic field generated by windings 1656 is reversed and magnetic element 1617 is retracted. In yet other embodiments, the trigger of handle assembly 1602 can be actuated once again in order to reverse the current within windings 1656 and retract magnetic element 1617.

In various embodiments, although not illustrated, a surgical instrument can include a handle, a shaft extending from the handle, and an end effector operably coupled to the shaft, wherein the shaft can include a rotatable drive shaft, and wherein the surgical instrument can further include a motor configured to rotate the drive shaft. Various surgical instruments including a motor and a rotatable drive shaft are disclosed in U.S. Pat. No. 7,422,139, entitled MOTOR-DRIVEN SURGICAL CUTTING FASTENING INSTRUMENT WITH TACTILE POSITION FEEDBACK, which issued on Sep. 9, 2008; and U.S. Pat. No. 7,416,101, entitled MOTOR-DRIVEN SURGICAL CUTTING AND FASTENING INSTRUMENT WITH LOADING FORCE FEEDBACK, which issued on Aug. 28, 2008, the entire disclosures of which are incorporated by reference herein. In at least one embodiment, the motor of the surgical instrument can comprise a stepper motor which can be configured to rotate a drive shaft through a predetermined range of rotation. In at least one embodiment, one or more magnetic elements, such as iron cores, for example, can be placed on or embedded within the drive shaft, wherein the magnetic elements can be configured to be detected by one or more sensors positioned within the shaft, for example. In certain embodiments, such sensors can comprise Hall Effect sensors, or coils, which can be configured to detect disruptions within one or more magnetic fields, i.e., disruptions created by the magnetic elements.

In various embodiments, although not illustrated, a surgical instrument can include a system of electromagnets and magnetic elements which can be configured to close and/or open an end effector of a surgical instrument. In at least one such embodiment, similar to the above, the end effector can comprise a staple cartridge channel configured to receive a staple cartridge and, in addition, an anvil rotatably coupled to the staple cartridge channel. In certain embodiments, one or more electromagnets can be positioned within the staple cartridge channel and, in addition, one or more magnetic elements can be positioned within the anvil, wherein, when the electromagnets are energized, or polarized, the electromagnets can generate a magnetic field which can move the magnetic elements toward the electromagnets and, as a result, move the anvil between an open position and a closed position. In some such embodiments, the polarity of the electromagnets can be reversed in order to repel the magnetic elements mounted to the anvil and, as a result, move the anvil between a closed position and an open position. In other embodiments, the current being supplied to the electromagnets can be sufficiently reduced, or disconnected, such that the electromagnets cannot produce a sufficient magnetic field to hold the anvil in its closed position. In at least one such embodiment, the end effector can further comprise a spring which can be configured to bias the anvil into its open position such that, when the electromagnets are sufficiently deenergized as described above, the spring can move the anvil into its open position. In various alternative embodiments, the electromagnets can be configured to bias the anvil into its open position and the spring can be configured to bias the anvil into its closed position.

While the present invention has been illustrated by the description of several embodiments and while the illustrative embodiments have been described in considerable detail, it is not the intention of the applicant to restrict or in any way limit the scope of the appended claims to such detail. Additional advantages and modifications may readily appear to those skilled in the art. Furthermore, although the embodiments disclosed herein have been described in connection with an endoscopic cutting and stapling instrument, other embodiments are envisioned in connection with any suitable medical device. While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Further to the above, the various embodiments of the present invention have been described above in connection with cutting-type surgical instruments. It should be noted, however, that in other embodiments, the surgical instruments disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Further to the above, the various staple cartridges disclosed herein can be disposable. In at least one embodiment, an expended staple cartridge, or an at least partially expended staple cartridge, can be removed from a surgical stapler and replaced with another staple cartridge. In other various embodiments, the staple cartridge may not be removable and/or replaceable during the ordinary use of the surgical instrument but, in some circumstances, may be replaceable while and/or after the surgical stapler is reconditioned as described in greater detail below. In various embodiments, the staple cartridge can be part of a disposable loading unit or end-effector which can further include a staple cartridge carrier, anvil, cutting member, and/or staple driver. In at least one such embodiment, the entire, or at least a portion of, the disposable loading unit or end-effector can be detachably connected to a surgical instrument and can be configured to be replaced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

What is claimed is:

1. A surgical stapling system, comprising:

a stapling assembly comprising:

a distal end;

a staple cartridge, wherein said staple cartridge comprises a plurality of staples removably stored therein; and an anvil configured to deform said staples, wherein said stapling assembly is configurable in an open configuration and a closed configuration by a closure member;

a firing member movable toward said distal end to eject said staples from said staple cartridge;

a shaft rotatable in a first rotation direction and a second rotation direction;

an articulation joint, wherein said stapling assembly is articulatable about said articulation joint in a first articulation direction and a second articulation direction; and a handle, wherein said shaft extends from said handle, and wherein said handle comprises:

a firing actuator configured to move said firing member toward said distal end;

a rotation actuator comprising a first initial position, wherein said rotation actuator is configured to:

rotate said shaft in said first rotation direction when said rotation actuator is rotated in a first rotation actuator direction; and rotate said shaft in said second rotation direction when said rotation actuator is rotated in a second rotation actuator direction which is opposite said first rotation actuator direction;

an articulation actuator comprising a second initial position, wherein said articulation actuator is rotatable about a longitudinal axis extending toward said distal end, wherein said articulation actuator is configured to:

rotate said stapling assembly in said first articulation direction when said articulation actuator is rotated in a first articulation actuator direction; and rotate said stapling assembly in said second articulation direction when said articulation actuator is rotated in a second articulation actuator direction which is opposite said first articulation actuator direction; and means for preventing the articulation of said stapling assembly and the rotation of said shaft when said firing actuator is being actuated, wherein said means is independent from said closure member.

* * * * *